United States Patent
McHenry et al.

(10) Patent No.: US 6,238,905 B1
(45) Date of Patent: May 29, 2001

(54) THERMOPHILIC POLYMERASE III HOLOENZYME

(75) Inventors: Charles S. McHenry; Mark Seville; Millard G. Cull, all of Denver, CO (US)

(73) Assignee: University Technology Corporation, CO (US)

( * ) Notice: Subject to any disclaimer, the term of this patent is extended or adjusted under 35 U.S.C. 154(b) by 0 days.

(21) Appl. No.: 08/928,213

(22) Filed: Sep. 12, 1997

(51) Int. Cl.$^7$ .............................. C12N 9/12; C12N 1/20; C12N 15/00; C07H 21/04

(52) U.S. Cl. ................. 435/252.3; 435/194; 435/254.11; 435/320.1; 435/325; 435/419; 530/326; 536/23.2; 536/23.7

(58) Field of Search ........................... 530/326; 536/23.2, 536/23.7; 435/194, 320.1, 325, 419, 252.3, 254.11

(56) References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,889,818 | 12/1989 | Gelfand et al. | 435/194 |
| 4,946,778 | 8/1990 | Ladner et al. | 435/69.6 |
| 4,965,188 | 10/1990 | Mullis et al. | 435/6 |
| 5,322,770 | 6/1994 | Gelfand | 435/6 |

FOREIGN PATENT DOCUMENTS

| | | |
|---|---|---|
| WO 91/09950 | 7/1991 | (WO) . |
| WO 93/03367 | 2/1993 | (WO) . |
| WO 93/15115 | 8/1993 | (WO) . |
| WO 94/05797 | 3/1994 | (WO) . |
| WO 98/454452 | 10/1998 | (WO) . |

OTHER PUBLICATIONS

Rudinger (1976) Characteristics of the amino acids as components of a peptide hormone sequence. In: Peptide Hormones. Ed. J. A. Parsons. University Park Press, Baltimore, MD. pp. 1–7, Jun. 1976.*
Ngo et al. (1994) Computational complexity, protein structure prediction, and the ILeventhal paradox. In: The Protein Folding Problem and Tertiary Structure Prediction. Eds. Merz et al. Birkhauser et al. Boston, MA. pp. 491–495, Jan. 1994.*
Thornton et al. (1995) Protein Engineering: Eidtorial Overview. Current Opinion in Biotechnology 6(4): 367–369, Aug. 1995.*
Wallace (1993) Understanding cytochrome c function: engineering protein structure by semisynthesis. The FASEB Journal 7: 505–515, Apr. 1993.*
Sellman et al., J. Bacteriol., 174:4350–4355 (1992).
Klimczak et al., Biochem., 25:4852–4855 (1986).

Alonso et al. Nuc. Acid Res. (1990) 18: 6771–6777 "Molecular cloning . . . of the recM region of *Bacillus subtilis*".*
Flower et al. Nuc. Acids Res. (1986) 14: 8091–8101. "The adjacent dnaZ and dnaX genes of *Escherichia coli* . . . ".*
McHenry et al. J. Mol. Biol. 272(2):178–189, 1997.*
Anderson and Young, Quantitative Filter Hybridization, in *Nucleic Acid Hybridization* (1985).
Ausubel et al., *Current Protocols in Molecular Biology*, John Wiley & Sons, New York NY (1995), sections 2.9.2 to 2.9.11, 6.1.1–6.1.3 and 6.3.1–6.3.4.
Blinkowa and Walker, "Programmed ribosomal frameshifting generates the *Escherichia coli* DNA polymerase III γ subunit from within the τ subunit reading frame," *Nucl. Acids Res.*, 18:1725–1729 (1990).
Boshart et al., "A Very Stong Enhancer is Located Upstream of an Immediate Early Gene of Human Cytomegalovirus," *Cell* 41:521–530 (1985).
Brush and Stillman, "Identification of Eukaryotic DNA Replication Proteins Using Simian Virus 40 in Vitro Replication System," *Meth. Enzymol.* 262:522–548 (1995).
Chamberlin et al., "New RNA Polymerase from *Escherichia coli* Infected with Bacteriophage T7," *Nature* 228:227–231 (1970).
Chien et al., "Deoxyribonucleic Acid Polymerase from the Extreme Thermophile *Thermus aquaticus*," *J. Bacteriol.* 127:1550–1557 (1976).
Cull and McHenry, "Purification of *Escherichia coli* DNA Polymerase III Holoenzyme," *Meth. Enzymol.* 262:22–35 (1995).
Dallmann and McHenry, "DnaX Complex of *Escherichia coli* DNA Polymerase III Holoenzyme, Physical Characterization of the DnaX Subunits and Complexes," *J. Biol. Chem.* 270:29563–29569(1995).
Dallmann et al., "DnaX Complex of *Escherichia coli* DNA Polymerase III Holoenzyme, Central Role of τ in Initiation Complex Assembly and in Determining the Functional Asymmetry of Holoenzyme," *J. Biol. Chem.* 270:29555–29562 (1995).
Dijkema et al., "Cloning and Expression of the Chromosomal Immune Interferon Gene of the Rat," *EMBO J.* 4(3):761–767 (1985).
Erlich (ed.), *PCR Technology*, Stockton Press (1989).
Flower and McHenry, "The τsubunit of DNA polymerase III holoenzyme of *Escherichia coli* is produced by ribosomal frameshifting," *Proc. Natl. Acad. Sci. USA* 87:3713–3717 (1990).

(List continued on next page.)

Primary Examiner—Einar Stole
(74) Attorney, Agent, or Firm—Medlen & Carroll, LLP

(57) ABSTRACT

The present invention relates to gene and amino acid sequences encoding DNA polymerase III holoenzyme subunits and structural genes from thermophilic organisms. In particular, the present invention provides DNA polymerase III holoenzyme subunits of *T. thermophilus*. The present invention also provides antibodies and other reagents useful to identify DNA polymerase III molecules.

39 Claims, 18 Drawing Sheets

OTHER PUBLICATIONS

Gorman et al., "The Rous Sarcoma Virus Long Terminal Repeat is a Strong Promoter when Introduced into a Variety of Eukaryotic Cells by DNA–Mediated Transfection," *Proc. Natl. Acad. Sci. USA* 79:6777–6781 (1982).

Hammond and Brown, "Overproduction and Purification of *Bacillus subtilis* DNA Polymerase III," *Protein Expression and Purification* 3:65 (1992).

Harlow and Lane, *Antibodies: A Laboratory Manual*, Cold Spring Harbor Laboratory Press, Cold Spring Harbor, NY.

Huse et al., "Generation of a Large Combinatorial Library of the Immunoglobulin Repertoire in Phage Lambda," *Science* 246:1275–1281. (1989).

Kacian et al., "A Replicating RNA Molecule Suitable for a Detailed Analysis of Extracellular Evolution and Replication," *Proc. Natl. Acad. Sci USA* 69(10):3038–3042 (1972).

Kaledin et al., "Isolation and Properties of DNA Polymerase From Extremely Thermophilic Bacterium *Thermus aquatics* YT1," *Biochem.* 45:494–501 (1981).

Kim et al., "Use of the Human Elongation Factor 1α Promoter as a Versatile and Efficient Expression System," *Gene* 91:217–223 (1990).

Kim and McHenry, "In Vivo Assembly of Overproduced DNA Polymerase III, Overproduction, Purification, and Characterization of the α, α–ε, and α–ε–θ Subunits," *J. Biol. Chem.* 271:20681–20689 (1996).

Köhler and Milstein, Nature 256:495–497 (1975).

Kong et al. "Three–Dimensional Structure of the β Subunit of *E. coli* DNA Polymerase III Holoenzyme: A Sliding DNA Clamp," Cell 69:425–437 (1992).

Kornberg and Baker, *DNA Replication*, 2nd ed. W.H. Freeman & Company,(1992), pp. 167.

Kornberg and Gefter, "Deoxyribonucleic Acid Synthesis in Cell–free Extracts, IV. Purification and Catalytic Properties of Deoxyribonucleic Acid Polymerase III," *J. Biol Chem.* 47:5369–5375 (1972).

LaDuca et al., "The β Subunit of the *Escherichia coli* DNA Polymerase III Holoenzyme Interacts Functionally with the Catalytic Core in the Absence of Other Subunits," *J. Biol. Chem.* 261:7550–7557 (1986).

Lasa et al., "Insertional mutagenesis in the extreme thermophilic eubacteria *Thermus thermophilus* HB8," *Molec. Microbiol.* 6:1555–1564 (1992).

Lawyer et al., "Isolation, Characterization, and Expression in *Escherichia coli* of the DNA Polymerase Gene from *Thermus aquaticus*," *J. Biol. Chem.* 264(11):6427–6437 (1989).

Low et al., "Purification and Characterization of DNA Polymerase III from *Bacillus subtilis*," *J. Biol. Chem.* 251:1311 (1976).

Maniatis et al., "Regulation of Inducible and Tissue–Specific Gene Expression," *Science* 236:1237–1245 (1987).

McHenry, "DNA Polymerase III Holoenzyme of *Escherichia coli*," *Ann. Rev. Biochem.* 57:519–550 (1988).

McHenry and Kornberg, "DNA Polymerase III Holoenzyme of *Escherichia coli*," *J. Biol. Chem.* 252:6478–6484 (1977).

McHenry, "Purification and Characterization of DNA Polymerase III, Identification of τ as a Subunit of the DNA Polymerase III Holoenzyme," *J. Biol. Chem.* 257:2657–2663 (1982).

Mizushima and S. Nagata, "pEF–BOS, a Powerful Mammalian Expression Vector," *Nucl. Acids. Res.* 18(17):5322 (1990).

Mok and Marians, "The *Escherichia coli* Preprimosome and DNA B Helicase Can Form Replication Forks That Move at the Same Rate," *J. Biol. Chem.* 262:16644–16654 (1987).

Molineux et al., "Purification and Properties of the *Escherichia coli* Deoxyribonucleic Acid–unwinding Protein, Effects on Deoxyribonucleic Acid Synthesis in Vitro," *J. Biol. Chem.* 249 6090–6098 (1974).

Mullis et al., "Specific Enzymatic Amplification of DNA In Vitro: The Polymerase Chain Reaction," *Cold Spring Harbor Symposia*, vol. LI, pp. 263–273 (1986).

Naktinis et al., "Assembly of a Chromosomal Replication Machine: Two DNA Polymerases, a Clamp Loader, and Sliding Clamps in One Holoenzyme Particle," *J. Biol. Chem.* 270:13358–13365 (1995).

Oi and Herzenberg, in Mishell and Shiigi (eds.), *Selected Methods in Cellular Immunology*, W.H. Freeman & Co., San Francisco (1980), pp. 351–371.

Sambrook et al., *Molecular Cloning: A Laboratory Manual*, 2nd ed., pp. 7.39–7.52, 9.31–9.58, 16.6–16.7, and 16.9–16.15, Cold Spring Laboratory Press, New York (1989).

Sherman et al., "Methionine or Not Methionine at the Beginning of a Protein," *Bioessays* 3:27–31 (1985).

Studencki and Wallace, "Allele–Specific Hybridization using Oligonucleotide Probes of Very High Specific Activity: Discrimination of the Human $\beta^A$– and $\beta^S$–Globin Genes," *DNA* 3:1–15 (1984).

Studencki et al., "Discrimination among the Human $\beta^A$, $\beta^S$, and $\beta^C$–Globin Genes Using Allele–Specific Oligonucleotide Hybridization Probes," *Human Genetics* 37:42–51 (1985).

Studwell–Vaughan and O'Donnell, "Consititution of the Twin Polymerase of DNA Polymerase II Holoenzyme," *J. Biol. Chem.* 266:19833–19841 (1991).

Tsuchihashi and Kornberg,"Translational frameshifting generates the γ subunit of DNA polymerase III holoenzyme," *Proc. Natl. Acad. Sci. USA* 87:2516–2520 (1990).

Uetsuki et al., "Isolation and Characterization of the Human Chromosomal Gene for Polypeptide Chain Elongation Factor–1α," *J.Biol. Chem.* 264(10):5791–5798 (1989).

Uhlmann et al., "In vitro reconstitution of human replication factor C from its five subunits," *Proc. Natl. Acad. Sci. USA* 93:6521–6526 (1996).

Voss et al., "The Role of Enhancers in the Regulation of Cell–Type–Specific Transcriptional Control," *Trends Biochem. Sci.* 11:287–289 (1986).

Wallace et al., "Application of synthetic oligonucleotides to the diagnosis of human genetic diseases," *Biochimie* 67:755–762 (1985).

Wickner, "Mechanism of DNA elongation catalyzed by *Escherichia coli* DNA polymerase III, dnaZ protein, and DNA elongation factors I and III (DNA replication/ATP or dATP cofactor)," *Proc. Natl. Acad. Sci. USA* 73:3511–3515 (1976).

Wu et al., "Coordinated Leading– and Lagging–strand Synthesis at the *Escherichia coli* DNA Replication Fork," *J. Biol. Chem.* 267:4030–4044 (1992).

Wu et al., "Monoclonal Antibodies Specific for the α Subunit of the *Escherichia coli* DNA Polymerase III Holoenzyme," *J. Biol. Chem.* 259:12117–12122 (1984).

Wu and Wallace, "The Ligation Amplification Reaction (LAR)—Amplification of Specific DNA Sequences Using Sequential Rounds of Template–Dependent Ligation," *Genomics* 4:560–569 (1989).

Yoder and Burgers, "*Saccharomyces cerevisiae* Replication Factor C, I. Purification and Characterization of its ATPase Activity," *J. Biol. Chem.* 266:22689–22697 (1991).

Sanjanwala and Ganesan, "DNA polymerase III gene of *Bacillus subtilis,*" *Proc. Natl. Acad. Sci. USA* 86:4421–4424 (1989).

Lancy et al., Nucleotide Sequences of dnaE, the gene for the polymerase subunit of DNA polymerase III in *Salmonella typhimurium,* and a variant that facilitates growth in the absence of another polymerase subunit, *J. Bacteriol.,* 171:5581–5586 (1989).

Barnes et al., "DNA Polymerase III of *Mycoplasma pulmonis:* isolation and characterization of the enzyme and its structural gene, polC," *Mol. Microbiol.,* 13:843–854 (1994).

Old et al., "Nucleotide sequence of the *Borrelia burgdorferi* dnaN gene encoding the β subunit of DNA polymerase III," *Nucleic Acids Res.* 21:3323 (1993).

O'Donnell et al., "Homology in accessory proteins of replicative polymerases–E. coli to humans," *Nucleic Acids Res.,* 21:1–3 (1993).

Wong et al., "Sequence of the dnaB Gene of *Salmonella typhimurium,*" *J. Bacteriol.,* 170(6):2668–2675 (1988).

Liao and Dennis, "The organization and expression of essential transcription translation component genes in the extremely thermophilic eubacterium *Thermotoga maritima,*" *J. Biol. Chem.,* 267(32):22787–22797 (1992).

Uemori et al., "Cloning of the DNA polymerase gene of *Bacillus caldotenax* and characterization of the gene product," *J. Biochem.,* 113:401–410 (1993).

Rüttimann et al., "DNA polymerases from the extremely thermophilic bacterium *Thermus thermophilus* HB–8," *Eur. J. Biochem.,* 149:41–46 (1985).

Myers and Gelfand, "Reverse transcription and DNA amplification by a *Thermus thermophilus* DNA polymerase," *Biochem.,* 30:7662–7666 (1991).

Carballeira et al., "Purification of a thermostable DNA polymerase from *Thermus thermophilus* HB8, useful in the polymerase chain reaction," *BioTechn.,* 9:276–281 (1990).

Glukhov et al.,"Amplification of DNA sequences of Epstein– Barr and human immunodeficiency viruses using DNA–polymerase from *Thermus thermophilus,*" *Mol. Cell. Probes* 4:435–443 (1990).

Sakaguchi and Yajima, "Thermophilic and stable DNA polymerase from *Thermus thermophilus,*" *Fed. Proc.,* 33:1519 (1974).

Maki et al., "DNA polymerase III holoenzyme of *Escherichia coli,* IV. The holoenzyme is an asymmetric dimer with twin active sites," *J. Biol. Chem.,* 263(14):6570–6578 (1988).

Livingston et al., "Deoxyribonucleic acid polymerase III of *Escherichia coli,*" *J. Biol. Chem.,* 250:461–469 (1975).

Sitney et al., "DNA polymerase III, a second essential DNA polymerase is encoded by the *S. cerevisiae* CDC2 gene," *Cell,* 56:599–605 (1989).

Otto et al., "Purification and properties of DNA polymerase III," *Eur. J. Biochem.,* 34:440–447 (1972).

McHenry and Johanson, "DNA polymerase III holoenzyme of *Escherichia coli:* an asymmetric dimeric replicative complex containing distinguishable leading and lagging strand polymerases," *In Proteins Involved in DNA Replication,* Ulrich Hubscher and Silvio Spadari (eds.), Plenum Publishing Corporation, pp. 315–319 (1984).

O'Donnell and Studwell, Total reconstitution of DNA polymerase III holoenzyme reveals dual accessory protein clamps, *J. Biol. Chem.,* 265:1179–1187 (1990).

Studwell and O'Donnell, "Processive replication is contingent on the exonuclease subunit of DNA polymerase III holoenzyme," *J. Biol. Chem.,* 265:1171–1178 (1990).

Bauer and Burgers, "The yeast analog of mammalian cyclin/proliferating–cell nuclear antigen interacts with mammalian DNA polymerase δ," *Proc. Natl. Acad. Sci. USA,* 85:7506–7510 (1988).

Hübscher et al., "Evidence that a high molecular weight replicative DNA polymerase is conserved during evolution," *Proc. Natl. Acad. Sci. USA* 11:6771–6775 (1981).

Turchi and Bambara, "Completion of mammalian lagging strand DNA replication using purified proteins," *J. Biol. Chem.* 268:15136–15141 (1993).

Abramson and Gelfand, "Characterization of the strand displacement and nick translation activities of *Thermus aquaticus* DNA polymerase," *Abstr. 72nd Gen. Mtg. Am. Soc. Microbiol.,* p. 200 (1992).

Stenesh and Roe, "DNA polymerase from mesophilic and thermophilic bacteria, I. Purification and properties of DNA polymerase from *Bacillus licheniformis* and *Bacillus stearothermophilus,*" *Biochim. Biophys. Acta* 272:156–166 (1972).

Stenesh et al., "DNA polymerase from mesophilic and thermophilic bacteria III. Lack of fidelity in the replication of synthetic polydeoxyribonucleotides by DNA polymerase from *Bacillus licheniformis* and *Bacillus stearothermophilus*", *Biochimia et Biophysicia Acta* 475:32–41 (1977).

Kaboev et al., "Purification and properties of deoxyribonucleic acid polymerase from *Bacillus stearothermophilus,*" *J. Bacteriol.,* 145:21–26 (1981).

Klimczak et al., "Purification and Characterizaion of DNA polymerase from the archaebacterium *Sulfolobus acidocoldarius,*" *Nucleic Acids Res.,* 13:5269–5282 (1985).

Forterre et al., "Studies on DNA polymerases and topoisomerases in Archaebacteria," *Can. J. Microbiol.,* 35:228–233 (1989).

Elie et al., "A DNA polymerase from a thermoacidophilic archaebacterium: evolutionary and technological interests," *Biochimica et Biophysica Acta* 951:261–267 (1988).

Rella et al., "Purification and properties of a thermophilic and thermostable DNA polymerase from the Archaebacterium *Sulfolobus Solfataricus,*" *Ital. J. Biochem.,* 39(2):83–99 (1990).

Rossi et al., "Structure and properties of a thermophilic and thermostable DNA polymerase isolated from *Sulfolobus solfataricus,*" *System. Appl. Microbiol.,* 7:337–341 (1986).

Salhi et al., "The DNA polymerase from the Archaebacterium *Sulfolobus acidocaldarius*: A thermophilic and thermoresistant enzyme which can Perform automated polymerase chain reaction," *Biochem. Biophys. Res. Commun.,* 167:1341–1347 (1990).

Salhi et al., "DNA polymerase from *Sulfolobus acidocaldarius,*" *J. Mol. Biol.,* 209:635–644 (1989).

Jannasch et al., "*Thermotoga neapolitana* sp. nov. of the extremely thermophilic, eubacterial genus Thermotoga," *Arch Microbiol.,* 150:103–104 (1988).

Simpson et al., "Purification and some properties of a thermostable DNA polymerase from a Thermotoga species," *Biochem. Cell Biol.,* 68:1292–1296 (1990).

Huber et al., "*Thermotoga maritima* sp. nov. represents a new genus of unique extremely thermophilic eubacteria growing up to 90° C," *Arch Microbiol.*, 144:324–333 (1986).

Windberger et al., "*Thermotoga thermarum* sp. nov. and *Thermotoga neapolitana* occurring in African continental solfataric springs," *Arch Microbiol.*, 151:506–512 (1989).

Hamal et al., "Purification and characterization of DNA polymerase from the archaebacterium *Thermoplasma acidophilum*," *Eur. J. Biochem.*, 190:517 (1990).

Sukhanov et al., "Physicochemical properties and sensitivity to inhibitors of Cyanobacterium *Plectonema boryanum* DNA–polymerases," *Mikrobiol. Zh.*, 55:42–45 (1993).

Bechtereva et al., "DNA sequencing with thermostable Tet polymerase from *Thermus thermophilus*," *Nucleic Acids Res.*, 17:10507 (1989).

Kaledin et al., "Isolation and properties of DNA polymerase from the extremely thermophilic bacterium *Thermus ruber*," *Biochem.*, 47:1515–1521 (1983); translated from *Biokhimiya* 47:1785–1791 (1982).

Scalice et al., "Monoclonal antibodies prepared against the DNA polymerase from *Thermus aquaticus* are potent inhibitors of enzyme activity," *J. Immunol. Meth.*, 172:147–163 (1994).

Barnes and Brown, "Antibody to *B. subtilis* DNA polymerase III: use in enzyme purification and examination of homology among replication–specific DNA polymerase," *Nucleic Acids Res.* 6:1203–1219 (1979).

McHenry et al., "A DNA Polymerase III Holenzyme–like Subassembly from an Extreme Thermophillic Eubacterium," *J. Mol. Biol.*, 272:12–12 (1997).

Yurieva et al., "*Thermus thermophilis dnaX* Homolog Encoding γ– and τ–like Proteins of the Chromosomal Replicase," *J. Biol. Chem.*, 272: 27131–27139 (1997).

\* cited by examiner

FIGURE 8

```
E. coli      3   LYRRFRPLTFQEVVGQEH    20
                 L R++RP TF +VVGQEH
Tth gamma    1   SALYRRFRPLTFQEVVGQE   19
Tth tau      1   SALYRRFRPLTFQEVVGQEH  20
                 ALYR FRP  F++VVGQEH
B. subtilis  5   ALYRVFRPQRFEDVVGQEH   23
```

FIGURE 9A

TCCGCCAGGCGCTTTCCCGTGAGGTAGAGGGCCATCTCCACCACCTCGAGCTGCTCC
GGGGGCGTCACCCGAAGCCCCCCCACGAAGCGGCTCTCGTACCCCAGGCGCCCAAGC
CAAGCCCCGATCTCGGGCCCGCCCCCGTGGACGAGAACCAAGGGACCAGGGTAGGC
GGCAAGCTCGTCCAATAGGGCCTCCGCCCCCCTAAGGCTTCCTCCCACCTTCACCAAAA
GGGCCTCACTCAAGGTAGACCACCTCCTCGGGCAGGCCCTCCTCCTCCTCGGCCTCCAG
GAGGTCGGCGAAGCCCAGAAGGGCGTGGTCCGGGTGGAGGCCGAAGCGGGCGGCGAG
GGCCCGGACCGCGTGCTCGGGCGGGAGGGCCTGGGCCCTCGTCAGGAGGGGGGCGAG
GTCGGCCGGGCCTTCAGGGCCGTCCCAAGCTCCGGACCCGCGCGAAGCTCCGCCCTC
ACCTCCCCCCCTCGGCCAGGAGGAAGAGGAGGTCCTCCTCGCTTAGTACCAGGAAGGC
CAAGGCCTGCCCTAGGCGGGAAAGCTCCCGCAGGAAGGCCCGGATGGCCTCCGGGTCC
TCCTCCGCCTCGAGGGCCTCGTGGTAGAGGCTCGTCCAAGGGGGTCGGGGACCAGGT
AGACCCCCGTCCCTCCCGTGCGCCCCTCGGCCCAGGCCGCCACCGCCTCCAGGGGGGC
CTGCAGGTGCAAGGAGAGGAAGCTCCGCACCACGCCCTATACTAGCCCTTGTGAGCGCC
CTCTACCGCCGCTTCCGCCCCCTCACCTTCCAGGAGGTGGTGGGGCAGGAGCACGTG
AAGGAGCCCCTCCTCAAGGCCATCCGGGAGGGGAGGCTCGCCCAGGCCTACCTCTTC
TCCGGGCCCAGGGGCGTGGGCAAGACCACCACGGCGAGGCTCCTCGCCATGGCGGT
GGGGTGCCAGGGGGAAGACCCCCCTTGCGGGGTCTGCCCCCACTGCCAGGCGGTGCA
GAGGGGCGCCCACCCGGACGTGGTGGAGATTGACGCCGCCAGCAACAACTCCGTGG
AGGACGTGCGGGAGCTGAGGGAAAGGATCCACCTCGCCCCCCTTTCTGCCCCCAGGA
AGGTCTTCATCCTGGACGAGGCCCACATGCTCTCCAAAAGCGCCTTCAACGCCCTCCT
CAAGACCCTGGAGGAGCCCCCGCCCCACGTCCTCTTCGTCTTCGCCACCACCGAGCC
CGAGAGGATGCCCCCCACCATCCTCTCCCGCACCCAGCACTTCCGCTTCCGCCGCCTC
ACGGAGGAGGAGATCGCCTTTAAGCTCCGGCGCATCCTGGAGGCCGTGGGGCGGGA
GGCGGAGGAGGAGGCCCTCCTCCTCCTCGCCCGCCTGGCGGACGGGGCCCTTAGGGA
CGCGGAAAGCCTCCTGGAGCGCTTCCTCCTCCTGGAAGGCCCCCTCACCCGGAAGGA
GGTGGAGCGCGCCCTAGGCCTCCCCCCCAGGGAGGCCCTGGCCGAGATCGCCGCCTC
CCTCGCGAGGGGGAAAACGGCGGAGGCCCTGGGCCTCGCCCGGCGCCTCTACGGGG
AAGGGTACGCCCCGAGGAGCCTGGTCTCGGGCCTTTTGGAGGTGTTCCGGGAAGGCC
TCTACGCCGCCTTCGGCCTCGCGGGAACCCCCCTTCCCGCCCCGCCCCAGGCCCTGAT
CGCCGCCATGACCGCCCTGGACGAGGCCATGGAGCGCCTCGCCCGCCGCTCCGACGC
CTTAAGCCTGGAGGTGGCCCTCCTGGAGGCGGGAAGGGCCCTGGCCGCCGAGGCCCT
GCCCCAGCCCACGGGCGCTCCCCCCCAGAGGTCGGCCCCAAGCCGGAAAGCCCCCC
GGCCCCGGAACCCCCAAGGCCCGAGGAGGCGCCCGACCTGCGGGAGCGGTGGCGGG
CCTTCCTCGAGGCCCTCAGGCCCACCCTACGGGCCTTCGTGCGGGAGGCCCGCCCGG
AGGTCCGGGAAGGCCAGCTCTGCCTCGCTTTCCCCGAGGACAAGGCCTTCCACTACC
GCAAGGCCTCGGAACAGAAGGCGAGGCTCCTCCCCCTGGCCCAGGCCCATTTCGGGG
TGGAGGAGGTCGTTCTCGTCCTGGAGGGAGAAAAAAAAAGCCTGAGCCCAAGGCCC
CGCTCGGCCCCACCTCCTGAAGCGCCCGCACCCCCGGGCCCTCCCGAGGAGGAGGTA
GAGGCGGAGGAAGCGGCGGAGGAGGCCCCGGAGGAGGCCTTGAGGCGGGTGGTCC
GCCTCCTGGGGGGGCGGGTGCTCTGGGTGCGGCGGCCCAGGACCCGGGAGGCGCCG
GAGGAGGAACCCCTGAGCCAAGACGAGATAGGGGGTACTGGTATATAATGGGGGCA
TGACGCGGACCACCGACCTCGGACAAGAGACCGTGGACAACATCCTCAAGCGCCTCC
GCCGTATTGAGGGCCAGGTGCGGGGGCTCCAAAAGATGGTGGCCGAGGGCCGCCCC
TGCGACGAGGTCCTCACCCAGATGACCGCCACCAAGAAGGCCATGGAGGCGGCGGC
CACCCTGATCCTCCACGAGTTCCTGAACGTCTGCGCCGCCGAGGTCTCCGAGGGCAA
GGTGAACCCCAAGAAGCCCGAGGAGATCGCCACCATGCTGAAGAAGTTCATCTAGAT
GGGTCGGCTTCGGGGGCGCCTCCGGCGCCTCCTCCGGGCCCTTCTCGCCCAGGAGGC

FIGURE 9B

SALYRRFRPLTFQEVVGQEHVKEPLLKAIREGRLAQAYLFSGPRGVGKTTTARLLAMA
VGCQGEDPPCGVCPHCQAVQRGAHPDVVEIDAASNNSVEDVRELRERIHLAPLSAPRKV
FILDEAHMLSKSAFNALLKTLEEPPPHVLFVFATTEPERMPPTILSRTQHFRFRRLTEEEIA
FKLRRILEAVGREAEEEALLLLARLADGALRDAESLLERFLLLEGPLTRKEVERALGLPPR
EALAEIAASLARGKTAEALGLARRLYGEGYAPRSLVSGLLEVFREGLYAAFGLAGTPLPA
PPQALIAAMTALDEAMERLARRSDALSLEVALLEAGRALAAEALPQPTGAPPPEVGPKPE
SPPAPEPPRPEEAPDLRERWRAFLEALRPTLRAFVREARPEVREGQLCLAFPEDKAFHYR
KASEQKARLLPLAQAHFGVEEVVLVLEGEKKSLSPRPRSAPPPEAPAPPGPPEEEVEAE
EAAEEAPEEALRRVVRLLGGRVLWVRRPRTREAPEEEPLSQDEIGGTGI

FIGURE 9C

```
Tth       1  ......SALY RRFRPLTFQE VVGQEHVKEP LLKAIREGRI AQAYLFSGPR GVGKT
E.coli    1  ...MSVQVLA RKVRPQTFAD VVGQEHVLTA LANCISLGRI HHAYLFSGTR GVGKT
B.sub     1  ...MSVQALY RVFRPQRFED VVGQEHITKT LQNALLQKKF SHAYLFSGPR GTGKT
Mycopl    1  ....MRKVLY QKVRPTKFSD TVGQDSIKRI IVNAITQDQL PHGYIFAGER GTGKT
Caulo     1  EKGDAYTVLA RKYRPRTFED LIGQEAVVRT LANAFSTGRI AHAFALIGVR GVGKT
Syn.sp.   1  ...MAYEPLH HKYRPQTFAD LVGQTAIAAT LSNAIEQERI VPAYLFIGPR GTGKT
consensus        y L  rkfRP tF d  vvGQe v  l nai  rl  haylfsG R  G GKT Tth      50  ITARI LAMAVGCQG. .....EDPPC GVCPHCQAVQ RGAHPDVVEI DAASNNSVEI
E.coli   53  SIARI LAKGINCETG ....ITATPC GVCDNCREIE QCRFVDIIEI DAASRTKVED
B.sub    53  SAAKI FAKAVNCEHA ....PVDEPC NECAACKCIT NGSISDVIEI DAASNNGVDE
Mycopl   52  TFAKI LAKAINCLN. ....WNGDVC NQCEACQAIN SNSAIDVFEI DAASKNGIND
Caulo    56  ITARI LARALNYETD TVKGPSVDLT TEGYHCRSII ECRHIDVIEL DAASRTKVDE
Syn.sp.  53  SSARI LAKSLNCIAG DR..PTATPC GQCATCRAIT NGSALDVIEI DAASNTGVLN
consensus      t Arl lAkavnc          pc    c  Crai   g  vDvvEi DAAS    ved Tth      99  VREIRPRIHL APLSAPRKVF IIDEAHMLSK SAFN.ALLKT LEEP..PPHV IFVF
E.coli  104  TRDLLDNVQY APARGRFKVY IIDEVHMLSR HSFN.ALLKT LEEP..PEHV KFIL
B.sub   104  IRDIRPKVKF APSAVTYKVY IIDEVHMLSI GAFN.ALLKT LEEP..PEHC IFIL
Mycopl  102  IREIAENVFN LPFKFKKKVY IIDEAHMLIP QSFS.GLLKT LEPA..PDYV LFIF
Caulo   111  VREILGVRY APVEARYKVY IIDEVHMLST AAFN.ALLKT LEEP..PPHA KFIF
Syn.sp. 106  IRDIIERAQF APVQCRYKVY VIDECLTGDS QVLTRNGLMS IDNPQIKGRE VLSY
consensus     vRel  e v y aP   rfKVy iiDE hmls    fn alLkt leep  p h  lfvf Tth     150  ATTEPE RMPPTILSRT QHFR....FR RITEEEIAFK IRRIFEAVGR EAEEEALLL
E.coli  155  ATTDPQ KIPVTILSRC LQFH....LK AIDVEQIRHQ IEIIENEDHI AHEPRALQI
B.sub   155  ATTEPH KIPLTILSRC QRFD....FK RITSQALVGR ENKIVDAPQL QVEEGSLEI
Mycopl  153  ATTEFN KIPVTILSRC QSFF....FK QITNDLIQQR IAEVAAKESI KITTDAIVK
Caulo   162  ATTEIR KVPVTILSRC QRFD....LR RVEPDVIVKH FDRISAKEGA RIEMDAIAL
Syn.sp. 160  NETLQQ WEYKKVIRWL DRGEKQTLSI KTKNSTVRCT ANILIRTEQG WTRAENITP
consensus     atTe   kmpvtilsrc qhf       r rl  ei  k l ril  e     e eal l Tth     201  I ARLADGAIRD AESLLERFIL L...EGPILR KEVERAICLP PI.........
E.coli  206  I ARAAEGSIRD ALSLTDQAIA SG..DGQYST QAVSAMICTL DDDQALSLVE AMV
B.sub   206  I ASAADGGIRD ALSLLDQAIS FS..GDIIKV EDALLITCAV SQ.........
Mycopl  204  I ADLAQGSIRD GLSLLDQISN FSE.SKTISL ADVEKTFNLL DIEQ......KF
Caulo   213  I ARAAEGSVRD GLSLLDQAIV QTERGQTVIS TVVRDMIGLA DI.........
Syn.sp. 215  G MKILSPASVD VDNLSQSTAL TAS.LGGESG AINYEAINTD KKNTTLSLSL KKQ
consensus     l ar adg lrD alsLldq l             lt    v  lg    r
```

FIGURE 9D

```
    GAAAAAAAAAGCCTGAGCCCAAGGCCCCGCTCGGCCCCACCTCCTGA
       E  K  K  S  L  S  P  R  P  R  S  A  P  P  P
    -1 E  K  K  K  P  E  P  K  A  P  L  G  P  T  S
    +1 E  K    K    A
```

FIGURE 10A

GGTTCCTCNAAGGTCTTGAGGAGGGCGTTGAAGGCGCTTTTGGAAAANCATGTGGGCCTCGTCCAGNATN
AAAACCTTCCTGGGGGCANAAAGGGGGGCGAGGTGGATCCTTTCCCTCAGCTCCCGCACNTCCTCCACG
GANTTGTTGCTGGCGGCGTCAATCTCCACCACGTCCGGGTGGGCGCCCCTCTGCACCGCCTGGCAGTGGG
GGCANACCCCGCAAGGGGGGTCTTCCCCCTGGCACCCCACCGCCATGGCNANGANCCTCNCCGTGGTGG
TCTTGCCCACNCCCCTGGGCCCGGAAAAAAAGTNGCCTGGGCGAACCTCCCCTCCCGGATGGCCTTGAN
GANGGGCTCCTTCACNTGCTCCTGACCCACAACCTCTTGAAA

FIGURE 10B

```
213 DPPCGVCPHCQAVQRGAHPDVVEIDAASNXSXXXXXXXXXXXIHLAPLXAPRKVXXLDEAH  34
    D PC  C  C+ +  G+  DV+EIDAASN              + AP    KV +DE H
 70 DEPCNECAACKGITNGSISDVIEIDAASNNGVDEIRDIRDKVKFAPSAVTYKVYIIDEVH  129

33 MXSKSAFNALL   1        T. thermophilus
    M S  AFNALL
130 MLSIGAFNALL 140        B. subtilis
```

FIGURE 11A

```
M.tuber    10    FVHLHNHTE
                 F HLH HT+
Tth:        4    RFAHLHQHTQ
                 RF HL  HT
H.infl      6    RFIHLRTHTD
```

FIGURE 11B

```
Tth (91)      FTGYQNLVRLASRAYLEGFYEK
              TGYQNL   L S+AY   G+
E.Coli:  92   TGYQNLTLLISKAYQRGY 109

Tth (676)     ILDETYGIPVYQEQQMQIAAAVGY
              +L+ TYGI +YQEQ MQIA
E.coli:676    VLEPTYGIILYQEQVMQIA 694

Tth (853)     GLDGGYFHLTLFD
                +GGYF+   LFD
E.coli:  853  RNKGGYFR-ELFD
```

FIGURE 12A

CATCTTCACCAGCACACCCAGTTCTCCCTCCTGGACGGGGCGGCGAARCTTTCCRACCTCCTCAAKTGGGTCA
AGGAGACGACCCCCCGAGGACCCCGCCTTGGCCATGACCGACCACGGCAACTTCTTCGGGGCCGKGGAKTTCT
ACAAGAAGGCCACCGAAATGGGCATCAAGCCCATCYTGGGCTACGAGGCCTAMGTGGCGGCGGAAAGCCGCTT
TGACCGCAAGCGGGGAAAGGGCYTAGACGGGGGCTACTTTCACYTCACCYTCYTCGCCAAGGACTTCACGGGG
TACCAGAACCTGGTGCGCCTGGCGAGCCGGGCTTACCTGGAGGGGTTTTACGAAAA

FIGURE 12B

```
Synechocy   12  YSLLDGASQLPALI 25
                +SLLDGA++L  L+
Tth          2  FSLLDGAAKLSXLLXWVK 55
                +S+LDGAAK++ +L  V+
M. tuber    19  YSMLDGAAKITPMLAEVE 36

Synechocy   34  PAIALTDHGVMYGAVELLKVCRGKPIKPIIGNEMYV 69
                PA+A+TDHG +GA   K      IKPI+G E   V
Tth         75  PALAMTDHGNFFGAXXFYKKATEMGIKPILGYEAXVAAESRFDRKR 212
                PA+ MTDHGN FGA   FY  AT+ GIKPI+G EA +A   SRFD +R
M. tuber    41  PAVGMTDHGNMFGASEFYNSATKAGIKPIIGVEAYIAPGSRFDTRR 86

Synechocy   83    FHQVVLAKNNQGYRNLVKLTT 103
                  FH   AK+   GY+NLV+L +
Tth        228  GGYFHXTXXAKDFTGYQNLVRLASRA 305
                G Y H T  A++ TG +NL +L+S A
M. tuber   103  GSYTHLTMMAENATGLRNLFKLSSHA 128
```

FIGURE 13A

```
ATGGGCCGCAAACTCCGCTTCGCCCACCTCCACCAGCACACCCAGTTCTCCCTCCTGGACGGGGCGGCGAARC
TTTCCRACCTCCTCAAKTGGGTCAAGGAGACGACCCCCCGAGGACCCCGCCTTGGCCATGACCGACCACGGCA
ACTTCTTCGGGGCCGKGGAKTTCTACAAGAAGGCCACCGAAATGGGCATCAAGCCCATCYTGGGCTACGAGGC
CTAMGTGGCGGCGGAAAGCCGCTTTGACCGCAAGCGGGGAAAGGGCYTAGACGGGGGCTACTTTCACYTCACC
YTCYTCGCCAAGGACTTCACGGGGTACCAGAACCTGGTGCGCCTGGCGAGCCGGGCTTACCTGGAGGGGTTTT
ACGAAAAGCCCCGGATTGACCGGGAGATCAYCCTGCGCGAGCACGCCGAGGGCCTCATCGCCCTCTCGGGGTG
CCTCGGGGCGGAGATCCCCCAGTTCATCCTCCAGGACCGTCTGGACCTGGCCGAGGCCCGGCTCAACGAGTAC
CTCTCCATYTTCAAGGACCGCTTCTTCATTGARATCCAGAACCACGGCCTCCCCGAGCAGAAAAAGGTCAACG
AGGTCCTCAAGGANTTCGCCCGAAANTACGGCCTGGGGATGGTGGCCACCAACGACGGCCATTACGTGAGGAA
GGAGGACGCCCGGGCCCACGAGGTCCTCCTCGCCATCCAGTCCAAGAGTACCYTGGACGACCCCGGGCGCTGG
CGCTTCCCCTGCGACGAGTTNTACGTGAAGACCCCSGANGAGATGCGGGCCATGTTCCCCCGAGGAGGAGTGG
GGGGACGAGCCCTTTGACAACACCGTGGAAGATCGCCCGCATGTGCAACGTGGAGCTGCCCATCGGGGGGACA
AGATGGTCTACCGCCATCCCCCCGCTTCCCCYTCCCCGCCCGTCGGAMCGARGCCCAGTTACTTCATGGAGCTCA
CNTTTAAGGGGCTCCTCCGCCGCTACCCGGACCGGATCACCGAGGGCTTCTACCGGGAGGTCTTCCGCCTTTT
GGGGAAGCTTCCCCCCCACGGGGACGGGGAGGCCCTGGCCGAGGCCTTGGCCCAGGTTGGAGCGGGAGGCTTG
GGAGAAGCTCATTG
```

FIGURE 13B

```
RKLRFAHLHQHTQFSLLDGAAKLSDLLNWVKETTPEDPALAMTDHGNFFGAVDFYKKATEMGIKPILGYEAYV
AAESRFDRKRGKGLDGGYFHFTLLAKDFTGYQNLVRLASRAYLEGFYEKPRIDREITLREHAEGLIALSGCLG
AEIPQFILQDRLDLAEARLNEYLSIFKDRFFIEIQNHGLPEQKKVNEVLKDFARKYGLGMVATNDGHYVRKED
ARAHEVLLAIQSKSTLDDPGRWRFPCDEFYVKTPDEMRAMFPPRRSGGTSPLTTPWKIARMCNVELPIGGTRW
STASPASPSPPVGPKPSYFMELTFKGLLRRYPDRITEGFYREVFRLLGKLPPHGDGEALAEALAQVGAGGLGE
A
```

FIGURE 13C

```
M.tuber   1 MSGSSAGSSF VHLHNHTEYS MLDGAAKITP MLAEVERLG. .MPAVGMTDH GNMFG
Tth       1 .....RKLRF AHLHQHTQES LLDGAAKLSD LLNWVKETTP EDPALAMTDH GNFFG
Syn.sp.   1 .......MSF VGLHIHSDYS LLDGASQLPA LIDRAIELG. .MPAIAITDH GVMYG M.tuber  54 ASEFY NSATKAGIKP IIGVEAYIAP GSRFDTRRIL WGDPSQKADD VSGSGSYTHL
Tth      51 AVDFY KKATEMGIKP ILGYEAYVAA ESRFD..... ......RKRG KGLDGGYFHF
Syn.sp.  47 AVELL KVCRGKPIKP IIGNEMYVIN G......... ........DIE INKRHRRFHQ M.tuber 109 TIMAENATGL RNLFKLSSHA SFEGQLSK.. WSR..MDAEL .IAEHAEGII ITIC
Tth      95 TLLAKDFTGY QNLVRLASRA YLEGFYEK.. .PR..IDREI TLREHAEGLI AISG
Syn.sp.  86 VVLAKNNQGY RNLVKLITIS NLKGIQGSGI BARPCINKEL .LECYKEGLI VTSA M.tuber 158 CPSGEV QTRKRLGQDR BALEAAAKWR EIVGPDNYFI EDMDHGITIE RRVRDGLLE
Tth     144 CLGAEI PQFILQD.RL DIAEARLNEY LSIFKDRFFI EIQNHGLPEQ KKVNEVLKD
Syn.sp.139 CLGGEV PQAILKG.DL DHAROVAKWY KNLFGDDYYL EIQDHCSVED RLVNINLVK
```

FIGURE 14A

CCTAGTTCTCCCTCCTGGACGGGGCGGCGAAGCTTTCCGACCTCCTCAAGTGGGTCAAGGAAACGACCCCCGA
GGGACCCCGCCTTGGCCATGACCGACCACGGCAACCTCTTCGGGGCCGTGGAGTTCTACAAGAAGGCCACCGA
AATGGGCATCAAGCCCATCCTGGGCTACGAGGCCTACGTGGCGGCGGAAAGCCGCTTTGACCGCAAGCGGGGG
AAAGGGCCTAGGACGGGGGCTACTTTCACCTCACCCTCCTCGCCAAGGACTTCACGGGGTACCAGAACCTGGT
GCGCCTGGCGAGCCGGGCTTACCTGGAGGGGTTTTACGAAAAGCCCCGGATTGACCGGGGAGATCCTGCGCGA
GCACGCCGAGGGCCTCATCGCCCTCTCGGGGTGCCTCGGGGCGGANATCCCCCAGTTCATCCTCCAGGACCGT
CTGGACCTGGCCGANGCCCGGCTCAACAAGTACCT

FIGURE 14B

CTGCACCGGGATGAGCTTGGCCAATTCCTCCGCCTTCTTGTGGGGGATGCCGTAGACCCGGGCCACGTCCTTG
AGGGCGGCCTTGGAGGCGAGGCTTCCCAGGGTGCCGATCTGGGCCACCTTGTCCTCGCCGTAGCGTTCCCGCA
CGTACTGGATCACCCGGTCCCGCTCCCGGTCGGAGAAGTCCGTGTCAATGTCGGGCATGGAGACCCTCTCGGG
GTTCAGGAAGCGCTCAAAGAGGAGGCCGAAGCGCAGGGGGTCAATGTTGGTGATCCCCACGGCGTAGGCCACC
AGGCTCCCGGCGGCGCTCCCCCTGCCGGGCCCCACGGAGACGCCGTTTCTCCGGGCCCAGTTGATGTATTCCT
GGACGATGAGGAAGTAGCCGGGNAAACCCCATGCGCTCTATCACGGGAAAGCTCGTAAAGGGCCCGGTGGAAA
ATGGCC

FIGURE 14C

```
Tth    393 GXPGYFLIVQEYINWARRNGVSVGPGRGSAAGSLVAYAVGITNIDPLRFGLLFERFLNPE 214
            G PGYFLIV E+I W++ NGV VGPGRGS AGSLVAYA+ IT++DPL F LLFERFLNPE
E.coli 336 GFPGYFLIVMEFIQWSKDNGVPVGPGRGSGAGSLVAYALKITDLDPLEFDLLFERFLNPE 395

Tth    213 RVSMPDIDTDFSDRERDRVIQYVRERYGEDKVAQIGTLGSLASKAALKDVARVYGIPHKK 34
            RVSMPD D DF    +RD+VI++V +  YG D V+QI T G++A+KA ++DV RV G P+
E.coli 396 RVSMPDFDVDFCMEKRDQVIEHVADMYGRDAVSQIITFGTMAAKAVIRDVGRVLGHPYGF 455

Tth     33 AEELAKLIP 7---Tth base#
            + ++KLIP
E.coli 456 VDRISKLIP 464----E. coli amino acid number
```

FIGURE 15A

TTGAAGGTGTGGAAAAGCTCCTCCTGGGTGCGCTCCTTTCCGGCGATGAACTGGACGTCGTCC
ACCAGCAGGAGGTCCACGGAGCGGTACCGCTCCCGGAACTCCGTCATCCGGTCCTCGCGGAT
GGCGTTGATGAGCTCGTTGGTGAAAGTTTCCGTGGAAACGTACTCAATCTTCAGGTGGGGGA
AGCGCTTGGCCACGGAGTGGCCCACGGCGTGCATCAGGTGGGTCTTCCCCAATCC

FIGURE 15B

```
E.coli:  181 LLHAVGNGIMARKPNAKVVYMHSERFVQDMVKALQNNAIEEFKRYYRSVDALLIDDIQFF 240
             L+HAVG+ +  R P+ K+ Y+ +E F   +++ A++ + + EF+   YRSVD LL+DD+QF
Tth:     204 LMHAVGHSVAKRFPHLKIEYVSTETFTNELINAIREDRMTEFRERYRSVDLLLVDDVQFI 25
             LMHA+GH V     P  K+ Y+S+E FTNE  IN+IR+++   +FR RYR+VD+LL+DD+QF+
B.Subt:  160 LMHAIGHYVIDHNPSAKVVYLSSEKFTNEFINSIRDNKAVDFRNRYRNVDVLLIDDIQFL 219

E.coli:   24 AGKERTQE 1
             A KER+QE
Tth:      24 AGKERTQE 1
             AGKE+TQE
B.Subt:  220 AGKEQTQE 227
```

FIGURE 16A

TCGAAGGCCGCGTTGTGGGCCACCAGCACCGTGTCCTGGACGAAGGCGCGGAAGGCGGGGAG
GACCGCCTCTAGGGGAGGCTTGTCCCGGANCATCTCCGCCGTGAGGCCGTGGACCGCCGTGG
CCGCGGGGANATGGGGCGCCCCGGGTTCACCAGGGCCTCGAACACCTCCTGCCGCAAGACC
CTTCGACCCAGGATATGGACCCCGGCGAGGGCCACCACGGCATCTTGCTCCGGGTCCAGGCC
CGTGGTCTCAGTGTC

FIGURE 16B

```
E. coli:     48 FHVYLKPDRLVDPEAFGVHGIADEFLLDKPTFAEVADEFMDYIRGAELV 96
                F   + P R   P A  VHG+   E   DKP    V  F  +++    LV
Tth         150 FEALVNPGRPXSPAATAVHGLTAEMXRDKPPLEAVLPAFRAFVQDTVLVA 1
                FEA  NP RP S      + G+T +M +D P +   V+  FR ++ D +LVA
B.Subtilis:455 FEAFANPHRPLSATIIELTGITDDMJQDAPDVVDVIRDFREWIGDDILVA 504
```

SEQUENCE LISTING (1) GENERAL INFORMATION:

(iii) NUMBER OF SEQUENCES: 195

(2) INFORMATION FOR SEQ ID NO: 1:

(i) SEQUENCE CHARACTERISTICS:
    (A) LENGTH: 19 amino acids
    (B) TYPE: amino acid
    (C) STRANDEDNESS: not relevant
    (D) TOPOLOGY: linear (ii) MOLECULE TYPE: protein (xi) SEQUENCE DESCRIPTION: SEQ ID NO: 1:

Ser Ala Leu Tyr Arg Arg Phe Arg Pro Leu Thr Phe Gln Glu Val Val
1               5                   10                  15

Gly Gln Glu (2) INFORMATION FOR SEQ ID NO: 2:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 2:

Ser Ala Leu Tyr Arg Arg Phe Arg Pro Leu Thr Phe Gln Glu Val Val
1               5                   10                  15

Gly Gln Glu His
            20

(2) INFORMATION FOR SEQ ID NO: 3:

(i) SEQUENCE CHARACTERISTICS:
        (A) LENGTH: 18 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 3:

Leu Tyr Arg Arg Phe Arg Pro Leu Thr Phe Gln Glu Val Val Gly Gln
1               5                   10                  15

Glu His (2) INFORMATION FOR SEQ ID NO: 4:

(i) SEQUENCE CHARACTERISTICS:
        (A) LENGTH: 19 amino acids
        (B) TYPE: amino acid
        (C) STRANDEDNESS: not relevant
        (D) TOPOLOGY: linear (ii) MOLECULE TYPE: protein (xi) SEQUENCE DESCRIPTION: SEQ ID NO: 4:

Ala Leu Tyr Arg Val Phe Arg Pro Gln Arg Phe Glu Asp Val Val Gly
1               5                   10                  15

Gln Glu His (2) INFORMATION FOR SEQ ID NO: 5:

(i) SEQUENCE CHARACTERISTICS:
        (A) LENGTH: 18 amino acids
        (B) TYPE: amino acid
        (C) STRANDEDNESS: not relevant
        (D) TOPOLOGY: not relevant

```
       (ii) MOLECULE TYPE: protein (ix) FEATURE:
            (A) NAME/KEY: Modified-site
            (B) LOCATION: 4
            (D) OTHER INFORMATION: /note= "The residue at this
                position is similar but not identical to arginine"

(ix) FEATURE:
            (A) NAME/KEY: Modified-site
            (B) LOCATION: 12
            (D) OTHER INFORMATION: /note= "The residue at this
                position is similar but not identical to glutamic acid"

(ix) FEATURE:
            (A) NAME/KEY: Modified-site
            (B) LOCATION: 5
            (D) OTHER INFORMATION: /note= "The residue at this
                position is similar but not identical to phenylalanine"

(xi) SEQUENCE DESCRIPTION: SEQ ID NO: 5:

Leu Xaa Arg Xaa Xaa Arg Pro Xaa Thr Phe Xaa Xaa Val Val Gly Gln
1               5                   10                  15

Glu His (2) INFORMATION FOR SEQ ID NO: 6:

(i) SEQUENCE CHARACTERISTICS:
           (A) LENGTH: 19 amino acids
           (B) TYPE: amino acid
           (C) STRANDEDNESS: not relevant
           (D) TOPOLOGY: not relevant (ii) MOLECULE TYPE: protein (ix) FEATURE:
            (A) NAME/KEY: Modified-site
            (B) LOCATION: 12
            (D) OTHER INFORMATION: /note= "The residue at this
                position is similar but not identical to glutamine
                and/or glutamic acid"

(ix) FEATURE:
            (A) NAME/KEY: Modified-site
            (B) LOCATION: 13
            (D) OTHER INFORMATION: /note= "The residue at this
                position is similar but not identical to aspartic acid
                and/or glutamic acid"

(xi) SEQUENCE DESCRIPTION: SEQ ID NO: 6:

Ala Leu Tyr Arg Xaa Phe Arg Pro Xaa Xaa Phe Xaa Xaa Val Val Gly
1               5                   10                  15

Gln Glu His (2) INFORMATION FOR SEQ ID NO: 7:

(i) SEQUENCE CHARACTERISTICS:
           (A) LENGTH: 2681 base pairs
           (B) TYPE: nucleic acid
           (C) STRANDEDNESS: double
           (D) TOPOLOGY: linear (ii) MOLECULE TYPE: other nucleic acid
            (A) DESCRIPTION: /desc = "DNA"

(xi) SEQUENCE DESCRIPTION: SEQ ID NO: 7:

TCCGCCAGGC GCTTTCCCGT GAGGTAGAGG GCCATCTCCA CCACCTCGAG CTGCTCCGGG     60

GGCGTCACCC GAAGCCCCCC CACGAAGCGG CTCTCGTACC CCAGGCGCCC AAGCCAAGCC    120

CCGATCTCGG GCCCGCCCCC GTGGACGAGA ACCAAGGGAC CAGGGTAGGC GGCAAGCTCG    180
```

-continued

| | |
|---|---|
| TCCAATAGGG CCTCCGCCCC CCTAAGGCTT CCTCCCACCT TCACCAAAAG GGCCTCACTC | 240 |
| AAGGTAGACC ACCTCCTCGG GCAGGCCCTC CTCCTCCTCG GCCTCCAGGA GGTCGGCGAA | 300 |
| GCCCAGAAGG GCGTGGTCCG GGTGGAGGCC GAAGCGGGCG GCGAGGGCCC GGACCGCGTG | 360 |
| CTCGGGCGGG AGGGCCTGGG CCCTCGTCAG GAGGGGGGCG AGGTCGGCCG GGGCCTTCAG | 420 |
| GGCCGTCCCA AGCTCCGGAC CCGCGCGAAG CTCCGCCCTC ACCTCCCCCC CCTCGGCCAG | 480 |
| GAGGAAGAGG AGGTCCTCCT CGCTTAGTAC CAGGAAGGCC AAGGCCTGCC CTAGGCGGGA | 540 |
| AAGCTCCCGC AGGAAGGCCC GGATGGCCTC CGGGTCCTCC TCCGCCTCGA GGGCCTCGTG | 600 |
| GTAGAGGCTC GTCCAAGGGG GGTCGGGGAC CAGGTAGACC CCCGTCCCTC CCGTGCGCCC | 660 |
| CTCGGCCCAG GCCGCCACCG CCTCCAGGGG GGCCTGCAGG TGCAAGGAGA GGAAGCTCCG | 720 |
| CACCACGCCC TATACTAGCC CTTGTGAGCG CCCTCTACCG CCGCTTCCGC CCCCTCACCT | 780 |
| TCCAGGAGGT GGTGGGGCAG GAGCACGTGA AGGACCCCCT CCTCAAGGCC ATCCGGGAGG | 840 |
| GGAGGCTCGC CCAGGCCTAC CTCTTCTCCG GGCCCAGGGG CGTGGGCAAG ACCACCACGG | 900 |
| CGAGGCTCCT CGCCATGGCG GTGGGGTGCC AGGGGGAAGA CCCCCCTTGC GGGGTCTGCC | 960 |
| CCCACTGCCA GGCGGTGCAG AGGGGCGCCC ACCCGGACGT GGTGGAGATT GACGCCGCCA | 1020 |
| GCAACAACTC CGTGGAGGAC GTGCGGGAGC TGAGGGAAAG GATCCACCTC GCCCCCCTTT | 1080 |
| CTGCCCCCAG GAAGGTCTTC ATCCTGGACG AGGCCCACAT GCTCTCCAAA AGCGCCTTCA | 1140 |
| ACGCCCTCCT CAAGACCCTG GAGGAGCCCC CGCCCCACGT CCTCTTCGTC TTCGCCACCA | 1200 |
| CCGAGCCCGA GAGGATGCCC CCCACCATCC TCTCCCGCAC CCAGCACTTC CGCTTCCGCC | 1260 |
| GCCTCACGGA GGAGGAGATC GCCTTTAAGC TCCGGCGCAT CCTGGAGGCC GTGGGGCGGG | 1320 |
| AGGCGGAGGA GGAGGCCCTC CTCCTCCTCG CCCGCCTGGC GGACGGGCC CTTAGGGACG | 1380 |
| CGGAAAGCCT CCTGGAGCGC TTCCTCCTCC TGGAAGGCCC CCTCACCCGG AAGGAGGTGG | 1440 |
| AGCGCGCCCT AGGCCTCCCC CCCAGGGAGG CCCTGGCCGA GATCGCCGCC TCCCTCGCGA | 1500 |
| GGGGAAAAC GGCGGAGGCC CTGGGCCTCG CCCGGCGCCT CTACGGGGAA GGGTACGCCC | 1560 |
| CGAGGAGCCT GGTCTCGGGC CTTTTGGAGG TGTTCCGGGA AGGCCTCTAC GCCGCCTTCG | 1620 |
| GCCTCGCGGG AACCCCCCTT CCCGCCCCGC CCCAGGCCCT GATCGCCGCC ATGACCGCCC | 1680 |
| TGGACGAGGC CATGGAGCGC CTCGCCCGCC GCTCCGACGC CTTAAGCCTG GAGGTGGCCC | 1740 |
| TCCTGGAGGC GGGAAGGGCC CTGGCCGCCG AGGCCCTGCC CCAGCCCACG GGCGCTCCCC | 1800 |
| CCCCAGAGGT CGGCCCCAAG CCGGAAAGCC CCCCGGCCCC GGAACCCCCA AGGCCCGAGG | 1860 |
| AGGCGCCCGA CCTGCGGGAG CGGTGGCGGG CCTTCCTCGA GGCCCTCAGG CCCACCCTAC | 1920 |
| GGGCCTTCGT GCGGGAGGCC CGCCCGGAGG TCCGGGAAGG CCAGCTCTGC CTCGCTTTCC | 1980 |
| CCGAGGACAA GGCCTTCCAC TACCGCAAGG CCTCGGAACA GAAGGCGAGG CTCCTCCCCC | 2040 |
| TGGCCCAGGC CCATTTCGGG GTGGAGGAGG TCGTTCTCGT CCTGGAGGGA GAAAAAAAA | 2100 |
| GCCTGAGCCC AAGGCCCCGC TCGGCCCCAC CTCCTGAAGC GCCCGCACCC CCGGGCCCTC | 2160 |
| CCGAGGAGGA GGTAGAGGCG GAGGAAGCGG CGGAGGAGGC CCCGGAGGAG GCCTTGAGGC | 2220 |
| GGGTGGTCCG CCTCCTGGGG GGGCGGGTGC TCTGGGTGCG GCGGCCCAGG ACCCGGGAGG | 2280 |
| CGCCGGAGGA GGAACCCCTG AGCCAAGACG AGATAGGGGG TACTGGTATA TAATGGGGGC | 2340 |
| ATGACGCGGA CCACCGACCT CGGACAAGAG ACCGTGGACA ACATCCTCAA GCGCCTCCGC | 2400 |
| CGTATTGAGG GCCAGGTGCG GGGGCTCCAA AAGATGGTGG CCGAGGGCCG CCCCTGCGAC | 2460 |
| GAGGTCCTCA CCCAGATGAC CGCCACCAAG AAGGCCATGG AGGCGGCGGC CACCCTGATC | 2520 |
| CTCCACGAGT TCCTGAACGT CTGCGCCGCC GAGGTCTCCG AGGGCAAGGT GAACCCCAAG | 2580 |

```
AAGCCCGAGG AGATCGCCAC CATGCTGAAG AAGTTCATCT AGATGGGTCG GCTTCGGGGG      2640

CGCCTCCGGC GCCTCCTCCG GGCCCTTCTC GCCCAGGAGG C                         2681

(2) INFORMATION FOR SEQ ID NO: 8:

(i) SEQUENCE CHARACTERISTICS:
        (A) LENGTH: 528 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 8:

Ser Ala Leu Tyr Arg Arg Phe Arg Pro Leu Thr Phe Gln Glu Val Val
1               5                   10                  15

Gly Gln Glu His Val Lys Glu Pro Leu Leu Lys Ala Ile Arg Glu Gly
                20                  25                  30

Arg Leu Ala Gln Ala Tyr Leu Phe Ser Gly Pro Arg Gly Val Gly Lys
            35                  40                  45

Thr Thr Thr Ala Arg Leu Leu Ala Met Ala Val Gly Cys Gln Gly Glu
        50                  55                  60

Asp Pro Pro Cys Gly Val Cys Pro His Cys Gln Ala Val Gln Arg Gly
65                  70                  75                  80

Ala His Pro Asp Val Val Glu Ile Asp Ala Ala Ser Asn Asn Ser Val
                85                  90                  95

Glu Asp Val Arg Glu Leu Arg Glu Arg Ile His Leu Ala Pro Leu Ser
                100                 105                 110

Ala Pro Arg Lys Val Phe Ile Leu Asp Glu Ala His Met Leu Ser Lys
            115                 120                 125

Ser Ala Phe Asn Ala Leu Leu Lys Thr Leu Glu Glu Pro Pro Pro His
        130                 135                 140

Val Leu Phe Val Phe Ala Thr Thr Glu Pro Glu Arg Met Pro Pro Thr
145                 150                 155                 160

Ile Leu Ser Arg Thr Gln His Phe Arg Phe Arg Arg Leu Thr Glu Glu
                165                 170                 175

Glu Ile Ala Phe Lys Leu Arg Arg Ile Leu Glu Ala Val Gly Arg Glu
                180                 185                 190

Ala Glu Glu Glu Ala Leu Leu Leu Ala Arg Leu Ala Asp Gly Ala
            195                 200                 205

Leu Arg Asp Ala Glu Ser Leu Leu Glu Arg Phe Leu Leu Leu Glu Gly
    210                 215                 220

Pro Leu Thr Arg Lys Glu Val Glu Arg Ala Leu Gly Leu Pro Pro Arg
225                 230                 235                 240

Glu Ala Leu Ala Glu Ile Ala Ala Ser Leu Ala Arg Gly Lys Thr Ala
                245                 250                 255

Glu Ala Leu Gly Leu Ala Arg Arg Leu Tyr Gly Glu Gly Tyr Ala Pro
                260                 265                 270

Arg Ser Leu Val Ser Gly Leu Leu Glu Val Phe Arg Glu Gly Leu Tyr
            275                 280                 285

Ala Ala Phe Gly Leu Ala Gly Thr Pro Leu Pro Ala Pro Pro Gln Ala
        290                 295                 300

Leu Ile Ala Ala Met Thr Ala Leu Asp Glu Ala Met Glu Arg Leu Ala
305                 310                 315                 320

Arg Arg Ser Asp Ala Leu Ser Leu Glu Val Ala Leu Leu Glu Ala Gly
```

```
                    325                 330                 335
Arg Ala Leu Ala Ala Glu Ala Leu Pro Gln Pro Thr Gly Ala Pro Pro
                340                 345                 350
Pro Glu Val Gly Pro Lys Pro Glu Ser Pro Pro Ala Pro Glu Pro Pro
                355                 360                 365
Arg Pro Glu Glu Ala Pro Asp Leu Arg Glu Arg Trp Arg Ala Phe Leu
                370                 375                 380
Glu Ala Leu Arg Pro Thr Leu Arg Ala Phe Val Arg Glu Ala Arg Pro
385                 390                 395                 400
Glu Val Arg Glu Gly Gln Leu Cys Leu Ala Phe Pro Glu Asp Lys Ala
                405                 410                 415
Phe His Tyr Arg Lys Ala Ser Glu Gln Lys Ala Arg Leu Leu Pro Leu
                420                 425                 430
Ala Gln Ala His Phe Gly Val Glu Glu Val Val Leu Val Leu Glu Gly
                435                 440                 445
Glu Lys Lys Ser Leu Ser Pro Arg Pro Arg Ser Ala Pro Pro Pro Glu
450                 455                 460
Ala Pro Ala Pro Pro Gly Pro Pro Glu Glu Val Glu Ala Glu Glu Glu
465                 470                 475                 480
Ala Ala Glu Glu Ala Pro Glu Glu Ala Leu Arg Arg Val Val Arg Leu
                485                 490                 495
Leu Gly Gly Arg Val Leu Trp Val Arg Arg Pro Arg Thr Arg Glu Ala
                500                 505                 510
Pro Glu Glu Glu Pro Leu Ser Gln Asp Glu Ile Gly Gly Thr Gly Ile
                515                 520                 525

(2) INFORMATION FOR SEQ ID NO: 9:

(i) SEQUENCE CHARACTERISTICS:
        (A) LENGTH: 273 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 9:

Xaa Xaa Xaa Xaa Xaa Xaa Ser Ala Leu Tyr Arg Arg Phe Arg Pro Leu
1                   5                   10                  15
Thr Phe Gln Glu Val Val Gly Gln Glu His Val Lys Glu Pro Leu Leu
                20                  25                  30
Lys Ala Thr Arg Glu Gly Arg Leu Ala Gln Ala Tyr Leu Phe Ser Gly
                35                  40                  45
Pro Arg Gly Val Gly Lys Thr Thr Thr Ala Arg Leu Leu Ala Met Ala
            50                  55                  60
Val Gly Cys Gln Gly Xaa Xaa Xaa Xaa Xaa Glu Asp Pro Cys
65                  70                  75                  80
Gly Val Cys Pro His Cys Gln Ala Val Gln Arg Gly Ala His Pro Asp
                85                  90                  95
Val Val Glu Ile Asp Ala Ala Ser Asn Asn Ser Val Glu Asp Val Arg
                100                 105                 110
Glu Leu Arg Glu Arg Ile His Leu Ala Pro Leu Ser Ala Pro Arg Lys
                115                 120                 125
Val Phe Ile Leu Asp Glu Ala His Met Leu Ser Lys Ser Ala Phe Asn
            130                 135                 140
Xaa Ala Leu Leu Lys Thr Leu Glu Glu Pro Xaa Xaa Pro Pro His Val
```

```
145                 150                 155                 160
Leu Phe Val Phe Ala Ala Thr Glu Pro Glu Arg Met Pro Pro Thr Ile
                165                 170                 175
Leu Ser Arg Thr Gln His Phe Arg Xaa Xaa Xaa Xaa Phe Arg Arg Leu
                180                 185                 190
Thr Glu Glu Glu Ile Ala Phe Lys Leu Arg Arg Ile Leu Glu Ala Val
                195                 200                 205
Gly Arg Glu Ala Glu Glu Ala Leu Leu Leu Ala Arg Leu Ala
                210                 215                 220
Asp Gly Ala Leu Arg Asp Ala Glu Ser Leu Leu Glu Arg Phe Ile Leu
225                 230                 235                 240
Leu Xaa Xaa Xaa Glu Gly Pro Leu Thr Arg Lys Glu Val Glu Arg Ala
                245                 250                 255
Leu Gly Leu Pro Pro Arg Xaa Xaa Xaa Xaa Xaa Xaa Xaa Xaa Xaa
                260                 265                 270
Xaa
```

(2) INFORMATION FOR SEQ ID NO: 10:

(i) SEQUENCE CHARACTERISTICS:
        (A) LENGTH: 273 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 10:

```
Xaa Xaa Xaa Met Ser Tyr Gln Val Leu Ala Arg Lys Trp Arg Pro Gln
1               5                   10                  15
Thr Phe Ala Asp Val Val Gly Gln Glu His Val Leu Thr Ala Leu Ala
                20                  25                  30
Asn Gly Leu Ser Leu Gly Arg Ile His His Ala Tyr Leu Phe Ser Gly
                35                  40                  45
Thr Arg Gly Val Gly Lys Thr Ser Ile Ala Arg Leu Leu Ala Lys Gly
        50                  55                  60
Leu Asn Cys Glu Thr Gly Xaa Xaa Xaa Xaa Ile Thr Ala Thr Pro Cys
65                  70                  75                  80
Gly Val Cys Asp Asn Cys Arg Glu Ile Glu Gln Gly Arg Phe Val Asp
                85                  90                  95
Leu Ile Glu Ile Asp Ala Ala Ser Arg Thr Lys Val Glu Asp Thr Arg
                100                 105                 110
Asp Leu Leu Asp Asn Val Gln Tyr Ala Pro Ala Arg Gly Arg Phe Lys
                115                 120                 125
Val Tyr Leu Ile Asp Glu Val His Met Leu Ser Arg His Ser Phe Asn
        130                 135                 140
Xaa Ala Leu Leu Lys Thr Leu Glu Glu Pro Xaa Xaa Pro Glu His Val
145                 150                 155                 160
Lys Phe Ile Leu Ala Thr Thr Asp Pro Gln Lys Leu Pro Val Thr Ile
                165                 170                 175
Leu Ser Arg Cys Leu Gln Phe His Xaa Xaa Xaa Xaa Leu Lys Ala Leu
                180                 185                 190
Asp Val Glu Gln Ile Arg His Gln Leu Glu His Ile Leu Asn Glu Glu
                195                 200                 205
His Ile Ala His Glu Pro Arg Ala Leu Gln Ile Leu Ala Arg Ala Ala
        210                 215                 220
```

```
Glu Gly Ser Leu Arg Asp Ala Leu Ser Leu Thr Asp Gln Ala Ile Ala
225                 230                 235                 240

Ser Gly Xaa Xaa Asp Gly Gln Val Ser Thr Gln Ala Val Ser Ala Met
            245                 250                 255

Leu Gly Thr Leu Asp Asp Asp Gln Ala Leu Ser Leu Val Glu Ala Met
                260                 265                 270

Val
```

(2) INFORMATION FOR SEQ ID NO: 11:

(i) SEQUENCE CHARACTERISTICS:
        (A) LENGTH: 273 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 11:

```
Xaa Xaa Xaa Met Ser Tyr Gln Ala Leu Tyr Arg Val Phe Arg Pro Gln
1               5                   10                  15

Arg Phe Glu Asp Val Val Gly Gln Glu His Ile Thr Lys Thr Leu Gln
                20                  25                  30

Asn Ala Ile Leu Gln Lys Lys Phe Ser His Ala Tyr Leu Phe Ser Gly
            35                  40                  45

Pro Arg Gly Thr Gly Lys Thr Ser Ala Ala Lys Ile Phe Ala Lys Ala
        50                  55                  60

Val Asn Cys Glu His Ala Xaa Xaa Xaa Xaa Pro Val Asp Glu Pro Cys
65                  70                  75                  80

Asn Glu Cys Ala Ala Cys Lys Gly Ile Thr Asn Gly Ser Ile Ser Asp
                85                  90                  95

Val Ile Glu Ile Asp Ala Ala Ser Asn Asn Gly Val Asp Glu Ile Arg
                100                 105                 110

Asp Ile Arg Asp Lys Val Lys Phe Ala Pro Ser Ala Val Thr Tyr Lys
            115                 120                 125

Val Tyr Ile Ile Asp Glu Val His Met Leu Ser Ile Gly Ala Phe Asn
130                 135                 140

Xaa Ala Leu Leu Lys Thr Leu Glu Glu Pro Xaa Xaa Pro Glu His Cys
145                 150                 155                 160

Ile Phe Ile Leu Ala Thr Thr Glu Pro His Lys Ile Pro Leu Thr Ile
                165                 170                 175

Ile Ser Arg Cys Gln Arg Phe Asp Xaa Xaa Xaa Xaa Phe Lys Arg Ile
            180                 185                 190

Thr Ser Gln Ala Ile Val Gly Arg Met Asn Lys Ile Val Asp Ala Glu
        195                 200                 205

Gln Leu Gln Val Glu Glu Gly Ser Leu Glu Ile Ile Ala Ser Ala Ala
    210                 215                 220

Asp Gly Gly Met Arg Asp Ala Leu Ser Leu Leu Asp Gln Ala Ile Ser
225                 230                 235                 240

Phe Ser Xaa Xaa Gly Asp Ile Ile Lys Val Glu Asp Ala Leu Leu Ile
            245                 250                 255

Thr Gly Ala Val Ser Gln Xaa Xaa Xaa Xaa Xaa Xaa Xaa Xaa Xaa
                260                 265                 270

Xaa
```

(2) INFORMATION FOR SEQ ID NO: 12:

(i) SEQUENCE CHARACTERISTICS:
        (A) LENGTH: 273 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 12:

```
Xaa Xaa Xaa Xaa Met Arg Lys Val Leu Tyr Gln Lys Tyr Arg Pro Thr
 1               5                  10                  15

Lys Phe Ser Asp Thr Val Gly Gln Asp Ser Ile Lys Arg Ile Ile Val
             20                  25                  30

Asn Ala Ile Thr Gln Asp Gln Leu Pro His Gly Tyr Ile Phe Ala Gly
         35                  40                  45

Glu Arg Gly Thr Gly Lys Thr Thr Phe Ala Lys Ile Ala Lys Ala
     50                  55                  60

Ile Asn Cys Leu Asn Xaa Xaa Xaa Xaa Xaa Trp Asn Gly Asp Val Cys
65                  70                  75                  80

Asn Gln Cys Glu Ala Cys Gln Ala Ile Asn Ser Asn Ser Ala Ile Asp
                 85                  90                  95

Val Phe Glu Ile Asp Ala Ala Ser Lys Asn Gly Ile Asn Asp Ile Arg
                100                 105                 110

Glu Leu Ala Glu Asn Val Phe Asn Leu Pro Phe Lys Phe Lys Lys Lys
            115                 120                 125

Val Tyr Ile Leu Asp Glu Ala His Met Leu Thr Pro Gln Ser Trp Ser
        130                 135                 140

Xaa Gly Leu Leu Lys Thr Leu Glu Glu Ala Xaa Xaa Pro Asp Tyr Val
145                 150                 155                 160

Leu Phe Ile Phe Ala Thr Thr Glu Phe Asn Lys Ile Pro Ile Thr Ile
                165                 170                 175

Leu Ser Arg Cys Gln Ser Phe Phe Xaa Xaa Xaa Xaa Phe Lys Gln Ile
            180                 185                 190

Thr Asn Asp Leu Ile Gln Gln Arg Leu Ala Glu Val Ala Ala Lys Glu
        195                 200                 205

Ser Ile Lys Ile Thr Thr Asp Ala Leu Val Lys Leu Ala Asp Leu Ala
    210                 215                 220

Gln Gly Ser Ile Arg Asp Gly Leu Ser Leu Leu Asp Gln Ile Ser Asn
225                 230                 235                 240

Phe Ser Glu Xaa Ser Lys Thr Ile Ser Leu Ala Asp Val Glu Lys Thr
                245                 250                 255

Phe Asn Leu Leu Asp Lys Glu Gln Xaa Xaa Xaa Xaa Xaa Xaa Xaa Lys
            260                 265                 270

Phe
```

(2) INFORMATION FOR SEQ ID NO: 13:

(i) SEQUENCE CHARACTERISTICS:
        (A) LENGTH: 273 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 13:

```
Glu Lys Gly Asp Ala Tyr Thr Val Leu Ala Arg Lys Tyr Arg Pro Arg
```

```
1               5                  10                 15
Thr Phe Glu Asp Leu Ile Gly Gln Glu Ala Met Val Arg Thr Leu Ala
                20                  25                  30

Asn Ala Phe Ser Thr Gly Arg Ile Ala His Ala Phe Lys Leu Thr Gly
                35                  40                  45

Val Arg Gly Val Gly Lys Thr Thr Ala Arg Leu Leu Ala Arg Ala
 50                  55                  60

Leu Asn Tyr Glu Thr Asp Thr Val Lys Gly Pro Ser Val Asp Leu Thr
65                  70                  75                  80

Thr Glu Gly Tyr His Cys Arg Ser Ile Ile Glu Gly Arg His Met Asp
                85                  90                  95

Val Leu Glu Ile Asp Ala Ala Ser Arg Thr Lys Val Asp Glu Met Arg
                100                 105                 110

Glu Leu Leu Asp Gly Val Arg Tyr Ala Pro Val Glu Ala Arg Tyr Lys
                115                 120                 125

Val Tyr Ile Ile Asp Glu Val His Met Leu Ser Thr Ala Ala Phe Asn
                130                 135                 140

Xaa Ala Leu Leu Lys Thr Leu Glu Glu Pro Xaa Xaa Pro Pro His Ala
145                 150                 155                 160

Lys Phe Ile Phe Ala Thr Thr Glu Ile Arg Lys Val Pro Val Thr Ile
                165                 170                 175

Leu Ser Arg Cys Gln Arg Phe Asp Xaa Xaa Xaa Xaa Leu Arg Arg Val
                180                 185                 190

Glu Pro Asp Val Leu Val Lys His Phe Asp Arg Ile Ser Ala Lys Glu
                195                 200                 205

Gly Ala Arg Ile Glu Met Asp Ala Leu Ala Leu Ile Ala Arg Ala Ala
                210                 215                 220

Glu Gly Ser Val Arg Asp Gly Leu Ser Leu Leu Asp Gln Ala Ile Val
225                 230                 235                 240

Gln Thr Glu Arg Gly Gln Thr Val Thr Ser Thr Val Val Arg Asp Met
                245                 250                 255

Leu Gly Leu Ala Asp Arg Xaa Xaa Xaa Xaa Xaa Xaa Xaa Xaa Xaa
                260                 265                 270

Xaa (2) INFORMATION FOR SEQ ID NO: 14:

(i) SEQUENCE CHARACTERISTICS:
        (A) LENGTH: 273 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 14:

Xaa Xaa Xaa Met Ala Tyr Glu Pro Leu His His Lys Tyr Arg Pro Gln
1               5                  10                  15

Thr Phe Ala Asp Leu Val Gly Gln Thr Ala Ile Ala Ala Thr Leu Ser
                20                  25                  30

Asn Ala Ile Glu Gln Glu Arg Ile Val Pro Ala Tyr Leu Phe Thr Gly
                35                  40                  45

Pro Arg Gly Thr Gly Lys Thr Ser Ser Ala Arg Ile Leu Ala Lys Ser
 50                  55                  60

Leu Asn Cys Ile Ala Gly Asp Arg Xaa Xaa Pro Thr Ala Thr Pro Cys
65                  70                  75                  80
```

```
Gly Gln Cys Ala Thr Cys Arg Ala Ile Thr Asn Gly Ser Ala Leu Asp
                85                  90                  95

Val Ile Glu Ile Asp Ala Ala Ser Asn Thr Gly Val Asp Asn Ile Arg
            100                 105                 110

Glu Ile Ile Glu Arg Ala Gln Phe Ala Pro Val Gln Cys Arg Tyr Lys
            115                 120                 125

Val Tyr Val Ile Asp Glu Cys Leu Thr Gly Asp Ser Gln Val Leu Thr
        130                 135                 140

Arg Asn Gly Leu Met Ser Ile Asp Asn Pro Gln Ile Lys Gly Arg Glu
145                 150                 155                 160

Val Leu Ser Tyr Asn Glu Thr Leu Gln Gln Trp Glu Tyr Lys Lys Val
                165                 170                 175

Leu Arg Trp Leu Asp Arg Gly Glu Lys Gln Thr Leu Ser Ile Lys Thr
            180                 185                 190

Lys Asn Ser Thr Val Arg Cys Thr Ala Asn His Leu Ile Arg Thr Glu
            195                 200                 205

Gln Gly Trp Thr Arg Ala Glu Asn Ile Thr Pro Gly Met Lys Ile Leu
        210                 215                 220

Ser Pro Ala Ser Val Asp Val Asp Asn Leu Ser Gln Ser Thr Ala Leu
225                 230                 235                 240

Thr Ala Ser Xaa Leu Gly Gly Leu Ser Gly Ala Ile Asn Tyr Glu Ala
                245                 250                 255

Ile Asn Thr Asp Lys Lys Asn Thr Thr Leu Ser Leu Ser Leu Lys Lys
            260                 265                 270

Gln (2) INFORMATION FOR SEQ ID NO: 15:

(i) SEQUENCE CHARACTERISTICS:
        (A) LENGTH: 273 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 15:

Xaa Xaa Xaa Xaa Xaa Tyr Xaa Xaa Leu Xaa Arg Lys Phe Arg Pro Xaa
1               5                   10                  15

Thr Phe Xaa Asp Val Val Gly Gln Glu Xaa Val Xaa Xaa Xaa Leu Xaa
            20                  25                  30

Asn Ala Ile Xaa Xaa Xaa Arg Leu Xaa His Ala Tyr Leu Phe Ser Gly
            35                  40                  45

Xaa Arg Gly Xaa Gly Lys Thr Thr Xaa Ala Arg Leu Leu Ala Lys Ala
    50                  55                  60

Val Asn Cys Xaa Xaa Xaa Xaa Xaa Xaa Xaa Xaa Xaa Xaa Xaa Pro Cys
65                  70                  75                  80

Xaa Xaa Cys Xaa Xaa Cys Arg Ala Ile Xaa Xaa Gly Xaa Xaa Val Asp
            85                  90                  95

Val Val Glu Ile Asp Ala Ala Ser Xaa Xaa Xaa Val Glu Asp Val Arg
            100                 105                 110

Glu Leu Xaa Glu Xaa Val Xaa Tyr Ala Pro Xaa Xaa Xaa Arg Phe Lys
        115                 120                 125

Val Tyr Ile Ile Asp Glu Xaa His Met Leu Ser Xaa Xaa Xaa Phe Asn
        130                 135                 140
```

```
Xaa Ala Leu Leu Lys Thr Leu Glu Glu Pro Xaa Xaa Pro Xaa His Xaa
145                 150                 155                 160

Leu Phe Val Phe Ala Thr Thr Glu Xaa Xaa Lys Met Pro Val Thr Ile
                165                 170                 175

Leu Ser Arg Cys Gln His Phe Xaa Xaa Xaa Xaa Xaa Arg Arg Leu
            180                 185                 190

Xaa Xaa Glu Xaa Ile Xaa Xaa Lys Leu Xaa Arg Ile Leu Xaa Xaa Glu
            195                 200                 205

Xaa Xaa Xaa Xaa Glu Xaa Glu Ala Leu Xaa Leu Leu Ala Arg Xaa Ala
            210                 215                 220

Asp Gly Xaa Leu Arg Asp Ala Leu Ser Leu Leu Asp Gln Xaa Leu Xaa
225                 230                 235                 240

Xaa Xaa Xaa Xaa Xaa Xaa Xaa Leu Thr Xaa Xaa Val Xaa Xaa Xaa
                245                 250                 255

Leu Gly Xaa Xaa Xaa Arg Xaa Xaa Xaa Xaa Xaa Xaa Xaa Xaa Xaa
            260                 265                 270

Xaa
```

(2) INFORMATION FOR SEQ ID NO: 16:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 16:

```
GAAAAAAAAA GCCTGAGCCC AAGGCCCCGC TCGGCCCCAC CTCCTGA            47
```

(2) INFORMATION FOR SEQ ID NO: 17:

(i) SEQUENCE CHARACTERISTICS:
        (A) LENGTH: 15 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 17:

```
Glu Lys Lys Ser Leu Ser Pro Arg Pro Arg Ser Ala Pro Pro Pro
1               5                   10                  15
```

(2) INFORMATION FOR SEQ ID NO: 18:

(i) SEQUENCE CHARACTERISTICS:
        (A) LENGTH: 15 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 18:

```
Glu Lys Lys Lys Pro Glu Pro Lys Ala Pro Leu Gly Pro Thr Ser
1               5                   10                  15
```

(2) INFORMATION FOR SEQ ID NO: 19:

(i) SEQUENCE CHARACTERISTICS:
        (A) LENGTH: 4 amino acids (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 19:

Glu Lys Lys Ala
1

(2) INFORMATION FOR SEQ ID NO: 20:

(i) SEQUENCE CHARACTERISTICS:
        (A) LENGTH: 371 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 20:

| | | | | | |
|---|---|---|---|---|---|
| GGTTCCTCAA | GGTCTTGAGG | AGGGCGTTGA | AGGCGCTTTT | GGAAACATGT | GGGCCTCGTC | 60 |
| CAGATAAAAC | CTTCCTGGGG | GCAAAAGGGG | GGCGAGGTGG | ATCCTTTCCC | TCAGCTCCCG | 120 |
| CACTCCTCCA | CGGATTGTTG | CTGGCGGCGT | CAATCTCCAC | CACGTCCGGG | TGGGCGCCCC | 180 |
| TCTGCACCGC | CTGGCAGTGG | GGGCAACCCC | GCAAGGGGGG | TCTTCCCCCT | GGCACCCCAC | 240 |
| CGCCATGGCA | GACCTCCCGT | GGTGGTCTTG | CCCACCCCCT | GGGCCCGGAA | AAAAAGTGCC | 300 |
| TGGGCGAACC | TCCCCTCCCG | GATGGCCTTG | AGAGGGCTCC | TTCACTGCTC | CTGACCCACA | 360 |
| ACCTCTTGAA | A | | | | | 371 |

(2) INFORMATION FOR SEQ ID NO: 21:

(i) SEQUENCE CHARACTERISTICS:
        (A) LENGTH: 20 base pairs
        (B) TYPE: nucleic acid
        (C) STRANDEDNESS: not relevant
        (D) TOPOLOGY: not relevant (ii) MOLECULE TYPE: protein (xi) SEQUENCE DESCRIPTION: SEQ ID NO: 21:

TTYCARGARG TNGTNGGWCA                                            20

(2) INFORMATION FOR SEQ ID NO: 22:

(i) SEQUENCE CHARACTERISTICS:
        (A) LENGTH: 17 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 22:

Gly Gly Tyr Thr Cys Tyr Thr Cys Asn Ala Arg Asn Gly Thr Tyr Thr
1               5                   10                  15

Thr (2) INFORMATION FOR SEQ ID NO: 23:

(i) SEQUENCE CHARACTERISTICS:
        (A) LENGTH: 71 amino acids
        (B) TYPE: amino acid
        (C) STRANDEDNESS: not relevant (D) TOPOLOGY: not relevant (ii) MOLECULE TYPE: protein (xi) SEQUENCE DESCRIPTION: SEQ ID NO: 23:

Asp Pro Pro Cys Gly Val Cys Pro His Cys Gln Ala Val Gln Arg Gly
 1               5                  10                  15

Ala His Pro Asp Val Val Glu Ile Asp Ala Ala Ser Asn Xaa Ser Xaa
                20                  25                  30

Xaa Xaa Xaa Xaa Xaa Xaa Xaa Xaa Xaa Ile His Leu Ala Pro Leu Xaa
            35                  40                  45

Ala Pro Arg Lys Val Xaa Xaa Leu Asp Glu Ala His Met Xaa Ser Lys
        50                  55                  60

Ser Ala Phe Asn Ala Leu Leu
 65                  70

(2) INFORMATION FOR SEQ ID NO: 24:

(i) SEQUENCE CHARACTERISTICS:
            (A) LENGTH: 71 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 24:

Asp Glu Pro Cys Asn Glu Cys Ala Ala Cys Lys Gly Ile Thr Asn Gly
 1               5                  10                  15

Ser Ile Ser Asp Val Ile Glu Ile Asp Ala Ala Ser Asn Asn Gly Val
                20                  25                  30

Asp Glu Ile Arg Asp Ile Arg Asp Lys Val Lys Phe Ala Pro Ser Ala
            35                  40                  45

Val Thr Tyr Lys Val Tyr Ile Ile Asp Glu Val His Met Leu Ser Ile
        50                  55                  60

Gly Ala Phe Asn Ala Leu Leu
 65                  70

(2) INFORMATION FOR SEQ ID NO: 25:

(i) SEQUENCE CHARACTERISTICS:
            (A) LENGTH: 71 amino acids
            (B) TYPE: amino acid
            (C) STRANDEDNESS: not relevant
            (D) TOPOLOGY: not relevant (ii) MOLECULE TYPE: protein (ix) FEATURE:
            (A) NAME/KEY: Modified-site
            (B) LOCATION: 17
            (D) OTHER INFORMATION: /note= "The residue at this
                location is similar but not identical to serine and/or
                alanine"

(ix) FEATURE:
            (A) NAME/KEY: Modified-site
            (B) LOCATION: 22
            (D) OTHER INFORMATION: /note= "The residue at this
                position is similar but not identical to isoleucine
                and/or valine"

(ix) FEATURE:
            (A) NAME/KEY: Modified-site
            (B) LOCATION: 42
            (D) OTHER INFORMATION: /note= "The residue at this
                position is similar but not identical to isoleucine

```
                and/or valine"

(ix) FEATURE:
         (A) NAME/KEY: Modified-site
         (B) LOCATION: 56
         (D) OTHER INFORMATION: /note= "The residue at this
             position is similar but not identical to leucine and/or
             isoleucine"

(ix) FEATURE:
         (A) NAME/KEY: Modified-site
         (B) LOCATION: 11
         (D) OTHER INFORMATION: /note= "The residue at this
             position is similar but not identical to glutamine
             and/or lysine"

(ix) FEATURE:
         (A) NAME/KEY: Modified-site
         (B) LOCATION: 13
         (D) OTHER INFORMATION: /note= "The residue at this
             location is similar but not identical to valine and/or
             isoleucine"

(xi) SEQUENCE DESCRIPTION: SEQ ID NO: 25:

Asp Xaa Pro Cys Xaa Xaa Cys Xaa Xaa Cys Xaa Xaa Xaa Xaa Xaa Gly
1               5                   10                  15

Xaa Xaa Xaa Asp Val Xaa Glu Ile Asp Ala Ala Ser Asn Xaa Xaa Xaa
            20                  25                  30

Xaa Xaa Xaa Xaa Xaa Xaa Xaa Xaa Xaa Xaa Xaa Ala Pro Xaa Xaa
        35                  40                  45

Xaa Xaa Xaa Lys Val Xaa Xaa Xaa Asp Glu Xaa His Met Xaa Ser Xaa
    50                  55                  60

Xaa Ala Phe Asn Ala Leu Leu
65                  70

(2) INFORMATION FOR SEQ ID NO: 26:

(i) SEQUENCE CHARACTERISTICS:
         (A) LENGTH: 10 amino acids
         (B) TYPE: amino acid
         (C) STRANDEDNESS: not relevant
         (D) TOPOLOGY: not relevant (ii) MOLECULE TYPE: protein (xi) SEQUENCE DESCRIPTION: SEQ ID NO: 26:

Arg Phe Ala His Leu His Gln His Thr Gln
1               5                   10

(2) INFORMATION FOR SEQ ID NO: 27:

(i) SEQUENCE CHARACTERISTICS:
         (A) LENGTH: 9 amino acids
         (B) TYPE: amino acid
         (C) STRANDEDNESS: not relevant
         (D) TOPOLOGY: not relevant (ii) MOLECULE TYPE: protein (xi) SEQUENCE DESCRIPTION: SEQ ID NO: 27:

Phe Val His Leu His Asn His Thr Glu
1               5

(2) INFORMATION FOR SEQ ID NO: 28:

(i) SEQUENCE CHARACTERISTICS:
         (A) LENGTH: 10 amino acids
         (B) TYPE: amino acid
         (C) STRANDEDNESS: not relevant
```

(D) TOPOLOGY: not relevant (ii) MOLECULE TYPE: protein (xi) SEQUENCE DESCRIPTION: SEQ ID NO: 28:

Arg Phe Ile His Leu Arg Thr His Thr Asp
1               5                  10

(2) INFORMATION FOR SEQ ID NO: 29:

(i) SEQUENCE CHARACTERISTICS:
            (A) LENGTH: 9 amino acids
            (B) TYPE: amino acid
            (C) STRANDEDNESS: not relevant
            (D) TOPOLOGY: not relevant (ii) MOLECULE TYPE: protein (ix) FEATURE:
            (A) NAME/KEY: Modified-site
            (B) LOCATION: 9
            (D) OTHER INFORMATION: /note= "The residue at this
                position is similar but not identical to glutamic acid,
                glutamine and/or aspartic acid"

(xi) SEQUENCE DESCRIPTION: SEQ ID NO: 29:

Phe Xaa His Leu His Xaa His Thr Xaa
1               5

(2) INFORMATION FOR SEQ ID NO: 30:

(i) SEQUENCE CHARACTERISTICS:
            (A) LENGTH: 10 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 30:

Arg Phe Xaa His Leu Xaa Xaa His Thr Xaa
1               5                  10

(2) INFORMATION FOR SEQ ID NO: 31:

(i) SEQUENCE CHARACTERISTICS:
            (A) LENGTH: 22 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 31:

Phe Thr Gly Tyr Gln Asn Leu Val Arg Leu Ala Ser Arg Ala Tyr Leu
1               5                  10                  15

Glu Gly Phe Tyr Glu Lys
            20

(2) INFORMATION FOR SEQ ID NO: 32:

(i) SEQUENCE CHARACTERISTICS:
            (A) LENGTH: 18 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 32:

Thr Gly Tyr Gln Asn Leu Thr Leu Leu Ile Ser Lys Ala Tyr Gln Arg
1               5                   10                  15

Gly Tyr (2) INFORMATION FOR SEQ ID NO: 33:

(i) SEQUENCE CHARACTERISTICS:
        (A) LENGTH: 22 amino acids
        (B) TYPE: amino acid
        (C) STRANDEDNESS: not relevant
        (D) TOPOLOGY: not relevant (ii) MOLECULE TYPE: protein (ix) FEATURE:
        (A) NAME/KEY: Modified-site
        (B) LOCATION: 13
        (D) OTHER INFORMATION: /note= "The residue at this
            position is similar but not identical to arginine
            and/or lysine"

(ix) FEATURE:
        (A) NAME/KEY: Modified-site
        (B) LOCATION: 19
        (D) OTHER INFORMATION: /note= "The residue at this
            position is similar but not identical to phenylalanine
            and/or tyrosine"

(xi) SEQUENCE DESCRIPTION: SEQ ID NO: 33:

Xaa Thr Gly Tyr Gln Asn Leu Xaa Xaa Leu Xaa Ser Xaa Ala Tyr Xaa
1               5                   10                  15

Xaa Gly Xaa Xaa Xaa Xaa
            20

(2) INFORMATION FOR SEQ ID NO: 34:

(i) SEQUENCE CHARACTERISTICS:
        (A) LENGTH: 24 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 34:

Ile Leu Asp Glu Thr Tyr Gly Ile Pro Val Tyr Gln Glu Gln Gln Met
1               5                   10                  15

Gln Ile Ala Ala Ala Val Gly Tyr
            20

(2) INFORMATION FOR SEQ ID NO: 35:

(i) SEQUENCE CHARACTERISTICS:
        (A) LENGTH: 19 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 35:

Val Leu Glu Pro Thr Tyr Gly Ile Ile Leu Tyr Gln Glu Gln Val Met
1               5                   10                  15

Gln Ile Ala (2) INFORMATION FOR SEQ ID NO: 36:

```
        (i) SEQUENCE CHARACTERISTICS:
            (A) LENGTH: 24 amino acids
            (B) TYPE: amino acid
            (C) STRANDEDNESS: not relevant
            (D) TOPOLOGY: not relevant (ii) MOLECULE TYPE: protein (ix) FEATURE:
            (A) NAME/KEY: Modified-site
            (B) LOCATION: 1
            (D) OTHER INFORMATION: /note= "The residue at this
                position is similar but not identical to isoleucine
                and/or valine"

(ix) FEATURE:
            (A) NAME/KEY: Modified-site
            (B) LOCATION: 3
            (D) OTHER INFORMATION: /note= "The residue at this
                position is similar but not identical to aspartic acid
                and/or glutamic acid"

(ix) FEATURE:
            (A) NAME/KEY: Modified-site
            (B) LOCATION: 10
            (D) OTHER INFORMATION: /note= "The residue at this
                position is similar but not identical to valine and/or
                leucine"

(xi) SEQUENCE DESCRIPTION: SEQ ID NO: 36:

Xaa Leu Xaa Xaa Thr Tyr Gly Ile Xaa Xaa Tyr Gln Glu Gln Xaa Met
1               5                  10                  15

Gln Ile Ala Xaa Xaa Xaa Xaa Xaa
            20

(2) INFORMATION FOR SEQ ID NO: 37:

(i) SEQUENCE CHARACTERISTICS:
            (A) LENGTH: 13 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 37:

Gly Leu Asp Gly Gly Tyr Phe His Leu Thr Leu Phe Asp
1               5                  10

(2) INFORMATION FOR SEQ ID NO: 38:

(i) SEQUENCE CHARACTERISTICS:
            (A) LENGTH: 12 amino acids
            (B) TYPE: amino acid
            (C) STRANDEDNESS: not relevant
            (D) TOPOLOGY: not relevant (ii) MOLECULE TYPE: protein (ix) FEATURE:
            (A) NAME/KEY: Modified-site
            (B) LOCATION: 9
            (D) OTHER INFORMATION: /note= "The residue at this
                position is similar but not identical to leucine"

(xi) SEQUENCE DESCRIPTION: SEQ ID NO: 38:

Arg Asn Lys Gly Gly Tyr Phe Arg Glu Leu Phe Asp
1               5                  10

(2) INFORMATION FOR SEQ ID NO: 39:

(i) SEQUENCE CHARACTERISTICS:
```

(A) LENGTH: 13 amino acids
(B) TYPE: amino acid
(C) STRANDEDNESS: not relevant
(D) TOPOLOGY: not relevant (ii) MOLECULE TYPE: protein (ix) FEATURE:
(A) NAME/KEY: Modified-site
(B) LOCATION: 3
(D) OTHER INFORMATION: /note= "The residue at this position is similar but not identical to aspartic acid and/or lysine"

(ix) FEATURE:
(A) NAME/KEY: Modified-site
(B) LOCATION: 8
(D) OTHER INFORMATION: /note= "The residue at this position is similar but not identical to histidine and/or arginine"

(xi) SEQUENCE DESCRIPTION: SEQ ID NO: 39:

```
Xaa Xaa Xaa Gly Gly Tyr Phe Xaa Xaa Xaa Leu Phe Asp
 1           5                   10
```

(2) INFORMATION FOR SEQ ID NO: 40:

(i) SEQUENCE CHARACTERISTICS:
(A) LENGTH: 348 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "DNA"

(xi) SEQUENCE DESCRIPTION: SEQ ID NO: 40:

```
CATCTTCACC AGCACACCCA GTTCTCCCTC CTGGACGGGG CGGCGAARCT TTCCRACCTC     60
CTCAAKTGGG TCAAGGAGAC GACCCCCCGA GGACCCCGCC TTGGCCATGA CCGACCACGG    120
CAACTTCTTC GGGGCCGKGG AKTTCTACAA GAAGGCCACC GAAATGGGCA TCAAGCCCAT    180
CYTGGGCTAC GAGGCCTAMG TGGCGGCGGA AAGCCGCTTT GACCGCAAGC GGGGAAAGGG    240
CYTAGACGGG GGCTACTTTC ACYTCACCYT CYTCGCCAAG GACTTCACGG GGTACCAGAA    300
CCTGGTGCGC CTGGCGAGCC GGGCTTACCT GGAGGGGTTT TACGAAAA                 348
```

(2) INFORMATION FOR SEQ ID NO: 41:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "DNA"

(xi) SEQUENCE DESCRIPTION: SEQ ID NO: 41:

```
CATCTTCACC AGCACACCCA                                                  20
```

(2) INFORMATION FOR SEQ ID NO: 42:

(i) SEQUENCE CHARACTERISTICS:
(A) LENGTH: 17 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "DNA"

(xi) SEQUENCE DESCRIPTION: SEQ ID NO: 42:

GAGGGGTTTT ACGAAAA                                                    17

(2) INFORMATION FOR SEQ ID NO: 43:

(i) SEQUENCE CHARACTERISTICS:
        (A) LENGTH: 14 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 43:

Tyr Ser Leu Leu Asp Gly Ala Ser Gln Leu Pro Ala Leu Ile
1               5                   10

(2) INFORMATION FOR SEQ ID NO: 44:

(i) SEQUENCE CHARACTERISTICS:
        (A) LENGTH: 14 amino acids
        (B) TYPE: amino acid
        (C) STRANDEDNESS: not relevant
        (D) TOPOLOGY: not relevant (ii) MOLECULE TYPE: protein (ix) FEATURE:
        (A) NAME/KEY: Modified-site
        (B) LOCATION: 1
        (D) OTHER INFORMATION: /note= "The residue at this
            position is similar but not identical to tyrosine and/or
            phenylalanine"

(ix) FEATURE:
        (A) NAME/KEY: Modified-site
        (B) LOCATION: 8
        (D) OTHER INFORMATION: /note= "The residue at this
            position is similar but not identical to alanine and/or
            serine"

(ix) FEATURE:
        (A) NAME/KEY: Modified-site
        (B) LOCATION: 9
        (D) OTHER INFORMATION: /note= "The residue at this
            position is similar but not identical to leucine and/or
            isoleucine"

(ix) FEATURE:
        (A) NAME/KEY: Modified-site
        (B) LOCATION: 14
        (D) OTHER INFORMATION: /note= "The residue at this
            position is similar but not identical to isoleucine
            and/or lysine"

(xi) SEQUENCE DESCRIPTION: SEQ ID NO: 44:

Xaa Ser Leu Leu Asp Gly Ala Xaa Xaa Leu Xaa Xaa Leu Xaa
1               5                   10

(2) INFORMATION FOR SEQ ID NO: 45:

(i) SEQUENCE CHARACTERISTICS:
        (A) LENGTH: 18 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 45:

Phe Ser Leu Leu Asp Gly Ala Ala Lys Leu Ser Xaa Leu Leu Xaa Trp

```
1               5                   10                  15
Val Lys
```

(2) INFORMATION FOR SEQ ID NO: 46:

(i) SEQUENCE CHARACTERISTICS:
        (A) LENGTH: 18 amino acids
        (B) TYPE: amino acid
        (C) STRANDEDNESS: not relevant
        (D) TOPOLOGY: not relevant (ii) MOLECULE TYPE: protein (ix) FEATURE:
        (A) NAME/KEY: Modified-site
        (B) LOCATION: 1
        (D) OTHER INFORMATION: /note= "The residue at this
            position is similar but not identical to phenylalanine
            and/or tyrosine"

(ix) FEATURE:
        (A) NAME/KEY: Modified-site
        (B) LOCATION: 3
        (D) OTHER INFORMATION: /note= "The residue at this
            position is similar but not identical to leucine and/or
            methionine"

(ix) FEATURE:
        (A) NAME/KEY: Modified-site
        (B) LOCATION: 10
        (D) OTHER INFORMATION: /note= "The residue at this
            position is similar but not identical to leucine and/or
            isoleucine"

(ix) FEATURE:
        (A) NAME/KEY: Modified-site
        (B) LOCATION: 11
        (D) OTHER INFORMATION: /note= "The residue at this
            position is similar but not identical to proline, serine
            and/or threonine"

(ix) FEATURE:
        (A) NAME/KEY: Modified-site
        (B) LOCATION: 13
        (D) OTHER INFORMATION: /note= "The residue at this
            position is similar but not identical to leucine and/or
            methionine"

(ix) FEATURE:
        (A) NAME/KEY: Modified-site
        (B) LOCATION: 18
        (D) OTHER INFORMATION: /note= "The residue at this
            position is similar but not identical to lysine and/or
            glutamic acid"

(xi) SEQUENCE DESCRIPTION: SEQ ID NO: 46:

```
Xaa Ser Xaa Leu Asp Gly Ala Ala Lys Xaa Xaa Xaa Xaa Leu Xaa Xaa
1               5                   10                  15
Val Xaa
```

(2) INFORMATION FOR SEQ ID NO: 47:

(i) SEQUENCE CHARACTERISTICS:
        (A) LENGTH: 18 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 47:

```
Tyr Ser Met Leu Asp Gly Ala Ala Lys Ile Thr Pro Met Leu Ala Glu
1               5                   10                  15
```

Val Glu (2) INFORMATION FOR SEQ ID NO: 48:

(i) SEQUENCE CHARACTERISTICS:
        (A) LENGTH: 36 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 48:

Pro Ala Ile Ala Leu Thr Asp His Gly Val Met Tyr Gly Ala Val Glu
1               5                   10                  15

Leu Leu Lys Val Cys Arg Gly Lys Pro Ile Lys Pro Ile Ile Gly Asn
            20                  25                  30

Glu Met Tyr Val
        35

(2) INFORMATION FOR SEQ ID NO: 49:

(i) SEQUENCE CHARACTERISTICS:
        (A) LENGTH: 36 amino acids
        (B) TYPE: amino acid
        (C) STRANDEDNESS: not relevant
        (D) TOPOLOGY: not relevant (ii) MOLECULE TYPE: protein (ix) FEATURE:
        (A) NAME/KEY: Modified-site
        (B) LOCATION: 3
        (D) OTHER INFORMATION: /note= "The residue at this
            location is similar but not identical to isoleucine,
            leucine and/or valine"

(ix) FEATURE:
        (A) NAME/KEY: Modified-site
        (B) LOCATION: 5
        (D) OTHER INFORMATION: /note= "The residue at this
            position is similar but not identical to leucine and/or
            methionine"

(ix) FEATURE:
        (A) NAME/KEY: Modified-site
        (B) LOCATION: 12
        (D) OTHER INFORMATION: /note= "The residue at this
            location is similar but not identical to tyrosine and/or
            phenylalanine"

(ix) FEATURE:
        (A) NAME/KEY: Modified-site
        (B) LOCATION: 30
        (D) OTHER INFORMATION: /note= "The residue at this
            position is similar but not identical to isoleucine
            and/or leucine"

(xi) SEQUENCE DESCRIPTION: SEQ ID NO: 49:

Pro Ala Xaa Ala Xaa Thr Asp His Gly Xaa Xaa Xaa Gly Ala Xaa Xaa
1               5                   10                  15

Xaa Xaa Lys Xaa Xaa Xaa Xaa Xaa Xaa Ile Lys Pro Ile Xaa Gly Xaa
            20                  25                  30

Glu Xaa Xaa Val
        35

(2) INFORMATION FOR SEQ ID NO: 50:

(i) SEQUENCE CHARACTERISTICS:

(A) LENGTH: 46 amino acids
                (B) TYPE: amino acid
                (C) STRANDEDNESS: not relevant
                (D) TOPOLOGY: not relevant (ii) MOLECULE TYPE: protein (xi) SEQUENCE DESCRIPTION: SEQ ID NO: 50:

Pro Ala Leu Ala Met Thr Asp His Gly Asn Phe Phe Gly Ala Xaa Xaa
1               5                   10                  15

Phe Tyr Lys Lys Ala Thr Glu Met Gly Ile Lys Pro Ile Leu Gly Tyr
            20                  25                  30

Glu Ala Xaa Val Ala Ala Glu Ser Arg Phe Asp Arg Lys Arg
        35                  40                  45

(2) INFORMATION FOR SEQ ID NO: 51:

(i) SEQUENCE CHARACTERISTICS:
                (A) LENGTH: 46 amino acids
                (B) TYPE: amino acid
                (C) STRANDEDNESS: not relevant
                (D) TOPOLOGY: not relevant (ii) MOLECULE TYPE: protein (ix) FEATURE:
                (A) NAME/KEY: Modified-site
                (B) LOCATION: 3
                (D) OTHER INFORMATION: /note= "The residue at this
                    position is similar but not identical to isoleucine,
                    leucine and/or valine"

(ix) FEATURE:
                (A) NAME/KEY: Modified-site
                (B) LOCATION: 23
                (D) OTHER INFORMATION: /note= "The residue at this
                    position is similar but not identical to glycine,
                    glutamic acid and/or lysine"

(ix) FEATURE:
                (A) NAME/KEY: Modified-site
                (B) LOCATION: 30
                (D) OTHER INFORMATION: /note= "The residue at this
                    position is similar but not identical to isoleucine
                    and/or leucine"

(ix) FEATURE:
                (A) NAME/KEY: Modified-site
                (B) LOCATION: 36
                (D) OTHER INFORMATION: /note= "The residue at this
                    position is similar but not identical to isoleucine
                    and/or valine"

(ix) FEATURE:
                (A) NAME/KEY: Modified-site
                (B) LOCATION: 45
                (D) OTHER INFORMATION: /note= "The residue at this
                    position is similar but not identical to arginine and/or
                    lysine"

(xi) SEQUENCE DESCRIPTION: SEQ ID NO: 51:

Pro Ala Xaa Xaa Met Thr Asp His Gly Asn Xaa Phe Gly Ala Xaa Xaa
1               5                   10                  15

Phe Tyr Xaa Xaa Ala Thr Xaa Xaa Gly Ile Lys Pro Ile Xaa Gly Xaa
            20                  25                  30

Glu Ala Xaa Xaa Ala Xaa Xaa Ser Arg Phe Asp Xaa Xaa Arg
        35                  40                  45

(2) INFORMATION FOR SEQ ID NO: 52:

(i) SEQUENCE CHARACTERISTICS:

(A) LENGTH: 46 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 52:

Pro Ala Val Gly Met Thr Asp His Gly Asn Met Phe Gly Ala Ser Glu
1               5                  10                  15

Phe Tyr Asn Ser Ala Thr Lys Ala Gly Ile Lys Pro Ile Ile Gly Val
             20                  25                  30

Glu Ala Tyr Ile Ala Pro Gly Ser Arg Phe Asp Thr Arg Arg
         35                  40                  45

(2) INFORMATION FOR SEQ ID NO: 53:

(i) SEQUENCE CHARACTERISTICS:
            (A) LENGTH: 23 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 53:

Xaa Xaa Phe His Gln Val Val Leu Ala Lys Asn Asn Gln Gly Tyr Arg
1               5                  10                  15

Asn Leu Val Lys Leu Thr Thr
             20

(2) INFORMATION FOR SEQ ID NO: 54:

(i) SEQUENCE CHARACTERISTICS:
            (A) LENGTH: 24 amino acids
            (B) TYPE: amino acid
            (C) STRANDEDNESS: not relevant
            (D) TOPOLOGY: not relevant (ii) MOLECULE TYPE: protein (ix) FEATURE:
            (A) NAME/KEY: Modified-site
            (B) LOCATION: 12
            (D) OTHER INFORMATION: /note= "The residue at this
                position is similar but not identical to asparagine
                and/or aspartic acid"

(ix) FEATURE:
            (A) NAME/KEY: Modified-site
            (B) LOCATION: 17
            (D) OTHER INFORMATION: /note= "The residue at this
                position is similar but not identical to arginine and/or
                glutamine"

(ix) FEATURE:
            (A) NAME/KEY: Modified-site
            (B) LOCATION: 21
            (D) OTHER INFORMATION: /note= "The residue at this
                position is similar but not identical to lysine and/or
                arginine"

(ix) FEATURE:
            (A) NAME/KEY: Modified-site
            (B) LOCATION: 24
            (D) OTHER INFORMATION: /note= "The residue at this
                position is similar but not identical to threonine
                and/or serine"

(xi) SEQUENCE DESCRIPTION: SEQ ID NO: 54:

Xaa Xaa Xaa Phe His Xaa Xaa Xaa Xaa Ala Lys Xaa Xaa Xaa Gly Tyr

```
1               5                  10                 15
Xaa Asn Leu Val Xaa Leu Xaa Xaa
            20
```

(2) INFORMATION FOR SEQ ID NO: 55:

(i) SEQUENCE CHARACTERISTICS:
        (A) LENGTH: 26 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 55:

```
Gly Gly Tyr Phe His Xaa Thr Xaa Xaa Ala Lys Asp Phe Thr Gly Tyr
1               5                  10                 15
Gln Asn Leu Val Arg Leu Ala Ser Arg Ala
            20                  25
```

(2) INFORMATION FOR SEQ ID NO: 56:

(i) SEQUENCE CHARACTERISTICS:
        (A) LENGTH: 26 amino acids
        (B) TYPE: amino acid
        (C) STRANDEDNESS: not relevant
        (D) TOPOLOGY: not relevant (ii) MOLECULE TYPE: protein (ix) FEATURE:
        (A) NAME/KEY: Modified-site
        (B) LOCATION: 11
        (D) OTHER INFORMATION: /note= "The residue at this
            position is similar but not identical to lysine and/or
            glutamic acid"

(ix) FEATURE:
        (A) NAME/KEY: Modified-site
        (B) LOCATION: 17
        (D) OTHER INFORMATION: /note= "The residue at this
            position is similar but not identical to arginine and/or
            glutamine"

(ix) FEATURE:
        (A) NAME/KEY: Modified-site
        (B) LOCATION: 21
        (D) OTHER INFORMATION: /note= "The residue at this
            position is similar but not identical to lysine and/or
            arginine"

(ix) FEATURE:
        (A) NAME/KEY: Modified-site
        (B) LOCATION: 23
        (D) OTHER INFORMATION: /note= "The residue at this
            position is similar but not identical to serine, alanine
            and/or threonine"

(ix) FEATURE:
        (A) NAME/KEY: Modified-site
        (B) LOCATION: 12
        (D) OTHER INFORMATION: /note= "The residue at this
            position is similar but not identical to asparagine
            and/or aspartic acid"

(xi) SEQUENCE DESCRIPTION: SEQ ID NO: 56:

```
Gly Xaa Tyr Xaa His Xaa Thr Xaa Xaa Ala Xaa Xaa Xaa Thr Gly Xaa
1               5                  10                 15
Xaa Asn Leu Xaa Xaa Leu Xaa Ser Xaa Ala
            20                  25
```

(2) INFORMATION FOR SEQ ID NO: 57:

(i) SEQUENCE CHARACTERISTICS:
        (A) LENGTH: 26 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 57:

```
Gly Ser Tyr Thr His Leu Thr Met Met Ala Glu Asn Ala Thr Gly Leu
1               5                   10                  15
Arg Asn Leu Phe Lys Leu Ser Ser His Ala
            20                  25
```

(2) INFORMATION FOR SEQ ID NO: 58:

(i) SEQUENCE CHARACTERISTICS:
        (A) LENGTH: 1109 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 58:

```
ATGGGCCGCA AACTCCGCTT CGCCCACCTC CACCAGCACA CCCAGTTCTC CCTCCTGGAC    60
GGGGCGGCGA ARCTTTCCRA CCTCCTCAAD TGGGTCAAGG AGACGACCCC CCGAGGACCC   120
CGCCTTGGCC ATGACCGACC ACGGCAACTT CTTCGGGGCC GKGGAKTTCT ACAAGAAGGC   180
CACCGAAATG GGCATCAAGC CCATCYTGGG CTACGAGGCC TAMGTGGCGG CGGAAAGCCG   240
CTTTGACCGC AAGCGGGGAA AGGGCYTAGA CGGGGGCTAC TTTCACYTCA CCYTCYTCGC   300
CAAGGACTTC ACGGGGTACC AGAACCTGGT GCGCCTGGCG AGCCGGGCTT ACCTGGAGGG   360
GTTTTACGAA AAGCCCCGGA TTGACCGGGA GATCAYCCTG CGCGAGCACG CCGAGGGCCT   420
CATCGCCCTC TCGGGGTGCC TCGGGGCGGA GATCCCCCAG TTCATCCTCC AGGACCGTCT   480
GGACCTGGCC GAGGCCCGGC TCAACGAGTA CCTCTCCATY TTCAAGGACC GCTTCTTCAT   540
TGARATCCAG AACCACGGCC TCCCCGAGCA GAAAAAGGTC AACGAGGTCC TCAAGGANTT   600
CGCCCGAAAN TACGGCCTGG GGATGGTGGC CACCAACGAC GGCCATTACG TGAGGAAGGA   660
GGACGCCCGG GCCCACGAGG TCCTCCTCGC CATCCAGTCC AAGAGTACCY TGGACGACCC   720
CGGGCGCTGG CGCTTCCCCT GCGACGAGTT NTACGTGAAG ACCCCSGANG AGATGCGGGC   780
CATGTTCCCC CGAGGAGGAG TGGGGGGACG AGCCCTTTGA CAACACCGTG GAAGATCGCC   840
CGCATGTGCA ACGTGGAGCT GCCCATCGGG GGACAAGAT GGTCTACCGC ATCCCCCGCT   900
TCCCCYTCCC CGCCCGTCGG AMCGARGCCC AGTTACTTCA TGGAGCTCAC NTTTAAGGGG   960
CTCCTCCGCC GCTACCCGGA CCGGATCACC GAGGGCTTCT ACCGGGAGGT CTTCCGCCTT  1020
TTGGGGAAGC TTCCCCCCCA CGGGGACGGG GAGGCCCTGG CCGAGGCCTT GGCCCAGGTT  1080
GGAGCGGGAG GCTTGGGAGA AGCTCATTG                                   1109
```

(2) INFORMATION FOR SEQ ID NO: 59:

(i) SEQUENCE CHARACTERISTICS:
        (A) LENGTH: 366 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 59:

```
Arg Lys Leu Arg Phe Ala His Leu His Gln His Thr Gln Phe Ser Leu
1               5                   10                  15

Leu Asp Gly Ala Ala Lys Leu Ser Asp Leu Ile Asn Trp Val Lys Glu
            20                  25                  30

Thr Thr Pro Glu Asp Pro Ala Leu Ala Met Thr Asp His Gly Asn Phe
        35                  40                  45

Phe Gly Ala Val Asp Phe Tyr Lys Lys Ala Thr Glu Met Gly Ile Lys
    50                  55                  60

Pro Ile Leu Gly Tyr Glu Ala Tyr Val Ala Ala Glu Ser Arg Phe Asp
65                  70                  75                  80

Arg Lys Arg Gly Lys Gly Leu Asp Gly Gly Tyr Phe His Phe Thr Leu
                85                  90                  95

Leu Ala Lys Asp Phe Thr Gly Tyr Gln Asn Leu Val Arg Leu Ala Ser
            100                 105                 110

Arg Ala Tyr Leu Glu Gly Phe Tyr Glu Lys Pro Arg Ile Asp Arg Glu
        115                 120                 125

Ile Thr Leu Arg Glu His Ala Glu Gly Leu Ile Ala Leu Ser Gly Cys
    130                 135                 140

Leu Gly Ala Glu Ile Pro Gln Phe Ile Leu Gln Asp Arg Leu Asp Leu
145                 150                 155                 160

Ala Glu Ala Arg Leu Asn Glu Tyr Leu Ser Ile Phe Lys Asp Arg Phe
                165                 170                 175

Phe Ile Glu Ile Gln Asn His Gly Leu Pro Glu Gln Lys Lys Val Asn
            180                 185                 190

Glu Val Leu Lys Asp Phe Ala Arg Lys Tyr Gly Leu Gly Met Val Ala
        195                 200                 205

Thr Asn Asp Gly His Tyr Val Arg Lys Glu Asp Ala Arg Ala His Glu
    210                 215                 220

Val Leu Leu Ala Ile Gln Ser Lys Ser Thr Leu Asp Asp Pro Gly Arg
225                 230                 235                 240

Trp Arg Phe Pro Cys Asp Glu Phe Tyr Val Lys Thr Pro Asp Glu Met
                245                 250                 255

Arg Ala Met Phe Pro Pro Arg Arg Ser Gly Gly Thr Ser Pro Leu Thr
            260                 265                 270

Thr Pro Trp Lys Ile Ala Arg Met Cys Asn Val Glu Leu Pro Ile Gly
        275                 280                 285

Gly Thr Arg Trp Ser Thr Ala Ser Pro Ala Ser Pro Ser Pro Pro Val
    290                 295                 300

Gly Pro Lys Pro Ser Tyr Phe Met Glu Leu Thr Phe Lys Gly Leu Leu
305                 310                 315                 320

Arg Arg Tyr Pro Asp Arg Ile Thr Glu Gly Phe Tyr Arg Glu Val Phe
                325                 330                 335

Arg Leu Leu Gly Lys Leu Pro His Gly Asp Gly Glu Ala Leu Ala
            340                 345                 350

Glu Ala Leu Ala Gln Val Gly Ala Gly Gly Leu Gly Glu Ala
        355                 360                 365
```

(2) INFORMATION FOR SEQ ID NO: 60:

(i) SEQUENCE CHARACTERISTICS:
        (A) LENGTH: 219 amino acids
        (B) TYPE: amino acid (C) STRANDEDNESS: not relevant
                (D) TOPOLOGY: not relevant (ii) MOLECULE TYPE: protein (xi) SEQUENCE DESCRIPTION: SEQ ID NO: 60:

Met Ser Gly Ser Ser Ala Gly Ser Ser Phe Val His Leu His Asn His
1               5                   10                  15

Thr Glu Tyr Ser Met Leu Asp Gly Ala Ala Lys Ile Thr Pro Met Leu
            20                  25                  30

Ala Glu Val Glu Arg Leu Gly Xaa Xaa Met Pro Ala Val Gly Met Thr
        35                  40                  45

Asp His Gly Asn Met Phe Gly Ala Ser Glu Phe Tyr Asn Ser Ala Thr
    50                  55                  60

Lys Ala Gly Ile Lys Pro Ile Ile Gly Val Glu Ala Tyr Ile Ala Pro
65                  70                  75                  80

Gly Ser Arg Phe Asp Thr Arg Arg Ile Leu Trp Gly Asp Pro Ser Gln
                85                  90                  95

Lys Ala Asp Asp Val Ser Gly Ser Gly Ser Tyr Thr His Leu Thr Met
                100                 105                 110

Met Ala Glu Asn Ala Thr Gly Leu Arg Asn Leu Phe Lys Leu Ser Ser
            115                 120                 125

His Ala Ser Phe Glu Gly Gln Leu Ser Lys Xaa Xaa Trp Ser Arg Xaa
    130                 135                 140

Xaa Met Asp Ala Glu Leu Xaa Ile Ala Glu His Ala Glu Gly Ile Ile
145                 150                 155                 160

Ile Thr Thr Gly Cys Pro Ser Gly Glu Val Gln Thr Arg Leu Arg Leu
                165                 170                 175

Gly Gln Asp Arg Glu Ala Leu Glu Ala Ala Lys Trp Arg Glu Ile
                180                 185                 190

Val Gly Pro Asp Asn Tyr Phe Leu Glu Leu Met Asp His Gly Leu Thr
            195                 200                 205

Ile Glu Arg Arg Val Arg Asp Gly Leu Leu Glu
        210                 215

(2) INFORMATION FOR SEQ ID NO: 61:

(i) SEQUENCE CHARACTERISTICS:
        (A) LENGTH: 219 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 61:

Xaa Xaa Xaa Xaa Xaa Arg Lys Leu Arg Phe Ala His Leu His Gln His
1               5                   10                  15

Thr Gln Phe Ser Leu Leu Asp Gly Ala Ala Lys Leu Ser Asp Leu Leu
            20                  25                  30

Asn Trp Val Lys Glu Thr Thr Pro Glu Asp Pro Ala Leu Ala Met Thr
            35                  40                  45

Asp His Gly Asn Phe Phe Gly Ala Val Asp Phe Tyr Lys Lys Ala Thr
    50                  55                  60

Glu Met Gly Ile Lys Pro Ile Leu Gly Tyr Glu Ala Tyr Val Ala Ala
65                  70                  75                  80

Glu Ser Arg Phe Asp Xaa Xaa Xaa Xaa Xaa Xaa Xaa Xaa Xaa Xaa
                85                  90                  95

```
Arg Lys Arg Gly Lys Gly Leu Asp Gly Gly Tyr Phe His Phe Thr Leu
            100                 105                 110

Leu Ala Lys Asp Phe Thr Gly Tyr Gln Asn Leu Val Arg Leu Ala Ser
            115                 120                 125

Arg Ala Tyr Leu Glu Gly Phe Tyr Glu Lys Xaa Xaa Xaa Pro Arg Xaa
            130                 135                 140

Xaa Ile Asp Arg Glu Ile Thr Leu Arg Glu His Ala Glu Gly Leu Ile
145                 150                 155                 160

Ala Leu Ser Gly Cys Leu Gly Ala Glu Ile Pro Gln Phe Ile Leu Gln
                165                 170                 175

Asp Xaa Arg Leu Asp Leu Ala Glu Ala Arg Leu Asn Glu Tyr Leu Ser
            180                 185                 190

Ile Phe Lys Asp Arg Phe Phe Ile Glu Ile Gln Asn His Gly Leu Pro
            195                 200                 205

Glu Gln Lys Lys Val Asn Glu Val Leu Lys Asp
            210                 215

(2) INFORMATION FOR SEQ ID NO: 62:

(i) SEQUENCE CHARACTERISTICS:
        (A) LENGTH: 219 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 62:

Xaa Xaa Xaa Xaa Xaa Xaa Xaa Met Ser Phe Val Gly Leu His Ile His
1               5                   10                  15

Ser Asp Tyr Ser Leu Leu Asp Gly Ala Ser Gln Leu Pro Ala Leu Ile
            20                  25                  30

Asp Arg Ala Ile Glu Leu Gly Xaa Xaa Met Pro Ala Ile Ala Leu Thr
            35                  40                  45

Asp His Gly Val Met Tyr Gly Ala Val Glu Leu Leu Lys Val Cys Arg
        50                  55                  60

Gly Lys Pro Ile Lys Pro Ile Ile Gly Asn Glu Met Tyr Val Ile Asn
65                  70                  75                  80

Gly Xaa Xaa Xaa Xaa Xaa Xaa Xaa Xaa Xaa Xaa Xaa Xaa Xaa Xaa Xaa
            85                  90                  95

Xaa Asp Ile Glu Ile Asn Lys Arg His Arg Phe His Gln Val Val
            100                 105                 110

Leu Ala Lys Asn Asn Gln Gly Tyr Arg Asn Leu Val Lys Leu Thr Thr
            115                 120                 125

Ile Ser Asn Leu Lys Gly Ile Gln Gly Ser Gly Ile Phe Ala Arg Pro
            130                 135                 140

Cys Ile Asn Lys Glu Leu Xaa Leu Glu Gln Tyr Lys Glu Gly Leu Ile
145                 150                 155                 160

Val Thr Ser Ala Cys Leu Gly Gly Glu Val Pro Gln Ala Ile Leu Lys
                165                 170                 175

Gly Xaa Asp Leu Asp His Ala Arg Gln Val Ala Lys Trp Tyr Lys Asn
            180                 185                 190

Leu Phe Gly Asp Asp Tyr Tyr Leu Glu Ile Gln Asp His Gly Ser Val
            195                 200                 205

Glu Asp Arg Leu Val Asn Ile Asn Leu Val Lys
            210                 215
```

(2) INFORMATION FOR SEQ ID NO: 63:

(i) SEQUENCE CHARACTERISTICS:
        (A) LENGTH: 473 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 63:

```
CCTAGTTCTC CCTCCTGGAC GGGGCGGCGA AGCTTTCCGA CCTCCTCAAG TGGGTCAAGG      60

AAACGACCCC CGAGGGACCC CGCCTTGGCC ATGACCGACC ACGGCAACCT CTTCGGGGCC     120

GTGGAGTTCT ACAAGAAGGC CACCGAAATG GGCATCAAGC CCATCCTGGG CTACGAGGCC     180

TACGTGGCGG CGGAAAGCCG CTTTGACCGC AAGCGGGGGA AAGGGCCTAG GACGGGGCT     240

ACTTTCACCT CACCCTCCTC GCCAAGGACT TCACGGGGTA CCAGAACCTG GTGCGCCTGG    300

CGAGCCGGGC TTACCTGGAG GGGTTTTACG AAAAGCCCCG GATTGACCGG GGAGATCCTG    360

CGCGAGCACG CCGAGGGCCT CATCGCCCTC TCGGGGTGCC TCGGGCGGA NATCCCCCAG     420

TTCATCCTCC AGGACCGTCT GGACCTGGCC GANGCCCGGC TCAACAAGTA CCT           473
```

(2) INFORMATION FOR SEQ ID NO: 64:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 64:

```
CCTAGTTCTC CCTCCTGGAC G                                                21
```

(2) INFORMATION FOR SEQ ID NO: 65:

(i) SEQUENCE CHARACTERISTICS:
        (A) LENGTH: 242 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 65:

```
TTGAAGGTGT GGAAAAGCTC CTCCTGGGTG CGCTCCTTTC CGGCGATGAA CTGGACGTCG     60

TCCACCAGCA GGAGGTCCAC GGAGCGGTAC CGCTCCCGGA ACTCCGTCAT CCGGTCCTCG    120

CGGATGGCGT TGATGAGCTC GTTGGTGAAA GTTTCCGTGG AAACGTACTC AATCTTCAGG    180

TGGGGGAAGC GCTTGGCCAC GGAGTGGCCC ACGGCGTGCA TCAGGTGGGT CTTCCCCAAT    240

CC                                                                   242
```

(2) INFORMATION FOR SEQ ID NO: 66:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: other nucleic acid
            (A) DESCRIPTION: /desc = "DNA"

(xi) SEQUENCE DESCRIPTION: SEQ ID NO: 66:

TTGAAGGTGT GGAAAAGCTC                                                    20

(2) INFORMATION FOR SEQ ID NO: 67:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO: 67:

GTGGGTCTTC CCCAATCC                                                      18

(2) INFORMATION FOR SEQ ID NO: 68:

(i) SEQUENCE CHARACTERISTICS:
            (A) LENGTH: 60 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 68:

Leu Leu His Ala Val Gly Asn Gly Ile Met Ala Arg Lys Pro Asn Ala
1               5                  10                  15

Lys Val Val Tyr Met His Ser Glu Arg Phe Val Gln Asp Met Val Lys
            20                  25                  30

Ala Leu Gln Asn Asn Ala Ile Glu Glu Phe Lys Arg Tyr Tyr Arg Ser
        35                  40                  45

Val Asp Ala Leu Leu Ile Asp Asp Ile Gln Phe Phe
    50                  55                  60

(2) INFORMATION FOR SEQ ID NO: 69:

(i) SEQUENCE CHARACTERISTICS:
            (A) LENGTH: 60 amino acids
            (B) TYPE: amino acid
            (C) STRANDEDNESS: not relevant
            (D) TOPOLOGY: not relevant (ii) MOLECULE TYPE: protein (ix) FEATURE:
            (A) NAME/KEY: Modified-site
            (B) LOCATION: 2
            (D) OTHER INFORMATION: /note= "The residue at this
                position is similar but not identical to leucine and/or
                methionine"

(ix) FEATURE:
            (A) NAME/KEY: Modified-site
            (B) LOCATION: 7
            (D) OTHER INFORMATION: /note= "The residue at this
                position is similar but not identical to asparagine
                and/or histidine"

(ix) FEATURE:
            (A) NAME/KEY: Modified-site
            (B) LOCATION: 9
            (D) OTHER INFORMATION: /note= "The residue at this
                position is similar but not identical to isoleucine

```
                and/or valine"
(ix) FEATURE:
    (A) NAME/KEY: Modified-site
    (B) LOCATION: 15
    (D) OTHER INFORMATION: /note= "The residue at this
        position is similar but not identical to asparagine,
        histidine and/or serine"

(ix) FEATURE:
    (A) NAME/KEY: Modified-site
    (B) LOCATION: 18
    (D) OTHER INFORMATION: /note= "The residue at this
        position is similar but not identical to valine and/or
        isoleucine"

(ix) FEATURE:
    (A) NAME/KEY: Modified-site
    (B) LOCATION: 21
    (D) OTHER INFORMATION: /note= "The residue at this
        position is similar but not identical to methionine,
        valine and/or leucine"

(ix) FEATURE:
    (A) NAME/KEY: Modified-site
    (B) LOCATION: 23
    (D) OTHER INFORMATION: /note= "The residue at this
        position is similar but not identical to serine and/or
        threonine"

(ix) FEATURE:
    (A) NAME/KEY: Modified-site
    (B) LOCATION: 29
    (D) OTHER INFORMATION: /note= "The residue at this
        position is similar but not identical to aspartic acid
        and/or glutamic acid"

(ix) FEATURE:
    (A) NAME/KEY: Modified-site
    (B) LOCATION: 30
    (D) OTHER INFORMATION: /note= "The residue at this
        position is similar but not identical to methionine,
        leucine and/or phenylalanine"

(ix) FEATURE:
    (A) NAME/KEY: Modified-site
    (B) LOCATION: 31
    (D) OTHER INFORMATION: /note= "The residue at this
        position is similar but not identical to valine and/or
        isoleucine"

(ix) FEATURE:
    (A) NAME/KEY: Modified-site
    (B) LOCATION: 34
    (D) OTHER INFORMATION: /note= "The residue at this
        position is similar but not identical to leucine and/or
        isoleucine"

(ix) FEATURE:
    (A) NAME/KEY: Modified-site
    (B) LOCATION: 35
    (D) OTHER INFORMATION: /note= "The residue at this
        position is similar but not identical to glutamine and/or
        arginine"

(ix) FEATURE:
    (A) NAME/KEY: Modified-site
    (B) LOCATION: 37
    (D) OTHER INFORMATION: /note= "The residue at this
        position is similar but not identical to asparagine
        and/or aspartic acid"

(ix) FEATURE:
    (A) NAME/KEY: Modified-site
    (B) LOCATION: 39
    (D) OTHER INFORMATION: /note= "The residue at this
        position is similar but not identical to isoleucine,
        methionine and/or alanine"
```

(ix) FEATURE:
    (A) NAME/KEY: Modified-site
    (B) LOCATION: 43
    (D) OTHER INFORMATION: /note= "The residue at this
        position is similar but not identical to lysine and/or
        arginine"

(ix) FEATURE:
    (A) NAME/KEY: Modified-site
    (B) LOCATION: 54
    (D) OTHER INFORMATION: /note= "The residue at this
        position is similar but not identical to isoleucine
        and/or valine"

(ix) FEATURE:
    (A) NAME/KEY: Modified-site
    (B) LOCATION: 57
    (D) OTHER INFORMATION: /note= "The residue at this
        position is similar but not identical to isoleucine
        and/or valine"

(xi) SEQUENCE DESCRIPTION: SEQ ID NO: 69:

```
Leu His Ala Val Gly Xaa Xaa Xaa Xaa Arg Xaa Pro Xaa Xaa
1               5                   10                  15

Lys Xaa Xaa Tyr Xaa Xaa Xaa Glu Xaa Phe Xaa Xaa Xaa Xaa Xaa Xaa
            20                  25                  30

Ala Xaa Xaa Xaa Xaa Xaa Xaa Xaa Glu Phe Xaa Xaa Xaa Tyr Arg Ser
        35                  40                  45

Val Asp Xaa Leu Leu Xaa Asp Asp Xaa Gln Phe Xaa
    50                  55                  60
```

(2) INFORMATION FOR SEQ ID NO: 70:

(i) SEQUENCE CHARACTERISTICS:
        (A) LENGTH: 60 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 70:

```
Leu Met His Ala Val Gly His Ser Val Ala Lys Arg Phe Pro His Leu
1               5                   10                  15

Lys Ile Glu Tyr Val Ser Thr Glu Thr Phe Thr Asn Glu Leu Ile Asn
            20                  25                  30

Ala Ile Arg Glu Asp Arg Met Thr Glu Phe Arg Glu Arg Tyr Arg Ser
        35                  40                  45

Val Asp Leu Leu Leu Val Asp Asp Val Gln Phe Ile
    50                  55                  60
```

(2) INFORMATION FOR SEQ ID NO: 71:

(i) SEQUENCE CHARACTERISTICS:
        (A) LENGTH: 60 amino acids
        (B) TYPE: amino acid
        (C) STRANDEDNESS: not relevant
        (D) TOPOLOGY: not relevant (ii) MOLECULE TYPE: protein (ix) FEATURE:
        (A) NAME/KEY: Modified-site
        (B) LOCATION: 5
        (D) OTHER INFORMATION: /note= "The residue at this
            position is similar but not identical to valine and/or
            isoleucine"

(ix) FEATURE:

```
          (A) NAME/KEY: Modified-site
          (B) LOCATION: 18
          (D) OTHER INFORMATION: /note= "The residue at this
              position is similar but not identical to valine and/or
              isoleucine"

(ix) FEATURE:
          (A) NAME/KEY: Modified-site
          (B) LOCATION: 21
          (D) OTHER INFORMATION: /note= "The residue at this
              position is similar but not identical to methionine,
              valine and/or leucine"

(ix) FEATURE:
          (A) NAME/KEY: Modified-site
          (B) LOCATION: 23
          (D) OTHER INFORMATION: /note= "The residue at this
              position is similar but not identical to serine and/or
              threonine"

(ix) FEATURE:
          (A) NAME/KEY: Modified-site
          (B) LOCATION: 33
          (D) OTHER INFORMATION: /note= "The residue at this
              position is similar but not identical to serine and/or
              alanine"

(ix) FEATURE:
          (A) NAME/KEY: Modified-site
          (B) LOCATION: 36
          (D) OTHER INFORMATION: /note= "The residue at this
              position is similar but not identical to aspartic acid,
              glutamic acid and/or asparagine"

(ix) FEATURE:
          (A) NAME/KEY: Modified-site
          (B) LOCATION: 27
          (D) OTHER INFORMATION: /note= "The residue at this
              position is similar but not identical to aspartic acid
              and/or asparagine"

(ix) FEATURE:
          (A) NAME/KEY: Modified-site
          (B) LOCATION: 38
          (D) OTHER INFORMATION: /note= "The residue at this
              position is similar but not identical to alanine,
              arginine and/or lysine"

(ix) FEATURE:
          (A) NAME/KEY: Modified-site
          (B) LOCATION: 41
          (D) OTHER INFORMATION: /note= "The residue at this
              position is similar but not identical to aspartic acid
              and/or glutamic acid"

(ix) FEATURE:
          (A) NAME/KEY: Modified-site
          (B) LOCATION: 48
          (D) OTHER INFORMATION: /note= "The residue at this
              position is similar but not identical to asparagine
              and/or serine"

(ix) FEATURE:
          (A) NAME/KEY: Modified-site
          (B) LOCATION: 51
          (D) OTHER INFORMATION: /note= "The residue at this
              position is similar but not identical to valine, leucine
              and/or alanine"

(ix) FEATURE:
          (A) NAME/KEY: Modified-site
          (B) LOCATION: 54
          (D) OTHER INFORMATION: /note= "The residue at this
              position is similar but not identical to valine and/or
              isoleucine"

(ix) FEATURE:
          (A) NAME/KEY: Modified-site
          (B) LOCATION: 57
```

(D) OTHER INFORMATION: /note= "The residue at this
                position is similar but not identical to valine and/or
                isoleucine"

(ix) FEATURE:
         (A) NAME/KEY: Modified-site
         (B) LOCATION: 60
         (D) OTHER INFORMATION: /note= "The residue at this
             position is similar but not identical to phenyalanine,
             isoleucine and/or leucine"

(xi) SEQUENCE DESCRIPTION: SEQ ID NO: 71:

Leu Met His Ala Xaa Gly His Xaa Val Xaa Xaa Xaa Xaa Pro Xaa Xaa
1               5                   10                  15

Lys Xaa Xaa Tyr Xaa Ser Xaa Glu Xaa Phe Thr Asn Glu Xaa Ile Asn
            20                  25                  30

Xaa Ile Arg Xaa Xaa Xaa Xaa Xaa Xaa Phe Arg Xaa Arg Tyr Arg Xaa
        35                  40                  45

Val Asp Xaa Leu Leu Xaa Asp Asp Xaa Gln Phe Xaa
50                  55                  60

(2) INFORMATION FOR SEQ ID NO: 72:

(i) SEQUENCE CHARACTERISTICS:
        (A) LENGTH: 60 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 72:

Leu Met His Ala Ile Gly His Tyr Val Ile Asp His Asn Pro Ser Ala
1               5                   10                  15

Lys Val Val Tyr Leu Ser Ser Glu Lys Phe Thr Asn Glu Phe Ile Asn
            20                  25                  30

Ser Ile Arg Asp Asn Lys Ala Val Asp Phe Arg Asn Arg Tyr Arg Asn
        35                  40                  45

Val Asp Val Leu Leu Ile Asp Asp Ile Gln Phe Leu
50                  55                  60

(2) INFORMATION FOR SEQ ID NO: 73:

(i) SEQUENCE CHARACTERISTICS:
        (A) LENGTH: 8 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 73:

Ala Gly Lys Glu Arg Thr Gln Glu
1               5

(2) INFORMATION FOR SEQ ID NO: 74:

(i) SEQUENCE CHARACTERISTICS:
        (A) LENGTH: 8 amino acids
        (B) TYPE: amino acid
        (C) STRANDEDNESS: not relevant
        (D) TOPOLOGY: not relevant (ii) MOLECULE TYPE: protein (ix) FEATURE:
         (A) NAME/KEY: Modified-site (B) LOCATION: 6
            (D) OTHER INFORMATION: /note= "The residue at this
                position is similar but not identical to threo..."

(ix) FEATURE:
            (A) NAME/KEY: Modified-site
            (B) LOCATION: 6
            (D) OTHER INFORMATION: /note= "The residue at this
                position is similar but not identical to threo..."

(xi) SEQUENCE DESCRIPTION: SEQ ID NO: 74:

Ala Xaa Lys Glu Arg Xaa Gln Glu
1               5

(2) INFORMATION FOR SEQ ID NO: 75:

(i) SEQUENCE CHARACTERISTICS:
        (A) LENGTH: 8 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 75:

Ala Gly Lys Glu Arg Thr Gln Glu
1               5

(2) INFORMATION FOR SEQ ID NO: 76:

(i) SEQUENCE CHARACTERISTICS:
        (A) LENGTH: 8 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 76:

Ala Gly Lys Glu Gln Thr Gln Glu
1               5

(2) INFORMATION FOR SEQ ID NO: 77:

(i) SEQUENCE CHARACTERISTICS:
        (A) LENGTH: 263 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 77:

TCGAAGGCCG CGTTGTGGGC CACCAGCACC GTGTCCTGGA CGAAGGCGCG GAAGGCGGGG      60

AGGACCGCCT CTAGGGGAGG CTTGTCCCGG ANCATCTCCG CCGTGAGGCC GTGGACCGCC     120

GTGGCCGCGG GGGANATGGG GCGCCCCGGG TTCACCAGGG CCTCGAACAC CTCCTGCCGC     180

AAGACCCTTC GACCCAGGAT ATGGACCCCG GCGAGGGCCA CCACGGCATC TTGCTCCGGG     240

TCCAGGCCCG TGGTCTCAGT GTC                                             263

(2) INFORMATION FOR SEQ ID NO: 78:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: other nucleic acid
              (A) DESCRIPTION: /desc = "DNA"

(xi) SEQUENCE DESCRIPTION: SEQ ID NO: 78:

TCGAAGGCCG CGTTGTG                                                              17

(2) INFORMATION FOR SEQ ID NO: 79:

(i) SEQUENCE CHARACTERISTICS:
              (A) LENGTH: 17 base pairs
              (B) TYPE: nucleic acid
              (C) STRANDEDNESS: double
              (D) TOPOLOGY: linear (ii) MOLECULE TYPE: other nucleic acid
              (A) DESCRIPTION: /desc = "DNA"

(xi) SEQUENCE DESCRIPTION: SEQ ID NO: 79:

CCCGTGGTCT CAGTGTC                                                              17

(2) INFORMATION FOR SEQ ID NO: 80:

(i) SEQUENCE CHARACTERISTICS:
              (A) LENGTH: 49 amino acids
              (B) TYPE: amino acid
              (C) STRANDEDNESS: not relevant
              (D) TOPOLOGY: not relevant (ii) MOLECULE TYPE: protein (xi) SEQUENCE DESCRIPTION: SEQ ID NO: 80:

Phe His Val Tyr Leu Lys Pro Asp Arg Leu Val Asp Pro Glu Ala Phe
 1               5                  10                  15

Gly Val His Gly Ile Ala Asp Glu Phe Leu Leu Asp Lys Pro Thr Phe
                20                  25                  30

Ala Glu Val Ala Asp Glu Phe Met Asp Tyr Ile Arg Gly Ala Glu Leu
            35                  40                  45

Val (2) INFORMATION FOR SEQ ID NO: 81:

(i) SEQUENCE CHARACTERISTICS:
              (A) LENGTH: 48 amino acids
              (B) TYPE: amino acid
              (C) STRANDEDNESS: not relevant
              (D) TOPOLOGY: not relevant (ii) MOLECULE TYPE: protein (ix) FEATURE:
              (A) NAME/KEY: Modified-site
              (B) LOCATION: 5
              (D) OTHER INFORMATION: /note= "The residue at this
                  position is similar but not identical to leucine, valine
                  and/or alanine"

(ix) FEATURE:
              (A) NAME/KEY: Modified-site
              (B) LOCATION: 21
              (D) OTHER INFORMATION: /note= "The residue at this
                  position is similar but not identical to isoleucine
                  and/or leucine"

(ix) FEATURE:
              (A) NAME/KEY: Modified-site
              (B) LOCATION: 42
              (D) OTHER INFORMATION: /note= "The residue at this
                  position is similar but not identical to tyrosine,
                  phenylalanine and/or tyrptophan"

```
    (ix) FEATURE:
        (A) NAME/KEY: Modified-site
        (B) LOCATION: 43
        (D) OTHER INFORMATION: /note= "The residue at this
            position is similar but not identical to isoleucine
            and/or valine"

(ix) FEATURE:
        (A) NAME/KEY: Modified-site
        (B) LOCATION: 44
        (D) OTHER INFORMATION: /note= "The residue at this
            position is similar but not identical to arginine,
            glutamine and/or glycine"

(xi) SEQUENCE DESCRIPTION: SEQ ID NO: 81:

Phe Xaa Xaa Xaa Xaa Xaa Pro Xaa Arg Xaa Xaa Xaa Pro Xaa Ala Xaa
1               5                   10                  15

Xaa Val His Gly Xaa Xaa Xaa Glu Xaa Xaa Xaa Asp Lys Pro Xaa Xaa
            20                  25                  30

Xaa Xaa Val Xaa Xaa Xaa Phe Xaa Xaa Xaa Xaa Xaa Xaa Xaa Leu Val
        35                  40                  45

(2) INFORMATION FOR SEQ ID NO: 82:

(i) SEQUENCE CHARACTERISTICS:
        (A) LENGTH: 50 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 82:

Phe Glu Ala Leu Val Asn Pro Gly Arg Pro Xaa Ser Pro Ala Ala Thr
1               5                   10                  15

Ala Val His Gly Leu Thr Ala Glu Met Xaa Arg Asp Lys Pro Pro Leu
            20                  25                  30

Glu Ala Val Leu Pro Ala Phe Arg Ala Phe Val Gln Asp Thr Val Leu
        35                  40                  45

Val Ala
    50

(2) INFORMATION FOR SEQ ID NO: 83:

(i) SEQUENCE CHARACTERISTICS:
        (A) LENGTH: 50 amino acids
        (B) TYPE: amino acid
        (C) STRANDEDNESS: not relevant
        (D) TOPOLOGY: not relevant (ii) MOLECULE TYPE: protein (ix) FEATURE:
        (A) NAME/KEY: Modified-site
        (B) LOCATION: 9
        (D) OTHER INFORMATION: /note= "The residue at this
            position is similar but not identical to valine and/or
            leucine"

(ix) FEATURE:
        (A) NAME/KEY: Modified-site
        (B) LOCATION: 21
        (D) OTHER INFORMATION: /note= "The residue at this
            position is similar but not identical to isoleucine
            and/or leucine"

(ix) FEATURE:
        (A) NAME/KEY: Modified-site
        (B) LOCATION: 24
```

```
              (D) OTHER INFORMATION: /note= "The residue at this
                  position is similar but not identical to glutamic acid
                  and/or aspartic acid"

(ix) FEATURE:
              (A) NAME/KEY: Modified-site
              (B) LOCATION: 27
              (D) OTHER INFORMATION: /note= "The residue at this
                  position is similar but not identical to leucine,
                  arginine and/or glutamine"

(ix) FEATURE:
              (A) NAME/KEY: Modified-site
              (B) LOCATION: 32
              (D) OTHER INFORMATION: /note= "The residue at this
                  position is similar but not identical to phenylalanine,
                  leucine and/or valine"

(ix) FEATURE:
              (A) NAME/KEY: Modified-site
              (B) LOCATION: 36
              (D) OTHER INFORMATION: /note= "The residue at this
                  position is similar but not identical to alanine, leucine
                  and/or isoleucine"

(ix) FEATURE:
              (A) NAME/KEY: Modified-site
              (B) LOCATION: 42
              (D) OTHER INFORMATION: /note= "The residue at this
                  position is similar but not identical to tyrosine,
                  phenylalanine and/or tryptophan"

(ix) FEATURE:
              (A) NAME/KEY: Modified-site
              (B) LOCATION: 43
              (D) OTHER INFORMATION: /note= "The residue at this
                  position is similar but not identical to isoleucine
                  and/or valine"

(ix) FEATURE:
              (A) NAME/KEY: Modified-site
              (B) LOCATION: 47
              (D) OTHER INFORMATION: /note= "The residue at this
                  position is similar but not identical to glutamic acid,
                  valine and/or isoleucine"

(xi) SEQUENCE DESCRIPTION: SEQ ID NO: 83:

Phe Glu Ala Xaa Xaa Asn Pro Xaa Arg Pro Xaa Ser Xaa Xaa Xaa Xaa
1               5                   10                  15

Xaa Xaa Xaa Gly Xaa Thr Xaa Xaa Met Xaa Xaa Asp Xaa Pro Xaa Xaa
            20                  25                  30

Xaa Xaa Val Xaa Xaa Xaa Phe Arg Xaa Xaa Xaa Xaa Asp Xaa Xaa Leu
        35                  40                  45

Val Ala
    50

(2) INFORMATION FOR SEQ ID NO: 84:

(i) SEQUENCE CHARACTERISTICS:
              (A) LENGTH: 50 amino acids
              (B) TYPE: amino acid
              (C) STRANDEDNESS: not relevant
              (D) TOPOLOGY: not relevant (ii) MOLECULE TYPE: protein (xi) SEQUENCE DESCRIPTION: SEQ ID NO: 84:

Phe Glu Ala Phe Ala Asn Pro His Arg Pro Leu Ser Ala Thr Ile Ile
1               5                   10                  15

Glu Leu Thr Gly Ile Thr Asp Asp Met Leu Gln Asp Ala Pro Asp Val
            20                  25                  30
```

```
Val Asp Val Ile Arg Asp Phe Arg Glu Trp Ile Gly Asp Asp Ile Leu
         35                  40                  45

Val Ala
     50

(2) INFORMATION FOR SEQ ID NO: 85:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 85:

TGACCCACAA CCTCTTGAAA                                                   20

(2) INFORMATION FOR SEQ ID NO: 86:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 86:

TTYTCRTARA ANCCYTC                                                      17

(2) INFORMATION FOR SEQ ID NO: 87:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 87:

CAYYTNCAYC ARCAYACNCA                                                   20

(2) INFORMATION FOR SEQ ID NO: 88:

(i) SEQUENCE CHARACTERISTICS:
        (A) LENGTH: 23 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 88:

Ala Arg Leu Leu Pro Leu Ala Gln Ala His Phe Gly Val Glu Glu Val
  1               5                  10                  15

Val Leu Val Leu Glu Gly Glu
                 20

(2) INFORMATION FOR SEQ ID NO: 89:

(i) SEQUENCE CHARACTERISTICS:
        (A) LENGTH: 7 amino acids
        (B) TYPE: amino acid
```

(C) STRANDEDNESS: not relevant
        (D) TOPOLOGY: not relevant (ii) MOLECULE TYPE: protein (xi) SEQUENCE DESCRIPTION: SEQ ID NO: 89:

Phe Gln Glu Val Val Gly Gln
1               5

(2) INFORMATION FOR SEQ ID NO: 90:

(i) SEQUENCE CHARACTERISTICS:
        (A) LENGTH: 6 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 90:

Lys Thr Leu Glu Glu Pro
1               5

(2) INFORMATION FOR SEQ ID NO: 91:

(i) SEQUENCE CHARACTERISTICS:
        (A) LENGTH: 20 base pairs
        (B) TYPE: nucleic acid
        (C) STRANDEDNESS: not relevant
        (D) TOPOLOGY: not relevant (ii) MOLECULE TYPE: protein (xi) SEQUENCE DESCRIPTION: SEQ ID NO: 91:

TTYCARGARG TNGTNGGSCA                                              20

(2) INFORMATION FOR SEQ ID NO: 92:

(i) SEQUENCE CHARACTERISTICS:
        (A) LENGTH: 16 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 92:

Lys Val Tyr Leu Ile Asp Glu Val His Met Leu Ser Arg His Ser Phe
1               5                   10                  15

(2) INFORMATION FOR SEQ ID NO: 93:

(i) SEQUENCE CHARACTERISTICS:
        (A) LENGTH: 16 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 93:

Lys Val Tyr Leu Ile Asp Glu Val His Met Leu Ser Ile Gly Ala Phe
1               5                   10                  15

(2) INFORMATION FOR SEQ ID NO: 94:

(i) SEQUENCE CHARACTERISTICS:
        (A) LENGTH: 16 amino acids
        (B) TYPE: amino acid (C) STRANDEDNESS: not relevant
            (D) TOPOLOGY: not relevant (ii) MOLECULE TYPE: protein (xi) SEQUENCE DESCRIPTION: SEQ ID NO: 94:

Lys Val Tyr Leu Ile Asp Glu Val His Met Leu Ser Arg His Ser Phe
1               5                   10                  15

(2) INFORMATION FOR SEQ ID NO: 95:

(i) SEQUENCE CHARACTERISTICS:
            (A) LENGTH: 16 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 95:

Lys Ile Ile Ile Leu Asp Glu Ala Asp Ser Met Thr Asp Gly Ala Gln
1               5                   10                  15

(2) INFORMATION FOR SEQ ID NO: 96:

(i) SEQUENCE CHARACTERISTICS:
            (A) LENGTH: 6 amino acids
            (B) TYPE: amino acid
            (C) STRANDEDNESS: not relevant
            (D) TOPOLOGY: not relevant (ii) MOLECULE TYPE: protein (ix) FEATURE:
            (A) NAME/KEY: Modified-site
            (B) LOCATION: 3
            (D) OTHER INFORMATION: /note= "The residue at this
                position can be either Ala or Val"

(xi) SEQUENCE DESCRIPTION: SEQ ID NO: 96:

Asp Glu Ala His Met Leu
1               5

(2) INFORMATION FOR SEQ ID NO: 97:

(i) SEQUENCE CHARACTERISTICS:
            (A) LENGTH: 17 base pairs
            (B) TYPE: nucleic acid
            (C) STRANDEDNESS: not relevant
            (D) TOPOLOGY: not relevant (ii) MOLECULE TYPE: protein (xi) SEQUENCE DESCRIPTION: SEQ ID NO: 97:

ARCATRTGNR CYTCRTC                                                        17

(2) INFORMATION FOR SEQ ID NO: 98:

(i) SEQUENCE CHARACTERISTICS:
            (A) LENGTH: 16 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 98:

Ser Phe Asn Ala Leu Leu Lys Thr Leu Glu Glu Pro Pro Glu His Val
1               5                   10                  15

(2) INFORMATION FOR SEQ ID NO: 99:

(i) SEQUENCE CHARACTERISTICS:
        (A) LENGTH: 16 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 99:

```
Ala Phe Asn Ala Leu Leu Lys Thr Leu Glu Glu Pro Pro Glu His Cys
1               5                   10                  15
```

(2) INFORMATION FOR SEQ ID NO: 100:

(i) SEQUENCE CHARACTERISTICS:
        (A) LENGTH: 16 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 100:

```
Ala Phe Asn Ala Leu Leu Lys Thr Leu Glu Glu Pro Pro Glu Tyr Val
1               5                   10                  15
```

(2) INFORMATION FOR SEQ ID NO: 101:

(i) SEQUENCE CHARACTERISTICS:
        (A) LENGTH: 6 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 101:

```
Lys Thr Leu Glu Glu Pro
1               5
```

(2) INFORMATION FOR SEQ ID NO: 102:

(i) SEQUENCE CHARACTERISTICS:
        (A) LENGTH: 19 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 102:

```
Ser Ala Leu Tyr Arg Arg Phe Arg Pro Leu Thr Phe Gln Glu Val Val
1               5                   10                  15
Gly Gln Glu
```

(2) INFORMATION FOR SEQ ID NO: 103:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 103:

```
GGCCGCAATT GCACGCGTTC GAATTCCATG ACGTCTTCCA GTGCACTGGT TAATTA         56
```

(2) INFORMATION FOR SEQ ID NO: 104:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 104:

```
CTAGTTAATT AACCAGTGCA CTGGAAGACG TCATGGAATT CGAACGCGTG CAATTG         56
```

(2) INFORMATION FOR SEQ ID NO: 105:

(i) SEQUENCE CHARACTERISTICS:
        (A) LENGTH: 7 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 105:

```
Gly Val Gly Lys Thr Thr Thr
1               5
```

(2) INFORMATION FOR SEQ ID NO: 106:

(i) SEQUENCE CHARACTERISTICS:
        (A) LENGTH: 6 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 106:

```
Glu Ile Asp Ala Ala Ser
1               5
```

(2) INFORMATION FOR SEQ ID NO: 107:

(i) SEQUENCE CHARACTERISTICS:
        (A) LENGTH: 11 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 107:

```
Phe Asn Ala Leu Leu Lys Thr Leu Glu Glu Pro
1               5                   10
```

(2) INFORMATION FOR SEQ ID NO: 108:

(i) SEQUENCE CHARACTERISTICS:
        (A) LENGTH: 23 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 108:

```
Ala Arg Leu Leu Pro Leu Ala Gln Ala His Phe Gly Val Glu Glu Val
1               5                   10                  15

Val Leu Val Leu Glu Gly Glu
                20
```

(2) INFORMATION FOR SEQ ID NO: 109:

(i) SEQUENCE CHARACTERISTICS:
        (A) LENGTH: 13 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 109:

```
Arg Lys Leu Arg Phe Ala His Leu His Gln His Thr Gln
1               5                   10
```

(2) INFORMATION FOR SEQ ID NO: 110:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 110:

CAYYTNCAYC ARCAYACNCA                                            20

(2) INFORMATION FOR SEQ ID NO: 111:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 111:

GARGGNTTYT AYGARAA                                              17

(2) INFORMATION FOR SEQ ID NO: 112:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 112:

TTYTCRTARA ANCCYTC                                              17

(2) INFORMATION FOR SEQ ID NO: 113:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
    (A) DESCRIPTION: /desc = "DNA"

(xi) SEQUENCE DESCRIPTION: SEQ ID NO: 113:

TAYCARGARC ARCARATGCA                                      20

(2) INFORMATION FOR SEQ ID NO: 114:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 114:

TGCATYTGYT CYTGRTA                                         17

(2) INFORMATION FOR SEQ ID NO: 115:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 115:

TGRAARTANC CNCCRTC                                         17

(2) INFORMATION FOR SEQ ID NO: 116:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 116:

CCGCGCTTAA TTAACCCAGT TCTCCCTCCT GGACG                      35

(2) INFORMATION FOR SEQ ID NO: 117:

(i) SEQUENCE CHARACTERISTICS:
        (A) LENGTH: 4 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 117:

Pro Asp Xaa Asp
1

(2) INFORMATION FOR SEQ ID NO: 118:

(i) SEQUENCE CHARACTERISTICS:
        (A) LENGTH: 6 amino acids
        (B) TYPE: amino acid
        (C) STRANDEDNESS: not relevant (D) TOPOLOGY: not relevant (ii) MOLECULE TYPE: protein (xi) SEQUENCE DESCRIPTION: SEQ ID NO: 118:

Gly Leu Gly Lys Thr His
1               5

(2) INFORMATION FOR SEQ ID NO: 119:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 119:

Pro Leu Phe Leu Tyr Gly Gly Thr Gly Leu Gly Lys Thr His Leu Leu
1               5                   10                  15

His Ala Val Gly
            20

(2) INFORMATION FOR SEQ ID NO: 120:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 120:

Pro Leu Phe Ile Tyr Gly Gly Val Gly Leu Gly Lys Thr His Leu Leu
1               5                   10                  15

Gln Ser Ile Gly
            20

(2) INFORMATION FOR SEQ ID NO: 121:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 121:

Pro Cys Leu Ile Tyr Gly Gly Val Gly Leu Gly Lys Thr His Leu Leu
1               5                   10                  15

Gln Ser Ile Gly
            20

(2) INFORMATION FOR SEQ ID NO: 122:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 122:

```
Pro Leu Phe Ile Tyr Gly Gly Val Gly Leu Gly Lys Thr His Leu Met
1               5                   10                  15

His Ala Ile Gly
            20

(2) INFORMATION FOR SEQ ID NO: 123:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 123:

Pro Leu Phe Leu Tyr Gly Gly Thr Gly Leu Gly Lys Thr His Leu Leu
1               5                   10                  15

His Ala Val Gly
            20

(2) INFORMATION FOR SEQ ID NO: 124:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 124:

Pro Leu Phe Leu Tyr Gly Gly Thr Gly Leu Gly Lys Thr His Leu Leu
1               5                   10                  15

His Ala Val Gly
            20

(2) INFORMATION FOR SEQ ID NO: 125:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 125:

Pro Leu Phe Leu Tyr Gly Gly Thr Gly Leu Gly Lys Thr His Leu Leu
1               5                   10                  15

His Ala Val Gly
            20

(2) INFORMATION FOR SEQ ID NO: 126:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 126:

Pro Leu Phe Leu Tyr Gly Gly Val Gly Leu Gly Lys Thr His Leu Met
1               5                   10                  15
```

```
His Ala Val Gly
        20

(2) INFORMATION FOR SEQ ID NO: 127:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 127:

Pro Leu Phe Leu Tyr Gly Gly Thr Gly Leu Gly Lys Thr His Leu Leu
1               5                   10                  15

His Ala Ile Gly
        20

(2) INFORMATION FOR SEQ ID NO: 128:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 128:

Pro Leu Phe Ile Tyr Gly Glu Ser Gly Leu Gly Lys Thr His Leu Leu
1               5                   10                  15

His Ala Ile Gly
        20

(2) INFORMATION FOR SEQ ID NO: 129:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 129:

Pro Leu Phe Ile Tyr Gly Glu Ser Gly Leu Gly Lys Thr His Leu Leu
1               5                   10                  15

His Ala Ile Gly
        20

(2) INFORMATION FOR SEQ ID NO: 130:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 130:

Pro Phe Phe Leu Tyr Gly Gly Thr Gly Leu Gly Lys Thr His Leu Leu
1               5                   10                  15

His Ala Ile Gly
        20
```

(2) INFORMATION FOR SEQ ID NO: 131:

(i) SEQUENCE CHARACTERISTICS:
        (A) LENGTH: 19 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 131:

```
Pro Leu Phe Ile His Ser Ser Val Gly Leu Gly Lys Thr His Leu Leu
1               5                  10                 15

Gln Ala Ile
```

(2) INFORMATION FOR SEQ ID NO: 132:

(i) SEQUENCE CHARACTERISTICS:
        (A) LENGTH: 19 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 132:

```
Pro Leu Phe Ile Tyr Gly Asp Ser Gly Leu Gly Lys Thr His Leu Leu
1               5                  10                 15

His Ala Ile
```

(2) INFORMATION FOR SEQ ID NO: 133:

(i) SEQUENCE CHARACTERISTICS:
        (A) LENGTH: 6 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 133:

```
Gly Leu Gly Lys Thr His
1               5
```

(2) INFORMATION FOR SEQ ID NO: 134:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 134:

GGNYTNGGNA ARACSCAT                                      18

(2) INFORMATION FOR SEQ ID NO: 135:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 135:

GGNYTNGGNA ARACSCAC                                               18

(2) INFORMATION FOR SEQ ID NO: 136:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 136:

GGNYTNGGNA ARACWCAT                                               18

(2) INFORMATION FOR SEQ ID NO: 137:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 137:

GGNYTNGGNA ARACWCAC                                               18

(2) INFORMATION FOR SEQ ID NO: 138:

(i) SEQUENCE CHARACTERISTICS:
        (A) LENGTH: 7 amino acids
        (B) TYPE: amino acid
        (C) STRANDEDNESS: not relevant
        (D) TOPOLOGY: not relevant (ii) MOLECULE TYPE: protein (ix) FEATURE:
        (A) NAME/KEY: Modified-site
        (B) LOCATION: 2
        (D) OTHER INFORMATION: /note= "The residue at this
            position can be either Leu or Phe"

(xi) SEQUENCE DESCRIPTION: SEQ ID NO: 138:

Glu Leu Phe His Thr Phe Asn
1               5

(2) INFORMATION FOR SEQ ID NO: 139:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 139:

Gln Glu Glu Phe Phe His Thr Phe Asn Ala Leu Leu Glu Gly Asn Gln
1               5                   10                  15

Gln Ile Ile Leu
            20

(2) INFORMATION FOR SEQ ID NO: 140:

(i) SEQUENCE CHARACTERISTICS:
        (A) LENGTH: 23 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 140:

```
Thr Gly Val Gln Thr Glu Leu Phe His Thr Phe Asn Glu Leu His Asp
1               5                   10                  15

Ser Gly Lys Gln Ile Val Ile
            20
```

(2) INFORMATION FOR SEQ ID NO: 141:

(i) SEQUENCE CHARACTERISTICS:
        (A) LENGTH: 22 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 141:

```
Gly Ile Gln Glu Glu Phe Phe His Thr Phe Asn Thr Leu His Asn Ala
1               5                   10                  15

Asn Lys Gln Ile Val Ile
            20
```

(2) INFORMATION FOR SEQ ID NO: 142:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 142:

```
Gln Thr Glu Phe Phe His Thr Phe Asn Thr Leu His Glu Glu Ser Lys
1               5                   10                  15

Gln Ile Val Ile
        20
```

(2) INFORMATION FOR SEQ ID NO: 143:

(i) SEQUENCE CHARACTERISTICS:
        (A) LENGTH: 21 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 143:

```
Gly Ile Gln Glu Glu Leu Phe His Thr Phe Asn Ala Leu Tyr Glu Asp
1               5                   10                  15

Asn Lys Gln Leu Val
            20
```

(2) INFORMATION FOR SEQ ID NO: 144:

(i) SEQUENCE CHARACTERISTICS:

(A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 144:

Gln Glu Glu Phe Phe His Thr Phe Asn Thr Leu His Asn Ala Asn Lys
1               5                   10                  15

Gln Ile Val Leu
        20

(2) INFORMATION FOR SEQ ID NO: 145:

(i) SEQUENCE CHARACTERISTICS:
        (A) LENGTH: 18 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 145:

Glu Phe Phe His Thr Phe Asn Thr Leu Tyr Asn Asn Asn Lys Gln Val
1               5                   10                  15

Val Ile (2) INFORMATION FOR SEQ ID NO: 146:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 146:

Gln Glu Glu Phe Phe His Ile Phe Asn Ser Leu Phe Glu Thr Gly Arg
1               5                   10                  15

Gln Ile Ile Leu
        20

(2) INFORMATION FOR SEQ ID NO: 147:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 147:

Gln Glu Glu Phe Phe His Thr Phe Asn Ala Leu Leu Glu Gly Gly Gln
1               5                   10                  15

Gln Val Ile Leu
        20

(2) INFORMATION FOR SEQ ID NO: 148:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 148:

Gln Glu Glu Phe Phe His Thr Phe Asn Ala Leu Leu Glu Gly Asn Gln
1               5                  10                  15

Gln Ile Ile Leu
            20

(2) INFORMATION FOR SEQ ID NO: 149:

(i) SEQUENCE CHARACTERISTICS:
            (A) LENGTH: 20 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 149:

Gln Glu Glu Phe Phe His Thr Phe Asn Ala Leu Leu Glu Gly Asn Gln
1               5                  10                  15

Gln Ile Ile Leu
            20

(2) INFORMATION FOR SEQ ID NO: 150:

(i) SEQUENCE CHARACTERISTICS:
            (A) LENGTH: 20 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 150:

Gln Glu Glu Phe Phe His Thr Phe Asn Ala Leu Leu Glu Gly Asn Gln
1               5                  10                  15

Gln Ile Ile Leu
            20

(2) INFORMATION FOR SEQ ID NO: 151:

(i) SEQUENCE CHARACTERISTICS:
            (A) LENGTH: 20 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 151:

Gln Glu Glu Phe Phe His Thr Phe Asn Ala Leu Leu Glu Gly Asn Gln
1               5                  10                  15

Gln Ile Ile Leu
            20

(2) INFORMATION FOR SEQ ID NO: 152:

(i) SEQUENCE CHARACTERISTICS:
            (A) LENGTH: 18 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 152:

Glu Phe Phe Lys Thr Phe Asn Ala Leu Ile Asp Gln Asn Lys Gln Leu
1               5                   10                  15

Val Ile (2) INFORMATION FOR SEQ ID NO: 153:

(i) SEQUENCE CHARACTERISTICS:
        (A) LENGTH: 21 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 153:

Ile Gln His Glu Phe Cys His Leu Leu Asn Met Leu Leu Asp Ser Ala
1               5                   10                  15

Lys Gln Val Val Val
            20

(2) INFORMATION FOR SEQ ID NO: 154:

(i) SEQUENCE CHARACTERISTICS:
        (A) LENGTH: 16 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 154:

Phe His Ile Phe Asn Ser Tyr Ile Glu Lys Asn Lys Gln Ile Val Ile
1               5                   10                  15

(2) INFORMATION FOR SEQ ID NO: 155:

(i) SEQUENCE CHARACTERISTICS:
        (A) LENGTH: 8 amino acids
        (B) TYPE: amino acid
        (C) STRANDEDNESS: not relevant
        (D) TOPOLOGY: not relevant (ii) MOLECULE TYPE: protein (ix) FEATURE:
        (A) NAME/KEY: Modified-site
        (B) LOCATION: 2
        (D) OTHER INFORMATION: /note= "The residue at this
            position could be either Leu or Phe"

(xi) SEQUENCE DESCRIPTION: SEQ ID NO: 155:

Glu Leu Phe Phe His Thr Phe Asn
1               5

(2) INFORMATION FOR SEQ ID NO: 156:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 156:

TTRAANGTRT GRAANAAYTC                                         20

(2) INFORMATION FOR SEQ ID NO: 157:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 157:

TTRAANGTRT GRAANAGYTC                                            20

(2) INFORMATION FOR SEQ ID NO: 158:

(i) SEQUENCE CHARACTERISTICS:
        (A) LENGTH: 13 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 158:

Ile Val Leu Asp Thr Glu Thr Thr Gly Met Asn Gln Ile
1               5                   10

(2) INFORMATION FOR SEQ ID NO: 159:

(i) SEQUENCE CHARACTERISTICS:
        (A) LENGTH: 13 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 159:

Leu Val Ile His Asn Ala Ala Phe Asp Ile Gly Phe Met
1               5                   10

(2) INFORMATION FOR SEQ ID NO: 160:

(i) SEQUENCE CHARACTERISTICS:
        (A) LENGTH: 13 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 160:

Ile Val Leu Asp Thr Glu Thr Thr Gly Met Asn Gln Ile
1               5                   10

(2) INFORMATION FOR SEQ ID NO: 161:

(i) SEQUENCE CHARACTERISTICS:
        (A) LENGTH: 13 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 161:

Leu Val Ile His Asn Ala Pro Phe Asp Ile Gly Phe Met 1            5                   10

(2) INFORMATION FOR SEQ ID NO: 162:

(i) SEQUENCE CHARACTERISTICS:
        (A) LENGTH: 13 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 162:

Ile Val Leu Asp Thr Glu Thr Thr Gly Met Asn Ser Val
1               5                   10

(2) INFORMATION FOR SEQ ID NO: 163:

(i) SEQUENCE CHARACTERISTICS:
        (A) LENGTH: 13 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 163:

Leu Val Ile His Asn Ala Ser Phe Asp Val Gly Phe Ile
1               5                   10

(2) INFORMATION FOR SEQ ID NO: 164:

(i) SEQUENCE CHARACTERISTICS:
        (A) LENGTH: 13 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 164:

Val Val Phe Asp Val Glu Thr Thr Gly Leu Ser Ala Val
1               5                   10

(2) INFORMATION FOR SEQ ID NO: 165:

(i) SEQUENCE CHARACTERISTICS:
        (A) LENGTH: 11 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 165:

Leu Val Ile His Asn Ala Ala Phe Asp Met Gly
1               5                   10

(2) INFORMATION FOR SEQ ID NO: 166:

(i) SEQUENCE CHARACTERISTICS:
        (A) LENGTH: 13 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 166:

```
Val Ile Phe Asp Ile Glu Thr Thr Gly Leu His Gly Arg
1               5                   10
```

(2) INFORMATION FOR SEQ ID NO: 167:

(i) SEQUENCE CHARACTERISTICS:
        (A) LENGTH: 14 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 167:

```
Met Val Ala His Asn Gly Ile Asn Phe Asp Leu Pro Phe Leu
1               5                   10
```

(2) INFORMATION FOR SEQ ID NO: 168:

(i) SEQUENCE CHARACTERISTICS:
        (A) LENGTH: 13 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 168:

```
Val Val Tyr Asp Ile Glu Thr Thr Gly Leu Ser Pro Met
1               5                   10
```

(2) INFORMATION FOR SEQ ID NO: 169:

(i) SEQUENCE CHARACTERISTICS:
        (A) LENGTH: 13 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 169:

```
Met Val Ala His Asn Ala Ala Phe Asp His Asn Phe Leu
1               5                   10
```

(2) INFORMATION FOR SEQ ID NO: 170:

(i) SEQUENCE CHARACTERISTICS:
        (A) LENGTH: 13 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 170:

```
Val Val Phe Asp Val Glu Thr Thr Gly Leu Ser Asn Gln
1               5                   10
```

(2) INFORMATION FOR SEQ ID NO: 171:

(i) SEQUENCE CHARACTERISTICS:
        (A) LENGTH: 13 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 171:

```
Phe Val Ala His Asn Ala Ser Phe Asp Met Gly Phe Ile
1               5                   10
```

(2) INFORMATION FOR SEQ ID NO: 172:

(i) SEQUENCE CHARACTERISTICS:
        (A) LENGTH: 6 amino acids
        (B) TYPE: amino acid
        (C) STRANDEDNESS: not relevant
        (D) TOPOLOGY: not relevant (ii) MOLECULE TYPE: protein (ix) FEATURE:
        (A) NAME/KEY: Modified-site
        (B) LOCATION: 2
        (D) OTHER INFORMATION: /note= "The residue in this
            position could be either Thr, Ile or Val"

(xi) SEQUENCE DESCRIPTION: SEQ ID NO: 172:

```
Asp Thr Glu Thr Thr Gly
1               5
```

(2) INFORMATION FOR SEQ ID NO: 173:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 173:

```
GAYACNGARA CNACNGG                                                17
```

(2) INFORMATION FOR SEQ ID NO: 174:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 174:

```
GAYRTNGARA CNACNGG                                                17
```

(2) INFORMATION FOR SEQ ID NO: 175:

(i) SEQUENCE CHARACTERISTICS:
        (A) LENGTH: 6 amino acids
        (B) TYPE: amino acid
        (C) STRANDEDNESS: not relevant
        (D) TOPOLOGY: not relevant (ii) MOLECULE TYPE: protein (ix) FEATURE:
        (A) NAME/KEY: Modified-site
        (B) LOCATION: 4
        (D) OTHER INFORMATION: /note= "The residue in this
            position could be either Ala, Ser or Ala"

(xi) SEQUENCE DESCRIPTION: SEQ ID NO: 175:

```
His Asn Ala Ala Phe Asp
1               5
```

(2) INFORMATION FOR SEQ ID NO: 176:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 176:

TCRAANGCNG CRTTRTG                                                          17

(2) INFORMATION FOR SEQ ID NO: 177:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 177:

TCRAANSWNG CRTTRTG                                                          17

(2) INFORMATION FOR SEQ ID NO: 178:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 178:

CTAGGAGGTT TTAATCGATG CGGCCGGATC CTCGAGTCTA GACACTGGCT CCAAAATTAG           60

CTACGCCGGC CTAGGAGCTC AGATCTGTG                                             89

(2) INFORMATION FOR SEQ ID NO: 179:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 179:

CTAGGAGGTT TTAATCGATG CGGCCGGATC CTCGAGTCTA GACACTGGNN NNCTCCAAAA           60

TTAGCTACGC CGGCCTAGGA GCTCAGATCT GTG                                        93

(2) INFORMATION FOR SEQ ID NO: 180:

(i) SEQUENCE CHARACTERISTICS:
        (A) LENGTH: 444 base pairs
        (B) TYPE: nucleic acid
        (C) STRANDEDNESS: double
        (D) TOPOLOGY: linear (ii) MOLECULE TYPE: other nucleic acid (A) DESCRIPTION: /desc = "DNA"

(ix) FEATURE:
       (A) NAME/KEY: modified_base
       (B) LOCATION: 1..5

(xi) SEQUENCE DESCRIPTION: SEQ ID NO: 180:

CTGCACCGGG ATGAGCTTGG CCAATTCCTC CGCCTTCTTG TGGGGGATGC CGTAGACCCG          60

GGCCACGTCC TTGAGGGCGG CCTTGGAGGC GAGGCTTCCC AGGGTGCCGA TCTGGGCCAG         120

CTTGTCCTCG CCGTAGCGTT CCCGCACGTA CTGGATCACC CGGTCCCGCT CCCGGTCGGA         180

GAAGTCCGTG TCAATGTCGG GCATGGAGAC CCTCTCGGGG TTCAGGAAGC GCTCAAAGAG         240

GAGGCCGAAG CGCAGGGGGT CAATGTTGGT GATCCCCACG GCGTAGGCCA CCAGGCTCCC         300

GGCGGCGCTC CCCCTGCCGG GCCCCACGGA GACGCCGTTT CTCCGGGCCC AGTTGATGTA         360

TTCCTGGACG ATGAGGAAGT AGCCGGGNAA ACCCCATGCG CTCTATCACG GGAAAGCTCG         420

TAAAGGGCCC GGTGGAAAAT GGCC                                               444

(2) INFORMATION FOR SEQ ID NO: 181:

(i) SEQUENCE CHARACTERISTICS:
       (A) LENGTH: 60 amino acids
       (B) TYPE: amino acid
       (C) STRANDEDNESS: not relevant
       (D) TOPOLOGY: not relevant (ii) MOLECULE TYPE: protein (xi) SEQUENCE DESCRIPTION: SEQ ID NO: 181:

Gly Xaa Pro Gly Tyr Phe Leu Ile Val Gln Glu Tyr Ile Asn Trp Ala
1               5                  10                  15

Arg Arg Asn Gly Val Ser Val Gly Pro Gly Arg Gly Ser Ala Ala Gly
            20                  25                  30

Ser Leu Val Ala Tyr Ala Val Gly Ile Thr Asn Ile Asp Pro Leu Arg
        35                  40                  45

Phe Gly Leu Leu Phe Glu Arg Phe Leu Asn Pro Glu
    50                  55                  60

(2) INFORMATION FOR SEQ ID NO: 182:

(i) SEQUENCE CHARACTERISTICS:
       (A) LENGTH: 60 amino acids
       (B) TYPE: amino acid
       (C) STRANDEDNESS: not relevant
       (D) TOPOLOGY: not relevant (ii) MOLECULE TYPE: protein (ix) FEATURE:
       (A) NAME/KEY: Modified-site
       (B) LOCATION: 12
       (D) OTHER INFORMATION: /note= "The residue at this
           position is similar but not identical to tyrosine and/or
           phenylalanine"

(ix) FEATURE:
       (A) NAME/KEY: Modified-site
       (B) LOCATION: 16
       (D) OTHER INFORMATION: /note= "The residue at this
           position is similar but not identical to alanine and/or
           serine"

(ix) FEATURE:
       (A) NAME/KEY: Modified-site
       (B) LOCATION: 17
       (D) OTHER INFORMATION: /note= "The residue at this
           position is similar but not identical to arginine and/or lysine"

(ix) FEATURE:
    (A) NAME/KEY: Modified-site
    (B) LOCATION: 39
    (D) OTHER INFORMATION: /note= "The residue at this
        position is similar but not identical to valine and/or
        leucine"

(ix) FEATURE:
    (A) NAME/KEY: Modified-site
    (B) LOCATION: 43
    (D) OTHER INFORMATION: /note= "The residue at this
        position is similar but not identical to asparagine
        and/or aspartic acid"

(ix) FEATURE:
    (A) NAME/KEY: Modified-site
    (B) LOCATION: 44
    (D) OTHER INFORMATION: /note= "The residue at this
        position is similar but not identical to isoleucine
        and/or leucine"

(xi) SEQUENCE DESCRIPTION: SEQ ID NO: 182:

```
Gly Xaa Pro Gly Tyr Phe Leu Ile Val Xaa Glu Xaa Ile Xaa Trp Xaa
1               5                   10                  15

Xaa Xaa Asn Gly Val Xaa Val Gly Pro Gly Arg Gly Ser Xaa Ala Gly
            20                  25                  30

Ser Leu Val Ala Tyr Ala Xaa Xaa Ile Thr Xaa Xaa Asp Pro Leu Xaa
            35                  40                  45

Phe Xaa Leu Leu Phe Glu Arg Phe Leu Asn Pro Glu
50                  55                  60
```

(2) INFORMATION FOR SEQ ID NO: 183:

(i) SEQUENCE CHARACTERISTICS:
        (A) LENGTH: 60 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 183:

```
Gly Phe Pro Gly Tyr Phe Leu Ile Val Met Glu Phe Ile Gln Trp Ser
1               5                   10                  15

Lys Asp Asn Gly Val Pro Val Gly Pro Gly Arg Gly Ser Gly Ala Gly
            20                  25                  30

Ser Leu Val Ala Tyr Ala Leu Lys Ile Thr Asp Leu Asp Pro Leu Glu
            35                  40                  45

Phe Asp Leu Leu Phe Glu Arg Phe Leu Asn Pro Glu
50                  55                  60
```

(2) INFORMATION FOR SEQ ID NO: 184:

(i) SEQUENCE CHARACTERISTICS:
        (A) LENGTH: 60 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 184:

```
Arg Val Ser Met Pro Asp Ile Asp Thr Asp Phe Ser Asp Arg Glu Arg
1               5                   10                  15

Asp Arg Val Ile Gln Tyr Val Arg Glu Arg Tyr Gly Glu Asp Lys Val
```

```
                    20                  25                  30
Ala Gln Ile Gly Thr Leu Gly Ser Leu Ala Ser Lys Ala Ala Leu Lys
                35                  40                  45

Asp Val Ala Arg Val Tyr Gly Ile Pro His Lys Lys
         50                  55                  60
```

(2) INFORMATION FOR SEQ ID NO: 185:

(i) SEQUENCE CHARACTERISTICS:
        (A) LENGTH: 60 amino acids
        (B) TYPE: amino acid
        (C) STRANDEDNESS: not relevant
        (D) TOPOLOGY: not relevant (ii) MOLECULE TYPE: protein (ix) FEATURE:
        (A) NAME/KEY: Modified-site
        (B) LOCATION: 15
        (D) OTHER INFORMATION: /note= "The residue at this
            position is similar but not identical to glutamic acid
            and/or lysine"

(ix) FEATURE:
        (A) NAME/KEY: Modified-site
        (B) LOCATION: 18
        (D) OTHER INFORMATION: /note= "The residue at this
            position is similar but not identical to arginine and/or
            glutamine"

(ix) FEATURE:
        (A) NAME/KEY: Modified-site
        (B) LOCATION: 21
        (D) OTHER INFORMATION: /note= "The residue at this
            position is similar but not identical to glutamine and/or
            glutamic acid"

(ix) FEATURE:
        (A) NAME/KEY: Modified-site
        (B) LOCATION: 22
        (D) OTHER INFORMATION: /note= "The residue at this
            position is similar but not identical to tyrosine and/or
            histidine"

(ix) FEATURE:
        (A) NAME/KEY: Modified-site
        (B) LOCATION: 25
        (D) OTHER INFORMATION: /note= "The residue at this
            position is similar but not identical to glutamic acid
            and/or aspartic acid"

(ix) FEATURE:
        (A) NAME/KEY: Modified-site
        (B) LOCATION: 33
        (D) OTHER INFORMATION: /note= "The residue at this
            position is similar but not identical to alanine and/or
            serine"

(ix) FEATURE:
        (A) NAME/KEY: Modified-site
        (B) LOCATION: 40
        (D) OTHER INFORMATION: /note= "The residue at this
            position is similar but not identical to serine and/or
            threonine"

(ix) FEATURE:
        (A) NAME/KEY: Modified-site
        (B) LOCATION: 41
        (D) OTHER INFORMATION: /note= "The residue at this
            position is similar but not identical to leucine and/or
            methionine"

(ix) FEATURE:
        (A) NAME/KEY: Modified-site
        (B) LOCATION: 43
        (D) OTHER INFORMATION: /note= "The residue at this

```
              position is similar but not identical to serine and/or
              alanine"

(ix) FEATURE:
         (A) NAME/KEY: Modified-site
         (B) LOCATION: 47
         (D) OTHER INFORMATION: /note= "The residue at this
              position is similar but not identical to leucine and/or
              isoleucine"

(ix) FEATURE:
         (A) NAME/KEY: Modified-site
         (B) LOCATION: 48
         (D) OTHER INFORMATION: /note= "The residue at this
              position is similar but not identical to lysine and/or
              arginine"

(ix) FEATURE:
         (A) NAME/KEY: Modified-site
         (B) LOCATION: 58
         (D) OTHER INFORMATION: /note= "The residue at this
              position is similar but not identical to histidine and/or
              tyrosine"

(xi) SEQUENCE DESCRIPTION: SEQ ID NO: 185:

Arg Val Ser Met Pro Asp Xaa Asp Xaa Asp Phe Xaa Xaa Xaa Xaa Arg
1               5                   10                  15

Asp Xaa Val Ile Xaa Xaa Val Xaa Xaa Xaa Tyr Gly Xaa Asp Xaa Val
            20                  25                  30

Xaa Gln Ile Xaa Thr Xaa Gly Xaa Xaa Ala Xaa Lys Ala Xaa Xaa Xaa
        35                  40                  45

Asp Val Xaa Arg Val Xaa Gly Xaa Pro Xaa Xaa Xaa
    50                  55                  60

(2) INFORMATION FOR SEQ ID NO: 186:

(i) SEQUENCE CHARACTERISTICS:
         (A) LENGTH: 60 amino acids
         (B) TYPE: amino acid
         (C) STRANDEDNESS: not relevant
         (D) TOPOLOGY: not relevant (ii) MOLECULE TYPE: protein (xi) SEQUENCE DESCRIPTION: SEQ ID NO: 186:

Arg Val Ser Met Pro Asp Phe Asp Val Asp Phe Cys Met Glu Lys Arg
1               5                   10                  15

Asp Gln Val Ile Glu His Val Ala Asp Met Tyr Gly Arg Asp Ala Val
            20                  25                  30

Ser Gln Ile Ile Thr Phe Gly Thr Met Ala Ala Lys Ala Val Ile Arg
        35                  40                  45

Asp Val Gly Arg Val Leu Gly His Pro Tyr Gly Phe
    50                  55                  60

(2) INFORMATION FOR SEQ ID NO: 187:

(i) SEQUENCE CHARACTERISTICS:
         (A) LENGTH: 9 amino acids
         (B) TYPE: amino acid
         (C) STRANDEDNESS: not relevant
         (D) TOPOLOGY: not relevant (ii) MOLECULE TYPE: protein (xi) SEQUENCE DESCRIPTION: SEQ ID NO: 187:

Ala Glu Glu Leu Ala Lys Leu Ile Pro
1               5
```

(2) INFORMATION FOR SEQ ID NO: 188:

(i) SEQUENCE CHARACTERISTICS:
        (A) LENGTH: 9 amino acids
        (B) TYPE: amino acid
        (C) STRANDEDNESS: not relevant
        (D) TOPOLOGY: not relevant (ii) MOLECULE TYPE: protein (ix) FEATURE:
        (A) NAME/KEY: Modified-site
        (B) LOCATION: 2
        (D) OTHER INFORMATION: /note= "The residue at this
            position is similar but not identical to glutamic acid
            and/or aspartic acid"

(ix) FEATURE:
        (A) NAME/KEY: Modified-site
        (B) LOCATION: 4
        (D) OTHER INFORMATION: /note= "The residue at this
            position is similar but not identical to leucine and/or
            isoleucine"

(ix) FEATURE:
        (A) NAME/KEY: Modified-site
        (B) LOCATION: 5
        (D) OTHER INFORMATION: /note= "The residue at this
            position is similar but not identical to alanine and/or
            serine"

(xi) SEQUENCE DESCRIPTION: SEQ ID NO: 188:

Xaa Xaa Xaa Xaa Xaa Lys Leu Ile Pro
1              5

(2) INFORMATION FOR SEQ ID NO: 189:

(i) SEQUENCE CHARACTERISTICS:
        (A) LENGTH: 9 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 189:

Val Asp Arg Ile Ser Lys Leu Ile Pro
1              5

(2) INFORMATION FOR SEQ ID NO: 190:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 190:

GGTTCCTCNA AGGTCTT                                    17

(2) INFORMATION FOR SEQ ID NO: 191:

(i) SEQUENCE CHARACTERISTICS:
        (A) LENGTH: 7 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 191:

His Leu His Gln His Thr Gln
1               5

(2) INFORMATION FOR SEQ ID NO: 192:

(i) SEQUENCE CHARACTERISTICS:
            (A) LENGTH: 6 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 192:

Glu Gly Phe Tyr Glu Lys
1               5

(2) INFORMATION FOR SEQ ID NO: 193:

(i) SEQUENCE CHARACTERISTICS:
            (A) LENGTH: 7 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 193:

Tyr Gln Glu Gln Gln Met Gln
1               5

(2) INFORMATION FOR SEQ ID NO: 194:

(i) SEQUENCE CHARACTERISTICS:
            (A) LENGTH: 6 amino acids
            (B) TYPE: amino acid
            (C) STRANDEDNESS: not relevant
            (D) TOPOLOGY: not relevant (ii) MOLECULE TYPE: protein (xi) SEQUENCE DESCRIPTION: SEQ ID NO: 194:

Asp Gly Gly Tyr Phe His
1               5

(2) INFORMATION FOR SEQ ID NO: 195:

(i) SEQUENCE CHARACTERISTICS:
            (A) LENGTH: 8 amino acids
            (B) TYPE: amino acid
            (C) STRANDEDNESS: not relevant
            (D) TOPOLOGY: not relevant (ii) MOLECULE TYPE: protein (ix) FEATURE:
            (A) NAME/KEY: Modified-site
            (B) LOCATION: 5
            (D) OTHER INFORMATION: /note= "The residue at this
                position is similar but not identical to arginine and/or
                glutamine"

(xi) SEQUENCE DESCRIPTION: SEQ ID NO: 195:

Ala Gly Lys Glu Xaa Thr Gln Glu
1               5

US 6,238,905 B1

THERMOPHILIC POLYMERASE III HOLOENZYME

FIELD OF THE INVENTION

The present invention relates to gene and amino acid sequences encoding DNA polymerase III holoenzyme subunits and structural genes from thermophilic organisms. In particular, the present invention provides DNA polymerase III holoenzyme subunits of *T. thermophilus*. The present invention also provides antibodies and other reagents useful to identify DNA polymerase III molecules.

BACKGROUND

Bacterial cells contain three types of DNA polymerases termed polymerase I, II and III. DNA polymerase III (pol III) is responsible for the replication of the majority of the chromosome. Pol III is referred to as a replicative polymerase; replicative polymerases are rapid and highly processive enzymes. Pol I and II are referred to as non-replicative polymerases although both enzymes appear to have roles in replication. DNA polymerase I is the most abundant polymerase and is responsible for some types of DNA repair, including a repair-like reaction that permits the joining of Okazaki fragments during DNA replication. Pol I is essential for the repair of DNA damage induced by WV irradiation and radiomimetic drugs. Pol II is thought to play a role in repairing DNA damage which induces the SOS response and in mutants which lack both pol I and III, pol II repairs UV-induced lesions. Pol I and II are monomeric polymerases while pol III comprises a multisubunit complex.

In *E. coli*, pol III comprises the catalytic core of the *E. coli* replicase. In *E. coli*, there are approximately 400 copies of DNA polymerase I per cell, but only 10–20 copies of Pol III (Kornberg and Baker, DNA Replication, 2d ed., W.H. Freeman & Company, [1992], pp. 167; and Wu et al. J. Biol. Chem., 259:12117–12122 [1984]). The low abundance of Pol III and its relatively feeble activity on gapped DNA templates typically used as a general replication assays delayed its discovery until the availability of mutants defective in DNA polymerase I (Kornberg and Gefter, J. Biol. Chem., 47:5369–5375 [1972]).

The catalytic subunit of Pol III is distinguished as a component of *E. coli* major replicative complex, apparently not by its intrinsic catalytic activity, but by its ability to interact with other replication proteins at the fork. These interactions confer upon the enzyme enormous processivity. Once the DNA polymerase III holoenzyme associates with primed DNA, it does not dissociate for over 40 minutes-the time required for the synthesis of the entire 4 Mb *E. coli* chromosome (McHenry, Ann. Rev. Biochem., 57:519–550 [1988]). Studies in coupled rolling circle models of the replication fork suggest the enzyme can synthesize DNA 150 kb or longer without dissociation in vitro (Mok and Marians, J. Biol. Chem., 262:16644–16654 [1987]; Wu et al., J. Biol. Chem., 267:4030–4044 [1992]). The essential interaction required for this high processivity is an interaction between the a catalytic subunit and a dimer of A, a sliding clamp processivity factor that encircles the DNA template like a bracelet, permitting it to rapidly slide along with the associated polymerase, but preventing it from falling off (LaDuca et al., J. Biol. Chem., 261:7550–7557 [1986]; Kong et al., Cell 69:425–437 [1992]). The β-α association apparently retains the polymerase on the template during transient thermal fluctuations when it might otherwise dissociate.

The β2 bracelet cannot spontaneously associate with high molecular weight DNA, it requires a multiprotein DnaX-complex to open and close it around DNA using the energy of ATP hydrolysis (Wickner, Proc. Natl. Acad. Sci. USA 73:35411–3515 [1976]; Naktinis et al., J. Biol. Chem., 270:13358–13365 [1985]; and Dallmann et al., J. Biol. Chem., 270:29555–29562 [1995]). In *E. coli*, the dnaX gene encodes two proteins, τ and γ. γ is generated by a programmed ribosomal frameshifting mechanism five-sevenths of the way through dnaX MRNA, placing the ribosome in a −1 reading frame where it immediately encounters a stop codon (Flower and McHenry Proc. Natl. Acad. Sci. USA 87:3713–3717 [1990]; Blinkowa and Walker, Nucl. Acids Res., 18:1725–1729 [1990]; and Tsuchihashi and Kornberg, Proc. Natl. Acad. Sci. USA 87:2516–2520 [1990]). In *E. coli*, the DnaX-complex has the stoichiometry $\gamma_2\tau_2\delta_1\delta'_1\chi_1\iota_1$ (Dallmann and McHenry, J. Biol. Chem., 270:29563–29569 [1995]). The τ protein contains an additional carboxyl-terminal domain that interacts tightly with the polymerase, holding two polymerases together in one complex that can coordinately replicate the leading and lagging strand of the replication fork simultaneously (McHenry, J. Biol. Chem., 257:2657–2663 [1982]; Studwell and O'Donnell, Biol. Chem., 266:19833–19841 [1991]; McHenry, Ann. Rev. of Biochem. 57:519–550 [1988]).

Pol IIIs are apparently conserved throughout mesophilic eubacteria. In addition to *E. coli* and related proteobacteria, the enzyme has been purified from the firmicute *Bacillus subtilis* (ow et al., J. Biol. Chem., 251:1311–1325 [1976]; Hammond and Brown [1992]). With the proliferation of bacterial genomes sequenced, by inference from DNA sequence, pol III exits in organisms as widely divergent as Caulobacter, Mycobacteria, Mycoplasma, *B. subtilis* and Synechocystis. The existence of dnaX and dnaN (structural gene for β) is also apparent in these organisms. These general replication mechanisms are conserved even more broadly in biology. Although eukaryotes do not contain polymerases homologous to Pol III, eukaryotes contain special polymerases devoted to chromosomal replication and β-like processivity factors (PCNA) and DnaX-like ATPases (RFC, Activator I) that assemble these processivity factors on DNA (Yoder and Burgers, J. Biol. Chem., 266:22689–22697 [1991]; Brush and Stillman, Meth. Enzymol., 262:522–548 [1995]; Uhlmann et al., Proc. Natl. Acad. Sci. USA 93:6521–6526 [1996]).

In spite of the apparent ubiquity of Pol Ills and their associated factors required to function as a replicase, the identification of such enzymes remains to be accomplished for many other organisms.

SUMMARY OF THE INVENTION

The present invention relates to gene and amino acid sequences encoding DNA polymerase III holoenzyme subunits and structural genes from thermophilic organisms. In particular, the present invention provides DNA polymerase III holoenzyme subunits of *T. thermophilus*. The present invention also provides antibodies and other reagents useful to identify DNA polymerase III molecules.

The present invention provides nucleotide sequences, including the nucleotide sequence set forth in SEQ ID NO: 7, as well as sequences comprising fragments of SEQ ID NO: 7, and sequences that are complementary to SEQ ID NO: 7. In alternative embodiments, the present invention provides the nucleotide sequence of SEQ ID NO: 7, wherein the nucleotide sequence further comprises 5' and 3' flanking sequences, and/or intervening regions.

The present invention also provides recombinant DNA vectors, such as vectors comprising SEQ ID NO: 7. In an alternative embodiment, the present invention provides host cells containing these recombinant vectors.

The present invention also provides a purified dnaX protein encoded by an oligonucleotide comprising a nucleotide sequence substantially homologous to the coding strand of the nucleotide sequence of SEQ ID NO: 7. The present invention provides full-length, as well as fragments of any size comprising the protein (i.e., the entire amino acid sequence of the protein, as well as short peptides). In particularly preferred embodiments, the dnaX protein is from *Thermus thermophilus*. In other preferred embodiments, the dnaX proteins comprises at least a portion of the amino acid sequence set forth in SEQ ID NO: 9.

The present invention also provides a fusion protein(s) comprising a portion of the dnax protein and a non-dnaX protein sequence. In some preferred embodiments, the dnaX protein comprises SEQ ID NO: 9.

The present invention also provides isolated amino acid sequences as set forth in SEQ ID NO: 2. In yet other embodiments, the present invention provides an isolated nucleotide sequence encoding the amino acid sequence set forth in SEQ ID NO: 2. In additional embodiments, the present invention provides a purified tau protein encoded by a polynucleotide sequence substantially homologous to the coding strand of the nucleotide sequences encoding tau protein. In alternative embodiments, the present invention provides nucleotide sequences encoding at least a portion of tau protein, wherein the nucleotide sequence further comprises 5' and 3' flanking regions and/or intervening regions. Thus, the present invention also encompasses fragments of any size, comprising tau protein amino acid or nucleic acid sequences. In preferred embodiments, the tau protein of the present invention is from *Thermus thermophilus*.

In an alternative embodiment, the present invention provides recombinant vectors comprising at least a portion of the nucleotide sequence encoding tau protein. In yet other embodiments, the present invention provides host cells containing at least one recombinant DNA vector comprising at least a portion of tau protein. In further embodiments, the present invention provides fusion protein(s) at least a portion of tau protein and a non-tau protein sequence.

The present invention also provides the amino acid sequence set forth in SEQ ID NO: 1. In one embodiment, the present invention provides an isolated nucleotide sequence encoding the amino acid sequence set forth in SEQ ID NO: 1. In other embodiments, the present invention provides at least a portion of purified gamma protein(s) encoded by a polynucleotide sequence substantially homologous to the coding strand of the nucleotide sequence that encodes gamma protein. In yet other embodiments, the present invention provides nucleotide sequences that further comprise 5' and 3' flanking regions and/or intervening regions. In preferred embodiments, the present invention provides gamma protein that is from *Thermus thermophilus*.

The present invention also provides recombinant vectors comprising at least a portion of a nucleotide sequence that encodes gamma protein. In yet other embodiments, the present invention also provides host cells containing the recombinant DNA vectors comprising at least a portion of nucleotide sequence encoding gamma protein. In alternative embodiments, the present invention provides fusion protein (s) comprising a portion of the gamma protein, and non-gamma protein sequence(s).

The present invention also provides methods for detecting DNA polymerase III comprising: providing in any order, a sample suspected of containing DNA polymerase III, an antibody capable of specifically binding to a at least a portion of the DNA polymerase III; mixing the sample and the antibody under conditions wherein the antibody can bind to the DNA polymerase III; and detecting the binding. In preferred embodiments of the methods, the sample comprises a thermophilic organism. In alternative preferred embodiments, the thermophilic organism is member of the genus Thermus. The methods of the present invention encompass any method for detection.

The present invention also provides methods for detection of polynucleotides encoding at least a portion of DNA polymerase III holoenzyme (or DNA polymerase III holoenzyme subunit) in a biological sample comprising the steps of: a) hybridizing at least a portion of the polynucleotide sequence comprising at least fifteen nucleotides, which hybridizes under stringent conditions to at least a portion of the polynucleotide sequence selected from the group consisting of the DNA sequences set forth in SEQ ID NOS: 7, 20, 21, 22, 40, 41, 42, 58, 63, 64, 65, 66, 67, 77, 78, 79, 88, 91, 92, 97, 110, 111, 112, 113, 114, 115, 116, 134, 135, 136, 137, 156, 157, 173, 174, 174, 176, 177, 178, 179, 180, and 190, to nucleic acid material of a biological sample, thereby forming a hybridization complex; and b) detecting the hybridization complex, wherein the presence of the complex correlates with the presence of a polynucleotide encoding at least a portion of DNA polymerase III holoenzyme (or DNA polymerase III holoenzyme subunit) in the biological sample. In one alternative embodiment of the methods, the nucleic acid material of the biological sample is amplified by the polymerase chain reaction.

The present invention also provides an antibody, wherein the antibody is capable of specifically binding to at least one antigenic determinant on the protein encoded by an amino acid sequence selected from the group comprising SEQ ID NOS: 1, 2, 8, 9, 26, 31, 34, 37, 59, 70, 75, 82, and 85. The present invention encompasses polyclonal, as well as monoclonal antibodies.

The present invention also provides methods for producing anti-DNA polymerase III holoenzyme and anti-DNA polymerase III holoenzyme subunit antibodies comprising, exposing an animal having immunocompetent cells to an immunogen comprising at least an antigenic portion of DNA polymerase III holoenzyme (or holoenzyme subunit) protein, under conditions such that immunocompetent cells produce antibodies directed against the portion of DNA polymerase III protein holoenzyme or holoenzyme subunit. In one embodiment, the method further comprises the step of harvesting the antibodies. In an alternative embodiment, the method comprises the step of fusing the immunocompetent cells with an immortal cell line under conditions such that an hybridoma is produced. In yet another embodiment, the portion of DNA polymerase III protein or subunit protein used as an immunogen to generate the antibodies is selected from the group consisting of SEQ ID NOS: 1, 2, 8, 9, 16, 17, 18, 19, 23, 26, 31, 34, 37, 45, 50, 55, 59, 601, 70, 75, 82, 88, 89, 90, 105, 106, 107, 109, 117, 181, 184, and 187. In other embodiments, the immunogen comprises a fusion protein. In yet another embodiment, the fusion protein comprises at least a portion of DNA polymerase III holoenzyme or holoenzyme subunit protein.

The present invention also provides methods for detecting DNA polymerase III holoenzyme or holoenzyme subunit expression comprising the steps of: a) providing a sample suspected of containing DNA polymerase III holoenzyme or holoenzyme III subunit; and a control containing a quantitated DNA polymerase III holoenzyme or holoenzyme III subunit protein, as appropriate; and b) comparing the test DNA polymerase III holoenzyme or holoenzyme subunit, in the sample with the quantitated DNA polymerase III holoenzyme or holoenzyme subunit in the control to determine the relative concentration of the test DNA polymerase III holoenzyme or holoenzyme III subunit in the sample. In addition, the methods may be conducted using any suitable means to determine the relative concentration of DNA polymerase III holoenzyme or holoenzyme subunit in the test and control samples, including but not limited to the means selected from the group consisting of Western blot analysis, Northern blot analysis, Southern blot analysis, denaturing polyacrylamide gel electrophoresis, reverse transcriptase-coupled polymerase chain reaction, enzyme-linked immunosorbent assay, radioimmunoassay, and fluorescent immunoassay. Thus, the methods may be conducted to determine the presence of DNA polymerase III holoenzyme or holoenzyme III subunit in the genome of the source of the test sample, or the expression of DNA polymerase III holoenzyme or holoenzyme subunit (mRNA or protein), as well as detect the presence of abnormal or mutated DNA polymerase holoenzyme or holoenzyme subunit proteins or gene sequences in the test samples.

In one preferred embodiment, the presence of DNA polymerase III holoenzyme or holoenzyme subunit is detected by immunochemical analysis. For example, the immunochemical analysis can comprise detecting binding of an antibody specific for an epitope of DNA polymerase III holoenzyme or holoenzyme subunit (e.g., SEQ ID NO: 2 or 3). In an another preferred embodiment of the method, the antibody comprises polyclonal antibodies, while in another preferred embodiment, the antibody is comprises monoclonal antibodies.

The antibodies used in the methods invention may be prepared using various immunogens. In one embodiment, the immunogen is DNA polymerase III holoenzyme or holoenzyme subunit peptide, to generate antibodies that recognize DNA polymerase III holoenzyme or holoenzyme subunit(s). Such antibodies include, but are not limited to polyclonal, monoclonal, chimeric, single chain, Fab fragments, and an Fab expression library.

Various procedures known in the art may be used for the production of polyclonal antibodies to DNA polymerase III holoenzyme or holoenzyme subunit. For the production of antibody, various host animals can be immunized by injection with the peptide corresponding to the DNA polymerase III holoenzyme or holoenzyme subunit epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin [KLH]). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, and dinitrophenol.

For preparation of monoclonal antibodies directed toward DNA polymerase III holoenzyme or holoenzyme subunit, any technique that provides for the production of antibody molecules by continuous cell lines in culture may be used (See, e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495–497 [1975]), as well as other techniques known in the art.

According to the invention, techniques described for the production of single chain antibodies (U.S. Pat. No. 4,946,778; herein incorporated by reference) can be adapted to produce DNA polymerase III holoenzyme or holoenzyme subunit-specific single chain antibodies. An additional embodiment of the invention utilizes the techniques described for the construction of Fab expression libraries (Huse et al., Science 246:1275–1281 [1989]) to allow rapid and easy identification of monoclonal Fab fragments with the desired specificity for DNA polymerase III holoenzyme or holoenzyme subunit.

Antibody fragments which contain the idiotype (antigen binding region) of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art (e.g., radioimmunoassay, ELISA [enzyme-linked immunosorbent assay], "sandwich" immunoassays, immunoradiometric assays, gel diffusion precipitin reactions, immunodiffusion assays, in situ immunoassays [using colloidal gold, enzyme or radioisotope labels, for example], Western Blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. (As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of DNA polymerase III holoenzyme or holoenzyme subunit (e.g., for Western blotting), measuring levels thereof in appropriate biological samples, etc. The biological samples can be tested directly for the presence of DNA polymerase III holoenzyme or holoenzyme subunit using an appropriate strategy (e.g., ELISA or radioimmunoassay) and format (e.g., microwells, dipstick [e.g., as described in International Patent Publication WO 93/03367], etc.). Alternatively, proteins in the sample can be size separated (e.g., by polyacrylamide gel electrophoresis (PAGE), in the presence or not of sodium dodecyl sulfate (SDS), and the presence of DNA polymerase III holoenzyme or holoenzyme subunit detected by immunoblotting (Western blotting). Immunoblotting techniques are generally more effective with antibodies generated against a peptide corresponding to an epitope of a protein, and hence, are particularly suited to the present invention.

The foregoing explanations of particular assay systems are presented herein for purposes of illustration only, in fulfillment of the duty to present an enabling disclosure of the invention. It is to be understood that the present invention contemplates a variety of immunochemical assay protocols within its spirit and scope.

DESCRIPTION OF THE FIGURES

In all of the following Figures that show alignments (DNA or amino acids), the "+" indicates similar, but not identical residues. In the DNA sequences with underlined regions, unless otherwise indicated, the underlining indicates bases generated by the degenerate primers used to generate the DNA of interest. Also unless otherwise indicated, the sequences between the sequences generated by the primers were used in the searches to generate deduced amino acid sequences (ie., the primer-generated sequences were excluded from the searches).

FIG. 8 shows the amino terminal sequence of the isolated candidate γ (SEQ ID NO: 1) and τ (SEQ ID NO: 2) T. thermophilus dnax gene products and comparison to the homologous sequences of E. coli (SEQ ID NO: 3) and B. subtilis (SEQ ID NO: 4). T. thermophilus is abbreviated as Tth. The sequences where identical or similar matches occur are also shown (SEQ ID NOS: 5 and 6).

FIG. 9A shows the DNA sequence (SEQ ID NO: 7) of T. thermophilus dnaX and flanking sequences.

FIG. 9B shows the deduced amino acid sequence (SEQ ID NO: 8) of the X gene product of T. thermophilus dnaX. The peptide sequences directly determined from the isolated T. thermophilus DnaX-proteins are underlined.

FIG. 9C shows a comparison of T. thermophilus dnaX (SEQ ID NO: 9); with homologous eubacterial dnaX sequences from E. coli (SEQ ID NO: 10), B. subtilis (SEQ ID NO: 1), Mycoplasma pneumoniae (SEQ ID NO: 12), Caulobacter crescentus (SEQ ID NO: 13), and Synechocystis sp. (SEQ ID NO: 14) (a consensus sequence is also shown [SEQ ID NO: 15]).

FIG. 9D shows the deduced sequence of the carboxyl-terminus of T. thermophilus γ subunit depending on whether the frameshift is −1 (as in E. coli) or +1 (SEQ ID NOS: 16–19).

FIG. 10A shows the nucleotide sequence (SEQ ID NO: 20) of T. thermophilus dnaX product obtained from PCR amplification of T. thermophilus chromosomal DNA with primers X1Fa (SEQ ID NO: 21) and X139R (SEQ ID NO: 22); the sequences generated by the primers are underlined in this Figure (SEQ ID NOS: 190 and 85).

FIG. 10B shows an alignment of the amino acid sequence (SEQ ID NO: 23) deduced from the underlined primers of 10A (ie., T. thermophilus DnaX product), with B. subtilis DNA polymerase dnax sequence (SEQ ID NO: 24). As with prior Figures, matching amino acids are indicated (SEQ ID NO: 25).

FIG. 11A shows an alignment of T. thermophilus 130 kDa polypeptide N-terminal amino acid sequence (dnaE) (SEQ ID NO: 26) with sequences from M tuberculosis (SEQ ID NO: 27) and H. influenzae (SEQ ID NO: 28) dnaE gene sequences. The sequences that are identical between the corresponding peptides are also shown (SEQ ID NOS: 29 and 30).

FIG. 11B shows comparisons between the internal amino acid sequences of three T. thermophilus dnaE regions compared with sequences from E. coli. In this Figure, the three T. thermophilus peptides were #91 (SEQ ID NO: 31), #676 (SEQ ID NO: 34), and #853 (SEQ ID NO: 37). For E. coli, the peptide number refers to the first amino acid residue in the amino acid sequence of the E. coli DNA Pol III a subunit with which the T. thermophilus 130 kDa polypeptide aligned (ie., 92 [SEQ ID NO: 32]; 676 [SEQ ID NO: 35]; and 38 [SEQ ID NO: 38]). As with other Figures, identical or similar amino acids are indicated between the T. thermophilus and E. coli sequences (SEQ ID NOS: 33, 36, and 39).

FIG. 12A shows the nucleotide sequence (SEQ ID NO: 40) of T. thermophilus dnaE product obtained from PCR amplification of T. thermophilus chromosomal DNA with primers E1F (SEQ ID NO: 87) and E91R (SEQ ID NO: 86). The sequences underlined in this Figure are the sequences are the regions recognized by these primers (SEQ ID NOS: 41 and 42).

FIG. 12B shows alignments of the T. thermophilus dnaE amino acid sequence (SEQ ID NOS: 45, 50, and 55) deduced from FIG. 12A (between the underlined primers), compared with Synechocystis sp. sequences (SEQ ID NO: 43, 48, and 53), and M tuberculosis sequences (SEQ ID NO: 47, 52, and 57). As with other Figures, identical or similar amino acids are also shown (SEQ ID NOS: 44, 46, 49, 51, 54, and 56).

FIG. 13A shows the nucleotide sequence (SEQ ID NO: 58) of the first approximately 1,109 bases of the T. thermophilus dnaE gene.

FIG. 13B shows the preliminary deduced amino acid sequence (SEQ ID NO: 59) corresponding to the N-terminal portion of the dnaE gene shown in FIG. 13A.

FIG. 13C shows an alignment of the T. thermophilus dnaE gene (SEQ ID NO: 61) with regions of homology in the M tuberculosis DNA polymerase III a subunit sequence (SEQ ID NO: 60) and Synechocystis sp. DNA polymerase III a subunit sequence (SEQ ID NO: 62).

FIG. 14A shows the region of asymmetric PCR product corresponding to the region close to the N-terminal end of the T. thermophilus dnaE gene (SEQ ID NO: 63) (i.e., the "front end of the clone"). In this Figure, the region corresponding to the sequence generated by the forward primer is underlined and shown in bold (SEQ ID NO: 64).

FIG. 14B shows the back end of the clone (SEQ ID NO: 180). In this Figure, the underlined bases correspond to part of the PstI site.

FIG. 14C shows the alignment of the amino acid sequence of T. thermophilus DnaE product deduced from the entire sequence shown in FIG. 14B (SEQ ID NOS: 181, 184, and 187), with E. coli DNA polymerase III sequences (SEQ ID NOS: 183, 186, and 189). As with prior Figures, identical and similar amino acids are indicated (SEQ ID NOS: 182, 185, and 188).

FIG. 15A shows the deduced nucleotide sequence (SEQ ID NO: 65) of T. thermophilus Dana product obtained from PCR amplification of T. thermophilus chromosomal DNA between the primers A177Fb (SEQ ID NO: 135) and A251Rb (SEQ ID NO: 157). The sequences recognized by the primers are underlined in this Figure (SEQ ID NOS: 66 and 67).

FIG. 15B shows an alignment of the deduced amino acid sequences (SEQ ID NOS: 70, 75) of T. thermophilus dnaA product, with E. coli dnaA sequence (SEQ ID NOS: 68, and 73), and B. subtilis dnaA sequence (SEQ ID NOS: 72 and 76). As with other Figures, identical and similar residues are also shown (SEQ ID NOS: 69, 71, 74and 195.).

FIG. 16A shows the nucleotide sequence (SEQ ID NO: 60) of T. thermophilus dnaQ product obtained from PCR amplification of T. thermophilus chromosomal DNA with primers Q12Fa (SEQ ID NO: 173) and Q98Ra (SEQ ID NO: 176). The sequences generated by these primers are underlined in this Figure (SEQ ID NOS: 78 and 79).

FIG. 16B shows an alignment of the deduced amino acid sequences (SEQ ID NO: 82) of T. thermophilus dnaQ product, with E. coli DNA polymerase III holoenzyme ε subunit sequence (SEQ ID NO: 80), and B. subtilis DNA polymerase III subunit sequence (SEQ ID NO: 84). As with other Figures, identical and similar residues are also shown (SEQ ID NOS: 81 and 83).

DEFINITIONS

Figure 1:
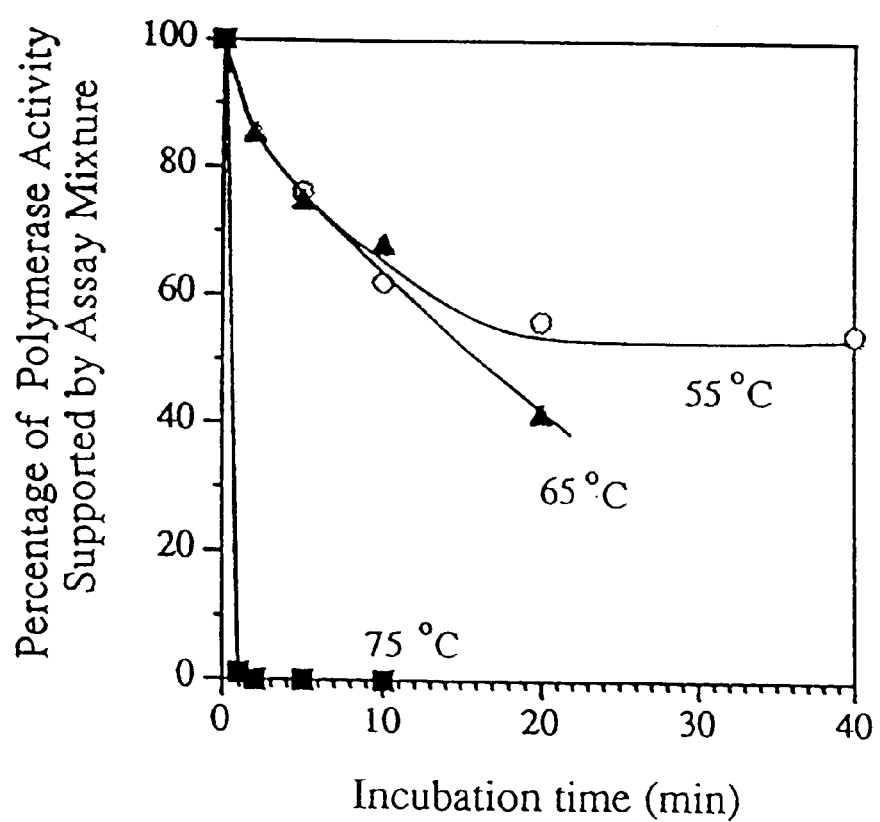
FIG. 1 shows a graph depicting the inactivation of the M13Gori assay mixture at elevated temperatures.

As used herein, the term "DNA polymerase III holoenzyme" refers to the entire DNA polymerase III entity (ie., all of the polymerase subunits, as well as the other associated accessory proteins required for processive replication of a chromosome or genome), while "DNA polymerase III" is just the core [α, ε, θ]). "DNA polymerase III holoenzyme subunit" is used in reference to any of the subunit entities that comprise the DNA polymerase III holoenzyme. Thus, the term "DNA polymerase III" encompasses "DNA polymerase III holoenzyme subunits" and "DNA polymerase III subunits."

The term "5' exonuclease activity" refers to the presence of an activity in a protein which is capable of removing nucleotides from the 5' end of an oligonucleotide. 5' exonuclease activity may be measured using any of the assays provided herein.

The term "3' exonuclease activity" refers to the presence of an activity in a protein which is capable of removing nucleotides from the 3' end of an oligonucleotide. 3' exonuclease activity may be measured using any of the assays provided herein.

The terms "DNA polymerase activity," "synthetic activity" and "polymerase activity" are used interchangeably and refer to the ability of an enzyme to synthesize new DNA strands by the incorporation of deoxynucleoside triphosphates. The examples below provide assays for the measurement of DNA polymerase activity. A protein which is can direct the synthesis of new DNA strands by the incorporation of deoxynucleoside triphosphates in a template-dependent manner is said to be "capable of DNA synthetic activity."

A "DNA synthesis terminating agent which terminates DNA synthesis at a specific nucleotide base" refers to compounds, including but not limited to, dideoxynucleosides having a 2', 3' dideoxy structure (e.g., ddATP, ddCTP, ddGTP and ddTTP). Any compound capable of specifically terminating a DNA sequencing reaction at a specific base may be employed as a DNA synthesis terminating agent.

The term "gene" refers to a nucleic acid (e.g., DNA) sequence that comprises coding sequences necessary for the production of a polypeptide or precursor (e.g., DNA polymerase III holoenzyme or holoenzyme subunit, as appropriate). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The term "gene" encompasses both cDNA and genomic forms of a gene. A genomic form or clone of a gene contains the coding region interrupted with non-coding sequences termed "intervening regions" or "intervening sequences." The MRNA functions during translation to specify the sequence or order of amino acids in a nascent polypeptide.

In particular, the terms "DNA polymerase III holoenzyme" and "holoenzyme subunit gene" refer to the full-length DNA polymerase III holoenzyme, and holoenzyme subunit nucleotide sequence(s), respectively. However, it is also intended that the term encompass fragments of the DNA polymerase III holoenzyme and holoenzyme subunit sequences, such as those that encode particular domains of interest, including subunit proteins, as well as other domains within the fill-length DNA polymerase III holoenzyme or holoenzyme subunit nucleotide sequence. Furthermore, the terms "DNA polymerase III holoenzyme," "holoenzyme subunit nucleotide sequence," "DNA polymerase III holoenzyme," and "holoenzyme subunit polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited proteins.

Genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the MRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (ie., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein the term "coding region" when used in reference to structural gene refers to the nucleotide sequences which encode the amino acids found in the nascent polypeptide as a result of translation of a mRNA molecule. The coding region is bounded on the 5' side by the nucleotide triplet "ATG" which encodes the initiator methionine and on the 3' side by one of the three triplets which specify stop codons (ie., TAA, TAG, TGA).

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the oligonucleotide or polynucleotide may be single-stranded (ie., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc., or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [1987]). Promoter and enhancer elements have been isolated from a variety of eukaryotic sources including genes in yeast, insect and mammalian cells and viruses (analogous control elements, ie., promoters, are also found in prokaryote). The selection of a particular promoter and enhancer depends on what cell type is to be used to express the protein of interest. Some eukaryotic promoters and enhancers have a broad host range while others are functional in a limited subset of cell types (for review see, S. D. Voss et al., Trends Biochem. Sci., 11:287 [1986]; and T. Maniatis et al., supra). For example, the SV40 early gene enhancer is very active in a wide variety of cell types from many mammalian species and has been widely used for the expression of proteins in mammalian cells (R. Dijkema et al., EMBO J. 4:761 [1985]). Two other examples of promoter/enhancer elements active in a broad range of mammalian cell types are those from the human elongation factor 1α gene (T. Uetsuki et al., J. Biol. Chem., 264:5791 [1989]; D. W. Kim et al., Gene 91:217 [1990]; and S. Mizushima and S. Nagata, Nuc. Acids. Res., 18:5322 [1990]) and the long terminal repeats of the Rous sarcoma virus (C. M. Gorman et al., Proc. Natl. Acad. Sci. USA 79:6777 [1982]) and the human cytomegalovirus (M. Boshart et al., Cell 41:521 [1985]).

As used herein, the term "promoter/enhancer" denotes a segment of DNA which contains sequences capable of providing both promoter and enhancer functions (ie., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (J. Sambrook, supra, at 16.6–16.7).

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the term "selectable marker" refers to the use of a gene which encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity which can be detected in any eukaryotic cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene which is used in conjunction with tk⁻ cell lines, the CAD gene which is used in conjunction with CAD-deficient cells and the mammalian hypoxanthine-guanine phosphoribosyl transferase (hprt) gene which is used in conjunction with hprt⁻ cell lines. A review of the use of selectable markers in mammalian cell lines is provided in Sambrook, J. et al., *Molecular Cloning: A Laboratory Manual*, 2nd ed., Cold Spring Harbor Laboratory Press, New York (1989) pp.16.9–16.15.

Eukaryotic expression vectors may also contain "viral replicons "or "viral origins of replication." Viral replicons are viral DNA sequences which allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral T antigen. Vectors which contain the replicons from bovine papillomavirus or Epstein-Barr virus replicate extrachromosomally at low copy number (~100 copies/cell).

The thermophilic DNA polymerase III holoenzyme or holoenzyme subunits may be expressed in either prokaryotic or eukaryotic host cells. Nucleic acid encoding the thermophilic DNA polymerase III holoenzyme or holoenzyme subunit may be introduced into bacterial host cells by a number of means including transformation of bacterial cells made competent for transformation by treatment with calcium chloride or by electroporation. If the thermophilic DNA polymerase III holoenzyme or holoenzyme subunit are to be expressed in eukaryotic host cells, nucleic acid encoding the thermophilic DNA polymerase III holoenzyme or holoenzyme subunit may be introduced into eukaryotic host cells by a number of means including calcium phosphate co-precipitation, spheroplast fusion, electroporation and the like. When the eukaryotic host cell is a yeast cell, transformation may be affected by treatment of the host cells with lithium acetate or by electroporation.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, (See e.g., Marmur and Lane, Proc. Natl. Acad. Sci. USA 46:453 [1960]); and Doty et al., Proc. Natl. Acad. Sci. USA 46:461 [1960]) have been followed by the refinement of this process into an essential tool of modem biology. Nonetheless, a number of problems have prevented the wide scale use of hybridization as a tool in diagnostics. Among the more formidable problems are: 1) the inefficiency of hybridization; 2) the low concentration of specific target sequences in a mixture of genomic DNA; and 3) the hybridization of only partially complementary probes and targets.

With regard to efficiency, it is experimentally observed that only a fraction of the possible number of probe-target complexes are formed in a hybridization reaction. This is particularly true with short oligonucleotide probes (less than 100 bases in length). There are three fundamental causes: a) hybridization cannot occur because of secondary and tertiary structure interactions; b) strands of DNA containing the target sequence have rehybridized (reannealed) to their complementary strand; and c) some target molecules are prevented from hybridization when they are used in hybridization formats that immobilize the target nucleic acids to a solid surface.

Even where the sequence of a probe is completely complementary to the sequence of the target (i.e., the target's primary structure), the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, continuous strand of bases (as opposed to hybridization between two different strands). Depending on the extent and position of intramolecular bonding, the probe can be displaced from the target sequence preventing hybridization.

Solution hybridization of oligonucleotide probes to denatured double-stranded DNA is further complicated by the fact that the longer complementary target strands can renature or reanneal. Again, hybridized probe is displaced by this process. This results in a low-yield of hybridization (low "coverage") relative to the starting concentrations of probe and target.

With regard to low target sequence concentration, the DNA fragment containing the target sequence is usually in relatively low abundance in genomic DNA. This presents great technical difficulties; most conventional methods that use oligonucleotide probes lack the sensitivity necessary to detect hybridization at such low levels.

One attempt at a solution to the target sequence concentration problem is the amplification of the detection signal. Most often this entails placing one or more labels on an oligonucleotide probe. In the case of non-radioactive labels, even the highest affinity reagents have been found to be unsuitable for the detection of single copy genes in genomic DNA with oligonucleotide probes. (See, Wallace et al., Biochimie 67:755 [1985]). In the case of radioactive oligonucleotide probes, only extremely high specific activities are found to show satisfactory results. (See, Studencki and Wallace, DNA 3:1 [1984] and Studencki et al., Human Genetics 37:42 [1985]).

With regard to complementarity, it is important for some diagnostic applications to determine whether the hybridization represents complete or partial complementarity. For example, where it is desired to detect simply the presence or absence of pathogen DNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, may require that the hybridization method distinguish between partial and complete complementarity. It may be of interest to detect genetic polymorphisms. For example, human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence.

Unless combined with other techniques (such as restriction enzyme analysis), methods that allow for the same level of hybridization in the case of both partial as well as complete complementarity are typically unsuited for such applications; the probe will hybridize to both the normal and variant target sequence. Hybridization, regardless of the method used, requires some degree of complementarity between the sequence being assayed (the target sequence) and the fragment of DNA used to perform the test (the probe). (Of course, one can obtain binding without any complementarity but this binding is nonspecific and to be avoided.)

As used herein, the terms "complementary" or "complementarity" are used in reference to polynucleotides (ie., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementarity. There may be partial homology or complete homology (ie., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (ie., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

A gene may produce multiple RNA species which are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe which can hybridize (i.e., it is the complement of) the single-stranded nucleic acid sequence under conditions of low stringency as described.

As used herein, the term "hybridization" is used in reference to the pairing of complementary nucleic acids.

Hybridization and the strength of hybridization (i.e. the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41$ (% G+C), when a nucleic acid is in aqueous solution at 1 M NaCl (See e.g., Anderson and Young, Quantitative Filter Hybridization, in *Nucleic Acid Hybridization* [1985]). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (M. Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids which may be amplified by any amplification method. It is contemplated that "amplifiable nucleic acid" will usually comprise "sample template." As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

As used herein, the term "nested primers" refers to primers that anneal to the target sequence in an area that is inside the annealing boundaries used to start PCR. (See, K. B. Mullis, et al., *Cold Spring Harbor Symposia*, Vol. LI, pp. 263–273 [1986]). Because the nested primers anneal to the target inside the annealing boundaries of the starting primers, the predominant PCR-amplified product of the starting primers is necessarily a longer sequence, than that defined by the annealing boundaries of the nested primers. The PCR-amplified product of the nested primers is an amplified segment of the target sequence that cannot, therefore, anneal with the starting primers.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "substantially single-stranded" when used in reference to a nucleic acid target means that the target molecule exists primarily as a single strand of nucleic acid in contrast to a double-stranded target which exists as two strands of nucleic acid which are held together by interstrand base pairing interactions.

Nucleic acids form secondary structures which depend on base-pairing for stability. When single strands of nucleic acids (single-stranded DNA, denatured double-stranded DNA or RNA) with different sequences, even closely related ones, are allowed to fold on themselves, they assume characteristic secondary structures. An alteration in the sequence of the target may cause the destruction of a duplex region(s), or an increase in stability of a thereby altering the accessibility of some regions to hybridization of the probes oligonucleotides. While not being limited to any particular theory, it is thought that individual molecules in the target population may each assume only one or a few of the structures (i.e., duplexed regions), but when the sample is analyzed as a whole, a composite pattern from the hybridization of the probes can be created. Many of the structures that can alter the binding of the probes are likely to be only a few base-pairs long and would appear to be unstable. Some of these structures may be displaced by the hybridization of a probe in that region; others may by stabilized by the hybridization of a probe nearby, such that the probe/substrate duplex can stack coaxially with the target intrastrand duplex, thereby increasing the stability of both. The formation or disruption of these structures in response to small sequence changes results in changes in the patterns of probe/target complex formation.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used in reference to amplification methods such as PCR, the term "polymerase" refers to any polymerase suitable for use in the amplification of nucleic acids of interest. It is intended that the term encompass such DNA polymerases as the polymerase III of the present invention, as well as Taq DNA polymerase (i.e., the type I polymerase obtained from *Thermus aquaticus*), although other polymerases, both thermostable and thermolabile are also encompassed by this definition.

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (ie., as in other PCR methods).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (ie., the oligonucleotide or polynucleotide may be double-stranded).

As used herein, the term "purified" or "to purify" refers to the removal of contaminants from a sample. For example, anti-DNA polymerase III holoenzyme and holoenzyme subunit antibodies are purified by removal of contaminating non-immunoglobulin proteins; they are also purified by the removal of immunoglobulin that does not bind DNA polymerase III holoenzyme or holoenzyme subunit. The removal of non-immunoglobulin proteins and/or the removal of immunoglobulins that do not bind DNA polymerase III holoenzyme or holoenzyme subunit results in an increase in the percent of DNA polymerase III holoenzyme or holoenzyme subunit-reactive immunoglobulins in the sample. In another example, recombinant DNA polymerase III holoenzyme or holoenzyme subunit polypeptides are expressed in bacterial host cells and the polypeptides are purified by the removal of host cell proteins; the percent of recombinant DNA polymerase III holoenzyme or holoenzyme subunit polypeptides is thereby increased in the sample.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "fusion protein" refers to a chimeric protein containing the protein of interest (i.e., DNA polymerase III holoenzyme or holoenzyme subunit and fragments thereof) joined to an exogenous protein fragment (the fusion partner which consists of a non-DNA polymerase III holoenzyme or holoenzyme subunit protein). The fusion partner may enhance solubility of the DNA polymerase III holoenzyme or holoenzyme subunit protein as expressed in a host cell, may provide an affinity tag to allow purification of the recombinant fusion protein from the host cell or culture supernatant, or both. If desired, the fusion protein may be removed from the protein of interest (i.e., DNA polymerase III holoenzyme, holoenzyme subunit protein, or fragments thereof) by a variety of enzymatic or chemical means known to the art.

A "variant" of DNA polymerase III holoenzyme or holoenzyme subunit, as used herein, refers to an amino acid sequence that is altered by one or more amino acids. The variant may have "conservative" changes, wherein a substituted amino acid has similar structural or chemical properties, (e.g., replacement of leucine with isoleucine). More rarely, a variant may have "nonconservative" changes (e.g., replacement of a glycine with a tryptophan). Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene. It is noted, however, that the invention does not require that a comparison be made between one or more forms of a gene to detect sequence variations. Because the method of the invention generates a characteristic and reproducible pattern of complex formation for a given nucleic acid target, a characteristic "fingerprint" may be obtained from any nucleic target without reference to a wild-type or other control. The invention contemplates the use of the method for both "fingerprinting" nucleic acids without reference to a control and identification of mutant forms of a target nucleic acid by comparison of the mutant form of the target with a wild-type or known mutant control.

As used herein, the term "target nucleic acid" refers to the region of nucleic acid bounded by the primers used for polymerase chain reaction. Thus, the "target" is sought to be sorted out from other nucleic acid sequences. A "segment" is defined as a region of nucleic acid within the target sequence.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to targets present in a PCR mixture refers to the use of nucleotides other than DATP, dGTP, dCTP and dTTP; thus, the use of dUTP (a naturally occurring dNTP) in a PCR would comprise the use of a nucleotide analog in the PCR. A PCR product generated using dUTP, 7-deaza-dATP, 7-deaza-dGTP or any other nucleotide analog in the reaction mixture is said to contain nucleotide analogs.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRS, RT-PCRs and the like.

A "consensus gene sequence" refers to a gene sequence which is derived by comparison of two or more gene sequences and which describes the nucleotides most often present in a given segment of the genes; the consensus sequence is the canonical sequence. "Consensus protein," "consensus amino acid," consensus peptide," and consensus polypeptide sequences refer to sequences that are shared between multiple organisms or proteins.

The term "biologically active," as used herein, refers to a protein or other biologically active molecules (e.g., catalytic RNA) having structural, regulatory, or biochemical functions of a naturally occurring molecule. Likewise, "immunologically active" refers to the capability of the natural, recombinant, or synthetic DNA polymerase III holoenzyme or holoenzyme subunit, or any oligopeptide or polynucleotide thereof, to induce a specific immune response in appropriate animals or cells and to bind with specific antibodies.

The term "agonist," as used herein, refers to a molecule which, when bound to DNA polymerase III holoenzyme or holoenzyme subunit, causes a change in DNA polymerase III holoenzyme or holoenzyme subunit, which modulates the activity of DNA polymerase III holoenzyme or holoenzyme subunit. Agonists may include proteins, nucleic acids, carbohydrates, or any other molecules which bind or interact with DNA polymerase III holoenzyme or holoenzyme subunit.

The terms "antagonist" or "inhibitor," as used herein, refer to a molecule which, when bound to DNA polymerase III holoenzyme or holoenzyme subunit, blocks or modulates the biological or immunological activity of DNA polymerase III holoenzyme or holoenzyme subunit. Antagonists and inhibitors may include proteins, nucleic acids, carbohydrates, or any other molecules which bind or interact with DNA polymerase III holoenzyme or holoenzyme subunit.

The term "modulate," as used herein, refers to a change or an alteration in the biological activity of DNA polymerase III holoenzyme or holoenzyme subunit. Modulation may be an increase or a decrease in protein activity, a change in binding characteristics, or any other change in the biological, functional, or immunological properties of DNA polymerase III holoenzyme or holoenzyme subunit.

The term "derivative," as used herein, refers to the chemical modification of a nucleic acid encoding DNA polymerase III holoenzyme or holoenzyme subunit, or the encoded DNA polymerase III holoenzyme or holoenzyme subunit. Illustrative of such modifications would be replacement of hydrogen by an alkyl, acyl, or amino group. A nucleic acid derivative would encode a polypeptide which retains essential biological characteristics of the natural molecule.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, N.Y., pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, J. et al., supra, pp 7.39–7.52 [1989]).

The term "Western blot" refers to the analysis of protein (s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (ie., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The terms "specific binding" or specifically binding" when used in reference to the interaction of an antibody and a protein or peptide means that the interaction is dependent upon the presence of a particular structure (ie., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labelled "A" and the antibody will reduce the amount of labelled A bound to the antibody.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

The terms "test DNA polymerase III holoenzyme" and "test holoenzyme subunit" refers to a sample suspected of containing DNA polymerase III holoenzyme or holoenzyme subunit, respectively. The concentration of DNA polymerase III holoenzyme or holoenzyme subunit in the test sample is determined by various means, and may be compared with a "quantitated amount of DNA polymerase III holoenzyme or holoenzyme subunit" (i.e., a positive control sample containing a known amount of DNA polymerase III holoenzyme or holoenzyme subunit), in order to determine whether the concentration of test DNA polymerase III holoenzyme or holoenzyme subunit in the sample is within the range usually found within samples from wild-type organisms.

The term "microorganism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

DESCRIPTION OF THE INVENTION

The present invention relates to gene and amino acid sequences encoding DNA polymerase III holoenzyme subunits and structural genes from thermophilic organisms. In particular, the present invention provides DNA polymerase III holoenzyme subunits of *T. thermophilus*. The present invention also provides antibodies and other reagents useful to identify DNA polymerase III molecules.

Prior to the present invention, only one type of DNA polymerase had been discovered in thermophilic eubacteria, even though others have been actively sought (See e.g., Lawyer et al., J. Biol. Chem., 264:6427–6437 [1989]; Chien et al., J. Bacteriol., 127:1550–1557 [1976]; and Kaledin et al., Biochem., 45:494–501 [1981]). The present invention provides a pol III-class polymerase and an associated Pol III holoenzyme auxiliary subunit homolog from the thermophile *T. thermophilus*.

This invention was developed in a step-wise fashion, using various techniques, including of general gap filling assays to monitor polymerase activity and the use of cross-reactive monoclonal antibodies against the α catalytic subunit of *E. coli* DNA polymerase III holoenzyme to distinguish the novel polymerase from the well characterized DNA polymerase I-like *Thermus thermophilus* DNA polymerase.

Indeed, a survey of 12 monoclonal antibodies directed against the 130 kDa ax subunit of the *E. coli* pol III holoenzyme revealed a subset that reacted with a protein of approximately the same size in Western blots of *T. thermophilus* extracts. These antibodies were used to distinguish the pol III polymerase of the present invention, from the characterized *T. thermophilus* polymerase during protein fractionation procedures.

Two proteins migrating with the polymerase and present in approximate stoichiometric ratio after three chromatographic steps were isolated and subjected to partial amino acid sequencing. The amino terminus of both were homologous to the two products of the *E. coli* dnaX gene, the γ and τ subunits of the DNA polymerase III holoenzyme. Using this information and sequences conserved among dnaX-like genes, a gene fragment was isolated by PCR, and used as a probe to isolate the full length *Thermus thermophilus* dnaX gene. The deduced amino acid sequence was found to be highly homologous to the DnaX proteins of other bacteria. Examination of the sequence permitted identification of a frameshift site similar to the one used in *E. coli* to direct the synthesis of the shorter y DnaX-gene product.

Conservation of a frameshifting mechanism to generate related ATPases is significant in that, by analogy to *E. coli*, can both assemble a β processivity factor onto primed DNA. Both a 63 kDa r subunit that has a molecular weight consistent with its being a full length dnaX translation product, and a 50 kDa τ subunit that likely arises by translational frameshifting was detected in enzyme purified from *T. thermophilus* extracts. Examination of the dnaX DNA sequence provided confirmation of this. In *E. coli*, ribosomes frameshift at the sequence A AAA AAG into a −1 frame where the lysine UUU anticodon tRNA can base pair with 6As before elongating (Flower and McHenry, Proc. Natl. Acad. Sci. USA 87:3713–3717 [1990]; Blinkowa and Walker, Nucl. Acids Res., 18:1725–1729 [1990]; and Tsuchihashi and Kornberg, Proc. Natl. Acad. Sci. USA 87:2516–2520 [1990]). In *T. thermophilus*, the putative frameshift site has the sequence A AAA AAA A, which would enable either a +1 or −1 frameshift. The +1 frameshift product would extend only one residue beyond the lys-lys encoding sequence where the frameshift occurs, similar to the *E. coli* −1 product. A −1 frameshift would encode a protein with a 12-amino acid extension. Such an extension could permit an interaction that may fer distinguish γ from τ functionally or could loop back to stabilize its structure in a thermal environment.

As mentioned above, *E. coli* Pol III holoenzyme can remain associated with primed DNA for 40 minutes and replicates DNA at 500–1000 nucleotides/second (McHenry, Ann. Rev. Biochem., 57:519–550 [1988]). Existing PCR technology is limited by relatively non-processive repair-like DNA polymerases. The present invention provides a thermophilic replicase capable of rapid replication and highly processive properties at elevated temperatures. It is contemplated that the compositions of the present invention will find use in many molecular biology applications, including megabase PCR by removing the current length restrictions, as well as enabling new technological advances in molecular biology.

Experimental

The following examples serve to illustrate certain preferred embodiments and aspects of the present invention and are not to be construed as limiting the scope thereof.

In the experimental disclosure which follows, the following abbreviations apply: g (gram); L (liter); μg (microgram); ml (milliliter); bp (base pair); ° C. (degrees Centigrade); kb or Kb (kilobases); kDa or kd (kilodaltons); EDTA (ethylenediaminetetraacetic acid); DTT (dithiothreitol); LB (Luria Broth); -mer (oligomer); DMV (DMV International, Frazier, NY); PAGE (polyacrylamide gel electrophoresis); SDS (sodium dodecyl sulfate); SDS-PAGE (sodium dodecyl sulfate polyacrylamide gel electrophoresis); SSPE (2×SSPE contains 0.36 mM NaCl, 20 mM $NaH_2PO_4$, pH 7.4, and 20 mM EDTA, pH 7.4; the concentration of SSPE used may vary), SOP media (20 g/l tryptone (Difco), 10 g/l yeast extract (Difco), 5 g/l NaCl, 2.5 g/l potassium phosphate, dibasic (Fisher), 1 g/l $MgSO_4.7H_2O$ (Fisher), pH 7.2); TE buffer (10 mM Tris, 1 mM EDTA); 50×TAE (242 g Tris base, 57.1 ml glacial acetic acid, 100 ml 0.5 M EDTA pH 8.0); Blotto (10% skim milk dissolved in $dH_2O$ and 0.2% sodium azide); Gel Loading Dye (0.25% Bromophenol blue, 0.25% xylene cyanol, 25% Ficoll (Type 400) in $dH_2O$); Pre-hybridization mix (50% Formamide, 5×SSPE, 1% SDS, 0.5% CARNATION1 non-fat dried milk, 10% skim milk, 0.2% Na Azide); FBS (fetal bovine serum); ABS, Inc. (ABS, Inc., Wilmington, Del.); Boehringer Mannheim (Boehringer Mannheim, Indianapolis, Ind.); Champion Industries (Champion Industries, Clifton, N.J.); Organon (Organon Teknika Corp., Durham N.C.); Difco (Difco, Detroit, Mich.); Enzyco (Enzyco Inc., Denver, Colo.); Fisher Scientific (Fisher Scientific, Fair Lawn, N.J.); FMC (FMC, Rockland, Me.); Gibco BRL (Gibco BRL Gaithersburg, Md.); Hyclone (Hyclone, Logan Utah); Intermountain or ISC (ISC BioExpress, Bountiful, Utah); Invitrogen (Invitrogen, Carlsbad, Calif.); Millipore (Millipore, Marlborough, Mass.); MJ Research (MJ Research, Watertown, Mass.); Molecular Probes (Molecular Probes, Eugene, Oreg.); National Diagnostics (National Diagnostics, Manville, N.J.); Pharmacia Biotech (Pharmacia Biotech., Piscataway, N.J.); Promega (Promega Corp., Madison, Wis.); Sigma (Sigma, St. Louis, Mo.); Stratagene (Stratagene, LaJolla Calif.); Tecan (Tecan, Research Triangle Park, N.C.); Whatman (Whatman, Maidstone, England); Lofstrand Labs (Lofstrand Labs, Ltd., Gaithersburg, Md.) and LSPI (LSPI Filtration Products, Life Science Products, Denver, Col.); Irvine (Irvine Scientific, Irvine Calif.); and Jackson Labs (Jackson Labs, Bar Harbor, Me.).

EXAMPLE 1

Selection of a DNA Polymerase Assay to Monitor the Purification of a Multi-Subunit DNA Polymerase HI from *Thermus thermophilus*

In order to monitor the purification of a multi-subunit DNA polymerase III from the thermophilic *Thermus thermophilus*, the suitability of a DNA polymerase assay which is commonly used for measurement of the activity of DNA polymerase III in mesophilic bacteria (e.g., *Escherichia coli*) was investigated. However, the unsuitability of the prior art assay for use at high temperatures necessitated the development of an alternative assay for DNA polymerase activity for use at high temperatures. This Example involved a) long single-stranded template mesophilic DNA polymerase assay, and b) development of a gap-filling assay for DNA polymerase activity.

A. Long Single-Stranded Template Mesophilic DNA Polymerase Assay

For mesophilic bacteria, such as *E. coli*, the assay system used to measure DNA replication employs a relatively long single-stranded DNA template, M13Gori, as substrate that is primed with RNA at a unique site by the action of dnaG primase (Cull & McHenry, Meth. Enzymol., 262:2235 [1995]). The ability to use this assay at high temperature for monitoring polymerase III activity from thermophilic organisms was investigated as follows.

The M13Gori template (Enzyco) was first primed with RNA as described below. The following components were mixed together on ice in the following order: 243 li of primer-template solution (60 mM HEPES (pH 7.5), 14 mM magnesium acetate, 2.8 mM ATP, GTP, CTP and UTP, 14% glycerol, 56 mM NaCl, 42 mM potassium glutamate, 84 $\mu$g/ml bovine serum albumin (BSA) and 4 mM DTT), with 7.2 $\mu$l M13Gori (2.98 mg/ml), 63 $\mu$l *E. coli* single-stranded binding protein (SSB) (Enzyco) (2.2 mg/ml) and 27 $\mu$l DnaG primase (Enzyco) (0.39 mg/ml). This mixture was then incubated for 15 min at 30° C. to form the "primer-template." The above mixture provided enough primed M13Gori for over 100 polymerase assays.

The DNA polymerase reaction mixture was assembled by adding the following components on ice: 300 $\mu$l of primer-template was added to 2.1 ml of polymerization reaction solution (180 mM Bicine (pH 8.0), 25% glycerol, 0.017% Nonidet-P40, 170 $\mu$g/ml BSA, 83 mM potassium glutamate, 8 mM DTT, 2.3 mM magnesium acetate, 10 $\mu$g/ml rifampicin, 57 $\mu$M each of dGTP, dATP and dCTP, and 21 $\mu$M TTP) and the solutions were mixed to form the "polymerase reaction mixture." This mixture can be used immediately or stored for several months at −80° C. by flash-freezing in liquid $N_2$.

To test the stability of the polymerase reaction mixture at elevated temperatures, 15 $\mu$l aliquots of the reaction mixture were incubated at 55° C., 65° C., or 75° C., for various periods of time varying between 1 and 40 min. The reaction tubes were then immediately placed on ice and allowed to cool to 0C. *E. coli* DNA polymerase III holoenzyme (Enzyco) was then added and the reaction tubes incubated for 5 min at 30° C. before measuring the amount of double-stranded (ds) DNA synthesized in the reaction.

The amount of ds DNA synthesized was measured using a fluorometric assay that relies on the properties of the fluorophor PicoGreen™ (Molecular Probes). This dye displays significant fluorescence in the presence only of ds DNA and is almost completely non-fluorescent in the presence of single stranded DNA. Two hundred fifty microliters of a 1:400 dilution of PicoGreen™ fluorophor in Tris-HCl (pH 7.5), 1 mM EDTA was added to each reaction tube. The fluorescence intensity was measured using an SLT fluorescent plate reader (Tecan) using a 385 nm filter for excitation and a 535 nm filter for emission.

The results of these polymerase assays are summarized in FIG. 1. In FIG. 1, the percentage of polymerase activity supported by the assay mixture was plotted against the incubation time in minutes. In this Figure, the time points indicated represent the length of time that the reaction mixture was incubated at the elevated temperature, before chilling, adding holoenzyme, and incubating for 5 minutes at 30° C. The solid squares, the solid triangles and the open circles represent assays conducted at 75° C., 65° C. and 55° C., respectively.

The data shown in FIG. 1 demonstrate that one or more components of the assay mixture were inactivated at the highest temperature tested. For example, at 75° C. complete inactivation occurred in less than 1 min. Thus, this system was unsuitable for the measurement of DNA polymerase activity at 75° C.

B. Development of a Gap-Filling Assay for DNA Polymerase

Because the polymerase reaction mixture in the M13Gori assay was found to be unstable at elevated temperatures, the DNA gap-filling assay was used to monitor polymerase activity during purification, although the DNA gap-filling assay does not discriminate between the different types of polymerases (e.g., polymerase I and III). The majority (>90%) of gap-filling activity in bacterial cells is due to the presence of DNA polymerase I, making it difficult to identify other polymerases, including DNA polymerase III. Nonetheless, as discussed below, this assay was found to be suitable to detect *T. thermophilus* pol III activity during the purification procedures described in the following Examples.

The gap-filling assay was performed as follows. An assay mixture containing 32 mM HEPES (pH 7.5), 13% glycerol, 0.01% Nonidet P40, 0.13 mg/ml BSA, 10 MM $MgCl_2$, 0.2 mg/ml activated calf-thymus DNA (Enzyco), 57 $\mu$M each of dGTP, dATP and dCTP, and 21 $\mu$M [$^3$H]TTP (360 cpm/pmol) was assembled.

The reaction was started by the addition of a 0.5 $\mu$l of a suitable dilution of DNA polymerase to 15 $\mu$l of reaction mix, and incubated at 37° C. for 5–50 min. The reaction was then stopped by placing the reaction tube on ice.

The amount of DNA synthesized in the assay was measured by first precipitating the polynucleotide with 2 drops of 0.2 M inorganic pyrophosphate (PPi) and 0.5 ml 10% TCA. Removal of unincorporated nucleotide triphosphates was accomplished by filtering the mixture through GFC filters (Whatman) and washing the filters with 12 ml 0.2 M PPi/1M HCl and then ethanol. The filters were then allowed to dry before scintillation counting; Ecoscint-0 (National Diagnostics) was used as the scintillant. One unit of enzyme activity is defined as one picomole of TTP incorporated per min at 37° C. Positive controls containing E. coli DNA Pol III were included in the assay since this assay does not distinguish the activity of Pol I, Pol II, and Pol III.

The gap-filling assay was selected instead of the long stranded template DNA polymerase assay to monitor the purification of DNA polymerase III activity from T. thermophilus. In the following Examples, the assay was performed at 37° C., in part for convenience, but also because the decrease in activity for Pol III at lower temperatures is less than that of the major T. thermophilus DNA polymerase activity, permitting more efficient detection of Pol III because it comprised a greater percentage of total polymerase activity when assayed this way. One unit of activity is equivalent to 1 pmol total nucleotide synthesis per minute at 37° C.

EXAMPLE 2

Purification of a DNA Polymerase Multi-Subunit Complex From T. thermophilus

This Example involved a) growth of T. thermophilus strain pMF48.kat cells, and b) large-scale purification of a DNA III polymerase multi-subunit complex from T thermophilus.

The MF48.kat strain (Lasa et al., Microbiol., 6:1555–1564 [1992]) was used for the purification of a polymerase multi-subunit complex. Strain pMF48.kat is a T thermophilus strain mutated to be deficient in the protective S-layer protein found on the outer coat. This mutation renders the strain susceptible to lysis by hen-egg white lysozyme. The lysis procedure of Cull and McHenry (Cull and McHenry, Meth. Enzymol., 262:22–35 [1995]) for isolation of E. coli DNA polymerase III holoenzyme (i.e., the replicative enzyme of E. coli) requires a gentle lysis procedure using lysozyme and the addition of spermidine to precipitate the chromosomal DNA with the cellular debris. The use of the S-layer mutant of T. thermophilus was found to allow the use of a modification of the standard E. coli gentle lysis procedure (Cull and McHenry supra), as described below.

A complex containing at least three proteins (α, τ, and γ) having DNA polymerase activity as determined by the gap-filling assay was purified from T. thermophilus MF48.kat Partial amino acid sequencing of these T. thermophilus proteins revealed that these proteins share homology with subunits of the E. coli DNA polymerase III holoenzyme.

A. Growth of T. thermophilus Strain pMF48.kat Cels

MF48.kat cells were grown as previously described in (Lasa et al., Molec. Microbiol., 6:1555–1564 [1992]), harvested, and the pellet stored at −80° C. as glycerol stock until ready for use. DNA polymerase was purified from large scale fermentation cultures of MF48.kat cells. These steps are further elaborated in the following sections.

1. Preparation of Media for Fermentation of T. thermophilus Strain pMF48.kat

T. thermophilus strain pMF48KAT (Lasa et al., 1992) was grown in 180 L batches with aeration in a 250 l fermentor at 72° C. in a medium containing (per L): 0.27 g ferric chloride hexahydrate, 0.294 g sodium citrate trisodium salt dihydrate, 0.025 g calcium sulfate dihydrate, 0.20 g magnesium chloride hexahydrate, 0.53 g ammonium chloride, 8 g pancreatic digest of casein (DMV International), 4 g yeast extract (Ardamine Z, Champlain Industries), 4.0 g glucose (Cerelose 2001, food grade (Corn Products, International), 0.5 L-glutamic acid monosodium salt, 0.254 g sodium phosphate monobasic (dissolved in 1000/180 ml water), 1.5 g dipotassium phosphate (dissolved in 2000/180 ml water). Following the addition of the final component to the fermentation medium, the pH of the broth was adjusted to pH 7.3 at 72° C. with 3N NaOH. Fermentation was conducted so as to avoid precipitation or turbidity, and achieve growth over 1.2 O.D.$_{600}$. During preparation of the fermentation medium, adequate time (approximately 4 minutes) was allowed for medium constituents to go into solution prior to the addition of the next medium component while constantly stirring.

2. Growth Conditions

Seed cultures were grown from frozen glycerol stock as follows and stored at −80° C. One ml of frozen glycerol stock was added to 250 ml fermentation medium prepared as described above and additionally containing kanamycin (30 µg/ml) at 72° C. in a baffled Fembach flask with 45 mm screw top closure, and the culture incubated overnight in an environmental shaker (New Brunswick) with low agitation (p100 rpm). At approximately 20 hours, the resulting seed culture was transferred to 180 L of fermentation medium in a fermenter (IF250 New Brunswick Scientific). Fermentation was carried out at 72° C., pH 7.3, 100% $O_2$ (measured with Ingold $O_2$ Transmitter 4300 with Ingold probes blanked on non-sparged, non-agitated medium, and at a pressure of 3 pounds per square inch, as determined by the pressure gauge on the fermenter) over atmospheric pressure with air flow at 40 L/min and rpm at 80.

A 5 L sugar mixture consisting of 480 g/L glucose and 60 g/L L-glutamic acid was added during the run. The sugar mixture was prepared by incrementally adding and dissolving the sugar and glutamic acid in hot, sterile deionized water. One liter of the sugar mixture was added at $OD_{600}$ 0.7–0.9, followed by the addition of 1 L of sugar mixture at each doubling thereafter (i.e., at the rate of approximately 50–100 ml sugar solution per minute). At the time of transfer of the seed culture from the flask to the large fermenter, the culture was mixed with aeration (sparge) only in the absence of agitation. Agitation was begun at $OD_{600}$ 0.7–0.9. As the culture density increased and the available oxygen approached zero (measured with Ingold $O_2$Transmitter 4300 with Ingold probes blanked on non-sparged, non-agitated medium), the agitation was increased to keep the detectable $O_2$ levels just above zero. pH control was not used during the initial static growth phase until $OD_{600}$ reached approximately 0.7–0.9, at which time pH was controlled with 3N sodium hydroxide to maintain a pH of 7.3 at 72° C. The pH was measured with an Ingold pH controller/transmitter 2500 with Ingold probes. Foaming was controlled mechanically.

Cells were harvested at $OD_{600}$ 2.5–3.0 by transferring the culture via a hose through an Alfa-Laval plate heat exchanger (72° C. culture: ~10° C. water exchange medium) to a Sharples A5 16 continuous flow centrifuge. A cell paste was obtained by centrifugation in a Sharples A5 16 continuous flow centrifuge for approximately 1 hour at 17,000 rpm (13,000×g) at room temperature. The cell paste was resuspended 1:1 (w/w) in Buffer TS (50 mM Tris-HCl, 10% sucrose (pH 7.5) and then frozen in liquid nitrogen as pellets and stored at −20° C.

B. Partial Purification of T. thermophilus DNA Polymerase III And Associated Proteins To avoid formation of a precipitate which was observed when protein solutions were kept at 4° C., all of the following operations for large scale purification were performed at room temperature unless otherwise stated. Cells were lysed with lysozyme, and an ammonium sulfate fraction collected. The ammonium sulfate fraction was first resolved by cation exchange chromatography, followed by hydrophobic chromatography. These steps are described below.

Cell Lysis and Ammonium Sulfate Fractionation

First, 4.7 kg of a 1:1 suspension of cells in Tris-sucrose were added to 6.5 l tris-sucrose that had been prewarmed to 55° C. To the stirred mixture, 117 ml of 0.5 M DTT, and 590 ml of 2M NaCl, 0.3M spermidine in Tris-sucrose adjusted to pH 7.5, were added. The pH of the slurry was adjusted to pH 8 by the addition of 2 M Tris base, and 2.35 g lysozyme was added. The slurry was distributed into 250 ml centrifuge bottles and incubated at 30° C. for 1 hour with occasional inversion, and then centrifuged at 23,000×g for 60 min. at 4° C. The recovered supernatant (8 l) constituted Fraction I (Table 1).

TABLE 1

Partial Purification of *T. thermophilus* Pol III and Associated Proteins

| Fraction | Method of Purification | Units ($\times 10^3$) | Protein[c] (mg) | Spec. Act. (Units/mg) |
|---|---|---|---|---|
| I. | Cell lysis | ND[a] | 73,800 | ND |
| II. | Amm. sulfate precipitation | 2,200 | 6,540 | 360 |
| III. | BioRex-70 chromatography | 6,700 | 686 | 10,000 |
| IV. | ToyoPearl ether chromatography | 1,400 | 54 | 25,000 |
| V. | Q-Sepharose chromatography | 760[c] | 4.8 | 160,000[b] |

[a]Fraction I was not assayed due to a non-linear response, presumably due to nuclease or inhibitory contaminants.
[b]Assays were conducted at 37° C. The specific activity is 5-fold higher (800,000 units/mg) if assayed at 60° C.
[c]The reported yield is normalized to a complete preparation using all of the material from Fraction IV. Only 50% of Fraction IV was used in the preparation of Fraction V.

To FrI ammonium sulfate (0.267 g/initial ml Fraction I) was added over a 15 min interval. The mixture was stirred for an additional 30 min at 4° C. and then centrifuged at 23,000×g for 60 min at 0° C. The recovered pellet was resupended (on ice) in 563 ml (0.07×Fraction I volume) 50 mM Tris-HCl (pH 7.5), 20% glycerol, 1 mM EDTA, 0.1 M NaCl, 5 mM DTT, 0.18 g (added to each ml of final solution) ammonium sulfate and the resulting suspension centrifuged at 23,000×g for 60 min at 0° C. resulting in Fraction II (Table 1).

The precipitate was thoroughly resuspended on ice in 563 ml (0.07×vol. of Fraction I) of backwash solution (50 mM Tris-HCl (pH 7.5), 20% glycerol, 1 mM EDTA, 0.1 M NaCl, 5 mM DTT, 0.18 g/initial ml ammonium sulfate [i.e., 0.18 g ammonium sulfate were added for each 1 ml of initial solution volume, and centrifuged at 12,000 rpm in a GSA rotor for 60 min at 0C. The pellet (Fraction II) was stored at 4° C.

C. Identification Of Monoclonal Antibodies Cross-Reactive With The a Subunit Of *T. thermophilus* DNA Polymerase m Using ELISA 1) Generation of Monoclonal Antibodies Monoclonal antibodies were generated by the University of Colorado Cancer Center Monoclonal Antibody Core. Standard procedures were used as described (See e.g., Oi and Herzenberg, in Mishell and Shiigi (eds.), *Selected Methods in Cellular Immunology*, W.H. Freeman & Co., San Francisco [1980], p 351–371). Briefly, 100 µg of DNA polymerase III a subunit (Enzyco) in complete Freund's Adjuvant was injected subcutaneously into the back of the neck of a BALB/c Bailey mouse (Jackson Labs). Four weeks later, each mouse was boosted intraperitoneally with 50 µg in Incomplete Freund's Adjuvant (IFA). Each animal was boosted again two weeks later with the same injection. Two weeks later, mice were bled from the tail and their polyclonal titer against a determined. The mouse giving the best response was selected for future sacrifice, was and given an additional 20 µg booster (without adjuvant). Three days later, the mouse was sacrificed, the spleen aseptically removed and processed by mincing into several 2–3 mm pieces. The spleen pieces were bathed in RPMI-serum free medium (1 10 L package RPMI Powder (Irvine), 20 g sodium bicarbonate, 43 g HEPES, 100 ml non essential amino acids (NEAA, Irvine), 1.1 g sodium pyruvate, 2.92 g L-Glutamine, 50 ml Pen-Strep (Irvine) adjusted to pH 7.05, in 10 L deionized $H_2O$, and filtered through a Gelman filter. Cells were transferred to a 50 ml conical tube, pelleted and washed in RPMI-serum free medium. Cells were manipulated to remove red blood cells and centrifuged for 5 min at 1400 rpm. Remaining red blood cells were removed by resuspending the spleen cell pellet in 10 ml of 0.83% $NH_4Cl$ at room temperature for 90 seconds. After 90 sec, 20 ml of RPMI-serum free medium was added, the cells were swirled to mix, and centrifuged at 1400 rpm for 5 min. The cell pellet was washed with RPMI-serum free medium, centrifuged (5 min, 1400 rpm) and resuspended in 20.3 ml RPMI-serum free medium.

Spleen cells and THT myeloma cells (Fox-NY Mouse Myeloma, ATCC 1732-CRL), cultured in RPMI with 10% FBS (Hyclone Lot 2334), and 15 µg/ml 8-azaguanine (pH 7.1–7.2) under 7% $CO_2$ at 37° C.), were mixed at a 4:1 ratio in a 50 ml conical tube. Mixed cells were centrifuged 10 min at 1400 rpm, and the supernatant was aspirated. PEG (50%) at room temperature was added drop-wide over 1 minute with gentle stirring. Approximately 1 ml was added to $2 \times 10^8$ cells. The PEG was then diluted by drop-wise addition of 9 ml RPMI-serum free medium. Cells were centrifuged at 1400 rpm for 10 min.

The supernatant from the centrifuged cells was aspirated and the cells were resuspended in 10 ml of RPMI containing 15% FBS. Then, 10 ml of cells were plated per 100 mm Petri dish, and the cells were incubated overnight at 37° C. in 7% $CO_2$. Cells were then harvested, collected by centrifugation and resuspended in 205 ml RPMI containing 15% FBS +AHAT medium (75 µM adenine, 0.1 mM hypoxanthine, 0.4 µM aminopterin, 16 µM thymine) in a T75 flask. In addition, 2 drops of this suspension were plated into the wells of a 96-well CoStar dish. This procedure was continued to generate twenty 96 well dishes. These were incubated at 37° C. in 7% $CO_2$. On the third day after plating 2 drops/well of fresh RPMI containing 15% FBS and AHAT, as well as 1×Hybridoma Cloning Supplement (Boehringer-Mannheim) medium were added, with fluid changes every three days thereafter by aspirating ½ of the medium from each well and feeding 2 drops/well of fresh RPMI with 15% FBS and AHAT. Screening was performed when the cells reached ⅓ confluency (ca 10 days post fusion).

2) Monoclonal Antibody Screening

Screening was performed by an ELISA procedure. Twenty 96-well dishes (Dynatech Laboratories) were coated with 50 µl/well of a 1 µg/ml solution of the a subunit of the *E. coli* DNA polymerase III holoenzyme diluted in PBS (8 g/l NaCl, 0.2 g/l KCl, 1.15 g/l $Na_2HPO_4$, 0.2 g/l $KH_2PO_4$ (pH 7.4)). Plates were washed (3×) in PBS with 0.1% Tween 20, and blocked by the addition of 200 µl/well of 1% BSA in PBS. After washing, hybridoma supernatant (50 µl/well) was added from the corresponding well of the 96-well culture dish. After washing, Fc specific goat anti-mouse IgG-horse radish peroxidase conjugated (Organon) (100 µl/well) antibody (diluted 1:5000 in 1% BSA in PBS) was added, and incubated for 3 hours at room temperature. Plates were washed and exposed to 100 μl substrate solution and incubated for 15 minutes in the dark. Substrate solution was prepared by adding 150 ml citric acid buffer (10.2 μl citric acid monohydrate, 26.8 g/l sodium phosphate dibasic, pH adjusted to 4.9 with phosphoric acid) to 60 mg O-phenylenediamine (Sigma). Just prior to use, 60 μl of 30% hydrogen peroxide was added. Reactions were quenched by the addition of 50 μl sulfuric acid/well, and read at 490 nm.

From the preliminary screening, 24 wells appeared positive (O.D. 490>1.0 Control wells containing only diluent (i.e., 1% BSA in PBS); growth medium and medium containing AHAT and myeloma cells only, gave an O.D. of 0.2 or less. Cells from 24 wells that produced monoclonal antibodies against the α subunit of DNA polymerase III holoenzyme were expanded in a well of a 24 well plate and tested again by ELISA for continued secretion of antibody against α. Three wells failed to show continued growth or secretion. The remaining candidates were also screened by a Western blot procedure with a mixture of the DNA polymerase III holoenzyme subunits (as described under section describing following *T. thermophilus* pol III by Western on hydrophobic column except 0.5 μg of each of the *E. coli* DNA polymerase III holoenzyme subunits were loaded in a mixture and blotted against undiluted serum).

From the 21 remaining candidates, 12 wells were selected that reacted strongly and specifically with α on Western Blots for cloning by limiting dilution (antibodies # 178, 210, 257, 279, 645, 889, 1018, 1104, 1171, 1283, 1950, 1976). The remaining polyclonal wells were frozen down by the procedure described below. The antibodies produced were isotyped using an ELISA and isotype-specific antibodies. The two antibodies used in this study, 1950 and 1104 were both IgG$_1$.

For cloning by the limiting dilution technique, cells were removed from the chosen positive wells and placed in a 15 ml conical tube. An aliquot of 600,000 cells was taken and added to a tube containing RPMI-serum free media to bring the final cell density to 60,000 cells/ml. Cells were diluted 1:10 successively with RPM-serum free media until a dilution of 600 cells/nl was achieved. Cells were then diluted with HCS (Hybridoma Cloning Supplement, Boehringer Mannheim) until concentrations of 50, 10 and 5 cells/ml were achieved. These were then aliquoted into wells of a 96 well plate (2 drops/well), incubated in a 37° C. incubator and visually scored after five days in an inverted microscope, by noting the wells that appear to have colonies that arose from a single cell (one colony/well). These wells were screened by ELISA to identify clones that are producing antibody directed against α.

The 12 candidate positive clones were expanded into 24 well plates and recreened by ELISA. These were expanded further into duplicate wells in a 24 well plate and then grown in 100 mm dishes and supernatant was collected. Cells were frozen away in 2×10$^6$ cell aliquots in 95% FBS +5% DMSO) and stored in a liquid nitrogen freezer.

3) ELISA Assay of an Ammonium Sulfate Fraction

In general, large asymmetric complexes are relatively insoluble in ammonium sulfate. Ammonium sulfate fractionation provides a 50-fold purification of the *E. coli* Pol III holoenzyme. A low ammonium sulfate cut of *T. thermophilus* extracts was used to provide a source of protein enriched sufficiently in Pol III that an ELISA assay could be used to screen 12 monoclonal antibodies directed against the *E. coli* Pol III α subunit to determine if they cross-reacted with a *T. thermophilus* protein. The ammonium sulfate fraction was prepared by addition of 0.246 g ammonium sulfate to each ml of Fraction I using the same approach as described for the preparation of Fraction II in the pol III preparation described under Methods. For the ELISA screening assay, all manipulations were conducted at room temperature. Into each well of a 96-well microtiter plate (Corning Costar High Binding EIA/RIA) was placed 4 μg protein in 150 μl Buffer E7 (10 mM Tris-HCl (pH 7.5), 150 mM NaCl, 0.05% Tween-20). After an overnight incubation, each well was blocked by incubation with buffer E7+10 μg/ml BSA for 3 h, followed by 3 washes with Buffer E7 containing 10 mg/ml BSA and the addition of 150 μl of hybridoma supernatant, incubated for 3.5 hours. Wells were then washed 3 times with Buffer E7 and once with an equivalent buffer that had been adjusted to pH 8.8 (Buffer E8). Then, 150 μl of a 1:3000 dilution of goat anti-mouse IgG antibody-alkaline phosphatase conjugate (BioRad) was added and incubated for 1 hour. Wells were washed 3 times with Buffer E7, once with Buffer E8 and developed in the presence of p-nitrophenyl phosphate for 10 min. Absorbance was read at 405. Monoclonal antibodies produced from hybridoma lines C1950-F3 and C1104-H2 (Enzyco) gave an absorbance of 0.17 and 0.16 respectively; on average, all other candidate monoclonal supernatants gave an absorbance of 0.06. Equal volumes of both supernatants were combined for future work.

In addition, 40 μg of the 0.246 ammonium sulfate fraction of *T. thermophilus* FrI was subjected to the Western Blotting procedure described below. A band migrating with the same mobility as the α subunit of Pol III of *E. coli* was detected.

These data demonstrated that Fraction II of *T. thermophilus* contained an α subunit of DNA polymerase III, and that a mixture of monoclonal antibodies from hybridoma cell lines C1950-F3 and C1104-H2 is capable of detecting the *T. thermophilus* DNA polymerase III α subunit. These data also demonstrated that the ammonium sulfate precipitations were optimized to provide a nearly quantitative precipitation of the candidate *T. thermophilus* α subunit (as judged by Western blots) while removing as much contaminating protein as possible (Fraction II; Table 1).

D. Cation Exchange Chromatography

Having established that a roughly 130 kDa protein cross-reacted with anti-*E. coli* α monoclonals, a lysis procedure and ammonium sulfate fractionation that partially purified the α subunit were optimized.

A BioRex 70 cation exchange chromatography step was developed that resolved polymerase activity from the majority of contaminating protein. Fraction II was resuspended in 100 ml buffer U (50 mM imidazole-HCl (pH 6.8), 20% glycerol, 35 mM ammonium sulfate, 1 mM magnesium acetate, 0.1 mM zinc sulfate, 5 mM 1-mercaptoethanol, 0.1 mM ATP) and dialyzed twice successively versus 2 L buffer U. Dialysate was applied to a 300 ml BioRex 70 (BioRad, 100–200 mesh, 5.5 cm diameter) column equilibrated in buffer U and washed with 0.9 l buffer U. Activity was eluted with a 1.5 l 0→300 mM NaCl gradient in buffer U. All gradient-eluted fractions containing greater than 20,000 units of gap-filling polymerase activity/ml were pooled, constituting Fraction III (Table 1).

Figure 2A:
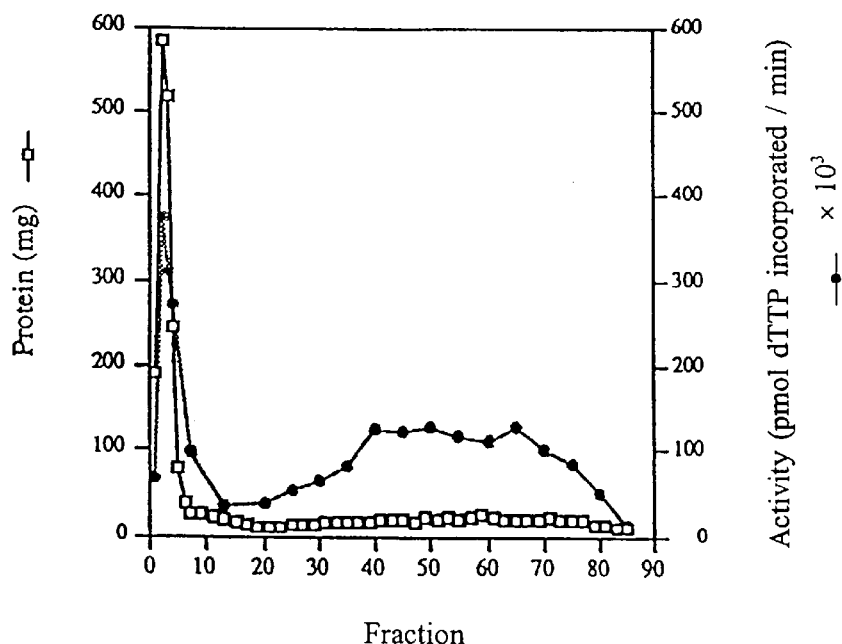
FIG. 2 shows the elution profile of Fraction II applied to a cation-exchange BioRex-70 column. Fraction II prepared from (A) 2.4 kg cells, and (B) 300 g of cells was applied at fraction I in both A and B.

FIG. 2 shows the column profile of protein, and DNA polymerase activity. Fractions 20–80 in FIG. 2A which contained bound DNA polymerase activity were pooled to generate Fraction III. Ammonium sulfate solution saturated at 4° C. was added to 50% (v/v), and centrifuged at 23,000×g for 60 min at 4° C. to obtain a precipitate.

Figure 2B:
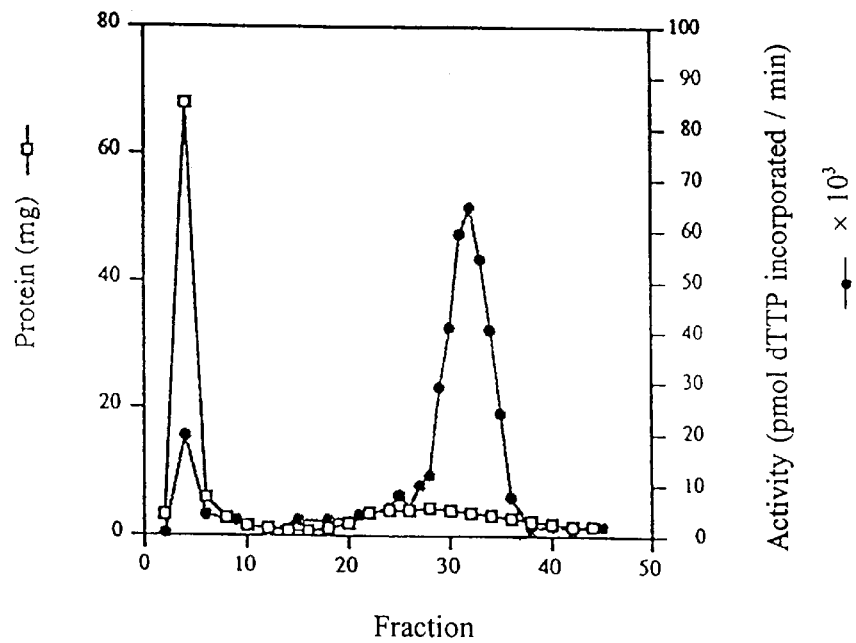

Although the BioRex-70 column separated a large amount of contaminating protein from the polymerase activity and resulted in enrichment of the polymerase fraction, it did not resolve different polymerases, since it did not resolve the Pol III antibody reactive fraction from the majority of polymerase activity. Nevertheless, a 25-fold increase in gap-filling polymerase specific activity was achieved (Fraction III, Table 1). Resolution of different DNA polymerase activities was achieved by hydrophobic interaction chromatography as described below. FIG. 2A shows the results from one column run, while FIG. 2B shows the results from another column run. Although the results are not completely reproducible, these Figures show that the DNA polymerase preparation was enriched by the BioRex-70 column.

E. Hydrophobic Chromatography

*E. coli* Pol III holoenzyme binds tightly to hydrophobic columns (McHenry and Kornberg, J. Biol. Chem., 252:6478–6484 [1977]). Thus, hydrophobic interaction chromatography was attempted to resolve *T. thermophilus* Pol III from the smaller and, presumably, more hydrophilic DNA polymerase I-like activity.

Figure 3:
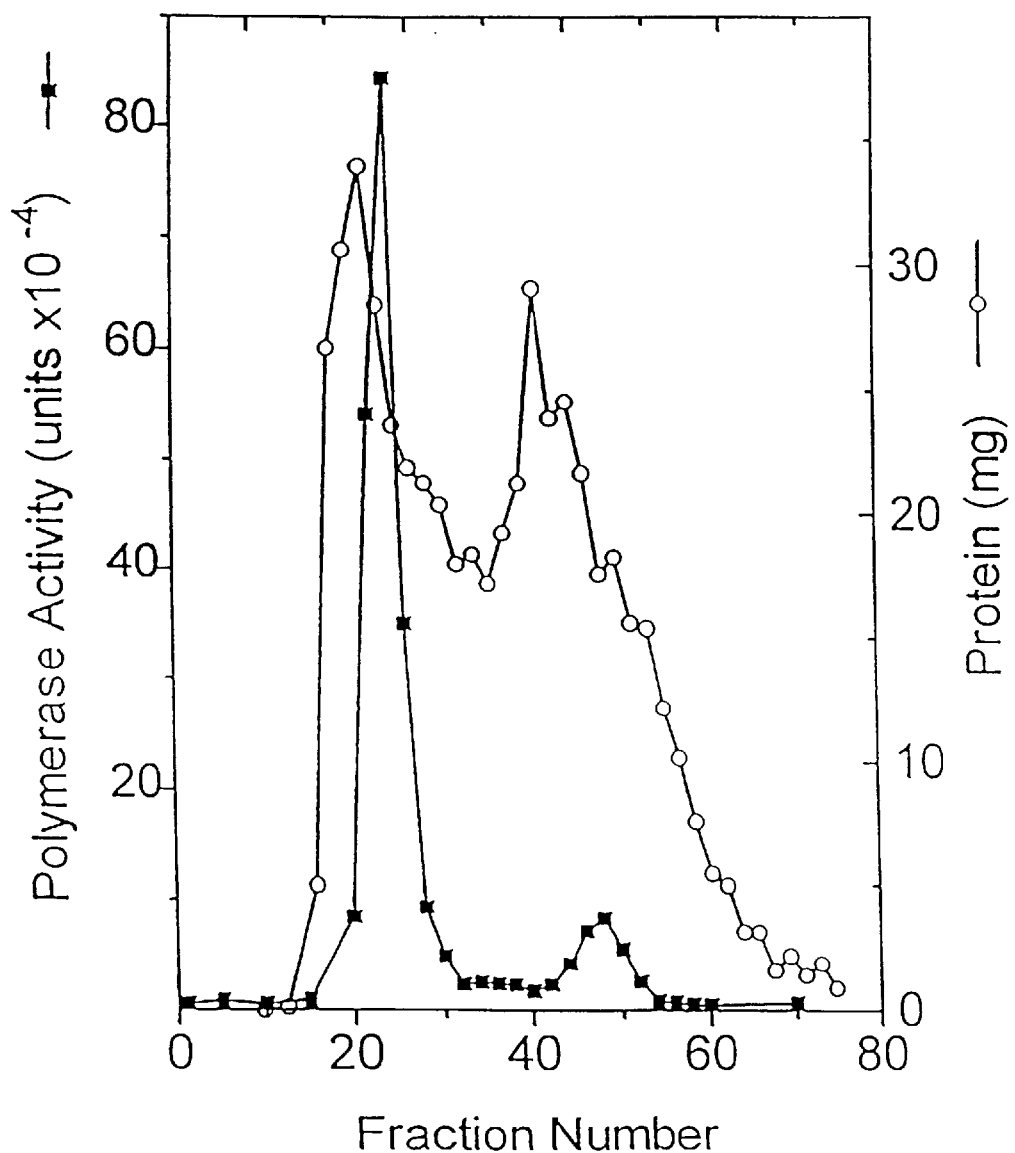
FIG. 3 shows the elution profile of Fraction III applied to a hydrophobic ToyoPearl-Ether 65-M column to separate the majority of T. thermophilus DNA polymerase form Pol III.

Hydrophobic interaction chromatography was used to resolve a unique polymerase that cross-reacted with antibody directed against *E. coli* Pol III cc subunit. Fraction III protein was precipitated by the addition of an equal volume of saturated ammonium sulfate and the pellet was collected by centrifugation 23,000×g, 1 h, 4 °C.). The pellet was dissolved in 40 ml buffer U, and 20 ml ToyoPearl-Ether 650M (Toso Haas) equilibrated in buffer U and 1.6 M ammonium sulfate was added. To the stirred suspension was added (dropwise) 33.6 ml 4 M ammonium sulfate and the entire mixture was applied to an 80 ml ToyoPearl-Ether column (3.5 cm diameter) equilibrated in buffer U with 1.6 M ammonium sulfate. The column was washed with 80 ml buffer U +1.1 M ammonium sulfate and polymerase activity eluted with a 1.5 1 1.1→0.3 M ammonium sulfate gradient in buffer U (FIG. 3). Fractions containing polymerase activity were subjected to the Western Blotting procedure. The second peak (fractions 45–50) that contained polymerase activity and reacted with monoclonal antibodies against *E. coli* Pol III α subunit was pooled, constituting Fraction IV (120 ml, Table 1, FIG. 3). Fractions were assayed for gap-filling polymerase activity as described above and for protein content using the Coomassie Protein Assay Reagent (Pierce) with BSA used as a standard.

FIG. 3 shows a profile of the hydrophobic column chromatography. Protein (open circles) and gap-filling polymerase activity (filled squares) were plotted against fraction numbers. The gap-filling assay revealed 2 peaks of polymerase activity, with the first peak eluting between fraction numbers 20–30, and the second peak eluting between fraction numbers 45–50. The major *T. thermophilus* DNA polymerase peak eluted early in the gradient, and did not react with anti-α monoclonal antibodies. The second peak, a minor peak comprising approximately 9% of the polymerase activity, bound more tightly to the column (Fraction IV, Table 1).

F. Western Blotting and Identification of Proteins Cross Reactive with Monoclonal Antibody Against *T. thermophilus* DNA Polymerase III Subunit α

In order to determine whether the fractions which eluted from the hydrophobic chromatography column contained *T. thermophilus* DNA polymerase III a subunit, fractions containing DNA polymerase activity as determined by the gap filling assay (described in Example 1) were further analyzed by Western blotting using monoclonal antibodies which were specific for *T. thermophilus* DNA polymerase III a subunit (described above). The following steps were carried out at room temperature unless otherwise indicated.

Aliquots of column fractions (50 μl) were subjected to electrophoresis on a 10% SDS-PAGE. Proteins were then transferred from the gel to a PVDF membrane (BioRad). The transfer buffer contained 25 mM Tris, 192 mM glycine, and 20% methanol, and was adjusted to pH 8.5 by the addition of HCl. Transfer was conducted for 2 h at 70V (0.7 A). The membrane was then washed in 10 mM Tris-HCl (pH 7.5), 150 mM NaCl, 0.05% Tween-20 followed by incubation for 1 h in the same buffer with 5% dried milk. The blot was then incubated overnight with C1950-F3, C1104 H2 hybridoma supernatant (Enzyco), washed (3-times) in 100 ml buffer TBS containing 0.5% Tween-20, incubated for 1 hour with a 1:2000 dilution of goat anti-mouse IgG alkaline phosphatase conjugate (BioRad) in buffer TBS containing 0.5% dried milk, washed (3-times) in 100 ml buffer TBS containing 0.5% Tween-20, and washed once in 100 ml buffer P (100 mM Tris-HCl (pH 9.5), 100 mM NaCl, 5 mM $MgCl_2$). The membrane was developed by incubating in a 1:150 dilution of a GIBCO nitroblue tetrazolium stock solution and a 1:300 dilution of a 5-bromo-4-chloro-3-indoyl phosphate stock solution in buffer B, until the ax band reached the desired intensity. The development of color was stopped by washing the membrane in water.

Figure 4:
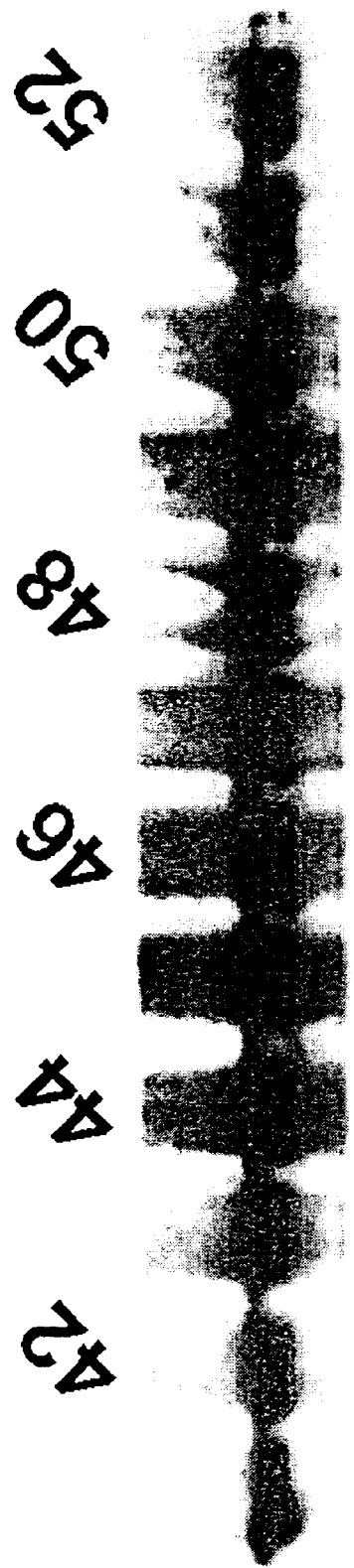
FIG. 4 shows a Western blot of ToyoPearl-Ether fractions 41–52 developed monoclonal antibodies specific for E. coli DNA polymerase III a subunit.

FIG. 4 shows the results of the SDS-PAGE/Western blot analysis for fractions 41–52. Lane numbers 41–52 contained ToyoPearl-Ether column fractions 41–52. Western blot analysis showed that the second peak (fractions 45–50) contained protein molecules with a molecular weight of approximately 130 kDa which cross-reacted with antibodies from cell lines C1950-F3 and C1104-H2 raised against the a subunit of *E. coli* DNA polymerase III holoenzyme (FIG. 4).

FIG. 4 shows that the cross-reactive 130 kDa band eluted with an intensity parallel to the polymerase activity in the second peak. This demonstrates that the second peak of activity contained a Pol III-like polymerase, which is distinct from the characterized *T. thermophilus* DNA polymerase. This is in contrast to fractions 20–30 in the first peak which did not result in detectable binding to *E. coli* DNA polymerase III antibody. Fractions 45–50 were used to generate Fraction IV (stored at 4° C.).

G. Anion Exchange Chromatography

To provide a higher level of purification, and to enable direct examination of the components, an additional chromatographic step was developed. One-half of Fraction IV was combined with an equal volume of saturated ammonium sulfate (4° C.) and the resulting precipitate collected by centrifugation and redissolved in 4 ml buffer U, and dialyzed overnight versus 250 ml buffer U (one buffer change). The dialysate was then applied to a 5 ml Q-Sepharose fast flow column (1.4 cm diameter) and equilibrated in buffer U. The column was washed with 15 ml buffer U, and the polymerase activity was eluted with a 75 ml 0→275 mM NaCl gradient in buffer U. A contaminating protein was found to elute toward the end of the activity peak; thus, fractions were carefully selected for pooling based on purity. All fractions that contained greater than 50 μg protein and a specific activity greater than 104,000, were pooled (Fraction 28–36) to yield Fraction V (25 ml, Table 1, FIG. 5). Fractions (1.5 ml each) were collected and assayed for polymerase activity using the gap-filling assay described above, and for conductivity using a Radiometer CDM83 conductivity meter on samples diluted 1:100 in distilled water equilibrated to room temperature. Standards were also run in parallel.

Figure 5:
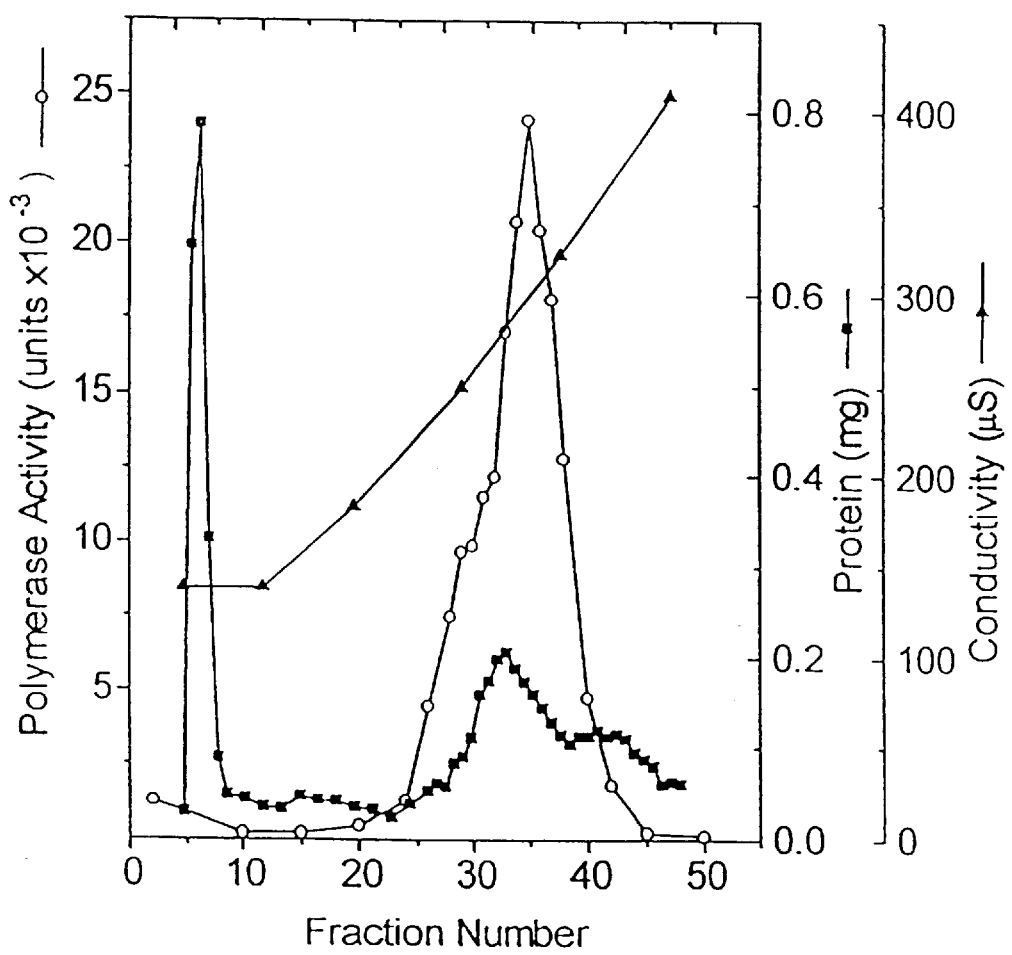
FIG. 5 shows the elution profile of Fraction IV applied to an anion exchange Q-Sepharose Fast Flow column. Fraction IV was applied at fraction 1.

FIG. 5 shows polymerase activity (open circles), protein (filled squares) and conductivity (filled triangles) across the column fractions. Chromatography on Q-Sepharose yielded a single peak of polymerase activity between fractions 28–40, and a 6-fold increase in specific activity (FIG. 5, Fraction V; Table 1).

Figure 6:
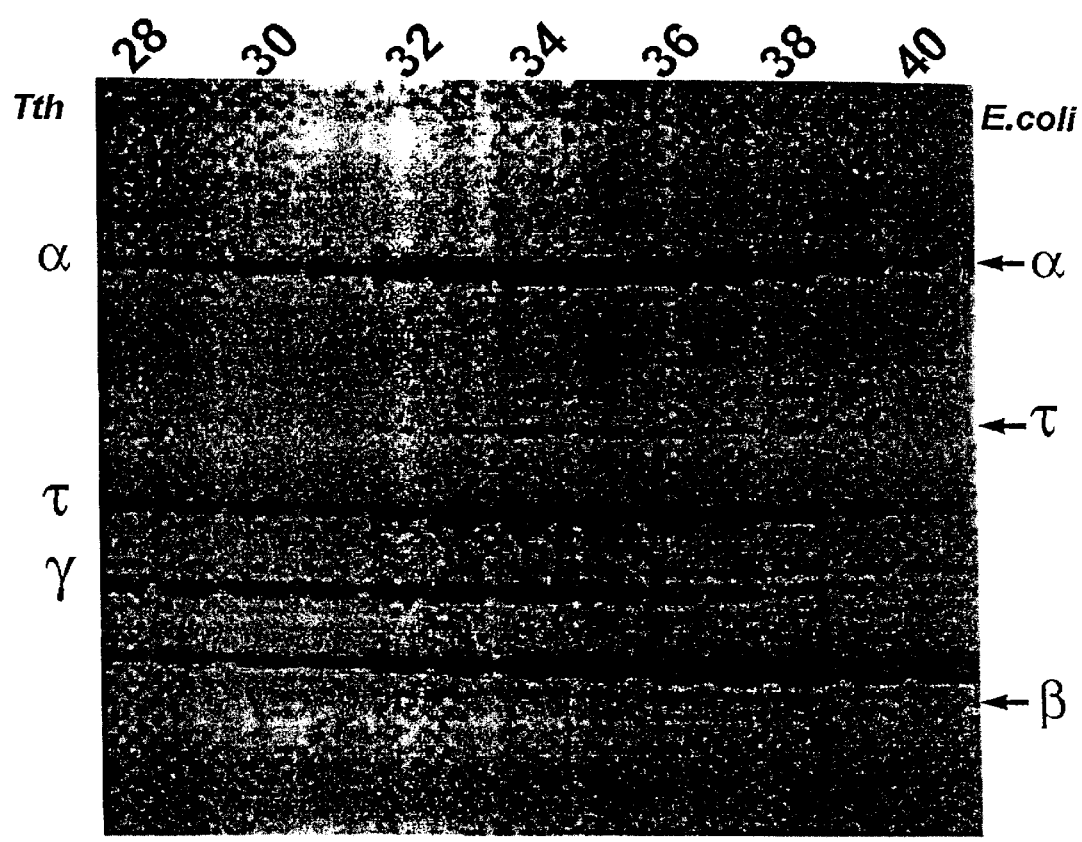
FIG. 6 shows a Coomassie blue-stained SDS-polyacrylamide gel containing Q-Sepharose fractions 28–40.

Samples (10 μl) of fractions 28–40 across the polymerase activity peak were analyzed by SDS-PAGE (10%). The Coomassie blue-stained gel is shown in FIG. 6. The migration position of the *E. coli* DNA polymerase III holoenzyme (Enzyco) subunits α(130 k), T (71.1 k) and P (40.5 k) are indicated with arrows on the right hand side of the gel (FIG. 6). A 130 kDa protein eluted in parallel to the activity profile (FIG. 6). A 43 kDa protein eluted later and did not parallel the eluted activity; this protein is presumably a contaminant. Two additional proteins of 63±6 and 50±5 kDa eluted roughly in parallel with the 130 kDa protein, providing candidates for polymerase III-associated proteins, possible subunits of a *T. thermophilus* Pol III holoenzyme. The candidate α and two apparently comigrating proteins of 63 kDa and 50 kDa comprised approximately 50% of the protein resolved on an SDS gel. The 63 kDa protein chromatographed in parallel with the polymerase. The 50 kDa protein was more strongly represented toward the early portion of the peak. These data suggest that the 63 kDa and 50 kDa bands correspond to the *T. thermophilus* τ and γ subunits, respectively.

Rigorous quantitation of the extent of purification of *T. thermophilus* polymerase III was not possible since the gap-filling assay used was not specific for the polymerase III holoenzyme. However, it is estimated that the *T. thermophilus* polymerase III was purified approximately 50,000-fold, assuming all of the DNA polymerase III activity was recovered in Fraction II and it represented 10% of the Fr II polymerase activity. The specific activity of purified *T. thermophilus* Pol III in Fraction V was 800,000 units/mg at 60° C. The specific activity of pure *E. coli* Pol III is known to be $2.5 \times 10^6$ at 30° C. (Kim and McHenry, J. Biol. Chem., 271:20681– 20689 [1996]). Thus, after correction for the mass of contaminants and the associated r and y proteins, the expected specific activity of *T. thermophilus* pol III core was estimated to be approximately $2 \times 10^6$ (ie., close to the activity of its *E. coli* counterpart when compared at temperatures slightly below their optimal growth temperature).

Fractions containing the highest polymerase specific activity (28–36) as determined from the gap-filling polymerase activity profile of FIG. 5 were pooled (Fraction V) and solid ammonium sulfate was added to 75% (w/v).

H. Enzyme Activity of *T. thermophilus* Fraction V as a Function of Temperature

Figure 7:
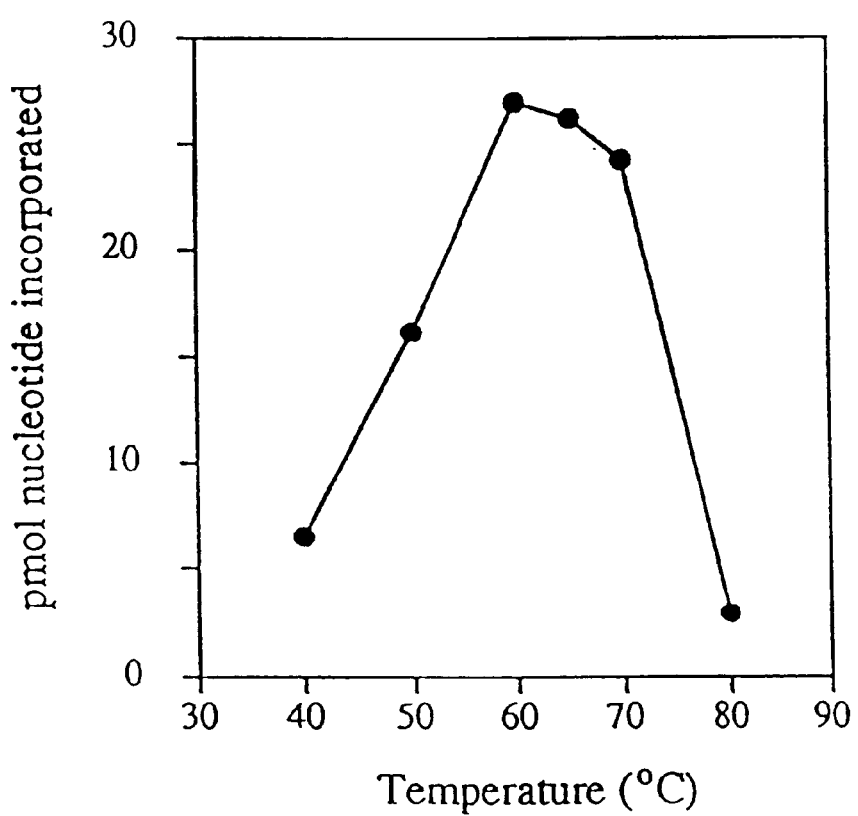
FIG. 7 shows the DNA polymerase gap-filling activity of T. thermophilus Fraction V at different temperatures.

In order to determine the stability of the *T. thermophilus* DNA polymerase III Fraction V, the DNA polymerase activity of the purified *T. thermophilus* DNA polymerase Fraction V was measured as a function of temperature. Polymerase activity was measured using the gap-filling assay described above with the exceptions that the incubation temperature was at selected temperatures between 37° C. to 80° C. and 0.14 μg of Fraction V protein. Polymerase activity (pmol TTP incorporated in 5 minutes) was plotted against the reaction temperature (FIG. 7). The results shown in FIG. 7 demonstrate that the gap-filling activity of the purified DNA polymerase complex (Fraction V) has a broad temperature optimum between 60–70° C.

EXAMPLE 3

Amino Acid Sequencing of the Purified *T. thermophilus* DNA Polymerase III τ and γ Proteins The τ and γ subunits of *E. coli* DNA polymerase III holoenzyme are both encoded by the same gene, dnax. The y subunit (47.4 kDa) arises as a result of translational frameshifting which yields a truncated version of the r (71.0 kDa) subunit. Both proteins have identical amino acid sequences at the N-terminus.

The SDS-PAGE analysis of the Q-Sepharose eluant (described in Example 2 and FIG. 6) showed that at least 2 other proteins of 63 kDa and 50 kDa, eluted together with the *T. thermophilus* a subunit. These molecular weights correspond closely to those of the τ and γ subunits of the *E. coli* DNA polymerase III holoenzyme. To confirm that the 63 kDa and 50 kDa proteins which co-eluted with the *T. thermophilus* a subunit corresponded to the r and y subunits of a DNA polymerase III holoenzyme, the 63 and 50 kDa proteins were subjected to N-terminal amino and internal amino acid sequence analysis as follows.

For N-terminal amino acid analysis, 120 μg of Fraction V was fractionated by SDS-PAGE (10%) and transferred to a Hyperbond PVDF membrane as described above. The protein bands at 50 kDa and 63 kDa were excised and subjected to N-terminal amino acid sequencing in an 477 Protein Sequence according to the manufacturer's (ABS, Inc.) instructions. The sequence (SEQ ID NO: 1) of the 19 N-terminal amino acids of the 50 kDa *T. thermophilus* protein was identical to the first 19 residues of the 20-amino acid sequence (SEQ ID NO: 2) obtained for the 63 kDa protein (i.e., this is consistent with both being the product of the same gene) (See, FIG. 8). The sequenced regions were 67% identical to the homologous 18-residue *E. coli* DnaX sequence (SEQ ID NO: 3), the only bacterial DnaX protein that has been directly characterized on the basis of activity, and 74% identical to the homologous 19-residue sequence within *B. subtilis* DnaX (SEQ ID NO: 4). In FIG. 8, homologous regions are also indicated (SEQ ID NOS: 5 and 6) between the T thermophilus, *E. coli*, and *B. subtilis* sequences.

The association of a *T. thermophilus* DnaX homolog with a protein that cross reacts with anti-pol III a monoclonal antibodies and which has the same molecular weight as the *E. coli* pol III a subunit in a 50% pure protein preparation establishes the existence of a multi-subunit Pol III holoenzyme in *T. thermophilus*. Furthermore, the results demonstrate that the 63 and 50 kDa proteins are the *T. thermophilus* τ and γ subunits of Pol III holoenzyme.

In addition, the 63 kDa band was blotted and treated with Lys-C as described above and an internal peptide was sequenced to yield the sequence ARLLPLAQAHFGVEE-WLVLEGE (SEQ ID NO: 88). This peptide did not exhibit detectable homology (i.e., no hits were identified in a BLAST search of the entire NR database) with known DnaX sequences), but was important for confirming the correctness of the DNA sequence of the *Thermus thermophilus* dnaX gene in subsequent experiments described below.

EXAMPLE 4

Cloning and Sequencing The *T. thermophilus* dnaX Gene

In order to determine whether the 63 kDa and 50 kDa proteins are products of the *T. thermophilus* dnaX gene, the structural genes were isolated by a reverse genetics approach using PCR to obtain a fragment of the gene. The gene fragment was used as a probe to obtain the full length of *T. thermophilus* dnaX, enabling its full sequence to be determined. From the N-terminal sequence, a peptide was selected, FQEWGQ (SEQ ID NO: 89), that would provide a PCR primer with the least degeneracy with all possible codons represented (512-fold). To provide an internal primer, a KTLEEP (SEQ ID NO: 90) amino acid sequence common to *E. coli, B. subtilis* (Carter et al., J. Bacteriol., 175:3812–3822 [1993]); and O'Donnell et al., Nuc. Acids Res. 21:1–3 [1993]) and many other eubacteria was exploited. From this consensus sequence a 17-mer primer with 256-fold degeneracy was designed that included all possible combinations of codons. A PCR fragment of the predicted size (388 nucleotides) was obtained. This fragment was close to the spacing of the corresponding regions in the *E. coli* dnaX gene (393 nucleotides). The PCR fragment was also highly homologous to dnaX genes in the fragment between the regions corresponding to the PCR primers, eliminating the bias imposed by primer selection. The PCR-generated probe led to the isolation to a full length gene (FIG. 9A) that is highly homologous to other eubacterial dnaX genes. The deduced amino acid sequence was 42% identical to the corresponding segment of the *B. subtilis* dnaX gene. These steps are discussed in detail below.

This example involved (A) Preparation of *T. thermophilus* genomic DNA; (B) Isolation of *T. thermophilus* dnaX probe by PCR; (C) Cloning PCR-amplified dnaX probe; (D) Restriction enzyme digestion of *T. thermophilus* genomic DNA; (E) Southern blotting; (F) Cloning the 7.1 kb PstI fragment; and (G) Colony hybridization and sequencing dnax.

A. Preparation of *T. thermophilus* Genomic DNA

*Thermus thermophilus* strain pMAF.kat (obtained from J. Berenguer; See, Lase et al, [1992]) genomic DNA was prepared using previously described methods (Ausubel FM et al., *Current Protocols in Molecular Biology*, John Wiley & Sons, New York NY [1995]). Briefly, *T. thermophilus* strain pMAF.kat was grown overnight at 70° C. from a single colony in 100 ml of Thermus rich media (8 g/l Bacto-tryptone (Difco), 4 g/l yeast extract (Difco), 3 g/l NaCl (Fisher Scientific) (pH 7.5) with vigorous shaking in a New Brunswick Model G25 incubator. The culture was centrifuged in a 250 ml centrifuge bottle in a Sorvall GSA rotor at 6000 rpm (5858×g) for 6 minutes, followed by resuspension of the pellet from a 100 ml overnight culture in 9.5 ml TE buffer (pH 7.5) in an SS34 centrifuge tube (Sorvall). 0.5 ml 10% SDS and 50 μl of fungal proteinase K (20 mg/ml in dH$_2$O) (GibcoBRL) was mixed with the suspension, the mixture was incubated at 37° C. for 1 h, followed by addition of 2.35 ml of 4M NaCl (Fisher Scientific), and 1.6 ml of cetyltrimethylammonium bromide (CTAB)/NaCl solution (10% CTAB in 0.7 M NaCl). The resulting mixture was incubated at 65° C. for 20 minutes followed by extraction with an equal volume of chloroform/isoamyl alcohol (30:1 mixture). The mixture was centrifuged in an SS34 rotor (Sorvall) for 10 minutes at 6000×g, 0.6 volumes of isopropanol (Fisher) was added to the pellet to form a stringy, white precipitate. The stringy white precipitate was placed into 25 ml 75% ethanol, centrifuged for 5 minutes at 10,000×g and the supernatant discarded. The pellet was resuspended in 4 ml of TE buffer (pH 7.5), the DNA concentration measured by determining the absorbance at a wavelength of 260 nm in a spectrophotometer, and the DNA concentration adjusted to 100 μg/ml with TE (pH 7.5). 4.3 g of cesium chloride (CsCl) (Sigma cat. # C-4036) and 200 μl of ethidium bromide (10 mg/ml) were added per 4 ml of TE (pH 7.5) used to resuspend the DNA pellet. The mixture was centrifuged in a Sorvall T-1270 rotor in a Sorvall RC70B ultracentrifuge at 55,000 rpm, at 15° C. overnight. The chromosomal DNA band (highlighted with UV light) was removed, the ethidium bromide extracted by adding an equal volume of H$_2$O saturated butanol, mixing thoroughly by inverting the tube, and briefly centrifuging the tube (30 seconds at 14,000 g) to separate the phases. The butanol extraction was repeated until pink color could not be detected, and then the extraction was repeated one more time. The remaining DNA/cesium chloride/TE (pH 7.5) mixture was dialyzed overnight in 500×volume of TE (pH 7.5) to remove the cesium chloride. DNA was precipitated by the addition of 1/10 volume of 2.5 M sodium acetate (pH adjusted to 5.2 with glacial acetic acid) and 1 volume of isopropanol, and centrifugation at 11,951×g for 10 minutes. The pellet was washed with 75% ethanol and centrifuged at 11,951×g for 2 minutes. The supernatant was removed, and the wash repeated. After the final wash, the supernatant was removed and the pellet allowed to dry until it became slightly translucent. The pellet was resuspended in 25 ml of TE (pH 7.5) by gentle rocking overnight at room temperature. DNA was quantitated by spectrophotometry by taking a spectrum of wavelengths from 220 nm to 340 nm. Two preparations were obtained. Preparation A diluted 1/70 in TE buffer gave an OD$_{260}$ of 0.175 consistent with a DNA concentration of 0.612 mg/ml using as a conversion factor A$_{260}$=1=50 μg/ml. Preparation B, with a DNA concentration of 0.906.

B. Isolation of *T. thermophilus* dnaX Probe by PCR

An amino-terminal peptide sequence of *T. thermophilus* that showed homology to DnaX from *E. coli*, *B. subtilis*, and *H. influenza* was used to design oligonucleotide primers which hybridized to the amino-terminal region of the putative *T. thermophilus* dnaX. Two oligonucleotide primers (X1Fa & X1Fb) were designed from the N-terminal peptide sequence to keep codon degeneracy at 512-fold. To design primers for regions located downstream from the N-terminal, conserved regions in DnaX were identified by comparing known sequences from bacteria and bacteriophage. These conserved regions were used to design primers that, with the amino terminal primer, could be used to amplify a portion of the *T. thermophilus* dnaX gene by PCR.

A sequence which was homologous to DnaX from *E. coli*, *B. subtilis*, and *H. influenza* had the sequence Ser Ala Leu Tyr Arg Arg Phe Arg Pro Leu Thr Phe Gln Glu Val Val Gly Gln Glu (SEQ ID NO: 102). The underlined amino acids were chosen for designing an oligonucleotide primer in order to give a primer of sufficient length with minimal degeneracy. The N-terminal primers were 20-mers with 512-fold degeneracy, ie., forward primer (X1Fa) [5'-TTY CAR GAR GTN GTN GGW CA-3' (SEQ ID NO: 21)] and forward primer (X1FB) [5'-TTY CAR GAR GTN GTN GGS CA-3' (SEQ ID NO: 91)].

The conserved DnaX amino acid sequences for design of reverse primer X126R were as follows:

| | | | | | | | | | | | | | | |
|---|---|---|---|---|---|---|---|---|---|---|---|---|---|---|
| *E. coli* | K | V | Y | L | I | D | E | V | H | M | L | S | R | H | S | F |
| *B. subtilis* | K | V | Y | L | I | D | E | V | H | M | L | S | I | G | A | F |
| *H. influenzae* | K | V | Y | L | I | D | E | V | H | M | L | S | R | H | S | F |
| 40 kDa subunit (human RFC) | K | I | I | I | L | D | E | A | D | S | M | T | D | G | A | Q |
| Consensus | | | | | | D | E | A/V | H | M | L | | | | | |

These above sequences correspond to SEQ ID NOS: 92–96. The 17-mer, 128-fold degeneracy reverse primer (X126R) had the sequence 5'-ARC ATR TGN RCY TCR TC-3' (SEQ ID NO: 97).

The conserved DnaX amino acid sequences for design of reverse primer X139R were as follows:

| E. coli | S | F | N | A | L | L | K | T | L | E | E | P | P | E | H | V |
|---|---|---|---|---|---|---|---|---|---|---|---|---|---|---|---|---|
| B. subtilis | A | F | N | A | L | L | K | T | L | E | E | P | P | E | H | C |
| H. influenzae | A | F | N | A | L | L | K | T | L | E | E | P | P | E | Y | V |
| Consensus | | | | | | | K | T | L | E | E | P | | | | |

The above sequences correspond to SEQ ID NOS: 98–101. The 17-mer, 256-fold degeneracy reverse primer (X139R) had the sequence 5'-GGY TCY TCN ARN GTY TT-3' (SEQ ID NO: 22).

For PCR reactions, the Boehringer Mannheim Expand™ long template PCR system was used and following the manufacturer's recommendations except as noted in the following. Reactions were conducted in Boehringer Expand™ buffer 1 supplemented with 0.5 mM extra $Mg^{++}$. The annealing steps were conducted at 48° C., elongation at 68° C. and the melting step at 94° C.; 26 total cycles were run. Products were separated on 2% FMC Metaphor agarose gels, visualized by Sybr green-1 staining, extracted and cloned into vector pCRII (Invitrogen).

Six $\mu l$ of gel loading dye was added to each 30 $\mu l$ PCR reaction described above. Thirty $\mu l$ of this mixture was loaded into wells of a 2% Metaphor gel in 1×TAE and subjected to gel electrophoresis at 250 volts for 4 hours.

Using the dnaX primers X1Fa and X139R, and *T. thermophilus* chromosomal DNA preparation A, approximately 10 bands were observed that ranged in size from 350 bp to greater than 1500 bp. Half of these bands were of equal or greater intensity than a band observed at 392 bp as estimated from the gel. Subsequent cloning and sequencing (described below) of the 392 bp gel band showed that this band was 388 bp.

Using dnaX primers X1Fa and X126R, approximately 18 bands were observed which ranged in size from 100 bp to greater than 1500 bp. Approximately half of the bands were of equal or greater size than the desired 357 bp band. A 329 bp band was selected for cloning as described below.

With the dnaX primers X1Fb and X126R, approximately 15 bands were observed. These included a band that migrated to the same position as the above described 329 bp product from X1Fa and X126R.

With the X1Fb and X139R primers, approximately 20 bands were observed, with one band at approximately 420 bp appearing near the desired product. However, since the 392 bp product from the X1Fa and X139R primer pair appeared more promising, the 420 bp product was not further pursued.

A plasmid isolate (pMGC/1FA-139A; DMSO 1327) containing an EcoRI fragment of the predicted size based upon the distance between the homologous region of the *E. coli* dnaX gene (approximately 393 bases) was sequenced (FIG. 10). In FIG. 10A, the sequences corresponding to primers are underlined. The DNA sequence shown in FIG. 10A is the complement of the message strand. The sequence shown is of relatively low quality (i.e., approximately 90% estimated accuracy), yet a BLAST search revealed strong homology to bacterial dnaX genes. *B. subtilis* (shown in the lower line of the alignment of FIG. 10B), showed 42% identity over a 71 amino acid stretch. In FIG. 10B, the upper peptide sequence is T thermophilus. For, *B. subtilis* the numbers refer to DnaX amino acid residues; numbers for *T. thermophilus* refer to the first base of the anticodon for the shown amino acid residue with base #1 being assigned to the C to the left of the corresponding primer sequence near the 3' end of the sequence shown (FIG. 10A).

C. Cloning PCR-Amplified dnaX Probe

PCR-amplified DNA which contained regions encoding the T and y subunits of *T. thermophilus* DNA polymerase III was cloned into a modified pCRII vector (Invitrogen) which was used to transform DH5a *E. coli*, and the plasmids containing the PCR-amplified DNA were analyzed by DNA sequencing. These steps are described in more detail in the following sections.

1. Cloning of PCR-Amplified DNA Into *E. coli*

PCR-amplified sequences were extracted from gel slices prepared as described above using freeze-squeeze extraction. Extraction was performed by placing the gel slice in a sterile micro-spin device (0.45 mm pore size cellulose acetate filter (LSPI) that was then inserted into a 2.0 ml Eppendorf tube and the assembly was placed in a −80° C. freezer for 10 minutes. The following steps were performed at room temperature. The frozen gel slice was then centrifuged in the micro-spin assembly for 4 minutes at maximum rpm in a microcentrifuge (14,000×g). The crushed gel slice was then resuspended in 100 $\mu l$ of 2.5 M Na Acetate, re-frozen for 10 minutes at −80° C., and centrifuged as before. The liquid containing the gel slice DNA was collected in the bottom of the Eppendorf tube (approximately 300 $\mu l$) and the DNA was precipitated by the addition of 1 $\mu l$ glycogen (Boehringer Mannheim) and an equal volume (300 $\mu l$) of isopropanol. The precipitate mixture was centrifuged (14,000×g) in a microcentrifuge for 10 minutes, the supernatant discarded, and the pellet washed with 75% ethanol. The ethanol wash supernatant was discarded, and the pellet was resuspended in 5 $\mu l$ TE (pH 7.5). The DNA was quantitated by adding 1 $\mu l$ of DNA to 300 $\mu l$ of a 1/400 dilution in TE (pH 7.5) of PicoGreen™ (Molecular Probes) in a well of a 96-well microtiter plate (Life Sciences), and compared to known concentrations of Thermus thermophilus genomic DNA by excitation on an SLT Fluostar Microplate Fluorometer of the PicoGreen™ at 480 nm and measuring emission at 520 nm.

DNA that PCR-amplified by the Expand High Fidelity enzyme mix had a I nucleotide addition (dATP) that allows a compatible cohesive annealing to a vector (pCRII vector, Invitrogen) with a 1 nucleotide T overhang. Fifty or 150 pmoles of PCR amplified DNA was added to 50 pmoles of vector DNA in a 10 $\mu l$ reaction mixture containing 1 $\mu l$ of 10× Ligation Buffer (Invitrogen), 1 $\mu l$ of T4 DNA ligase (1 Weiss unit/l, GibcoBRL), and sterile $dH_2O$ to bring the volume to 10 $\mu l$. Ligation was carried out at 14° C. overnight. The DNA in the ligation mixture was precipitated by the addition of 1 $\mu l$ of glycogen (20 mg/ml, Molecular Biology Grade, Boehringer Mannheim), 1/10 volume (1 $\mu l$) 2.5 M sodium acetate (pH 5.2), and 2.5 volumes of ethanol. The precipitate was recovered by centrifugation at 14,000×g for 10 minutes, the supernatant was removed, and the pellet washed with 0.3 ml of 75% ethanol. The washed pellet was re-centrifuged at 14,000×g for 2 minutes, the supernatant removed completely with a fine tipped pipet, and the pellet was resuspended in 5 μl of dH$_2$O. The DNA was used to transform electrocompetent DH5a E. coli by electroporation as described below.

Electrocompetent DH5a E. coli cells were prepared by picking an isolated colony of DH5a (Gibco-BRL) and growing overnight in 10 ml SOP media. 1 ml of overnight culture was added to 500 mL SOP media, grown to an OD$_{600}$ reading of 0.6–0.8. The culture was placed immediately in an ice water bath to chill rapidly and left on ice for least 15 min. The following steps were carried out in the cold room at 4° C. Cells were centrifuged at 4000 rpm for 15 min, washed with 500 mL ice cold dH$_2$O and allowed to sit on ice for 30 min. before spinning down in 500 mL centrifuge bottles at 4000 rpm for 15 min. The pellet was washed with 500 ml ice cold dH$_2$O, spun down in 500 mL centrifuge bottles at 4000 rpm for 15 min. and the pellet resuspended in 20 mL 10% glycerol. The cells were spun down in a 50 mL tube at 5000 rpm for 10 min., resuspended in approximately 0.5 mL 10% glycerol, and 0.2 mL aliquots of competent cell preparation frozen quickly in 1.7 μL centrifuge tubes by placing in liquid nitrogen, then storing at -80° C.

For electroporation, electrocompetent cells were transformed as follows. Cells were removed from the -80° C. freezer and thawed on ice. 40 μl of electrocompetent cells were placed into a 1.5 ml Eppendorf tube (pre-chilled for at least 5 minutes on ice) and 2 μl of the dH$_2$O re-suspended ligated DNA (ligated DNA+5 μl H$_2$O) was added and allowed to sit for 5 minutes. The transformation mixture was removed from the 1.5 ml Eppendorf tube and added to pre-chilled electroporation cuvettes (0.2 cm electrode gap, BioRad). The electroporation was performed in an Eppendorf Electroporator 2510 at 2500 V. Then, 1 ml of SOP media was immediately added to the cuvette following electroporation, and the electroporated cells in SOP media were transferred to a capped tube and incubated for 1 h with shaking at 37° C. After 1 hour, aliquots of 2×200 μl, 1×50 μl, and 1×5 μl were plated by spreading onto LB plates containing carbenicillin (50 μg/ml), and incubated overnight at 37° C. in a convection heat incubator.

2. Large Scale Plasmid Purification

Large scale plasmid purification was performed in order to obtain enough DNA for sequencing, restriction digestion, etc. Large scale (i.e., 50 ml) plasmid purification was performed using Qiagen plasmid preps (Qiagen, Chatsworth, Calif.). An isolated E. coli colony was picked from an LB-carbenicillin (70 μg/ml) plate and grown overnight in 50 ml of SOP media. The culture was centrifuged at 12,000×g in a Sorvall SS34 rotor for 10 minutes in a 50 ml polypropylene tube. The supernatant was discarded. The pellet was resuspended in 4 ml Buffer P1 (50 mM Tris (pH 8.0), 10 mM EDTA, 100 μg/ml Rnase A). 4 ml of Buffer P2 (200 mM NaOH, 1% SDS) was added, mixed gently by inverting the tube 4 to 6 times, and the mixture incubated at room temperature for 5 min. 4 ml of chilled Buffer P3 (3.0 M potassium acetate (pH 5.5)) was added, mixed immediately but gently, the mixture incubated on ice for 15 min., centrifuged at approximately 20,000 g for 30 min at 4° C. and the supernatant removed promptly. The supernatant was centrifuged at approximately 20,000×g for 15 min at 4° C., and the resulting supernatant promptly removed and applied to a Qiagen-tip 100 (Quiagen) which had been previously equilibrated by applying to the resin 4 ml of buffer QBT (750 mM NaCl, 50 mM MOPS (pH 7.0), 15% ethanol, 0.15% Triton X-100). The supernatant was allowed to flow through the resin under gravity. The Qiagen-tip 100 was washed with 2×10 ml of Buffer QC (1.0 M NaCl, 50 mM MOPS (pH 7.0), 15% ethanol), and the DNA eluted with 5 ml Buffer QF (1.25 M NaCl, 50 mM Tris-HCl (pH 8.5), 15% ethanol). The eluate was collected in a 12 ml centrifuge tube and the DNA precipitated with 0.7 volumes of isopropanol at room-temperature, and centrifuged immediately at approximately 15,000×g for 30 min at 4° C. The DNA pellet was washed with 2 ml of 70% ethanol, air-dried for 5 min, and re-dissolved in 500 Ill of dH$_2$O. DNA was quantitated by spectrophotometry over the optical range of 220 nm to 340 nm by blanking against 700 μl dH$_2$O followed by the addition 10 μl of DNA into the 700 μl dH$_2$O for the measurement. The ratio of OD at 260 nm to OD at 280 nm was between 1.8 and 2.0. Typically, 5 μg was obtained from a 50 ml culture. The above procedure was used when plasmids were sequenced or used for further cloning steps. The alternative DNA preparation method provided herein was used just for screening methods.

D. Restriction Enzyme Digestion of T. thermophilus Genomic DNA

Since a large probe that was identical to the gene had been prepared, a directed approach was used to clone the full length T. thermophilus dnaX rather than screening of a full library. A Southern blot against digested T. thermophilus DNA was performed in order to detect a restriction fragment that was large enough to contain the entire T. thermophilus dnaX gene. This fragment was extracted, cloned, and the resulting colonies were screened by colony hybridization and a candidate clone selected for sequencing. These steps are described as follows.

Restriction endonuclease digests of Thermus thermophilus DNA were carried out in order to run the resulting digests on agarose gels and to blot for Southern analysis using PCR-amplified fragments which had been cloned in E. coli as described above. Restriction digestion was carried out at 37° C. overnight in a 100 μl reaction volume containing 20 μl of genomic DNA (18 jig preparation B chromosomal DNA), 10 pi 10× restriction endonuclease buffer (NEB), 5 Ill restriction endonuclease (25 to 50 Units) (NEB), and 65 μl dH$_2$O. An additional 5 μl of restriction endonuclease was then added and the mixture incubated at 37° C. for an additional 2 hours. The digest was precipitated with 1 μl glycogen (20mg/ml, Boehringer Mannheim), 1/10 volume 2.5 M sodium acetate (pH 5.2), 3 volumes of ethanol and centrifuged for 30 minutes at 14,000×g. The supernatant was removed and the pellet washed with 0.5 ml 75% ethanol prior to resuspension of the pellet in 40 μl TE (pH 7.5).

The prepared genomic DNA was run on agarose gels together with 60,000 cpm of $^{32}$p end-labelled DNA Molecular Weight Marker VII (Boehringer Mannheim) and 1.75 μg (7 μl) of DNA Molecular Weight Marker VII (Boehringer Mannheim). End-labeled molecular weight markers were prepared by incubating an end-labeling reaction mixture [8 μl of DNA Molecular Weight Standard (2 μg, Boehringer Mannheim), 8 μl dH$_2$, 3 μl 0.5M Tris (pH 7.5), 0.3 μl 1M MgCl$_2$, 0.3 μl 1M DTT, 1 μl (2 units/l), 1.5 μl 1.5 mM each of dCTP, dGTP, and dTTP, 8 μl $^{32}$P-dATP (80 μCi, 3000 Ci/mmole in 5 mM Tris-HCl (pH 7.5), for 1 hour at 37° C. To this mixture was added 2 μl glycogen (20 mg/ml, Boehringer Mannheim), 1/10 volume 2.5 M sodium acetate (pH 5.2) with glacial acetic acid, 3 volumes of ethanol and the resulting mixture was centrifuged in a microcentrifuge at 14,000×g for 5 minutes, the supernatant discarded and the pellet washed with 400 μl of ethanol. The pellet was resuspend in 50 μl TE (pH 7.5), 1 μl was spotted onto a 24 mm diameter GF/C filter (Whatman), the filter paper dried, and counted with 5 ml scintillation fluid in a scintillation counter, yielding DNA of approximately $10^8$ cpm/μg.

To 10 μl of digested genomic DNA (3 μg) was added 2 μl of gel loading dye and the mixture run on a 0.7% Seakem GTG (FMC) agarose gel in 1× TAE for 14.2 hours, at room temperature, at 35 V constant voltage. The gels were stained for 1 h with gentle rocking with Sybr green in 1× TAE.

E. Southern Blotting

Southern blotting of *T. thermophilus* genomic DNA with PCR-amplified probes was performed by linking genomic DNA to a positively charged nylon membrane for colony and plaque hybridization (Boehringer Mannheim) using an alkaline transfer buffer as previously described (Ausubel F M et al. [1995] supra). Briefly, the gel was rinsed with distilled water, and the gel gently shaken with 10 gel volumes of 0.4 M NaOH on a platform shaker for 20 min. The positively charged nylon membrane was placed without prewetting directly onto the gel and alkaline transfer was carried out in 0.4 M NaOH. Since alkaline transfer is quicker than high-salt transfer, the blot could be taken apart any time after 2 h, but the blot was generally performed overnight. The membrane was rinsed in 2×SSPE, and allowed to air dry in order to remove agarose fragments that may adhere to the membrane and to neutralize the membrane. The membrane filters were baked at 80° C. in a vacuum oven and were ready to use for hybridization with a labeled probe.

1. Preparation of Probe

Probe DNA was prepared from vectors (pCRII, Invitrogen) containing genomic DNA segments which encode portions of subunits of the *Thermus thermophilus* DNA polymerase III holoenzyme subunits, as described above. The gene segments were released from the vector by digestion of 10 μg of the cloned DNA's in a 300 μl reaction with EcoRI (100 Units, Gibco BRL) in 1× Boehringer Mannheim High Salt restriction digest buffer H at 37° C. for 2 hours 60 II of gel loading dye was added to each digest, the entire 360 μl digest was loaded into 260×1.5 mm wells, and the digests were electrophoresed in 4% NuSieve GTG agarose (FMC) in 1×TAE buffer, and the gel was run at 100 V (constant voltage) for 4 hours. The gel was stained with 300 ml Sybr green (Molecular Probes, diluted 1/10,000 in 1×TAE) for 1 h with gentle rocking. Bands containing the gene fragments were excised with a clean scalpel, placed into a tared 4 ml Nunc tube (Nunc 4.5 ml Cryotube, NUNC), and the bands were weighed. The slices were melted by putting the tubes in a gravity convection incubator at 72° C. for 30 minutes or until the slice was completely melted. Once melted the tubes were cooled to 45° C. in a temperature block and 1/10 volume of 10× β-agarase buffer (Gibco BRL; 100 mM Bis-Tris (pH 6.5), 10 mM EDTA) was added, followed by the addition of 4 μl of β-Agarase (GibcoBRL, 1 unit/μl). The mixture was incubated overnight in a gravity convection incubator at 42° C. To precipitate the DNA, 1/10 vol. of 3 M NaOAc (pH 5.2), was added and the mixture chilled on ice. Any remaining undigested agarose was removed by centrifugation for 2 minutes in 2 ml Eppendorf tubes at 14,000×g in an Eppendorf microcentrifuge. The supernatant was removed and the DNA precipitated by the addition of 1 ml glycogen (Boehringer Mannheim, molecular biology grade, 20 mg/ml) and 2.5 volumes of ethanol, followed by centrifugation at 14,000×g in an Eppendorf microcentrifuge for 10 minutes. The supernatant was removed and the pellet washed with 0.5 ml of 75% ethanol and centrifuged at 14,000×g in an Eppendorf microcentrifuge for 2 minutes. The pellets were resuspended in 10 μl of a 1/10 dilution of TE (1 mM Tris (pH 7.5), 0.1 mM EDTA final concentration). The DNA was quantitated by adding 1 μl of DNA to 300 PI of a 1/400 dilution of PicoGreen™ in a well of a 96-well microtiter plate (Life Sciences), and compared to known concentrations of Thermus thermophilus genomic DNA by excitation of the PicoGreen™ at 480 nm and measuring emission at 520 nm, on an SLT Fluostar Microplate Fluorometer.

2. Labelling of Probe

The probe was labeled by adding 50 ng of DNA to a random hexamer priming reaction mixture (Random Primed DNA Labeling Kit, Boehringer Mannheim) following the manufacture's instructions. Briefly, 50 ng DNA in 10 Pi dH$_2$O was placed into a 0.2 ml thin-walled PCR tube, overlaid with 25 pi mineral oil and the DNA denatured by heating at 95° C. for 10 minutes in a thermal cycler (MJ Research). At 9 minutes through the 10 minute denaturation, 2 μl of Boehringer Mannheim hexanucleotide reaction mix (tube 6 in kit) was added and the denaturation continued for an additional minute. Just prior to the end of the 10 minute denaturation, the mixture was rapidly cooled by removing the tube from the thermal cycler and immediately placing it in a beaker of ice-water. One μl each of dATP, dTTP, dGTP (0.5 mM in Tris buffer, final concentration 25 FM) was added to the reaction, followed by 5 μl of $^{\alpha32}$P-dCTP (50 μCi, 3000 Ci/mmole, in 5 mM Tris-HCl (pH 7.5)), and 1 μl of Klenow DNA polymerase (Boehringer Mannheim, 2 units/el in 50% glycerol), and the mixture was incubated at 37° C. in a water bath for 1 h.

3. Removing Unincorporated Label

The unincorporated label was removed using the PCR Clean-up Kit (Boehringer Mannheim). Briefly, the 20 μl reaction was removed from the mineral oil overlay with a fine-tipped micropipette and the volume adjusted to 100 μl with TE (7.5) in a 0.5 ml Eppendorf tube. 400 l of the nucleic acid binding buffer was added to the DNA along with 10 μl of the silica suspension mix. The mixture was incubated for 10 minutes at room temperature with frequent vortexing. The mixture was centrifuged for 30 seconds in a microcentrifuge and the supernatant discarded. The matrix containing the DNA was resuspended with 400 μl of nucleic acid binding buffer by vortexing. The mixture was centrifuged and the supernatant discarded as before. The pellet was washed with 400 μl of washing buffer, centrifuged and the supernatant discarded as before. This step was repeated once more. After the final spin the pellet was re-centrifuged and any remnants of supernatant were removed with a fine-tipped micropipette. The pellet was allowed to dry at room temperature for 15 minutes. The DNA was eluted from the silica matrix by the addition of TE (10 mM Tris (pH 8.4), 1 mM EDTA) and incubation at 65° C. for 10 minutes with occasional vortexing After centrifugation for 2 minutes at maximum speed in the microcentrifuge, the supernatant was removed to a clean tube and the silica matrix was again re-suspended in 100 II dH$_2$O. The elution procedure was repeated and the supernatant combined with the first supernatant to give a final volume of 200 μl. It was then determined that $2 \times 10^7$ cpm was incorporated. The estimated specific activity of the DNA is 1089 cpm/μg.

4. Hybridization

Membranes with bound *Thermus thermophilus* DNA were blocked by incubation with 50 ml blocking fluid (50% formamide, 5×SSPE (20×SSPE comprises 3 M NaCl, 200 mM NaH$_2$PO$_4$, 0.02 M Na$_2$EDTA adjusted to pH 7.4 with NaOH), 1% SDS, and a 1/20 dilution of milk solution (10% skim milk dissolved in dH$_2$O, 0.2% sodium azide)) at 42° C. for at least 2 h in a hybridization bag with spout (Boehringer Mannheim, cat#1666 649). Two ill of the labelled probe was spotted onto 2.4 cm diameter circle GFC filters, placed in 5 ml of scintillation fluid in a scintillation tube, and counted in a scintillation counter. The specific activity of the probe should be around $1 \times 10^9$ cpm/g DNA.

The blocking fluid was replaced with 20 ml of fresh blocking buffer fluid. The labeled probe (200 μl as described above in section 3; $1-3 \times 10^7$ cpm) was denatured by the addition of ⅕ volume (40 μl) of 0.2 N NaOH and the mixture was incubated at room temperature for 10 minutes. The denatured probe was added to the hybridization bag. Neutralization of this mixture to allow hybridization was accomplished by the addition of ⅕ volume (40 μl) of 2 M Tris-HCl (pH unadjusted). The hybridization mixture was incubated at 42° C. with rocking overnight. The filters were washed at least 3×100 ml each in the bag with 2×SSPE, 0.1% SDS, and placed in a pyrex dish with 500 ml of 0.1×SSPE, 0.1% SDS pre-heated to 42° C. for 30 minutes. This wash was repeated 1 more time and the filters were air dried, and exposed to Kodak X-OMAT film or exposed to a phosphorimager plate (Molecular Dynamics) and viewed in a phosphorimager (Molecular Dynamics).

Using as a probe the cloned fragment amplified with dnaX 1Fa and X1Fb primers, Southern blot hybridization showed a 7.1 kb band with genomic DNA digested with PstI. The results of these experiments were 1) The probe hybridized to a 7.1 kb PstI band made by digestion of (22.5 μg of Preparation B chromosomal DNA with 10 μl PstI (100 units), in 25 μl NEB Buffer 3 (NEB) and 190 μl H₂O, overnight at 37° C.; and an 8.5 kb band hybridized to the HindIII digest (22.5 μg of Preparation B chromosomal DNA digested with 10 μl HindIII (100 units) in 25 μl NEB Buffer 2 (NEB) and 190 μl H₂O, overnight at 37° C.

F. Cloning The 7.1 kb PstI Fragment

PstI-digests of *T. thermophilus* genomic DNA were prepared in order to clone large restriction fragments of a size which was expected to contain the full length T thermophilus dnaX gene. The restriction fragments were cloned into a modified pCRII vector (pMGC 707), transformed into *E. coli* and cells containing plasmids that carried dnaX encoding sequences complementary to probe were identified by a colony hybridization procedure.

1. PstI-Restriction Enzyme Digestion of *T. thermophilus* Genomic DNA To Prepare the Library A 250 μl restriction digest reaction mixture was prepared by incubating overnight at 37° C. 22.5 μg genomic DNA (Preparation B, prepared as described above), 25 μl of 10× restriction endonuclease buffer, 10 μl PstI (10 units/μl), and 190 μl dH₂O. Fifty μl of gel loading dye was added to the digest, and the entire 300 μl sample was loaded into a 1.5 mm thickness×4.3 cm well in a 0.7% SeaPlaque low melt agarose at 45V constant voltage overnight at 4° C. with the DNA Molecular Weight Standards VII (Boehringer Mannheim). The dye front was run until it had reached ⅔ the length of the gel, the gel was stained in Sybr green in 1×TAE for 1 h with gentle shaking. A gel slice that contained at least 2 mm on either side of the region corresponding to a 7.1 kb fragment was excised with a clean scalpel.

The DNA was recovered from the gel by incubating the gel slice at 72° C. in a convection heat incubator for 30 minutes or until the gel slice was completely melted. The melted gel slice was placed into a tube which was inserted into a 45° C. temperature block and allowed to cool for 5 minutes. Then, ¹⁄₁₀ volume of 10×β-agarase buffer was added along with 4 μl of β-agarase (1 unit/el, GibcoBRL) per 200 μl of volume. Digestion was carried out at 42° C. overnight in a convection heat incubator and the sample was precipitated by adding 1 μl glycogen (20 mg/ml, Boehringer Mannheim), ¹⁄₁₀ volume of 2.5 M sodium acetate (pH 5.2) with glacial acetic acid, and 1 volume of isopropanol. The precipitate was centrifuged at 14,000×g for 15 minutes and the supernatant discarded. The pellet was washed once with 1 ml of 75% ethanol, the pellet centrifuged at 14,000×g for 2 minutes and the supernatant discarded. The pellet was resuspended in 10 μl of millQ de-ionized H₂O.

2. Cloning dnaX PstI Fragment into pMGC707

A 7.1 kb fragment that hybridized with the partial dnaX probe generated by PCR was extracted and cloned into vector pMGC707. pMGC707 was prepared by cutting pCRII (Invitrogen) with SpeI and NotI and inserting a polylinker resulting from the annealing oligonucleotides (5' GGCCGCAATTGCACGCGTTCGAATTC-CATGACGTCTTCCAGTGCACTGGTTAATTA) (SEQ ID NO: 103) and (5° CTAGTTAATTAACCAGTGCACTG-GAAGACGTCATGGAATTCGAACGCGTG CAATTG) (SEQ ID NO: 104). The polylinker region of the resulting plasmid was cleaved with BstXI to generate PstI compatible termini to receive the extracted 7.1 kb population of fragments. As BstXI does not itself give Pst-compatible termini, this vector was designed so that it would give PstI compatible termini.

Vector pMGC707 was cut with BstXI, and gel purified to remove the small digestion product. The cut pMGC707 was ligated with a PstI restriction fragment of genomic digest prepared as described above, in a 20 μl Ligation Reaction [2 μl vector DNA (100 ng), 2 μl insert DNA (1000 ng), 2 μl of 10× ligation buffer (Invitrogen), 1 μl ligase (GibcoBRL, 3 units/μl), and 13 μl dH₂O] by incubating for 1 h at room temperature and overnight at 14° C. The reaction mixture was precipitated with 1 μl glycogen (20 mg/ml, Boehringer Mannheim), ¹⁄₁₀ volume of 2.5M sodium acetate (pH 5.2), and 3 volumes ethanol, and washed once with 1 ml 75% ethanol. The resulting plasmids were used to transform DH5α *E. coli* by electroporation as described supra. Electroporated cells were incubated for 1 h prior to selection overnight on LB plates containing carbenicillin (50 μg/ml) at 37° C. in a convection heat incubator. Transformed cells which grew on carbenicillin-containing plates were ready for colony hybridization to detect the presence of sequences encoding *T. thermophilus* DNA polymerase III holoenzyme subunits. (i.e., "DNA polymerase III holoenzyme" refers to the whole entity, while "DNA polymerase III" is just the core [α, ε, θ]).

G. Colony Hybridization And Sequencing of *T. thermophilus* dnaX

Colonies were screened by colony hybridization (Ausubel et al. [1995] supra) using the *T. thermophilus* dnaX PCR-generated probe. Plasmid from positive colonies were purified and those containing 7.1 kb inserts and also a BamHI site as indicated from the sequence of the PCR probe were retained for further characterization. One was submitted for full DNA sequencing (Lark Sequencing Technologies, Houston, Tex.), resulting in the sequence of the full length gene. These steps are elaborated in detail below.

1. Preparation of Replica Filters Containing Transformed Colonies

Replica filters were prepared by filter-to-filter contact with a master filter. A master filter was prepared by placing a sterile dry nylon membrane filter for colony and plaque hybridization (Boehringer Mannheim) onto a one day-old LB agar plate containing carbenicillin (50 μg/ml; Gibco-BRL). The bacteria were applied in a small volume of liquid (<0.8 ml, containing up to 20,000 bacteria for a 137-mm filter; <0.4 ml, containing up to 10,000 bacteria for an 82-mm filter), and spread over the surface of the filter leaving a border 2–3 mm wide at the edge of the filter free of bacteria. The plates were allowed to stand at room temperature until all of the liquid had been absorbed. The plates were inverted and incubated at 37° C. until very small colonies (0.1-mm diameter) appeared (about 8–10 hours) on the filter.

Using sterile, blunt-ended forceps (e.g, Millipore forceps), the master filter was gently removed from the first plate and placed on a stack of sterile MC filter paper colony side up. The second, wetted filter was placed on top of the master filter, being careful not to move filters once contact has been made. The filters were pressed together using sterile blotting paper and by applying pressure to a 140 mm petri-dish lid placed on top of the sterile blotting paper. Before filters were peeled apart, 3 to 11 holes were poked through the wedded filters with an 18 gauge hypodermic needle around the perimeter of the filters to aid in orienting the master and replica filters with respect to each other. The filters were gently peeled apart and the filter replica returned to an LB-agar-carbenicillin plate, colony side up, while the master filter was placed back onto an LB-agar-carbenicillin plate.

The plates (containing master filter and replica filter) were incubated at 37° C. until colonies 1–2 mm in diameter appeared. Colonies on the master plate reached the desired size more rapidly (6–8 hours). At this stage, while the bacteria were still growing rapidly, the replica filters were transferred to agar plates containing chloramphenicol (170–250 µg/ml) and incubated for a further 8 hours at 37° C. The chloramphenicol plate does not allow growth of the bacterial cell but the plasmid in the cell continues to replicate giving a better signal when the DNA from the colonies is hybridized. The master plates were sealed with parafilm and stored at 4° C. in an inverted position until the results of the hybridization reaction were available. Bacteria on the replica filters were lysed and the liberated DNA bound to the replica filters for subsequent hybridization as follows.

2. Lysis And Binding Liberated DNA To Filters

Using blunt-ended forceps (e.g, Millipore forceps), the replica nylon membrane filter was peeled from the plate and placed for 3 minutes, colony side up, on MC filter paper impregnated with 10% SDS. The filter was transferred to a second sheet of MC paper that had been saturated with denaturing solution (0.5 M NaOH, 1.5 M NaCl) and left for 5 minutes, then to a third sheet of MC paper that had been saturated with neutralizing solution (1.5 M NaCl, 0.5 M Tris•Cl (pH 8.0)) and left for 5 minutes. The filter was allowed to dry, colony side up, at room temperature on a sheet of dry MC paper for 30–60 minutes. The dried filter was sandwiched between two sheets of dry MC paper and baked for 2 hours at 80° C. in a vacuum oven prior to hybridization to a $^{32}$P-labeled probe. Colony hybridization with a probe demonstrates that the colony contained plasmids with inserts which contained sequences of *T. thermophilus* DNA that were complementary to the probe.

The hybridization was performed as described for Southern blots. One to two filters were placed in a hybridization bag. If two filters were placed in the bag, the filters were placed back-to-back with the filter surfaces that had not come into contact with the colonies against each other. After completion of the hybridization procedure, the filters were air-dried at least one hour, and the filters were marked with a small dab phosphorescent paint over each of the needle holes. When the filters are exposed to X-ray film, the phosphorescent paint produces a dark spot on the X-ray film that can be used to align the X-ray image with the master filter to identify specific *E. coli* containing plasmids that hybridize to the probe.

The hybridized filters were taped to a piece of Whatman 3 MM paper with Scotch brand Magic tape and the taped filters and Whatman 3MM paper covered with plastic wrap to prevent contamination of the film cassette. In the darkroom, the filters were placed in an X-ray film cassette with an intensifying screen and Kodak XR Omat X-ray film was placed over the top and the cassette sealed. The cassette was placed in a black garbage bag and sealed with tape to act as a secondary barrier to light exposure of the film. The bag was placed overnight at −80° C. for exposure of the film.

The film was developed by removing the film in the darkroom, and dipping the film into Kodak developing solution for 3 minutes, followed by a 23 minute soak in cool tap water, and finished by soaking for 3 minutes in fixer (all developing reagents used were Kodak). The film was then rinsed with tap water and allowed to air dry for 15 to 30 minutes.

To align the film with the master filter, the developed X-ray film was placed on a white light box and covered with Plastic wrap. The master filter was identified by the number and orientation of the black spots on the film that aligned with the holes poked in the master filter. The master filter was then carefully removed from the agar plate with sterile forceps and placed on the plastic wrap covered X-ray film to line up the darkened spots on the film with the holes in the master filter. Dark spots on the film were correlated to colonies on the filter, and colonies were picked and struck with a sterile toothpick to LB-agar plates containing carbenicillin at 150 µg/ml.

Isolated colonies from each streak were grown and plasmid isolated as described previously (Promega). For dnaX, 4 strongly hybridizing colonies on one filter from the HindIII 8.4 to 8.6 Kb fragment clones were chosen for plasmid preparations. Four colonies each from 3 separate filters from the PstI 7.1 Kb fragment clones, (12 total PstI clones) were selected for plasmid preparations. The plasmid DNA from HindIII and PstI clones was digested with BamHI restriction endonuclease as previously described, and only 1 colony, designated "pAX2-S," showed evidence of an insert. The BamHI digest was repeated on pAX2-S clone, and the restriction pattern gave bands that were roughly estimated against the VII DNA molecular weight standards as 6 Kb, 2 Kb, 1.9 Kb, 0.8 Kb. The addition of these fragments gave a plasmid size of around 10.7 Kb, roughly the size of plasmid that would be expected from a 7.1 Kb insert into pMGC707. BamHI restriction endonuclease digests were used because sequence data from the dnaX partial clone obtained by PCR described previously indicated the presence of a BamHI site. This clone was verified to be dnaX by sequencing.

3. Restriction Digestion of Clones

In order to confirm the presence of inserts in the plasmids which had been identified as "positives" by colony hybridization, the plasmids were purified and analyzed by restriction enzyme digestion.

a. Plasmid Purification

Plasmid was prepared and purified from 1–3 ml bacterial culture. Plasmid preparation was performed using a Promega Plus Miniprep technique (Promega). Briefly, 1–3 ml of bacterial cell culture was centrifuged for 1–2 minutes at 10,000×g in a microcentrifuge, the supernatant poured off and the tube blotted upside-down on a paper towel to remove excess media. The cell pellet was completely resuspended in 200 µl of Cell Resuspension Solution (Promega, A71 1E) (50 mM Tris (pH 7.5); 10 mM EDTA; 100 µg/ml RNase A). 200 µl of Cell Lysis Solution (Promega, A712E) (0.2M NaOH and 1% SDS) was added and mixed by inverting the tube 4 times followed by the addition of 200 µl of Neutralization Solution (Promega, A713J) (1.32M potassium acetate) and mixing by inverting the tube 4 times. The lysate was centrifuged at 10,000×g in a microcentrifuge for 5 minutes. If a pellet has not formed by the end of the centrifugation, centrifugation was carried out for an additional 15 minutes.

The plasmid preparation was purified using a vacuum manifold by using ProMega Plus Minipreps (Promega, A721C) which can be easily processed simultaneously with Promega's Vac-Man™ or Vac-Man™ Jr. Laboratory Vacuum Manifold. One ProMega Plus Minipreps column was prepared for each miniprep. The ProMega Plus Minipreps resin (Promega, A767C) was thoroughly mixed before removing an aliquot. If crystals or aggregates were present, they were dissolved by warming the resin to 25–37° C. for 10 minutes, then cooling to 30° C. before use. One ml of the resuspended resin was pipetted into each barrel of the Minicolumn/Syringe assembly (i.e., the assembly formed by attaching the Syringe Barrels to the Luer-Lok® extension of each Minicolumn), and all of the cleared lysate from each plasmid preparation was transferred to the barrel of the Minicolumn/Syringe assembly containing the resin. A vacuum was applied to pull the resin/lysate mix into the Minicolumn until all of the sample has completely passed though the column. Extended incubation of the resin and lysate was not necessary since at the concentration of plasmid present in most lysates, plasmid binding to the resin was immediate. 320 ml of 95% ethanol was added to the Column Wash solution bottle to yield a Column Wash Solution (Promega, A810E) having a final concentration of 80 mM Potassium acetate, 8.3 mM Tris-HCl (pH 7.5), 40CM EDTA and 55% ethanol. 2 ml of the Column Wash Solution was added to the Syringe Barrel and the vacuum reapplied to draw the solution though the Minicolumn. The resin was dried by continuing to draw a vacuum for a maximum of 30 seconds after the solution has been pulled though the column. The Minicolumn was transferred to a 1.5 ml microcentrifuge tube and the Minicolumn centrifuged at 10,000×g in a microcentrifuge for 2 minutes to remove any residual Column Wash Solution. The Minicolumn was transferred to a new microcentrifuge tube, and eluted with 50 µl water or TE buffer (elution in TE buffer was not used if the DNA was subsequently used in an enzyme reaction, particularly if the DNA was dilute and if large volumes of the DNA solution were required to be added to a reaction, since EDTA may inhibit some enzymes by chelating magnesium required as a co-factor for activity). DNA was eluted by centrifuging the tube at 10,000×g in a microcentrifuge for 20 seconds. For large plasmids (≧10 kb), water or TE buffer preheated to 65–70° C. was used since it may increase yields. For plasmids >20kb, water or TE buffer preheated to 80° C. was used. Plasmids were eluted as soon as possible off the column since, although DNA remains intact on the Minicolumn for up to 30 minutes. The eluted plasmid DNA was stored in the microcentrifuge tube at 4° C. or -20° C. (50 µl). Typically, the yield was 0.5–2 µg from a 2 ml culture. For plasmids that underwent additional investigation, the process was scaled up, and they were purified using Quiagen's preparation methods.

b. Restriction Digest Analysis of Plasmids

Plasmids were analyzed for the presence of insert by restriction digestion with EcoRI restriction endonuclease. EcoRI restriction sites flank insert DNA in the pCRII vector system. For EcoRI restriction digestion, 5 µl of ProMega Plus Miniprep-isolated plasmid (from 50 µl total) was added to a 10 µl reaction with 1 µl of 10 High Salt reaction buffer (10×H buffer, Boehringer Mannheim), 1 µl of EcoRI restriction endonuclease (10 units/µl, GibcoBRL), and 3 µl of dH$_2$0. The mixture was incubated at 37° C. for 2 hours. 2 µl of 6×gel loading dye was added, and all 12 µl of the reaction and dye were electrophoresed in 0.7% SeaKem GTG agarose (FMC) in 1×TAE for 4 hs at 80 V constant voltage. The presence of a gel band of the expected size confirmed the presence of the insert in the plasmid. Using primers XF1b and X136R, seven colonies were selected for further screening. Six had inserts of approximately the correct size. One (clone A) was selected for sequencing (DMSO 1386, DH5α/pAX2.S). Six colonies were also obtained with the X1Fa-X126R primer pair. The longer X139R-derived sequences were pursued since they were longer.

c. Sequencing and Analysis

Sequencing was performed by Lark Technologies (Houston Tex.) as described below. Standard direction for the use of DyeDeoxy termination reaction kit (Perkin Elmer Applied Biosystems Division, Foster City, Calif.). Base specific fluorescent dyes were used as labels. Some reaction mixtures were modified to contain DMSO to decrease the formation of secondary structure and allow the determination of sequence in regions of high G-C base content. Sequencing reactions were analyzed on 4.75% PAGE by an ABI 373-S using ABI Sequencing Analysis Software version 2.1.2. Data analysis was performed using Sequencer™ 2.1 software (GeneCodes, Ann Arbor, Mich.).

A 2142 bp open reading frame (FIG. 9A) (SEQ ID NO: 7) was detected. Within the candidate open reading frame, GUG (the 186th codon) was identified as the actual initiation codon from the sequence of the amino-terminus since it was immediately followed by the previously determined amino-terminal sequence shown in FIG. 8, and since GUG is occasionally used as an initiation codon in *T. thermophilus*. Methionine amino-peptidases would be expected to cleave off the terminal methionine (Sherman et al., Bioessays 3:27–31 [1985]), revealing serine as determined experimentally. The initiating GTG could only be conclusively identified by use of the amino-terminal sequence of protein purified from *T. thermophilus*. The preceding sequences in the open reading frame are italicized in FIG. 9A. Also in bold and underlined is the AAAAA sequence that, by analogy to *E. coli*, is probably the frameshifting site that permits synthesis of the shorter γ product. The potential stop codons for γ in the +1 (first) and −1 reading frame are underlined. The stop codon for the full length τ translation product is double-underlined.

Alignment of the resulting DNA sequence with the identified *E. coli* dnaX gene and putative homologous genes from other eubacteria revealed a high level of identity in the amino-terminal region of all bacteria, confirming the identity of the isolated gene to be a dnaX homolog (FIG. 9C). To provide the most useful and concise presentation, only examples from widely divergent organisms are presented in FIG. 9C. The amino acid sequences for the organisms listed from the top are: Tth (*T. thermophilus* Chloroflexaceae/Deinococcaceae group) (SEQ ID NO: 9); E.coli (proteobacteria group, gamma division) (SEQ ID NO: 10), *B.sub.* (*B. subtilis*, firmicute group, low G+C gram-positive bacteria division) (SEQ ID NO: 1 1), Mycopl (*Mycoplasma pneumoniae*, firmicute group, mycoplasma division) (SEQ ID NO: 12), Caulo (*Caulobacter crescentus*, proteobacteria group, alpha division) (SEQ ID NO: 13), Syn.sp. (Synechocystis sp., Cyanobacteria group, (blue green algae) (SEQ ID NO: 14)). Sequences shaded in black are identical among the indicated bacteria; sequences shaded in gray are similar. The consensus sequence is shown in SEQ ID NO: 15.

The deduced amino acid sequence (SEQ ID NO: 8) of the T: thermophilus r subunit is shown in FIG. 9B. The peptide sequences directly determined from the isolated T. thermophilus DnaX-proteins are underlined. A perfect match was observed with the internal peptide sequence obtained from sequencing of the 63 kDa candidate y subunit between residues 428 to 450, further confirming the isolation of the structural gene for the protein associated with T. thermophilus Pol III. The molecular weight of the predicted T. thermophilus T subunit is 58 kDa, in reasonable agreement with the 63±6 kDa determined from SDS PAGE.

In E. coli, the shorter γ product of the dnaX gene is produced by a translational frameshifting mechanism at the sequence A AAA AAG containing two adjacent lysine codons read by the Lys UUU anticodon tRNA. A potential frameshift site that exploits adjacent AAA lys codons flanked by A residues(A AAA AAA A) was observed at codons 451 and 452 (FIG. 9A). Frameshifting into the −1 reading frame at this site would result in a 51 kDa protein, close to the 50 kDa candidate observed in Fraction V (FIG. 9D). If, instead, a +1 frameshift occurred, a 50 kDa protein would be produced, indistinguishable within experimental error from the −1 frameshift alternative.

Every region conserved among other eubacterial dnaX genes is found represented in T. thermophilus dnaX. These sequences include the Walker-type ATP binding site, represented by GVGKTTT (SEQ ID NO: 105) in T. thermophilus dnaX, and highly conserved EIDAAS (SEQ ID NO: 106), and FNALLKTLEEP sequences (SEQ ID NO: 107) (FIG. 9C). The conservation beyond the first 220 residues falls off for all dnaX genes. Thus, the internal peptide sequence obtained that starts at residue 427 (SEQ ID NO: 108; the second underlined sequence in FIG. 9B) was useful in confirming that the sequence was in the correct reading frame and in providing further confirmation of the isolation of the structural gene for the same proteins isolated in association with T. thermophilus pol III.

EXAMPLE 5

Cloning and Sequencing the T. Thermophilus dnaE Gene

The dnaE gene sequence of the T. thermophilus DNA polymerase III was obtained using a PCR amplification approach. In this approach, oligonucleotide primers that could be used for amplifying genomic DNA encoding a portion of the a subunit of Thermus thermophilus were designed using one of two strategies. The first strategy relied on designing PCR primers which hybridized to DNA polymerase III sequences that were homologous among several species of bacteria. However, insufficient homology was observed between diverse bacterial dnaes, rendering this approach problematic.

The second strategy relied on designing PCR primers based on the amino acid sequence information which was obtained by sequencing T. thermophilus DNA III polymerase a subunit which had been partially purified on protein SDS-PAGE gel (as described in Example 3, supra). The designed PCR primers were used to isolate T. thermophilus genomic sequences which encoded T. thermophilus DNA III polymerase subunit a. First, the PCR primers were used to amplify T. thermophilus genomic DNA, and the PCR-amplified sequences were used to create clones which contained dnaE sequences. Second, these clones were used as probes against restriction nuclease digested T. thermophilus DNA in a Southern reaction that would allow isolation and cloning of larger segments of genomic DNA of a size expected to contain the entire coding region of dnaE. Third, downstream sequences were isolated by asymmetric PCR. Fourth, downstream sequences were used to probe X libraries of T. thermophilus chromosomal DNA to isolate full length dnae clones.

This Example involved (A) Partial amino acid sequencing, (B) Isolation of T. thermophilus dnaE probe by PCR amplification of a segment of T. thermophilus dnaE, (C) Cloning PCR-amplified dnaE probe, (D) Southern analysis of T. thermophilus DNA using isolated 1F-91R dnaE probe, (E) Cloning and sequencing of the 5' approximately 1100 bp of T. thermophilus dnaE gene, (F) Isolation of downstream sequences by asymmetric PCR, (G) Southern analysis of T. thermophilus using approximately 300 BspHI/EcoRI dnaE probe isolated from plasmid pB5, (H) Sequencing full-length T. thermophilus dnaE.

As described below, a segment of the T. thermophilus DnaE gene was isolated by PCR and confirmed by DNA sequencing (FIG. 13B shows the estimated sequence for the first 366 amino acids T. thermophilus DnaE (SEQ ID NO: 59). The full-length gene is isolated by using the sequences identified during the development of the present invention to probe lambda T. thermophilus chromosomal DNA libraries, subcloning hybridizing sequences, and confirming their identity by DNA sequencing. The isolated and sequenced full length dnaE gene is engineered to overexpress wild type and N- and C-terminal fusions with a peptide containing a hexahistidine sequence, as well as a biotinylation site. The N- and/or C-terminal fusion proteins are purified and used to obtain T. thermophilus DnaE-specific monoclonal antibodies and fusion proteins.

The fusion proteins are also used to make affinity columns for the isolation of proteins that bind to DnaE alone, and in a complex with the isolated T protein, and/or associated factors of the T. thermophilus DnaX complex. The structural genes for novel proteins identified by this method are isolated, sequenced, expressed, purified and used to determine whether they make contributions to the functional activity of the T. thermophilus DNA polymerase III holoenzyme. Wild type DnaE is purified and used for the reconstitution of DNA polymerase III holoenzyme. In addition, it is developed as an additive to improve the fidelity of thermophilic polymerases that do not contain proofreading exonucleases.

A. Partial Amino Acid Sequencing

The amino acid sequence at the N-terminus and internal amino acid sequences was determined as follows.

1. N-Terminus

An aliquot of Fraction IV containing 500 jig of protein was precipitated by the addition of an equal volume of saturated ammonium sulfate at 4° C., centrifuged at 15,000 rpm at 4° C. in a SS-34 rotor, resuspended in 50 µl Buffer U and dialyzed overnight versus Buffer U at room temperature. The sample was applied to a 5% SDS polyacrylamide tube gel (0.5 cm diameter) and subjected to electrophoresis in an 230A High Performance Electrophoretic Chromatography module (ABS, Inc.). Fractions (25 µl) were collected, aliquots (5 µl), subjected to 7.5% slab SDS-PAGE, and the proteins visualized by silver staining. Fractions containing the highest concentration of 130 kDa protein were pooled, concentrated approximately 30-fold on a Centricon-10 membrane (Amicon) and analyzed by preparative gel electrophoresis on 7.5% SDS-polyacrylamide gels. The gel-fractionated proteins were transferred to a Hyperbond PVDF membrane (Biorad), and the 130 kd protein band excised and subjected to N-terminal amino acid sequence analysis in an 477A Protein Sequencer according to the manufacturer's (ABS, Inc.) instructions. A sequence of 13 amino-acids was obtained: RKLRFAHLHQHTQ (SEQ ID NO: 109). This sequence was aligned with 6/13 residues from the amino terminus M tuberculosis and H. influenzae in a BLAST search, and the alignments are shown in FIG. 11. In this Figure, "M. tuber" refers to *M. tuberculosis*, while "Tth" refers to *T. thermophilus*, and "H. infl." refers to "H. influenzae." The numbers in this Figure indicate the amino acid numbers for the respective residues.

2. Internal Amino Acid Sequence

Internal peptide sequences were determined at the Harvard Microchemistry facility as described above. An aliquot of Fraction V (same as that used in the DnaX Examples) (230 μg) was subjected to electrophoresis on a 10% polyacrylamide gel, and the fractionated proteins transferred to a PVDF membrane (BioRad) as described above, the Ponseau-S stained 130 kDa band was cut out, subjected to digestion by endo Lys-C, and the resultant peptide separated by HPLC. Three peptides were chosen for sequencing (FIG. 11). The peptide sequences aligned with sequences of *E. coli* dnaE. The peptides were named by the first amino acid in *E. coli* that corresponded to the first residue of the *T. thermophilus* peptide. The peptide sequences obtained were 61% identical (peptide #91) (SEQ ID NOS: 31 and 32); 84% identical (peptide #676) (SEQ ID NOS: 34 and 35); and 54% identical (peptide #853) (SEQ ID NOS: 37 and 38). Sequences of homology between these peptides are shown in SEQ ID NOS: 33, 36, and 39, respectively.

B. Isolation Of *T. thermophilus* dnaE Probe By PCR And PCR Amplification of *T. thermophilus* dnaE Primers were selected from the amino-terminal protein sequence that would provide the least degeneracy. Because the order of the sequences was known by their alignment with other eubacterial dnaE sequences, only one primer was made for the extreme amino- and carboxyl sequences, 1F and 853R, respectively. Both forward and reverse primers were made for the internal sequences to enable performing PCR reactions with all possible primer combinations. The peptide sequences selected and the corresponding oligonucleotide probes are summarized in Table 2.

chromosomal DNA preparation A following the manufacturer's recommendations except as noted. Buffer 1 contained 2 μl of 10 mM dNTP mix (Gibco/BRL; 200 μM final); 4 μl of the forward and reverse primers (3 μM initially; 240 nM final in 100 μl reaction); 1 μl of a ⅟30 dilution of *T. thermophilus* genomic DNA (20 ng total), 39 μl distilled H₂0. Buffer 2 contained 10 μl of 10-fold concentrated Boehringer Mannheim Expand HF Buffer with 15 mM MgCl₂, 39 μl H₂O), and 1 μl Expand High Fidelity enzyme mix (mixture of Taq and Pwo DNA Polymerase—3.5 units total). Buffers 1 and 2 were combined in a 0.2 ml thin walled tube (Intermountain) and the PCR reaction was conducted in an MJ Research thermal cycler as follows: annealing steps were conducted at 48° C., elongation at 68° C. and the melting step at 94° C., 26 total cycles were run. Reactions were initiated by placing the reaction mixture in a block pre-warmed to 95° C., incubated for 5 min. and the following cycle was initiated: (a) reactions were incubated at 94° C. for 30 s (melting step); (b) primer annealing was permitted to occur for 45 s at 48° C.; (c) primers were elongated at 68° C. for 2 min. After the conclusion of step (c), the reaction block was cycled to 94° C. and the cycle was restarted at step (a). After ten cycles, step (c) was increased 20 s for each successive cycle until it reached 7 min.; 26 cycles total were run. The block was then cycled to 4° C. and held there until the sample was removed for further use.

DNA was precipitated by the addition of 1 μl glycogen (Boehringer-Mannheim) and 100 μl isopropanol, centrifuged in a microfuge for 2 min. at 14,000×g; the supernatant was discarded and the pellet was washed with 300 μl 75% ethanol (room temperature). The pellet was resuspended in 10 μl TE and 2 μl of gel loading dye (0.25% Bromophenol Blue, 0.25% Xylene cyanol, 25% Ficoll (Type 400) in distilled H₂O) was added. The entire sample was loaded onto a 3% Metaphor agarose gel (FMC) in TAE buffer (0.04 M Tris-acetate, 1 mM EDTA (pH 8.5) along with a 123 bp standard and a 100 bp ladder (Gibco/BRL) in separate lanes. The gel was run at 30 V overnight, stained with ⅟10,000 dilution of Sybr Green I (Molecular Probes) in TAE buffer for 1 h at room temperature with gentle shaking, and

TABLE 2

PCR primers used for isolation of *T. thermophilus* dnaE probes

| Peptide # | Sequenced used for PCR primer | Primer number[1] | Primer Sequence(s) 5'→3' | Primer Degeneracy (-fold) |
|---|---|---|---|---|
| 2 | HLHQHTQ (SEQ ID NO:191) | 1F | CAY YTN CAY CAR CAY ACN CA (SEQ ID NO:110) | 512 |
| 91 | EGFYEK (SEQ ID NO:192) | 91F | GAR GGN TTY TAY GAR AA (SEQ ID NO:111) | 64 |
|  |  | 91R | TT YTC RTA RAA NCC YTC (SEQ ID NO:112) | 64 |
| 676 | YQEQQMQ (SEQ ID NO:193) | 676F | TAY CAR GAR CAR CAR ATG CA (SEQ ID NO:113) | 320 |
|  |  | 676R | TG CAT YTG YTC YTG RTA (SEQ ID NO:114) | 16 |
| 853 | DGGYFH (SEQ ID NO:194) | 853R | TG RAA RTA NCC NCC RTC (SEQ ID NO:115) | 128 |

[1]F, forward primer; R, reverse primer

For PCR reactions, the Boehringer Mannheim Expand™ High Fidelity PCR system was used with *T. thermophilus* photographed ugder short uv irradiation. The results of the analysis are summarized below.

Primer pair: 1F-91R. Size of band(s) 330 near 314 expected band. Two other faint bands were visible at approximately 250 and 980 bp.

Primer pair: 91F-676R. Blank lane on gel—no band produced.

Primer pair: 676F-853R. Size of band 520–550 near 522 expected band. 11 bands ranging from 200 to >1500 bp. 9 bands were of equal or greater than the intensity of the desired band. (This band did not result in a clone that provided dnae sequence information.)

Primer pair: 1F-676R. Size of band 2100 near 2050 expected band.

Only one other band was visible near 1200 bp. (After cloning, this band was sequenced and found to be incorrect—that is, not dnaE gene.)

Primer pair: 91F-853R. Blank lane—no bands visible.

C. Cloning PCR-Amplified dnaE Probe

The products resulting from primer pairs 1F-91R and 1F-676R were extracted using the freeze squeeze technique (described in Example 4, section D) and cloned into vector pCRII (Invitrogen) as described above.

Plasmid isolates were prepared using the Promega Plus Minipreps technique and examined by restriction analysis to determine whether they yielded an EcoRI fragment approximately the same size as the desired cloned PCR product (EcoRI is flanked by the cloning site). From 8 colonies picked from the IF-91R cloning, 7 yielded a fragment around the expected 320 bp. From 8 colonies picked from the 1F-676R cloning, 8 yielded a fragment around the expected size. Plasmid DNA was prepared from the IF-91R and IF-676R clonings, using the Qiagen Plasmid Midi Kit and sequenced (Colorado State University DNA Sequencing Facility, Ft. Collins, Colo.).

The sequence of the PCR product (SEQ ID NO: 40) resulting from amplification of *T. thermophilus* chromosomal DNA with primers IF and 91R (plasmid pMGC/E1-91.B; DMSO 1322) are shown in FIG. 12A. In this Figure, the sequences resulting from the primers underlined and shown in bold (SEQ ID NOS: 41 and 42). In FIG. 12, a portion of the BLAST search results using only the sequence between the primers is shown. The first segment aligned (base 2-55) in the *T. thermophilus* query sequence) aligned with M. tuberculosis and Synechocystis sp. DnaE in the +2 reading frame; the remainder of the alignment is in the +3 reading frame indicating a frameshift error in the DNA sequence. The percent identity for three homology stretches was found to be 50%, 63%, and 46% (M. tuberculosis) and 57%, 47%, and 47% (Synechocystis sp.).

D. Southern Analysis Of *T. thermophilus* DNA Using Isolated 1F-91R dnaE Probe A Southern Analysis of *T. thermophilus* chromosomal DNA was conducted as described above (Example 4, section F) to determine the restriction fragments most likely to contain a full-length *T. thermophilus* dnaE gene. *T. thermophilus* chromosomal DNA was digested with the indicated restriction enzymes alone and in combination as described above. Approximately 3 µg DNA was subjected to electrophoresis, transfer to membranes and blotting as previously described (Ausubel et al. [1995] supra). Probe preparation and amount used was as described above.

The size of the bands which hybridized with the probe in restriction enzyme-digested DNA was as follows:

| | |
|---|---|
| PstI | 10.2 kb |
| PstI/HindIII | 0.95 kb |
| Hind III | 0.95 kb |

-continued

| | |
|---|---|
| BspHI | 8.5 kb |
| MscI/BspHI | 2.6 and 2.2 kb |
| MscI | 3.2, 2.2 kb |
| MscI/Hind III | 0.95 kb |

E. Cloning And Sequencing Of The 5' Approximately 1100 bp of *T. thermophilus* dnaE Gene A BspHI digest of *T. thermophilus* chromosomal DNA (preparation B) was subjected to electrophoretic separation on an agarose gel and the region corresponding to the 8.5 kb fragment that hybridized with the dnaE IF-91R probe cut out of plasmid pE1-91B.

The isolated 8.5 kb population of BspHI fragments was cloned into pMGC707 as described above, except that the cleavage site was not within the polylinker. The BspHI site is at nucleotide 3088 in the parental pCRII vector, approximately 1120 nucleotides away from the polylinker.

Colonies were screened by colony hybridization (Ausubel et al [1995] supra, sections 6.1.1–6.1.3 and 6.3.1–6.3.4; See also, production of *T. thermophilus* 1F-91R probe isolated from plasmid pE1-91B. A total of approximately 4,000 colonies from 2 plates was screened. Two positive colonies were selected and restruck on LB plates containing 150 µg/ml carbenicillin to ensure purity of the selected clones. Two separate colonies were selected from each for further examination. Of these, only two (DMSO 708B and 709A) had approximately 8 Kb inserts as judged by HindIII digestion of plasmids isolated by the ProMega Plus Minipreps. Plasmid pBspHIdnaE (DMSO 708B) was sequenced (Colorado State University DNA sequencing facility), resulting in the approximate sequence of the first 1,109 bases of the *T. thermophilus* dnaE gene (SEQ ID NO: 58) (FIG. 13A). In this Figure, the apparent start of this preliminary sequence is underlined; the upstream sequence is not shown in this Figure. The start of this sequence was estimated by alignment with the N-terminal protein sequence. Apparently the initiating Met and the following Gly were removed by proteolysis.

The BLAST search using this sequence indicated that there were at least two frarneshift errors in the sequence, since the first part aligned in frame 1, then a long stretch aligned in frame 2, and then a final stretch aligned in frame 1. From these alignments, it was determined that the first frameshift error probably occurred between bases 102 and 119, and the second occurred between bases 787 and 832. The sequences were edited in order to bring all of the homology into one open reading frame, by deleting $C_{108}$, that was a part of a string of 6 Cs. An "N" (ie., any base) was added after base 787, to produce the sequence shown in FIG. 13B (SEQ ID NO: 59). The best alignments resulting from a BLAST search with the amino acid sequence shown in FIG. 13B are shown in FIG. 13C (SEQ ID NOS: 60–62. In this Figure, the grey boxes indicate bases that are similar, but not identical between the sequences, while black boxes indicate identical bases.

F. Isolation Of Downstream Sequences By Asymmetric PCR

Experiments attempting to use primer E853R in combination with primers 91F and 676F failed to isolate downstream dnaE sequences. Thus, in an attempt to obtain further downstream sequence the following asymmetric PCR procedure was developed so that only relied on an upstream primer and a knowledge of a downstream Pst I restriction site through Southern analysis.

Asymmetric PCR uses one primer to extend a stretch of DNA rather than two primers normally used. The advantage of this technique is useful in that it allows amplification of either a region upstream or downstream of the primer and subsequent cloning without further knowledge of DNA sequence. A single DNA primer is mixed with genomic DNA, and the polymerase used to make a single strand copy of the template DNA as far as it could extend. The single-strand DNA was then made double-stranded by a random hexamer-primer annealing and extension with Klenow polymerase, and the double stranded DNA was cloned directly into the vector after creating the appropriate ends by digestion of the double-stranded DNA with the chosen restriction enzymes.

1. Primer Design

The primer was selected from known *T. thermophilus* dnaE sequence; and additionally was biotinylated at the 5' end and contained a PacI restriction site to allow cloning. The primer sequence was 5'-biotin-CCGCGCTTAATTAACCCAGTTCTCCCTCCTGGACG-3' (SEQ ID NO: 116). The PacI restriction site, highlighted in bold, has a rare 8-base recognition sequence (ie., only contains As and Ts), and would be expected to be extremely rare in Thermus thermophilus with its highly (69%) GC rich genome. This is important because it restricts possible clones into the PacI site of the vector to DNA containing the primer. The GCGC region preceding the PacI site clamps the DNA, thus allowing a highly efficient cleavage of the PacI site, and PacI is known to cleave efficiently with as little as 2 base pairs of DNA flanking the cleavage site. Biotin on the 5' end was used to purify the amplified DNA containing the primer, as explained below.

2. PCR Amplification

For the single-stranded amplification step, the Boehringer Mannheim Expand™ PCR system was used and following the manufacturer's recommendations except as noted in the following. Buffer A contained 3.5 Al of 10 mM dNTP mix (Gibco/BRL; 350 $\mu$M final); 0.5 $\mu$l of the forward primer (80 $\mu$M stock concentration; 400 nM final in 100 $\mu$l reaction), 46 $\mu$l distilled H$_2$O). Buffer B contained 10 $\mu$l of 10-fold concentrated Boehringer Mannheim Long Template PCR System Buffer 2 (500 mM Tris-HCl (pH 9.2 at 25° C.), 160 mM ammonium sulfate, 22.5 mM MgCl$_2$), 37.5 III H$_2$O), and 1.5 $\mu$l Expand Long Template enzyme mix (mixture of Taq and Pwo DNA Polymerase—5 units total) and 1 $\mu$l of *T. thermophilus* genomic DNA (preparation A, 0.6 $\mu$g total). Buffers A and B were combined in a 0.2 ml thin walled tube (Intermountain) and the single primer extension reaction was conducted in an MJ Research thermal cycler as follows.

Annealing steps were conducted at 55° C., elongation at 68° C. and the melting step at 95° C.; 60 total cycles were run. Reactions were initiated by placing the reaction mixture in a block pre-warmed to 95° C., incubated for 5 min. and the following cycle was initiated: (a) reactions were incubated at 95° C. for 30 s (melting step); (b) primer annealing was permitted to occur for 30 s at 55° C.; (c) primers were elongated at 68° C. for 12 min. After the conclusion of step (c), the reaction block was cycled to 94° C. and the cycle was restarted at step (a). Upon completion of 60 cycles, the block was cycled to 4° C. and held there until the sample was removed for workup.

After completion of the PCR reaction, the Boehringer Mannheim PCR cleanup kit was used to remove unextended primer. The PCR cleanup kit efficiently binds DNA that contains greater than 100 bp of double stranded DNA. Most long single-stranded DNA would be expected to contain enough secondary structure to bind to the silica beads, while the primers would not. The PCR cleanup kit was used as described above. Bound DNA was eluted overnight in 50 $\mu$l TE, pH 8.4 followed by an additional wash with 50 $\mu$l of distilled H$_2$O.

The extended, biotinylated DNA was removed from the remaining genomic DNA by binding the biotinylated DNA to agarose beads coated with monomeric avidin (Soft-Link, Promega). Soft-Link resin (100 $\mu$l settled beads) was incubated 2x w/0.4 mls 10 mM biotin washed 6x with 10% acetic acid by resuspending gel in 1 ml and spinning dry in 0.45 $\mu$M spin filters (Life Sciences). The resin was then washed once with 0.5 mls of 0.5 M potassium phosphate (pH 7.0), 3x with 50 mM potassium phosphate (pH 7.0), then resuspended in 0.5 mls 50 mM potassium phosphate (pH 7.0). DNA from the single primer elongation reaction was added to 20 $\mu$l of the beads (packed volume) (final reaction volume 120 $\mu$l), incubated 30 min. with gentle agitation every few minutes, washed with 0.5 ml TE (pH 7.5) followed by centrifugation (14,000×g, 30 s) in the spin filters to remove unbiotinylated DNA. The wash was repeated 5 times. The biotinylated DNA was eluted by the addition of 40 $\mu$l 10 mM biotin to the beads and incubation in a capped spin filter for 5 min. in a 42° C. water bath. The DNA was recovered by centrifugation (14,000×g, 320 s); the elution step was repeated once more. To ensure complete removal of DNA, the beads were washed with 0.1 M NaOH, spun as before and the basic mixture neutralized by the addition of 2 M Tris-HCl. The neutralized solution had a final pH of 7.8 as tested by pH paper. The DNA resulting from the alkaline-eluted and biotin-eluted fractions was ethanol by the addition of 1 $\mu$l glycogen, ¹⁄₁₀ volume sodium acetate (adjusted by the addition of acetin acid to pH 5.2), and 3 volumes ethanol followed by centrifugation at 14,000×g for 10 min. The samples were suspended in 50 I distilled H$_2$O and combined.

To convert the single stranded DNA to double-stranded DNA the random hexamer priming was used as previously described, following the protocol of the manufacturer (Boehringer-Mannheim). A 5x reaction mixture was used (100 $\mu$l reaction volume) with the following components: approximately 40 $\mu$l DNA, 3 [1 each dATP, dTTP, dGTP and 5 $\mu$l dCTP, 10 $\mu$l Boehringer Mannheim random primed DNA labeling kit component 6 "reaction mixture" (containing random hexamer oligonucleotides, 25 $\mu$l water, and 5 $\mu$l Klenow polymerase (Boehringer, 10 U). The reaction was incubated for 30 min. at 37° C.

DNA from the random-hexamer priming was precipitated using 1 $\mu$l glycogen, ¹⁄₁₀ volume sodium acetate, and 3 volumes of ethanol. The pellet was washed 2xwith 0.2 mls of 75% ethanol and the pellet resuspended in 200 $\mu$l TE, pH 7.5. About 15 $\mu$g of total DNA was recovered, quantitated with PicoGreen™ as described above.

A PacI digest on 6.5 $\mu$g of the recovered DNA was performed to prepare the primer end of the product for cloning. In reaction containing 90 $\mu$l DNA (6.5 $\mu$g), was digested (3h, 37° C.) in the presence of 25 $\mu$l 10 NEB buffer 1 (10 mM Bis Tris Propane-HCl, 10 mM MgCl$_2$, 1 mM DTT (pH 7.0 at 25° C.), 10 Ill PacI enzyme (NEB, 100 units), 125 $\mu$l distilled H$_2$O). The cleaved DNA was precipitated by the addition of 1 Al glycogen, 25 $\mu$l sodium acetate, and 3 volumes of ethanol. The product recovered by centrifugation (5 min., 14,000×g) was dissolved in 75 $\mu$l distilled H$_2$O.

Analysis of Southern digests showed that there was a PstI site downstream of the BspHI site that defined the end of the longest *T. thermophilus* dnaE clone. Therefore, the asymmetric PCR product was digested with PstI, to provide a distal cloning site to enable cloning more downstream sequence.

PacI digested DNA (37 $\mu$l containing 3.25 $\mu$g DNA) was combined with 12.5 $\mu$l 10xNEB buffer #3 50 mM Tris HCl, 10 MM MgCl$_2$, 100 mM NaCl, 1 mM DTT (pH 7.9 at 25° C.), 5 $\mu$l PstI (NEB, 25 units), 65.5 $\mu$l dH$_2$O) and digested for 2 h at 37° C. The digested DNA was precipitated by the addition of 1 $\mu$l glycogen, 25 $\mu$l sodium acetate and 3 volumes of ethanol, recovered by centrifugation, dissolved in 125 $\mu$l dH$_2$O, and quantitated with PicoGreen™ as described. The concentration was 9 ng/$\mu$l (i.e., 1125 ng total recovery). DNA was precipitated again as before and dissolved in 2 $\mu$dH$_2$O.

The vector was digested with PacI and BstXI (gives a PstI compatible end for cloning) as follows: 10 $\mu$l DNA (pMGC707, 30 μg) was digested (4h, 55° C.) in the presence of 25 μl 10× NEB buffer #3, 10 μl BstXI (NEB, 100 units), 205 μl distilled H₂O). The product was precipitated by the addition of 2 μl glycogen, 1/10 vol. sodium acetate (2.5 M, pH 5.2), 2 volumes ethanol, collected by centrifugation, and redissolved in 50 μl TE (pH 7.5). The redissolved DNA (15 μg) was further digested (37° C. overnight) with PacI (5 μl PacI 50 units, NEB) in the presence of 10 μl 10×NEB buffer #1 and 60 μl distilled H₂0.

DNA was run preparatively in 0.6% Seakem agarose in lx TAE at 85V for 4 hrs. A single band was obtained and recovered by the freeze/squeeze technique described above. DNA was precipitated with ethanol by the standard procedure described above.

3. Ligation of PacI/PstI-digested Asymmetric PCR product into PacI/BstXI-digested pMGC707 DNA to make pB5

Digested pMGC707 vector DNA (2 μl (0.1 μg) was mixed with 2 μl of PacI/PstI digested asymmetric PCR product (1 pg) together with 2 μl 10× ligation buffer (Invitrogen), 1 μl T4 DNA ligase (Invitrogen, 4 Weiss units) and 13 μl distilled H₂O and incubated 1 h at 23° C. and then overnight at 14° C. DNA was precipitated with ethanol, centrifuged and resuspended in 10 ill distilled H₂O. 4 μl of this mixture was transformed by electroporating as described above. To enrich the population for kanamycin-resistant bacteria, the transformation mixture was grown in liquid culture for 1 hr without selection and 2.5 brs in the presence of kanamycin (50 μg/ml), then streaked for isolated colonies on LB. Ten colonies were picked and DNA was prepared using Promega Plus minipreps. Two of the ten had inserts of roughly 1.8 kb as judged by comparison of PacI-digested DNA with linearized vector.

The candidate inserts from isolates pB4 and pB5 also released a 0.95 kb fragment upon HindIII digestion as predicted from the Southern blot of T. thermophilus chromosomal DNA against a dnaE probe. One (pB5, DMSO 1335) was sequenced and shown to have homology to E. coli dnaE. The region of asymmetric PCR product corresponding to the more N-terminal end (ie., the "front end" of the clone) of the T. thermophilus dnaE gene is shown in FIG. 14A (SEQ ID NO: 63). In this Figure, the region corresponding to the forward primer is underlined and shown in bold. The distal end of the PCR clone was also sequenced (i.e., the "back end" of the clone), in order to provide an indication of whether extensive new sequence had been gained, or if the full-length gene was obtained by the asymmetric PCR. The sequence of this clone is shown in FIG. 14B (SEQ ID NO: 180). The PstI sequence that defined the front end of the T. thermophilus DNA is underlined in FIG. 14A. BLAST alignment (FIG. 14B; SEQ ID NO: 180) indicated that the most distal end corresponded to roughly residue 464 of E. coli DnaE, considerably short of the full-length 1160 amino acid protein. Thus, this approach to identify the T. thermophilus dnaE sequence was abandoned. However, this alignment did reveal the critical "PDXD" motif (SEQ ID NO: 1 17) that defines two critical aspartate residues making up part of the eubacterial DNA polymerase III active site. This motif is bolded and underlined in FIG. 14. T. thermophilus DnaE was found to be 62% identical to E. coli sequences in this region.

G. Southern Analysis Of T. thermophilus Using Approximately 300 BspHI/EcoRI dnaE Probe Isolated From Plasmid pB5 AND Sequencing Full-Length T. thermophilus dnaE Sequence analysis of the BspHI T. thermophilus dnaE clone indicated that it encoded only the amino-terminal portion of the sought gene. After obtaining a portion of the T. thermophilus dnaE gene further downstream sequence by use of the asymmetric PCR cloning method, a probe was designed that was more internal to the gene, enhancing the chances of detecting a restriction fragment that encoded downstream regions of T. thermophilus dnaE. The distal most C-terminal encoding fragment of pB5 bounded by the terminal vector EcoRI site and a BspIH site internal to dnaE was used as a probe for more Southern blots. T. thermophilus chromosomal DNA was digested with the indicated restriction enzymes alone and in combination. Approximately 3 μg DNA was subjected to electrophoresis, transferred and blotted as previously described (Ausubel, supra, section 2.9.2 to 2.9.11). Following hybridization procedures described and using 120 ng of a probe labeled by the random hexamer priming method ($2.5 \times 10^7$ cpm) we determined the size of the bands which hybridized with the probe following restriction digestion as follows (all sizes of restriction fragments from this and all Southerns is ±20%):

| | |
|---|---|
| BamHI | 4.9 kb |
| BamHI/KpnI | 4.2 kb |
| KpnI | 7.4 kb |
| BglII | 13.8 kb |
| BglII/NcoI | 2.1 kb |
| NcoI | 2.1 kb |
| BamHI/BglII | 4.9 kb |
| BamHI/NcoI | 2.1 kb |

PvuI, SpeI and XhoI digests yielded only very high molecular weight DNA

A critical part of the restriction map gleaned from the above (with distances here and as determined from all Southerns was ±20%) was:

BamHI—700 bp—KpnI—4200bp—BamHI—3200 bp—KpnI

This method was used to isolate the putative fill length T. thermophilus dnaE clones (Lofstrand Labs) as described briefly below. The bacterial DNA was randomly cut with SauA1 (i.e., a 4 base cutter) by partial digestion and ligated into phage vector lambda GEM 12 at the Xho I site (Promega). The library was packaged using Epicenter Technologies packaging extract and plated out for screening. The plaques were lifted in duplicate and probed using $^{32}$p random primed pB5E insert DNA (780bp fragment was isolated from low melt agarose using KpnI and BspHI). The six primary plates containing greater than 20,000 pfu per plate demonstrated about 100 duplicate positives each. Twelve duplicate positive primary plaque areas were picked and replated to enrich the clones. A third plating was performed using duplicates from the second screen and four duplicate positive isolated plaques were chosen for amplification and DNA purification. The phage were grown in liquid lysate cultures and the virus was purified by two CsCl density gradient centrifugations. The four DNA clones were digested using KpnI and BamHI, and KpnI and BamHI. The ethidium bromide stained 0.8% TBE gel indicated that clones BGP2 7.1 and BGP2 8.1 appear to contain full length genes based on the restriction patterns present. A Southern blot was also performed on the four clones cut with BamHI and BamHI+KpnI using the pB5E (probe 2) which showed strong signals in the predicted 4.9 Kb BamHI fragment and 7.4 Kb KpnI fragment. The 4.9 Kb Bam HI fragment was subcloned into plasmid (pBSIIKS+) for sequencing.

EXAMPLE 6

Cloning and Sequencing the T. thermophilus dnaA Gene

A. Design of PCR Primers

The PCR primers for dnaA were designed by using highly conserved amino acid sequences from regions of the dnaA gene in a variety of bacteria. For the design of the forward primers, the consensus sequence (SEQ ID NO: 118) was derived from the following regions of homology (SEQ ID NOS: 119–132):

```
Concensus for dnaA                            |G  L  G  K  T  H|
forward PCR primer
E. coli           P  L  F  L  Y  G  G  T   G  L  G  K  T  H  L  L  H  A  V
T. maritima       P  L  F  I  Y  G  G  V   G  L  G  K  T  H  L  L  Q  S  I
B. burgdorfori    P  C  L  I  Y  G  G  V   G  L  G  K  T  H  L  L  Q  S  I
B. subtilis       P  L  F  I  Y  G  G  V   G  L  G  K  T  H  L  M  H  A  I
Serratia          P  L  F  L  Y  G  G  T   G  L  G  K  T  H  L  L  H  A  V
S. typhimurium    P  L  F  L  Y  G  G  T   G  L  G  K  T  H  L  L  H  A  V
P. mirabilis      P  L  F  L  Y  G  G  T   G  L  G  K  T  H  L  L  H  A  V
P. putida         P  L  F  L  Y  G  G  V   G  L  G  K  T  H  L  M  H  A  V
B. aphidicola     P  L  F  L  Y  G  G  T   G  L  G  K  T  H  L  L  H  A  I
M. luteus         P  L  F  I  Y  G  E  S   G  L  G  K  T  H  L  L  H  A  I
S. coelicolor     P  L  F  I  Y  G  E  S   G  L  G  K  T  H  L  L  H  A  I
H. influenza      P  F  F  L  Y  G  G  T   G  L  G  K  T  H  L  L  H  A  I
R. melioti        P  L  F  I  H  S  S  V   G  L  G  K  T  H  L  L  Q  A  I
S. ciiri          P  L  F  I  Y  G  D  S   G  L  G  K  T  H  L  L  H  A  I
```

The amino acid sequence used for the design of dnaA forward primers was Gly Leu Gly Lys Thr His (SEQ ID NO: 133). The Forward Primer A177Fa had the sequence 5'-GGN YTN GGN AAR ACS CAT-3' (SEQ ID NO: 134); the Forward Primer A177Fb had the sequence 5'-GGN YTN GGN AAR ACS CAC-3' (SEQ ID NO: 135); the Forward Primer A177Fc had the sequence 5'-GGN YTN GGN AAR ACW CAT-3' (SEQ ID NO: 136); while the Forward Primer A177Fc had the sequence 5'-GGN YTN GGN AAR ACW CAC-3' (SEQ ID NO: 137). Four primers were used to keep degeneracy at or under 512-fold. They varied in codon 5 and 6.

For the design of the reverse primers, the consensus sequence (SEQ ID NO: 138) was derived from the following regions of homology (SEQ ID NOS: 139–154):

```
Consensus Sequence              E  L  F  H  T  F  N
for dnaA reverse                   F
PCR primer
E. coli                  Q  E  E  F  F  H  T  F  N  A  L  L  E  G  N  Q  Q  I  I  L
T. maritima     T  G  V  Q  T  E  L  F  H  T  F  N  E  L  H  D  S  G  K  Q  I  V  I
M. leprae          G  I  Q  E  E  F  F  H  T  F  N  T  L  H  N  A  N  K  Q  I  V  I
B. subtilis              Q  T  E  F  F  H  T  F  N  T  L  H  E  E  S  K  Q  I  V  I
B. burgdorferi     G  I  Q  E  E  L  F  H  T  F  N  A  L  Y  E  D  N  K  Q  L  V
S. coelicolor            Q  E  E  F  F  H  T  F  N  T  L  H  N  A  N  K  Q  I  V  L
M. luteus                   E  F  F  H  T  F  N  T  L  Y  N  N  N  K  Q  V  V  I
H. influenza             Q  E  E  F  F  H  I  F  N  S  L  F  E  T  G  R  Q  I  I  L
P. putida                Q  E  E  F  F  H  T  F  N  A  L  L  E  G  G  Q  Q  V  I  L
B. aphidicola            Q  E  E  F  F  H  T  F  N  A  L  L  E  G  N  Q  Q  I  I  L
S. marcesens             Q  E  E  F  F  H  T  F  N  A  L  L  E  G  N  Q  Q  I  I  L
S. typhimurium           Q  E  E  F  F  H  T  F  N  A  L  L  E  G  N  Q  Q  I  I  L
p. mirabilis             Q  E  E  F  F  H  T  F  N  A  L  L  E  G  N  Q  Q  I  I  L
Wolbachia                   E  F  F  K  T  F  N  A  L  I  D  Q  N  K  Q  L  V  I
R. melioti           I   Q  H  E  F  C  H  L  L  N  M  L  L  D  S  A  K  Q  V  V  V
S. ciiri                       F  H  I  F  N  S  Y  I  E  K  N  K  Q  I  V  I
```

The amino acid sequence for dnaA reverse primers was Glu Leu/Phe Phe His Thr Phe Asn (SEQ ID NO: 155). The reverse PCR primers for dnaa were reverse primer A25IRa [5'-TTR AAN GTR TGR AAN AAY TC-3' (SEQ ID NO: 156)]; reverse primer A251Rb [5'-TTR AAN GTR TGR AAN AGY TC-3' (SEQ ID 30 NO: 157)] (SEQ ID NO: 67).

B. PCR Amplification of T. Thermophilus dnaA probe

PCR amplification of dnaA was carried out using the Boehringer Mannheim Expand™ long template PCR system as described above except that the following conditions were used: The annealing steps were conducted at 55° C., elongation at 68° C. and the melting step at 94° C.; 26 total cycles were run. PCR-amplified dnaA probe was separated on 2% FMC Metaphor agarose gels, visualized by Sybr green-1 staining, cloned into vector pCRII (Invitrogen), and sequenced as described above. The primer pair that yielded product of the expected length (237 bp) was A177 Fb and A 25IRb.

A roughly 237 bp and a 210 bp band were excised from the gel and cloned into pCrII (Invitrogen) as previously described for dnax and dnaE. Five colonies from each of the 2 ligations were tested for the presence of insert by digestion with EcoRI, which releases cloned inserts from the pCRII vector. All five of the dnaA clones from the 237 bp DNA ligation had inserts. Four out of 5 clones using the 210 bp DNA had inserts. Two colonies from the 237 bp insert clones were chosen at random, clones (A237.A and clone A237.E). These clones were grown up for plasmid purification using the Qiagen procedure (described previously). Plasmid pA237.A (DMSO dnaA L-A) was sent for sequencing (Fort Collins) and shown by sequence to have homology to dnaA.

The results are shown in FIG. 15. FIG. 15A shows the deduced nucleotide sequence of a portion of T. thermophilus dnaA (SEQ ID NO: 65). In this Figure, the sequences corresponding to primers are underlined (SEQ ID NOS: 66 and 67). The DNA sequence in FIG. 15A was found to be equivalent to the message. A BLAST search of the sequence between the regions corresponding to the primers was conducted. These results revealed a strong homology to the structural genes encoding bacterial DnaA origin binding protein. The corresponding segment of B. subtilis dnaA showed 58% identity over a 68 amino acid stretch. The corresponding E. coli dnaA showed 45% identity over 68 residues. As with other Figures, the intervening designations indicate identical residues. FIG. 15B shows the alignment results for T thermophilus, *E. coli*, and *B. subtilis*. In FIG. 15B, the numbers refer to *B. subtilis* (SEQ ID NOS: 72 and 76) and *E. coli* (SEQ ID NOS: 68 and 73) amino acid residues, as appropriate; the numbers for *T. thermophilus* (SEQ ID NOS: 70 and 75) refer to the first base of the anticodon for the shown amino acid residue to the left of the corresponding primer sequence near the 3' end of the shown sequence. In FIG. 15, homologous sequences are indicated (SEQ ID NOS: 69, 71, and 74).

Probe A237 was also used to screen a lambda library using the methods described above for dnaE (i.e., probe isolated and labeled as for the other oligonucleotides). Over 100 candidate positive clones were identified; two were grown up and the DNA purified as described for dnaE. The first clone was sequenced using a primer designed from the sequence of plasmid pA237.A (See, FIG. 15A). It was discovered that the clone terminated and vector sequence was encountered before the carboxyl terminus of dnaA was reached. The second clone is sequenced to the end of the gene. The sequence aligns with other bacterial dnaAs.

An EcoRI fragment was removed from plasmid pA237.A and labeled as previously described in the generation of PCR probes for dnaX, and used to probe restriction enzyme digestions of *T. thermophilus* chromosomal DNA preparation B in Southern Blots, as described for the dnaE and dnaX genes in this application. The estimated sizes of hybridizing bands were:

| | |
|---|---|
| ApaLI | 4.1 kb |
| ApaLI/HindIII | 4.1 kb |
| HindIII | 12 kb |
| EheI/HindIII | 3 kb |
| MluI/ApaLI | 4.1 kb |
| MluI | 14 kb |
| EheI/MluI | 3.9 kb |
| MfeI | 14 kb |
| MfeI/HindIII | 12 kb |

EXAMPLE 7

Cloning and Sequencing the *T. thermophilus* dnaQ Gene

A. Design of PCR Primers

Primers for dnaQ were designed from sequences conserved in the epsilon subunits of bacteria and phage.

TABLE 3

Primers for dnaQ

| CONSENSUS | DTETTG | HNAA FD |
|---|---|---|
| *E. coli* | IVLDTETTGMNQI (SEQ ID NO:158) | LVIHNAA-FDIGFM (SEQ ID NO:159) |
| *H. haemolyticus* | IVLDTETTGMNQI (SEQ ID NO:160) | LVIHNAP-FDIGFM (SEQ ID NO:161) |
| *B. aphidicola* | IVLDTETTGMNSV (SEQ ID NO:162) | LVIHNAS-FDVGFI (SEQ ID NO:163) |
| *B. subtilis* | VVFDVETTGLSAV (SEQ ID NO:164) | LVIHNAA-FDMG (SEQ ID NO:165) |
| *M. genitalium* | VIFDIETTGLHGR (SEQ ID NO:166) | MVAHNGINFDLPFL (SEQ ID NO:167) |
| *M. pulmonis* | VVYDIETTGLSPM (SEQ ID NO:168) | MVAHNAA-FDHNFL (SEQ ID NO:169) |
| *S. aureus* | VVFDVETTGLSNQ (SEQ ID NO:170) | FVAHNAS-FDMGFI (SEQ ID NO:171) |

Two forward primers were designed for each forward and reverse sequence for dnaQ in order to reduce degeneracy. The amino acid sequence used for the design of forward primers was Asp Thr Glu Thr Thr Gly ((SEQ ID NO: 172). The first forward primer (Q12Pa) had the sequence 5'-GAY ACN GAR ACN ACN 0G-3' (SEQ ID NO: 173), while the second forward primer (Q12Fb) had the sequence 5'-GAY RTN GAR ACN ACN GG-3' (SEQ ID NO: 174). Both forward primers were equivalent except for the second codon which encodes Thr, in order to keep the degeneracy below 512-fold, since Thr was found in the gram negative bacteria (primer Q12Fa), while Ile or Val were found in some gram positive bacteria (primer Q12Fb). The amino acid sequence for the reverse primers was His Asn Ala Ala Phe Asp (SEQ ID NO: 175). The first reverse primer (Q98Ra) had the sequence 5'-TCR AAN GCN GCR TTR TG-3' (SEQ ID NO: 176), while the second reverse primer (Q98Rb) had the sequence 5'-TCR AAN SWN GCR TTR TG-3' (SEQ ID NO: 177). Both the reverse primers were equivalent except for the fourth codon (from the 3' end) which encoded Ala (primer Q98Ra) and Ser (primer Q98Rb).

B. PCR Amplification of T. Thermophilus dnaQ probe

PCR amplification, gel analysis and sequencing of a dnaQ probe was carried out as described above for the dnaA probe. Only primer combinations Q12Fa and Q98Ra gave a PCR product of the expected size. The Q12Fa/98Ra primer combination gave a single intense sharp band of approximately 270 bp and 8 additional bands of high molecular weight (6 to 14 kb).

An approximately 264 bp band resulting from amplification of *T. thermophilus* chromosomal DNA preparation B using primers Q12Fa and Q98Ra was excised from a 2% Metaphor agarose (1×TAE) and cloned as described for the PCR probes for dnaE and dnaX. Five colonies from the clones were chosen and plasmid isolated using the Promega plus Minipreps. The plasmid DNA from the five colonies were tested for the presence of insert by digestion with restriction endonuclease EcoRI, which releases cloned inserts from the pCRII vector. Four out of five showed the presence of insert. Two clones, named plasmid pMGC/QFA11A and QFA11E were chosen for further analysis. Plasmid pMGC/QFA11A (DMSO 1329) was sent was sent for sequencing (Fort Collins) and was shown to have sequence homology to dnaQ (FIG. 16). The results are shown in FIG. 16A (SEQ ID NO: 77). In this Figure, sequences corresponding to primers are underlined (SEQ ID NOS: 78 and 79); the sequence shown in this Figure is the complement of the message strand. A BLAST search of the sequence between the regions corresponding to the primers revealed strong homology to the structural genes encoding bacterial proofreading exonucleases. The exonuclease domain of *B. subtilis* DNA polymerase III (SEQ ID NO: 84) showed 40% identity over a 50 amino acid stretch. The epsilon proofreading subunit (F) of the *E. coli* DNA polymerase III holoenzyme (dnaQ) (SEQ ID NO: 80), showed 32% identity over 49 amino acid residues. The amino acid sequences are shown in FIG. 16B. In FIG. 16B, for *B. subtilis* and *E. coli*, the numbers refer to amino acid residues, while for *T. thermophilus* (SEQ ID NO: 82), the numbers refer to the first base of the anticodon for the shown amino acid residue to the left of the corresponding primer sequence near the 3' end of the shown sequence. As with other Figures, the intervening designations indicate identical residues (SEQ ID NOS: 81 and 83).

Southern Blots were also conducted as described above, using above probe and digest of *T. thermophilus* DNA preparation B.

| | |
|---|---|
| HindIII | 7.55 Kb |
| HindIII/EheI | 2.25 kb |
| EheI | 3.4 kb |
| ApaLI | Very high molecular weight |
| ApaLI/HindIII | 1.1 kb |
| ApaLI/EheI | 2.2 kb |

Plasmid pMGC/QFA11A (DMSO 1329) was also used as a probe screen a lambda library using the same techniques described for dnaE. However, experiments using this probe failed to produce positive colonies as it had for dnaE and dnaA. Next, an oligonucleotide probe was designed, based on the sequence shown in FIG. 16. With this probe, over 100 strong positive plaques were identified and verified by replating. Three were grown up and the DNA purified as described for dnaE.

In addition, the full length gene is isolated using the sequences identified during the development of the present invention, to probe lambda *T. thermophilus* chromosomal DNA libraries, subclone hybridizing sequences, and confirm their identity by DNA sequencing.

The isolated and sequenced full length dnaQ gene is engineered to overexpress wild type and N- and C-terminal fusions with a peptide containing a hexahistidine sequence and a biotinylation site as described for DnaX below. The N- and/or C-terminal fusion proteins are purified, and used to obtain *T. thermophilus* DnaQ-specific monoclonal antibodies and fusion proteins. The fusion proteins are also used to make affinity columns for the isolation of proteins that bind to DnaQ alone and in a complex with the isolated DnaE protein. The structural genes for novel proteins found by this method are isolated, sequenced, expressed, purified and used to determine whether they make contributions to the functional activity of the *T. thermophilus* DNA polymerase III holoenzyme. Native DnaQ is also purified and used for the reconstitution of DNA polymerase III holoenzyme, and developed as an additive to improve the fidelity of thermophilic polymerases that do not contain proofreading exonucleases.

EXAMPLE 8

Construction of Vectors Expressing Native *T. thermophilus* τ and γ Subunits

As the sequence of the *T. thermophilus* dnaX gene is complete (See, FIG. 9A), vectors are constructed that overproduce both the τ and γ subunits of the *T. thermophilus* DNA polymerase III holoenzyme in *E. coli*. Methods used to construct these vectors are similar to those followed previously for the corresponding *E. coli* subunits to overproduce native τ and γ (See e.g., H. G. Dallmann et al, J. Biol. Chem., 270:29555–29562 [1995]).

1. Construction of the Starting Vectors

First, a vector, pDRK-C, (See, D. R. Kim and C. McHenry, J. Biol. Chem., 271: 20690–20698 [1996]) containing a pBR322 origin of replication, a gene expressing the lac IQ repressor protein, and a semisynthetic *E. coli* promoter (pA1) that is repressed by the lacI repressor is modified. Plasmid pDRKC DNA is prepared and digested with XbaI and DraIII to remove a small polylinker (this removed polylinker contains XbaI-NcoI-NotI-DraIII sites). The following oligonucleotide is synthesized and inserted into the digested plasmid:
CTAGGAGGTTTTAATCGATGCGGCCGGATCCTCGAGTCTAGACACTGG—
CTCCAAAATTAGCTACGCCGGCCTAG-GAGCTCAGATCTGTG (SEQ ID NO: 178).

The resulting plasmid pA1-CB-CEBXXDS contains the restriction sites within a polylinker to enable the following cloning steps. The following is a reproduction of the above oligonucleotides with the relevant sequences annotated:
5° CTAGGAGGTTTTAATCGATGCGGCCGGATCCTC-GAGTCTAGACACTGG—
CTCCAAAATTAGCTACGCCGGCCTAGGAGCTCA-GATCTGTG-5' (SEQ ID NO: 179). In this sequence, the following annotations apply:
CTAG—Sticky end for XhaI, but destroys site, so it is not recleaved
AGGAGG=rbs
ATCGAT=ClaI site
ATG=initiation codon
CGGCCG=EagI site
GGATCC=BamHI site
CTCGAG=XhoI site
TCTAGA=XbaI site
CACTGG=3'-overhang to regenerate DraIII site In parallel, a T7 promoter cloning vector is developed, such that the determination of which (i.e., T7 or pA1) provides the best levels of soluble protein in a form amenable to further purification. The starting vector, pET11-KC contains a pBR322 replication origin, a copy of lacI and a T7 promoter. A ClaI site in the vector is destroyed and the polylinker is replaced with a synthetic one to enable further cloning steps. PET11-KC is prepared and cut with ClaI, then filled in and religated to destroy the site. The resulting plasmid, pET11-KC-Cla, is then cut with XbaI, DraIII and the same duplex replacement oligonucleotide described above are cloned into it, resulting in plasmid pET-CB-CEBXXDS.

2. Construction of Plasmids that Overexpress *T. thermophilus* τ and γ From pA1 Promoter Plasmid (for dnaX) is prepared and a 300 bp segment containing the amino-terminal end of the gene amplified using PCR. The priming oligonucleotide used in the forward direction contains a ClaI site followed by an overlapping ATG to replace the *T. thermophilus* GTG start codon, followed by *T. thermophilus* dnax sequence from nucleotides 4–26. The reverse primer is located downstream of the unique BamHI site within *T. thermophilus* dnaX. The PCR product is then cut with ClaI and BamHI, and cloned into corresponding sites in pA1-CB-CEBXXDS. The resulting plasmid has the 5'-end of the dnaX gene linked to the pA1 promoter, as well as an optimal ribosome binding site and an ATG initiation codon. The rest of the gene is then reconstructed by insertion of an approximately 2 Kb BamHI-XbaI fragment isolated from plasmid pAX2.S into the corresponding sites of the plasmid to generate plasmid pA1-TX. The product is verified by sequencing the upstream polylinker region, as well as the first several hundred bases of inserted DNA downstream from the ClaI site through the BamHI site. The recleavage of the XbaI site is also verified.

3. Construction of pA1 Promoter-Containing Plasmids that Overexpress *T. thermophilus* τ Fused to a Carboxyl-Terminal Peptide That Contains Hexahistidine and a Biotinylation Site The present invention also provides methods and compositions for expression *T. thermophilus* τ fused on its carboxyl-terminus to tagged peptides. This permits rapid purification and oriented immobilization to create an affinity column for isolation of additional *T. thermophilus* proteins that bind τ. During the development of the present invention, it was determined that *E. coli* τ tolerates fusion of foreign proteins to its C-terminus with preservation of activity. These observations are utilized to produce the fused *T. thermophilus* τ.

The vector pDRK-C described above encodes a 30-residue peptide that is brought into frame with the C-terminus of dnaX. This is accomplished by engineering a PCR product to contain a properly phased SpeI site in place of the normal termination codon of *T. thermophilus* dnaX. PCR is then conducted using pAX2.S as a template. One PCR primer is internal to the dnaX AflII site, while the second primer contains a cleavable SpeI site followed by final 8 codons of *T. thermophilus* dnaX (excluding the stop codon). The approximately 600 nucleotide product is then cleaved with SpeI and AflII, and inserted into the corresponding sites of the vector to generate the plasmid "pA1-CB-TX." The presence of restriction sites is verified, and the sequence of the DNA generated by PCR through the flanking restriction site confirmed.

4. Placing the Sequences Expressing *T. thermophilus* τ and τ-Biotin/Hexahistidine Polypeptide Under Control of the T7 Promoter Next, the ClaI-SpeI fragment is removed from plasmids pA1-TX and pA1-CB-TX and inserted into the ClaI-SpeI sites of pET-CB-CEBXXD generating plasmids pET-TX and pET-CB-TX, using methods known in the art.

5. Comparing Overproduction of Soluble *T. thermophilus* dnaX Protein From pA1-TX, pA1-CB-TX, pET-TX and pET-CB-TX Next, strains carrying pA1-CB-TX and pET-CB-TX are grown, induced with IPTG, lysed, and run on SDS PAGE. The SDS-PAGE gels are stained (e.g., with Coomassie), and biotin blots of the products also conducted. Uninduced cells and cells lacking plasmid are included as controls. Cells are grown at 25° C., 37° C. and 43° C. to determination which gives the highest levels of protein expression consistent with no or limited degradation. Once a candidate optimal set of conditions is established, the determinate is made whether the protein is soluble by growing cells in a flask, subjecting them to the lysis methods described in previous Examples, centrifuging to remove debris and insoluble protein, and precipitating protein from the cleared supernatant by the addition of ammonium sulfate to 50% saturation. The protein is then redissolved, subjected to SDS-PAGE, and the percent *T. thermophilus* dnaX directly assessed by staining with Coomassie blue, and the percent of total protein is determined by densitometry. A control with cells lacking a plasmid is also included. If the percent of total protein is approximately the same as with the SDS lysis of whole cells, large scale growth at a 180 l scale in a fermentor is possible. If the level of *T. thermophilus* τ protein is low in the redissolved ammonium sulfate precipitate, induction at the other temperatures that gave acceptable production in the preliminary experiments are used.

6. Purification of *T. thermophilus* τ Subunit Fusion with a Biotinylated Peptide Containing Hexahistidine In these experiments, all purification procedures (unless otherwise specified) are generally conducted at 4° C. However, in cases where the protein dissociates or is judged to have lost activity in this or any subsequent purifications, room temperature may be used. Cells are grown and lysed as described with modifications made in the growth conditions to yield optimal levels of soluble undegraded protein as determined in section 5 above. DnaX protein containing in the cleared lysate is precipitated using ammonium sulfate added to 60% saturation, or higher, as necessary to precipitate all of the DnaX protein. The *T. thermophilus* τ protein fused to a C-terminal biotinylated hexahistidine-containing peptide is purified by ammonium sulfate fractionation, chromatography on $Ni^{++}$-NTA ion chelating chromatography much as described above.

If necessary, additional purification can be achieved by affinity chromatography on monomeric avidin affinity columns as known in the art.

The purified protein is used to generate a battery of monoclonal antibodies that react with it by the procedures described in Example 2, above. Antibody producing cell lines are selected that express antibody that reacts strongly with *T. thermophilus* τ fusion protein as shown in ELISA assays and Western blots, as known in the art and described in previous Examples. The latter assay system is used to distinguish antibodies that react with contaminants present in the *T. thermophilus* τ fusion protein preparation. As a control, the *E. coli* α subunit that has the same fusion peptide is included in the screen, in order to eliminate antibodies that are directed against the fusion peptide. Selected hybridomas are grown up at the 3 liter level to produce an abundant quantity of antibody.

7. Purification of Natural *T. thermophilus* τ and γ Subunits

Natural τ and γ subunits expressed from the modified *T. thermophilus* dnaX gene in *E. coli* are purified by column chromatographic procedures and assayed by SDS-PAGE, with confirmation of the identity of the authentic τ protein by Western blots using the above monoclonal antibodies. Cell growth and lysis are conducted as described above (See e.g., Dallmann et al., supra) with modifications in growth conditions to yield optimal levels of soluble undegraded protein as determined in section 5 above. The ammonium sulfate precipitation conditions are optimized in order to maximize the amount of *T. thermophilus* DnaX protein precipitated and minimize the total level of protein precipitated. Protein determinations are conducted by the method of Bradford with modifications following the instructions that come with the reagent supplied by Pierce. The level of *T. thermophilus* DnaX protein is determined by quantitative Western blots using methods as described in previous Examples (e.g., those used to monitor the levels of *T. thermophilus* DnaE protein), with the exception being that antibodies to DnaX prepared as described above will be used. While the optimum level of ammonium sulfate determined by experiment is used, the following provides a representative procedure: Fr. I (cleared lysate) is precipitated with 107 g of ammonium sulfate (0.226 g for each mL of Fr. I, 40% saturation) and centrifuged at 22,000×g for approximately 30 min. Pellets are backwashed by resuspension in a Dounce homogenizer with 100 mL of Buffer TBP containing 0.1 M NaCl, and 0.2 g/mL ammonium sulfate (35% saturation), and re-centrifuged. The final pellets are stored at 4° C. until used and referred to as Fr. II.

The chromatography columns (e.g., hydrophobic, ion exchange, and/or sizing columns) are chosen so as to yield maximally pure protein and provide the highest yield. Portions of Fr II are dissolved in Buffer SP (50 mM Tris-HCl (pH 7.5), 10% (w/v) glycerol, 5 mM dithiothreitol) (approximately 7 mg/ml final), clarified by centrifugation (28,000×g, 30 min), and diluted with the same buffer to a conductivity equivalent to 50 mM NaCl. In experiments where the desired DnaX protein does not remain soluble as judged by remaining in the supernatant after gentle centrifugation, it is dissolved in larger quantities of buffer, adding additional salt and diluting just before application to the column, and/or adding low levels of various detergents (i.e., 0.02% NP-40).

This material is loaded onto a Q Sepharose (Pharmacia; 2 mg protein/ml resin) column equilibrated in buffer SP. After loading, the column is washed with one column volume of Buffer SP, then developed with a 12 column volume gradient of 50 to 600 mM NaCl in Buffer SP at a flow rate of 1 column volume/h, and 100 fractions are collected. The elution position of *T. thermophilus* γ and X are determined by quantitative Western blots, and total protein determined by the method of Bradford. Fractions with the highest ratio of DnaX protein to total protein are pooled. Generally, this results in pooling fractions of ½ peak height or greater. In the situation where the protein fails to bind to the column, buffers with lower salt (down to O NaCl with dialysis to decrease endogenous levels of salt) are used, and, if that fails, buffers with higher pH are used. In the situation where the protein fails to elute, the ionic strength of the gradient is increased until it does so. Once the elution position is determined, the gradient is optimized, so that the total ionic strength change is not more than what is needed (generally no more than a 400 mM NaCl change) and the dnax protein elutes ½ way through the gradient. The pooled peak is then precipitated by the addition of sufficient ammonium sulfate to precipitate all protein (generally 60% saturation) and the pellet collected by centrifugation (28,000×g for 30 min) to yield Fr. III.

The Fr. III pellet is the dissolved in Buffer SP to a concentration of approximately 2 mg/ml, and centrifuged (28,000×g, 30 min) to clarify. Fr. III is then be loaded onto a SP Sepharose (Pharmacia; approximately 5 mg protein/ml resin) column equilibrated with buffer SP. After loading, the column is washed with one column volume of Buffer SP, and developed with a 12 column volume gradient of 50 to 600 mM NaCl in Buffer SP at a flow rate of 1 column volume/h; 100 fractions are collected. Chromatography is quantitated and optimized as described for the Q-Sepharose column. Additionally, this column resolves τ and γ, and conditions are optimized to enable this resolution. In situation where τ and γ are not separated by this procedure or the preceding Q Sepharose procedure, hydrophobic chromatography using commercially available resins is conducted. The resulting pooled fractions of γ and τ are precipitated with ammonium sulfate as described to Q-Sepharose resulting in Fr. IV.

Fr IV is dissolved in Buffer H (25 mM Hepes-KOH (pH 7.5), 25 mM NaCl, 5% glycerol, 0.1 mM EDTA) (approximately 7 mg protein/ml), and applied to a S-400 HR (Pharmacia) column (44:1 height:diameter ratio, total column volume 50-times sample volume) equilibrated with Buffer H. The column is developed in the same buffer at a flow rate of 1 column volume/day, and 100 fractions collected. DnaX protein (τ and γ run on separate columns since resolved in a preceding column) are quantitated as described for the Q-Sepharose column These fractions are pooled, and distributed in aliquots, which are then flash-frozen in liquid nitrogen and stored at −80° C. as Fr. IV. This material provides reagents for reconstituted *T. thermophilus* DNA polymerase III holoenzyme.

EXAMPLE 9

Use of *T. thermophilus* DnaX Proteins to Obtain Additional Components of the DnaX Complex and Reconstitution of *T. thermophilus* Dnax Complex In other cellular systems examined to date, the ATPase that transfers the sliding clamp processivity factor (i.e., $\beta_2$ in *E. coli*, PCNA in eukaryotes) contains five different proteins that are tightly and cooperatively bound in a complex. In this Example, *T. thermophilus* DnaX protein is immobilized on a column and cleared T. thermophilus lysates are passed over the column, in order to permit subunit exchange and assembly of a full DnaX complex on the immobilized protein. Contaminants are washed away, and the specifically bound proteins eluted, separated by SDS-PAGE, transferred to a membrane, and both amino-terminal and internal peptide sequences determined, using methods known in the art. These sequences are used to isolate the structural gene for the isolated proteins. These proteins are expressed and purified, their ability to form a specific complex with *T. thermophilus* DnaX confirmed, and used to reconstitute *T. thermophilus* DnaX complex to provide a functional *T. thermophilus* DNA polymerase III holoenzyme.

EXAMPLE 10

Isolation of *T. thermophilus* SSB and Expression of Purification of SSB

*T. thermophilus* SSB is isolated by chromatography of DNA cellulose columns using modifications of the methods of Molineux et al. (Molineux et al., J. Biol. Chem., 249 6090–6098 [1974]). Lysates (Fraction I) are prepared by the methods described in Example 2. Fraction II is prepared by addition of 0.24 g to each ml of Fraction I and precipitates collected as described in Example 2. The collected ammonium sulfate precipitate is dissolved in 20 mM Tris-HCl (pH 7.5), 50 mM NaCl, 10% glycerol, 5 mM β-mercaptoethanol at a concentration of 1 mg protein/ml and applied to a denatured DNA cellulose column equilibrated in the same buffer. A 1.5×13 cm column is run for each 100 g of *T. thermophilus* used as starting material. The column is then washed successively with two column volumes of equilibration buffer at 0.5 column volume/E containing 100, 200, 400, 800, 1600 and 2000 mM NaCl respectively. Fractions eluting from the column are monitored by SDS-PAGE, and the tightest binding fractions that contain proteins between 15,000 Da and 30,000 Da are pooled individually for each protein and subjected to further purification by Q-Sepharose (Pharmacia) chromatography. The pooled fractions are dialyzed against 20 mM Tris-HCl (pH 7.5), 10% glycerol, 5 mM β-mercaptoethanol, and then applied to a Q Sepharose column equilibrated in the same buffer at a load ratio of 2 mg protein/ml resin. The column is eluted with a 20-column gradient from 0–1 M NaCl in the equilibration buffer and the fractions containing the sought protein selected by SDS-PAGE in the preceding step pooled. This procedure is repeated for each major candidate.

Each of the pooled candidate fractions are concentrated by ammonium sulfate precipitation (60% saturation) and collected as described under Example 2. The protein is as concentrated as possible (e.g., consistent with its being soluble after centrifugation in a bench top microcentrifuge for 2 minutes as judged by protein determination with the Bradford reagent as described in the above Examples), dialyzed against the Q-Sepharose equilibration buffer, and then subjected to SDS-PAGE, and blotted onto a membrane.

Both N-terminal and internal peptide sequencing are conducted as described above for DnaX and DnaE. For the protein that contains sequences that show the best homology to SSB from other eubacteria (i e., as judged by the most favorable score using the NIH's BLAST server), oligonucleotides are designed for obtaining a fragment of the *T. thermophilus* ssb gene using methods described for dnaX, E, Q and A. Success in obtaining a fragment of the sought ssb gene is judged by a favorable score of a sequence obtained by DNA sequencing the cloned PCR products (i.e., better than $1 \times 10^{-2}$) in a BLAST search of the sequences between primers against the nr database at NIH's server. This fragment is used to probe a lambda library for a fall length clone as described for DnaE.

The candidate full length fragment is subjected to DNA sequencing and its identity confirmed by recognizable homology to other eubacterial ssbs using the default parameters in the NIH BLAST server. The full length gene is modified and overexpressed using the strategies outlined for DnaX above. The isolated homogeneous protein (e.g., either from purification from an overproducing strain or frame non-overproducing T. thermophilus) is then used to support reconstituted T thermophilus replication systems.

EXAMPLE 11

Isolation of the T. thermophilus DnaN Protein

As once the core DNA polymerase III, SSB and DnaX complexes are in hand, the only factor presumed to be missing required for reconstitution of a processive polymerase is the sliding clamp processivity factor DnaN (C). In this Example, an assay is set up that employs a long single stranded template and a single primer. This assay system is used to assay for an activity in T. thermophilus extracts (or ammonium sulfate or column fractions) that stimulates replication by limiting levels of DNA polymerase III in the presence of DnaX complex and SSB. This assay is used to guide purification of T. thermophilus DnaN. The isolated protein is partially sequenced (N-terminus and internal sequences), a fragment isolated by PCR, the entire gene full length gene isolated from chromosomal libraries in lambda vectors as described for DnaE, the dnaN gene sequenced, expressed and the resulting DnaN protein purified by ammonium sulfate fractionation and chromatographic procedures. Then, conditions for reconstitution of DNA polymerase III holoenzyme activity on long single-stranded templates are optimized.

In an alternative method, the sequence downstream from the T. thermophilus dnaA gene is determined and, if homologous to dnaN genes of other eubacteria, used to express T. thermophilus β subunit. The dnaN gene resides downstream of the dnaA gene in most, but not all, eubacteria.

EXAMPLE 12

Additional Assay Systems

In this Example, methods that assay specifically for processive DNA replication on long single-stranded templates are described. These assays are useful a they permit further optimization of the systems described above to maximize processive synthesis. These steps include the assaying cleared lysates, ammonium sulfate and chromatographic fractions for factors that further increase the yield of long replication products. Once identified, these factors are purified, their structural genes isolated and expression vectors constructed to provide larger quantities of these stimulatory factors.

In addition, the processive assays are modified to include regions of high secondary structure at a defined point in the template. In a second assay, long single-stranded DNA that contains extensive complementarity to internal regions ranging from 100–1000 bases are added. Conditions that increase readthrough of these regions including the assaying for T. thermophilus protein factors that enable this readthrough.

Furthermore, the initial optimizations is conducted on lambda clones containing inserts up to 23 Kb. Primers are selected from insert sequence or flanking lambda sequences. Optimum protocols to amplify DNA to provide optimal yields are developed.

Once optimization has been performed on lambda isolate, the procedure is extended to 100 Kb or longer isolates using longer vectors. The optimal conditions are determined for these vectors, and the methodology is extended to isolated chromosomal DNA to determine the practical limitations of these methods.

Optimal elongation protocols are developed, and cycling protocols that enable reconstituted T. thermophilus DNA polymerase III holoenzyme plus isolated accessory factors used in PCR methods using substrates (i.e., targets) beyond 10 kb, 50 kb, and 200 kb, and larger, are also established. Conditions that permit the component proteins to remain stable during repeated denaturation steps to approximately 95° C., in standard protocols as known in the art are also established. In the alternative, capillary technology requiring very short denaturation times (i.e., a few seconds at approximately 95° C.) are developed. In addition, methods and conditions for isothermal amplification, wherein the polymerase is coupled to the action of thermophilic helicase and associated assembly factors are also obtained.

From the above, it is clear that the present invention provides novel thermophilic DNA polymerases and preparations from T thermophilus. In particular, the present invention provides T. thermophilus polymerase III preparations and means to identify Pol IIIs present in other species.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant arts are intended to be within the scope of the following claims.

What is claimed is:

1. An isolated nucleotide sequence comprising the nucleotide sequence set forth in SEQ ID NO: 7.

2. A recombinant DNA vector comprising the nucleotide sequence of claim 1.

3. A host cell containing the recombinant DNA vector of claim 2.

4. A purified dnaX protein comprising the amino acid sequence set forth in SEQ ID NO: 8.

5. A fusion protein comprising dnax protein encoded by SEQ ID NO: 8, and a non-dnaX protein sequence.

6. An isolated amino acid sequence comprising the amino acid sequence set forth in SEQ ID NO: 8.

7. An isolated nucleotide sequence encoding the amino acid sequence of claim 6.

8. The nucleotide sequence of claim 7, wherein said nucleotide sequence further comprises 5' and 3' flanking regions.

9. A recombinant vector comprising the nucleotide sequence of claim 7.

10. A host cell containing the recombinant vector of claim 9.

11. An isolated amino acid sequence comprising the amino acid sequence set forth in SEQ ID NO: 1.

12. An isolated nucleotide sequence encoding the amino acid sequence of claim 11.

13. The purified protein encoded by the isolated nucleic acid sequence of claim 12, wherein said protein is *Thermus thermophilus* gamma protein.

14. The nucleotide sequence of claim 12, wherein said nucleotide sequence further comprises 5' and 3' flanking regions.

15. A recombinant vector comprising the nucleotide sequence of claim 12.

16. A host cell containing the recombinant vector of claim 15.

17. A fusion protein comprising the protein of claim 11.

18. Purified *Thermus thermophilus* DNA polymerase holoenzyme III, wherein said DNA polymerase III holoenzyme comprises alpha subunit.

19. The purified Thermus thermophilus DNA polymerase holoenzyme III of claim 18, wherein said DNA polymerase III holoenzyme further comprises gamma and tau subunits.

20. An isolated nucleotide sequence comprising the sequence of nucleotide 744 to 2333 of SEQ ID NO: 7.

21. The isolated nucleotide sequence of claim 20, wherein said nucleotide sequence encodes dnaX.

22. An isolated amino acid encoded by the nucleotide sequence of claim 20.

23. The isolated nucleotide sequence of claim 20, wherein said sequence comprises the sequence of nucleotide 744 to 1853 of SEQ ID NO: 7.

24. An isolated amino acid sequence encoded by the nucleotide sequence of claim 23.

25. The isolated amino acid sequence of claim 24, wherein said sequence comprises the tau subunit of *Thermus thermophilus* DNA polymerase III holoenzyme.

26. An isolated polypeptide comprising the gamma subunit of *Thermus thermophilus* DNA polymerase III holoenzyme.

27. The amino acid sequence of claim 26, wherein said sequence comprises the sequences set forth in SEQ ID NOS: 17–19.

28. A fusion protein comprising the sequence of claim 27.

29. An isolated nucleotide sequence encoding the amino acid sequence set forth in claim 27.

30. A recombinant vector comprising the nucleotide sequence of claim 29.

31. An isolated amino acid sequence comprising the sequence set forth in SEQ ID NO: 26.

32. The amino acid sequence of claim 31, wherein said sequence is a *Thermus thermophilus* DNA polymerase III alpha subunit.

33. A fusion protein comprising the Thermus thermophilus DNA polymerase III alpha subunit of claim 32.

34. An isolated nucleotide sequence encoding the amino acid sequence of claim 31.

35. A recombinant vector comprising the sequence set forth in claim 34.

36. An isolated polypeptide comprising at least one functionally active subunit of *Thermus thermophilus* DNA polymerase III holoenzyme, wherein said subunit is selected from the group consisting of alpha, tau, and gamma.

37. A fusion protein comprising said functionally active subunit of *Thermus thermophilus* DNA polymerase III holoenzyme of claim 36.

38. An isolated nucleotide sequence encoding at least one functionally active subunit of *Thermus thermophilus* DNA polymerase III holoenzyme, wherein said subunit is selected from the group consisting of alpha, tau, and gamma.

39. A recombinant vector encoding said functionally active subunit of *Thermus thermophilus* DNA polymerase III holoenzyme of claim 38.

* * * * *